(12) United States Patent
Mercier et al.

(10) Patent No.: US 10,920,237 B2
(45) Date of Patent: Feb. 16, 2021

(54) INCREASE IN MEIOTIC RECOMBINATION IN PLANTS BY INHIBITING AN RECQ4 OR TOP3A PROTEIN OF THE RTR COMPLEX

(71) Applicant: INSTITUT NATIONAL DE LA RECHERCHE AGRONOMIQUE, Paris (FR)

(72) Inventors: Raphaël Mercier, Fontenay le Fleury (FR); Mathilde Seguela-Arnaud, Bois d'Arcy (FR); Wayne Crismani, West Des Moines, IA (US)

(73) Assignee: INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 435 days.

(21) Appl. No.: 15/311,151

(22) PCT Filed: Mar. 27, 2015

(86) PCT No.: PCT/IB2015/052276
§ 371 (c)(1),
(2) Date: Nov. 14, 2016

(87) PCT Pub. No.: WO2015/181647
PCT Pub. Date: Dec. 3, 2015

(65) Prior Publication Data
US 2017/0073697 A1 Mar. 16, 2017

(30) Foreign Application Priority Data
May 30, 2014 (FR) ........................ 1454944

(51) Int. Cl.
*C12N 15/82* (2006.01)
*C12N 9/90* (2006.01)
*C07K 14/415* (2006.01)

(52) U.S. Cl.
CPC ........ *C12N 15/8242* (2013.01); *C07K 14/415* (2013.01); *C12N 9/90* (2013.01); *C12N 15/8218* (2013.01); *C12N 15/8241* (2013.01); *C12Y 599/01002* (2013.01)

(58) Field of Classification Search
CPC ............................................. C12N 15/8242
See application file for complete search history.

(56) References Cited

U.S. PATENT DOCUMENTS 8,399,254 B2 * 3/2013 Que .................. C12N 15/8213
435/325

FOREIGN PATENT DOCUMENTS

| WO | 2013/038376 A1 | 3/2013 | |
| WO | WO 2013/038376 | * 3/2013 | ........... C07K 14/415 |
| WO | WO-2013038376 A1 | * 3/2013 | ............... A01H 5/00 |

OTHER PUBLICATIONS

Hartung, F. et al., PNAS Nov. 20, 2007; vol. 104, No. 47, pp. 18836-18841.*
Crismani, W. et al., Science Jun. 22, 2012; vol. 336, pp. 1588-1590.*
Crismani, W. et al., Science Jun. 22, 2012; vol. 336, pp. 1588-1590. (Year: 2012).*
Bagherieh-Najjar, M. et al. The Plant Journal (2005) vol. 43, pp. 789-798. (Year: 2005).*
Hartung, F. et al. PNAS Nov. 20, 2007; vol. 104, No. 47, pp. 18836-18841. (Year: 2007).*
Higgins, J.D. et al., THe Plant Journal, Dec. 30, 2010; vol. 65, pp. 492-502. (Year: 2010).*
Hartung, F. et al. PNAS (Nov. 20, 2007); 104:18836-188841. (Year: 2007).*
Bagherieh-Najjar, M.B., et al., "*Arabidopsis* RecQl4A Suppresses Homologous Recombination and Modulates DNA Damage Responses," The Plant Journal 43(6):789-798, Sep. 2005.
Crismani, W., and R. Mercier, "What Limits Meiotic Crossovers?" Cell Cycle 11(19):3527-3528, Oct. 2012.
Hartung, F., and H. Puchta, "The RecQ Gene Family in Plants," Journal of Plant Physiology 163(3):287-296, Feb. 2006.
Hartung, F., et al., "Two Closely Related RecQ Helicases Have Antagonistic Roles in Homologous Recombination and DNA Repair in *Arabidopsis thaliana*," Proceedings of the National Academy of Sciences of the USA (PNAS) 104(47):18836-18841, Nov. 2007.
International Search Report dated Sep. 9, 2015, issued in corresponding International Application No. PCT/IB2015/052276, filed Mar. 27, 2015, 3 pages.

* cited by examiner

*Primary Examiner* — Russell Kallis
(74) *Attorney, Agent, or Firm* — Christensen O'Connor Johnson Kindness PLLC

(57) ABSTRACT

The invention relates to a method for increasing the frequency of meiotic recombination in plants, by inhibiting the RECQ4 or TOP3A protein, especially by mutagenesis or extinction of the RECQ4 or TOP3A gene coding for said protein. The invention can be used especially in the field of plant breeding and genetic mapping.

Figure 1:
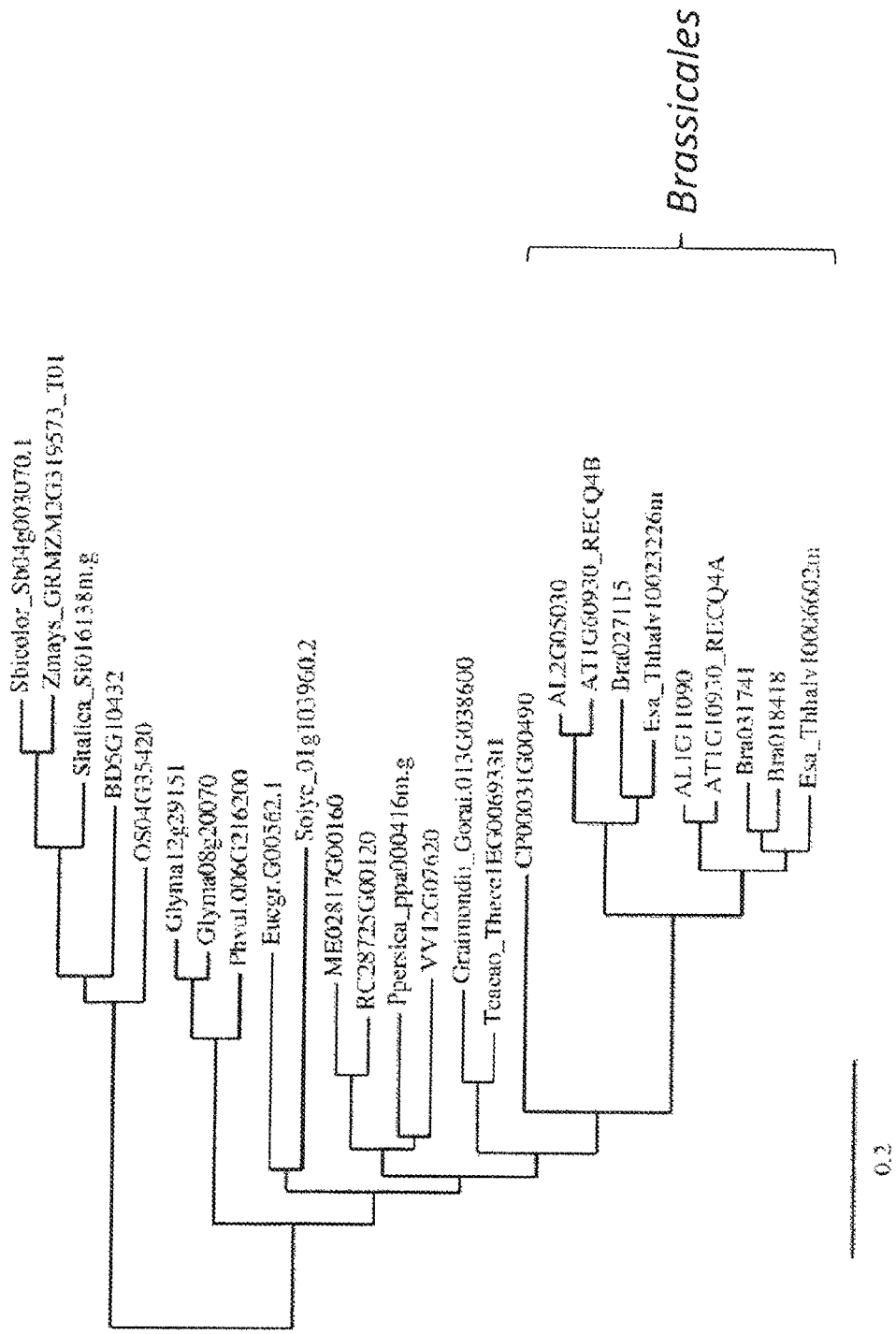

9 Claims, 8 Drawing Sheets
Specification includes a Sequence Listing.

FIGURE 2

Figure 2 (continued)

INCREASE IN MEIOTIC RECOMBINATION IN PLANTS BY INHIBITING AN RECQ4 OR TOP3A PROTEIN OF THE RTR COMPLEX

STATEMENT REGARDING SEQUENCE LISTING

The sequence listing associated with this application is provided in text format in lieu of a paper copy and is hereby incorporated by reference into the specification. The name of the text file containing the sequence listing is 56981_Sequence_Revised_final_2017-04-17. The text file is 452 KB; was created on Apr. 17, 2017; and is being submitted via EFS-Web with the filing of the specification.

The present invention relates to a method for increasing meiotic recombination in plants.

Meiotic recombination is an exchange of DNA between homologous chromosomes during meiosis; it occurs during the prophase of the first meiotic division. One of the products of recombination is crossing over (or crossover), which leads to a reciprocal exchange of continuity between two homologous chromatids. This prophase (prophase I) comprises five successive stages: leptotene, zygotene, pachytene, diplotene and diakinesis. At the leptotene stage, the chromosomes become individualized, each chromosome being made up of two sister chromatids resulting from the duplication which occurred before the prophase. During the zygotene stage, the homologous chromosomes pair up, forming a structure known as "bivalent" which contains four chromatids, two maternal sister chromatids and two paternal sister chromatids, which are homologous to the maternal chromatids. At the pachytene stage, the chromosomes are completely paired, and recombination nodules form between the homologous chromatids which are tightly linked to one another by the synaptonemal complex (SC); at the diplotene stage, the SC gradually dissociates, and the homologous chromosomes begin to separate from one another, but remain attached at the chiasmas, which correspond to the sites of crossovers (COs). The chromosomes condense during diakinesis; the chiasmas remain until metaphase I, during which they maintain the pairing of the bivalents on either side of the equatorial plate.

Meiotic recombination is triggered by the formation of double-stranded breaks (DSBs) in one or other of the homologous chromatids, and results from the repairing of these breaks, using, as template, a chromatid of the homologous chromosome.

The result of meiotic recombination is to cause a rearrangement of the alleles of paternal and maternal origin in the genome, which contributes to generating genetic diversity. It is therefore of particular interest in plant breeding programs (Wijnker & de Jong, Trends in Plant Science, 2008, 13, 640-646; Crismani et al., Journal of Experimental Botany, 2013, 64, 55-65). In particular, the possibility of increasing the recombination rate can make it possible to obtain new combinations of characteristics; it can also make it possible to facilitate the introgression of genes of interest from one line to the other, and also the genetic mapping and the positional cloning of genes of interest.

Various methods for controlling meiotic recombination have been proposed, based on the overexpression or the silencing of one or other of the very large number of genes identified as being involved or potentially involved in this mechanism. For example, PCT application WO/0208432 proposes the overexpression of the RAD51 protein, which is involved in homologous recombination, for stimulating meiotic recombination; application US 2004/023388 proposes overexpressing an activator of meiotic recombination, chosen from: SPO11, MRE11, RAD50, XRS2/NBS1, DMC1, RAD51, RPA, MSH4, MSHS, MLH1, RAD52, RAD54, TID1, RAD5S, RADS7, RADS9, a resolvase, a single-stranded DNA-binding protein, a protein involved in chromatin remodeling, or a protein of the synaptonemal complex, for increasing the frequency of recombination between homologous chromatids; PCT application WO 2004/016795 proposes increasing the recombination between homologous chromosomes by expressing an SPO11 protein fused to a DNA-binding domain; PCT application WO 03/104451 proposes increasing the potential for recombination between homologous chromosomes by overexpression of a protein (MutS) involved in mismatch repair; PCT application WO 2010/071418 proposes reducing the expression or the activity of the RecQ15 (RECQ5) protein.

However, in most cases, the effect of these candidate genes on the formation of meiotic COs in planta has not been confirmed, and it is therefore necessary to identify other genes involved in this phenomenon.

One of the factors known to act on the meiotic recombination rate is the interference phenomenon: the formation of a CO at a site on the chromosome inhibits the formation of other COs close by. However, it has been shown that there are in fact two distinct pathways for meiotic CO formation (Hollingsworth & Brill, Genes Dev., 2004, 18, 117-125; Berchowitz & Copenhaver, Current genomics, 2010, 11, 91-102). The first generates interfering COs known as type I COs (COI), and involves a set of genes collectively denoted as BA/genes (ZIP1, ZIP2/SHOC1, ZIP3, HEI10, ZIP4, MER3, MSH4, MSH5, PTD) and also the MLH1 and MLH3 proteins; the second pathway generates non-interfering COs, known as type II COs (COII), and is dependent on the MUS81 gene.

The use of one and/or the other of these two pathways is variable from one organism to another. In higher plants, represented by the model plant *Arabidopsis thaliana*, the two pathways coexist, that of the type I COs being predominant; it has been observed that the inactivation of the AtMSH4, AtMSH5, AtMER3, SHOC1, PTD, AtHEI10 or AtZIP4 genes induces up to an 85% reduction in CO frequency (Higgins et al., Genes Dev., 2004, 18, 2557-2570; Mercier et al., Curr. Biol., 2005, 15, 692-701; Chelysheva et al., PLoS Genet. 2007, 3, e83; Higgins et al., Plant J., 2008, 55, 28-39; Macaisne et al., Current Biology, 2008, 18, 1432-1437; Wijeratne et al., Molecular Biology of the Cell, 2006, 17, 1331-43; Chelysheva et al., PLoS Genetics, 2012, 8, e1002799). Some homologous chromosomes are as a result no longer paired in the form of bivalents, but pair in the form of univalents. This decrease in the number of bivalents is accompanied by a strong reduction in fertility.

Previously, the inventors have identified a gene, known as FANCM (for "Fanconi Anemia Complementation Group M"), the inhibition of which compensated for the effects of that of AtMSH5, of SHOC1, or of AtZIP4, and made it possible to increase the number of meiotic COs (PCT application WO 2013/038376; Crismani et al., Science 2012, 336, 6088, 1588-90).

In continuing their research, the inventors have now identified two other genes of which the inhibition produces effects similar to that of FANCM.

These are the TOP3A (for DNA TOPOISOMERASE III alpha) and RECQ4 genes, encoding two of the proteins of the RTR complex.

The RTR complex is a conserved complex, consisting of a helicase of the RecQ family, of a DNA Topoisomerase III (Topoisomerase type I, sub-type IA) and of a structural protein of the RMI1 family. This complex, which is involved in the resolution of DNA recombination intermediates in all eukaryotes, is essential for maintaining the integrity of the genome (Mankouri and Hickson, Trends Biochem Sci., 2007, 32, 538-46).

The helicases of the RecQ family are proteins involved in the maintaining and the stability of the genome in all organisms such as bacteria, yeasts, animals and plants. In eukaryotes, the number of RecQ (or RECQ) genes and the structure of the RecQ (or RECQ) proteins vary enormously between organisms. In *Arabidopsis thaliana*, there are seven RECQ genes, including AtRECQ4A which encodes a protein homologous to the RecQ helicase of *Escherichia coli*, Sgs1 from yeast and human BLM (Hartung F. and Puchta, H., J. Plant. Physiol., 2006, 163, 287-296; Hartung et al., Nucleic Acids Res., 2000, 28, 4275-4282). The AtRECQ4B gene, a paralog of AtRECQ4A probably derived from a gene duplication that occurred only in Brassicaceae, encodes a protein which exhibits 70% identity with AtRECQ4A (FIG. 1). The AtRECQ4A and AtRECQ4B proteins comprise three conserved domains: a helicase domain, which is the most important, and comprises eight motifs (0, I, Ia, II, III, IV, V and VI), having a total length of approximately 300 to 450 amino acids, containing the sequences required for the binding of ATP, the hydrolysis and DNA unfolding (NCBI cd00079 and cd00046); an RQC domain (smart00956), conserved in almost all RECQ proteins; and an HRDC domain (pfam00570), conserved in more than 50% of RECQ proteins and also at the C-terminal of RNase D.

While in the yeast *S. cerevisiae*, meiotic recombination is increased in the absence of the Sgs1 helicase by a factor of 1.17-1.6 (Jessop et al., PLoS Genetics, 2006, 2, e155; Oh et al., Cell, 2007, 130(2), 259-272), the mutation of AtRECQ4A (recq4a-5/SALK_069672) or AtRECQ4B is described as producing no significant effect on meiotic CO formation (Higgins et al., The Plant Journal, 2011, 65, 492-502). It has in particular been observed that the mutation of AtRECQ4A (recq4a-5/SALK_069672) or of AtRECQ4B is incapable of restoring fertility and the formation of bivalents in an msh4 mutant of the Columbia strain. On the other hand, it has been suggested that RECQ4A plays a role in the maintaining of the telomeres, and a role in the integrity of the genome, previously unknown for a protein of the RecQ family.

Figure 2:
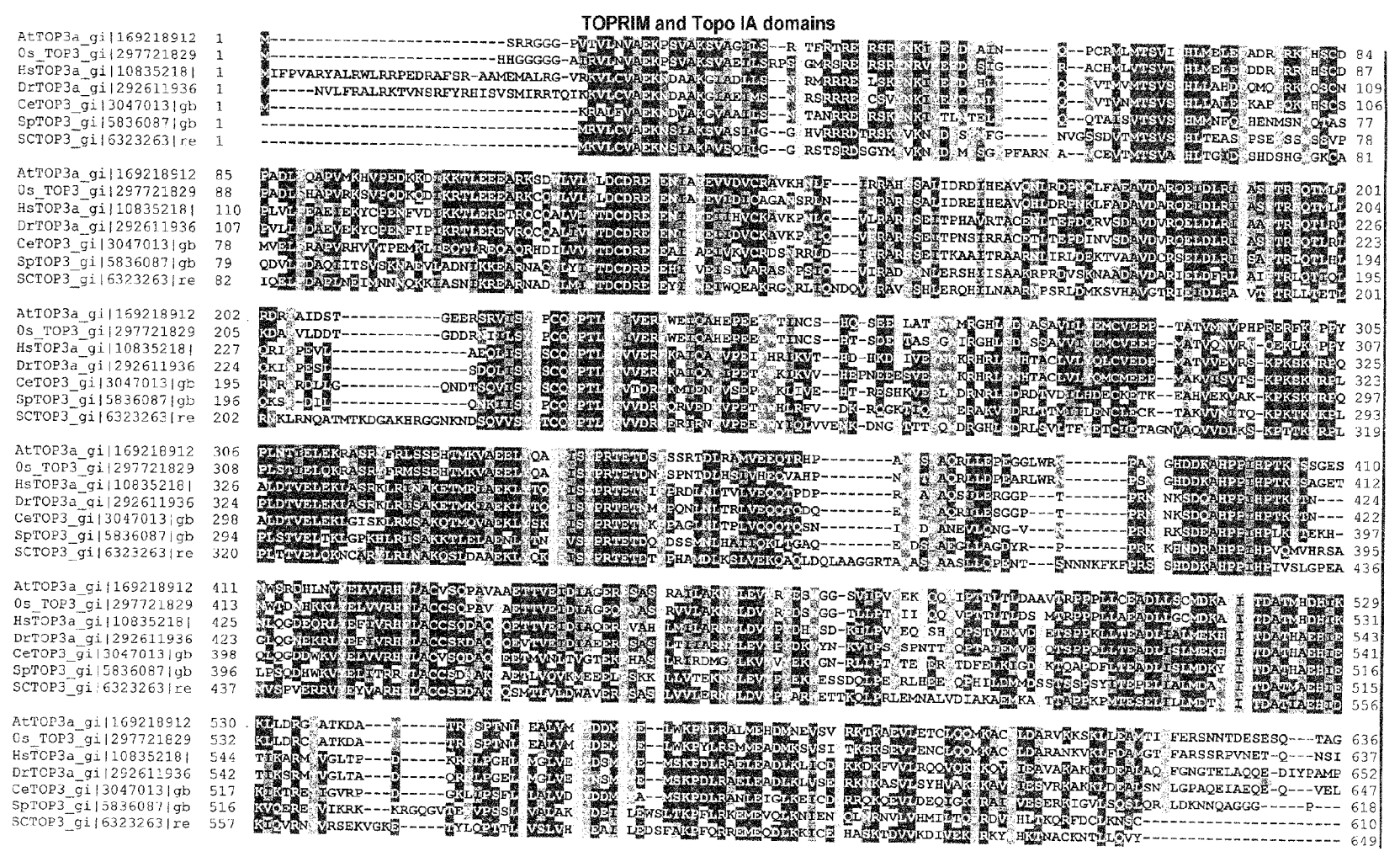
Figure 2:
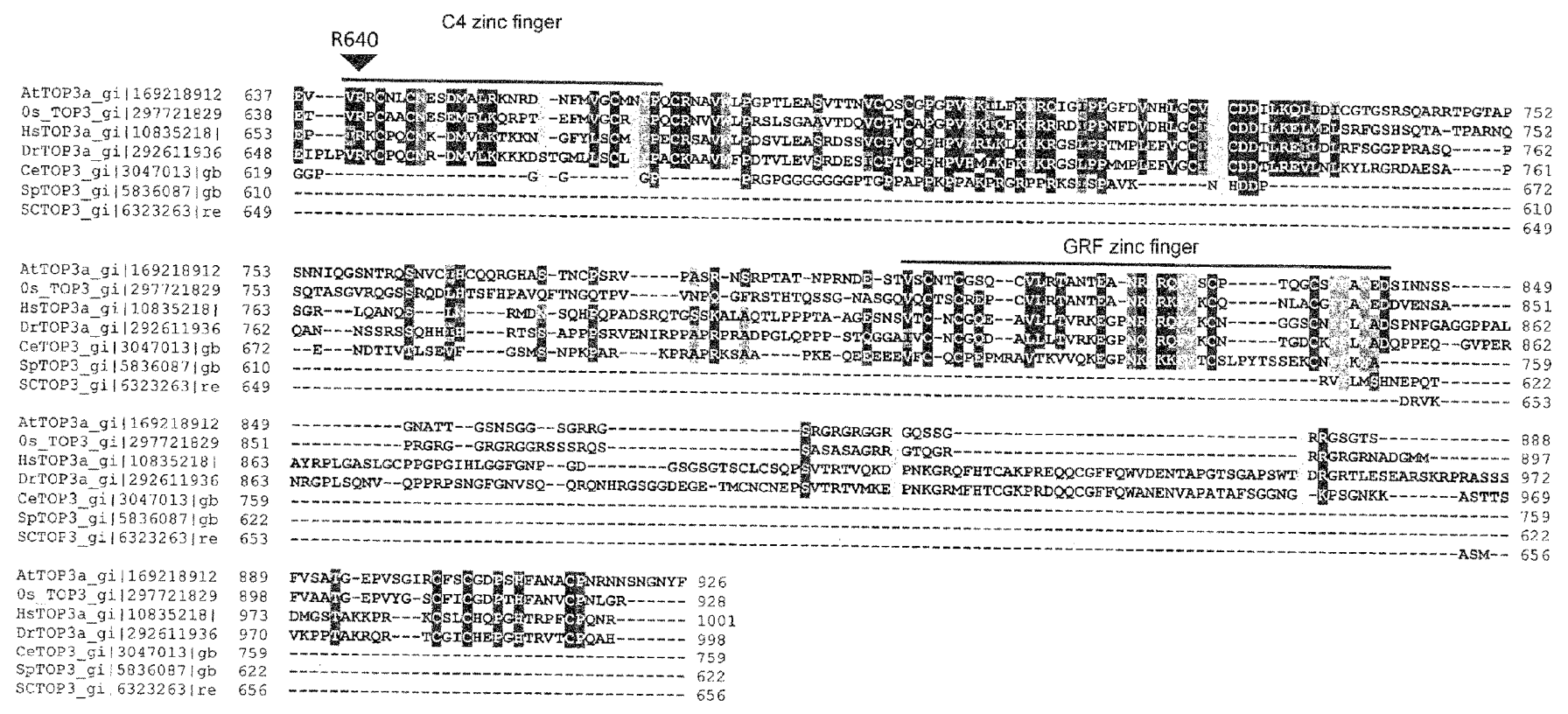

The AtTOP3A protein (TOP3a, TOP3, Top3a, Top3 alpha, TOP3 alpha or TOP3a, for DNA TOPOISOMERASE III alpha or DNA TOPOISOMERASE 3-alpha) contains four conserved domains: in its N-terminal region, a TOPRIM domain (NCBI cd03362) and a DNA Topoisomerase subtype IA domain (NCBI cd00186), both conserved in all TOP3 homologs; in its C-terminal region, two zinc finger domains (pfam01396 and pfam06839), which are conserved in plants and animals but not in yeasts (FIG. 2).

Two mutant alleles of top3a (top3a-1 and top3a-2) have previously been described in *Arabidopsis* (Hartung et al., PLoS Genet., 2008, 4, e1000285, Hartung et al., PNAS 2007, 104, 47, 18836-41). The top3a-1 mutation is probably null given that it results in early lethality during development. The second allele, top3a-2, is a hypomorphic mutant which is viable but shows somatic growth defects, and is completely sterile (Hartung et al., PLoS Genet., 2008, 4, e1000285). The severe phenotypes associated with the inactivation of TOP3A in *Arabidopsis* and varied species (Goodwin et al., *Nucleic Acids Res.*, 1999, 27, 4050-8; Kim et al., *Nucleic Acids Res.*, 2000, 28, 2012-7; Li and Wang, *Proc. Natl. Acad. Sci. U. S. A*, 1998, 95, 1010-3, Plank et al., *J. Biol. Chem.*, 2005, 280, 3564-73) emphasize an essential role of TOP3A in the resolution of DNA repair mitotic and meiotic intermediates, but do not suggest an anti-meiotic co activity of this protein.

On the contrary, as demonstrated in the present invention, inhibition of the AtRECQ4A and AtRECQ4B or TOP3A genes increases the number of meiotic COs, not only in zmm mutants, but also in plants which are wild-type for the ZMM genes.

Indeed, the inventors have shown that the inhibition of AtRECQ4A and of AtRECQ4B compensates the effects of that of AtMSH4 or of AtZIP2/SHOC1 and makes it possible to increase the number of meiotic COs and to restore fertility in the zmm mutants Atmsh4−/− and shoc1−/−.

The inhibition of TOP3A compensates for the effects of that of AtHEI10 or of AtMSH5 and makes it possible to increase the number of meiotic COs and to restore fertility in the zmm mutants Athei10−/− and Atmsh5−/−.

The inventors have also discovered that the effects of inhibiting the TOP3A or RECQ4 gene on the increase in the number of meiotic COs occurred not only in the zmm mutants, but also in plants having functional ZMM genes.

The FIDG proteins belong to the family of AAA-ATPases (ATP-ases Associated with various Activities), and more particularly to subgroup 7 (Beyer, Protein Sci., 1997, 6, 2043-58; Frickey & Lupas, J. Struct. Biol., 2004, 146, 2-10). A single representative of this family has been identified in the genome of most plants. The FIDG proteins have two conserved protein domains: an AAA-ATPase domain, with a putative ATP hydrolysis role; and also a VSP4 domain, known to play an important role in microtubule binding. These two domains are respectively listed under references PF00004 and PF09336 in the PFAM database (Punta et al., Nucleic Acids Res., 2012, Database Issue 40:D290-D301).

The FIDG proteins are described as microtubule severing enzymes, involved in the regulation of microtubule number and size in many animal and plant species (*C. elegans* (Yakushiji et al., FEBS Lett., 2004, 578, 191-7); *D. melanogaster* (Zhang et al., J. Cell. Biol., 2007, 177, 231-42); *H. sapiens* (Mukherjee et al., Cell Cycle, 2012, 11, 2359-66); *A. thaliana* (Stoppin-Mellet et al., Biochem J., 2002, 365, 337-42)).

The inventors have also discovered that, when inhibition of the TOP3A or RECQ4 gene is combined with that of the FANCM or FIDG gene, the number of meiotic COs is further increased compared with those observed when these genes are inactivated separately.

A subject of the present invention is a method for increasing the frequency of meiotic COs in a plant, characterized in that it comprises the inhibition, in said plant, of at least one protein of the RTR complex, chosen from a protein known as RECQ4 and a protein known as TOP3A, said RECQ4 protein having at least 40%, and in order of increasing preference, at least 45, 50, 55, 60, 65, 70, 75, 80, 85, 90, 95 or 98% sequence identity with the RECQ4 protein of sequence SEQ ID NO: 1, and said TOP3A protein having at least 50%, and in order of increasing preference, at least 55, 60, 65, 70, 75, 80, 85, 90, 95 or 98% sequence identity with the TOP3A protein of sequence SEQ ID NO: 2.

The RECQ4 protein can also comprise a region having at least 60%, and in order of increasing preference, at least 65, 70, 75, 80, 85, 90, 95 or 98% sequence identity with the region which extends from positions 407 to 959 of the sequence SEQ ID NO: 1.

Alternatively, the RECQ4 protein can be defined as a protein comprising a region having at least 60%, and in order of increasing preference, at least 65, 70, 75, 80, 85, 90, 95 or 98% sequence identity with the region which extends from positions 407 to 959 of the sequence SEQ ID NO: 1.

The sequence identities of the RECQ4 and TOP3 proteins are calculated over the whole length of the longest of the two proteins that are compared, after alignment using T-Coffee (v6.85) with the default parameters (http://tookit.tuebin-gen.mpg.de/t_coffee). The percentage identity of the RECQ4 and TOP3 proteins is obtained on the basis of this alignment using Bioedit 7.2.5 (Hall, T. A. 1999. BioEdit: a user-friendly biological sequence alignment editor and analysis program for Windows 95/98/NT. Nucl. Acids. Symp. Ser. 41:95-98). The percentage identity of the region of the RECQ4 protein is calculated on the sequence of positions 407-959 of the sequence SEQ ID NO: 1 after alignment of the RECQ4 protein with the sequence SEQ ID NO: 1.

The sequences of the RECQ4 and TOP3A genes and proteins are available on the public databases, such as, in a non-limiting manner, the PLAZA (http://bioinformatics.ps-b.ugent.be/plaza/) and phytozome http://www.phytozome.net/ (phytosome v9.1) databases.

For the purposes of the present invention, the expression "RECQ4 protein" corresponds to the RECQ4A and RECQ4B proteins in plants of the family Brassicaceae (*Brassica* sp) which have two RECQ4 genes (RECQ4A and RECQ4B), and to the RECQ4 protein in plants other than Brassicaceae, which have only one RECQ4 gene. However, in certain Brassicaceae lines in which one of the RECQ4 proteins is not functional, only the RECQ4 protein that is functional is inhibited.

The sequence SEQ ID NO: 1 represents the sequence of the RECQ4A protein of *Arabidopsis thaliana* (AT1G10930 in the PLAZA database). The sequences of orthologs of RECQA and of paralogs RECQB in various flowering plant species are indicated in the table below:

TABLE I

RECQ4 sequences

| Plant | Accession number* | SEQ ID NO: |
|---|---|---|
| *Arabidopsis thaliana* | AT1G10930 | 1 |
| *Arabidopsis lyrata* | AL1G11090 | 3 |
| *Arabidopsis lyrata* | AL2G05030 | 4 |
| *Arabidopsis thaliana* | AT1G60930** | 5 |
| *Brachypodium distachyon* | BD5G10432 | 6 |
| *Brassica rapa* | Bra031741 | 7 |
| *Brassica rapa* | Bra027115 | 8 |
| *Brassica rapa* | Bra018418 | 9 |
| *Carica papaya* | CP00031G00490 | 10 |
| *Thellungiella halophila* | Thhalv10006602m | 11 |
| *Thellungiella halophila* | Thhalv10023226m | 12 |
| *Eucalyptus grandis* | Eucgr.G00562.1 | 13 |
| *Glycine max* | Glyma12g29151 | 14 |
| *Glycine max* | Glyma08g20070 | 15 |
| *Gossypium raimondii* | Gorai.013G038600 | 16 |
| *Manihot esculenta* | ME02817G00160 | 17 |
| *Oryza sativa* | OS04G35420 | 18 |
| *Phaseolus vulgaris* | Phyul.006G216200 | 19 |
| *Prunus persica* | ppa000416m.g | 20 |
| *Ricinus communis* | RC28725G00120 | 21 |
| *Sorghum bicolor* | Sb04g003070.1 | 22 |
| *Setaria italica* | Si016138m.g | 23 |
| *Solanum lycopersicum* | 01g103960.2 | 24 |
| *Theobroma cacao* | Thecc1EG006933t1 | 25 |
| *Vitis vinifera* | VV12G07620 | 26 |

*in the PLAZA or phytozome database
**RECQ4B

In accordance with the invention, said RECQ4 protein comprises three conserved domains: a helicase domain, which is the most important, and comprises eight motifs (0, I, Ia, II, III, IV, V and VI), having a total length of approximately 300 to 450 amino acids, containing the sequences required for the binding of ATP, the hydrolysis and the DNA unfolding (NCBI cd00079 and cd00046); an RQC domain (smart00956); and an HRDC domain (pfam00570).

The sequence SEQ ID NO: 2 represents the sequence of the TOP3A protein of *Arabidopsis thaliana* (AT5G63920 in the PLAZA database). The sequences of orthologs in various flowering plant species are indicated in the table below:

TABLE II

TOP3A sequence

| Plant | Accession number* | SEQ ID NO: |
|---|---|---|
| *Arabidopsis thaliana* | AT5G63920 | 2 |
| *Arabidopsis lyrata* | AL8G30570 | 27 |
| *Brachypodium distachyon* | BD1G74120 | 28 |
| *Fragaria vesca* | FV0G21450 | 29 |
| *Oryza sativa* | OS03G06900 | 30 |
| *Populus trichocarpa* | PT05G06620 | 31 |
| *Ricinus communis* | RC30149G00070 | 32 |
| *Sorghum bicolor* | SB01G046210 | 33 |
| *Zea mays* | ZM01G04670 | 34 |
| *Thellungiella halophila* | Thhalv10003618m.g | 35 |
| *Capsella rubella* | Carubv10025845m | 36 |
| *Brassica rapa* | Bra031944 | 37 |
| *Gossypium raimondii* | Gorai.007G066700. | 38 |
| *Theobroma cacao* | Thecc1EG001553t1 | 39 |
| *Eucalyptus grandis* | Eucgr.H05141.1 | 40 |
| *Glycine max* | Glyma06g16175.1 | 41 |
| *Mimulus guttatus* | mgv1a000984m.g | 42 |
| *Aquilegia caerula* | Aquca_069_00036.1 | 43 |
| *Setaria italica* | Si034218m.g | 44 |

*in the PLAZA or phytozome database

In accordance with the invention, TOP3A protein comprises four conserved domains: in its N-terminal region, a TOPRIM domain (NCBI cd03362) and a DNA Topoisomerase sub-type IA domain (NCBI cd00186); in its C-terminal region, two zinc finger domains (pfam01396 and pfam06839; FIG. 2). The first zinc finger domain is located in the region of said TOP3A protein which extends from position 639 to position 677 of the sequence SEQ ID NO: 2. The second zinc finger domain is located in the region of said TOP3A protein which extends from position 804 to position 844 of the sequence SEQ ID NO: 2.

The invention encompasses the simultaneous inhibition of the RECQ4 and/or TOP3A proteins.

The inhibition of the RECQ4 and/or TOP3A protein is obtained by abolishing, blocking or inhibiting the expression of the RECQ4 or TOP3A gene or else the function of said RECQ4 or TOP3A protein. In addition, the inhibition of the TOP3A protein in the plant is carried out in such a way that the plant necessarily expresses, from the mutated TOP3A gene or from a transgene, a mutated TOP3A protein comprising a mutation in its C-terminal region which inhibits at least one of the two zinc finger domains, while its N-terminal region comprising the TOPRIM and DNA topoisomerase IA domains is intact.

The inhibition can in particular be obtained by mutagenesis of the RECQ4 or TOP3A gene. For example, a mutation in the coding sequence can, depending on the nature of the mutation, induce the expression of an inactive protein, or of a protein with reduced activity; a mutation in a splice site can also impair or abolish the function of the protein; a mutation in the promoter sequence can induce an absence of expression of said protein, or a decrease in its expression.

The mutagenesis can be carried out for example by deleting all or part of the coding sequence or of the promoter of RECQ4 or TOP3A, or by inserting an exogenous sequence, for example a transposon or a T-DNA, into said coding sequence or said promoter. It can also be carried out by inducing point mutations, for example by EMS mutagenesis, by radiation, or by site-directed mutagenesis, for example using TALEN (Transcription Activator-Like Effector Nuclease) nucleases, CRISPR-CAS systems or zinc finger nucleases (Christian et al., Genetics, 186, 757-61, 2010; Curtin et al., Plant Gen., 5, 42-50, 2012).

The mutated alleles can be detected for example by PCR, using primers specific for the RECQ4 or TOP3A gene.

Various methods of mutagenesis and of high-throughput screening are described in the prior art. By way of examples, mention may be made of methods of "Tilling" (Targeting Induced Local Lesions In Genome) type, described by McCallum et al., Plant Physiol., 2000, 123, 439-442). The absence of functionality of RECQ4 or TOP3A in the mutants can be verified on the basis of the phenotypic characteristics of their descendence; plants which are homozygous for a mutation that inactivates the RECQ4 or TOP3A gene have a meiotic CO rate that is higher than that of the wild-type plants (not carrying the mutation in the RECQ4 or TOP3A gene) from which they are derived. Generally, this meiotic CO rate is at least 50% higher, preferably at least twice as high as that of the wild-type plants from which they are derived.

According to one advantageous embodiment of said method, it comprises the introduction, into an allele of the TOP3A gene, of a mutation which results in the inhibition of at least one zinc finger domain of the TOP3A protein, said domain being located in the region of said protein which extends from position 639 to position 677 or position 804 to position 844 of the sequence SEQ ID NO: 2. The mutation preserves the TOPRIM and DNA topoisomerase IA domains but inhibits, and preferably inactivates, at least one of the two zinc finger domains. It is in particular an insertion or a deletion in the C-terminal region of TOP3A comprising said domains. Preferably, said mutation is a deletion of the C-terminal sequence of said TOP3A protein, starting from one of the residues of said protein located from position 610 to position 803 of the sequence SEQ ID NO: 2, preferably starting from the residue of said protein located in position 640 of the sequence SEQ ID NO: 2 (production of a C-terminal-truncated TOP3A protein).

Alternatively, the inhibition of the RECQ4 or TOP3A protein is obtained by silencing the RECQ4 or TOP3A gene. Various techniques for silencing genes in plants are known in themselves (for a review, see for example: Watson & Grierson, Transgenic Plants: Fundamentals and Applications (Hiatt, A, ed.) New York: Marcel Dekker, 255-281, 1992; Chicas & Macino, EMBO reports, 2001, 21, 992-996; Puchta, H and Fauser, F, Int. J. Dev. Biol., 2013, 57, 629-37; Ali et al., GM crops, 2010, 1, 207-213). Mention may be made of the antisense inhibition or co-suppression that are described for example in U.S. Pat. Nos. 5,190,065 and 5,283,323. It is also possible to produce ribozymes which target the mRNA of the RECQ4 or TOP3A protein.

Preferably, the silencing of the RECQ4 or TOP3A gene is induced by RNA interference targeting said gene.

An interfering RNA (iRNA) is a small RNA which can silence a target gene in a sequence-specific manner. Interfering RNAs comprise in particular "small interfering RNAs" (siRNAs) and micro-RNAs (miRNAs).

Initially, the DNA constructs for expressing interfering RNAs in plants contain a fragment of 100 bp or more (generally from 100 to 800 bp) of the cDNA of the targeted gene, under the transcriptional control of a suitable promoter. Constructs widely used are those which can produce a hairpin RNA (hpRNA) transcript. In these constructs, the fragment of the target gene is inversely repeated, generally with a spacing region between the repeats (for a review, cf. Watson et al., FEBS Letters, 2005, 579, 5982-5987). Use may also be made of artificial micro-RNAs (amiRNAs) directed against the RECQ4 or TOP3A gene (Ossowski et al., The Plant Journal, 2008, 53, 674-690; Schwab et al., Methods Mol Biol., 2010, 592, 71-88; Wei et al., Funct Integr Genomics, 2009, 9, 499-511).

To inhibit the TOP3A protein, the method of the invention is advantageously carried out with one of the following genetically modified plants:

(i) a mutant plant which is homozygous for the TOP3A mutation, as defined above, which results in the expression of a TOP3A protein that is mutated in the C-terminal domain, for example a truncated TOP3A protein, of which the TOPRIM and Topoisomerase IA domains are intact but at least one or both of the zinc finger domains are inhibited, and preferably inactivated, (ii) a mutant and transgenic plant, which is homozygous for a mutation which inhibits the TOP3A gene and which comprises a TOP3A transgene encoding a C-terminal-mutated TOP3A protein, for example a truncated TOP3A protein, as defined above, and (iii) a double transgenic plant, comprising a first transgene encoding an iRNA which targets the TOP3A gene and a second transgene comprising a recombinant TOP3A gene encoding a mutated TOP3A protein, for example a C-terminated-truncated TOP3A protein, as defined above; the second transgene not being sensitive to the iRNA produced by the first transgene. To do this, use may be made, in a nonlimiting manner, of an iRNA targeting the C-terminal region of TOP3A The inhibition of the RECQ4 or TOP3A protein can also be obtained by abolishing, blocking or decreasing the function of said protein. In order to inhibit the activity of said protein, use may be made of inhibitors which specifically bind to a functional domain of said protein and block its activity. They are in particular protein inhibitors, such as peptides or antibodies or functional antibody fragments, or else small molecules. By way of nonlimiting example, mention may be made of small molecule inhibitors of RecQ such as described in Nguyen et al., Chemistry & Biology, 2013, 20, 1, 24, 55-62. Advantageously, these inhibitors are applied to plants.

A subject of the present invention is recombinant DNA constructs, and in particular expression cassettes, producing: (i) an iRNA which makes it possible to silence the RECQ4 or TOP3A gene and/or (ii) a C-terminal-mutated TOP3A protein, in particular a truncated TOP3A protein as defined above.

An expression cassette in accordance with the invention comprises a recombinant DNA sequence of which the transcript is an iRNA, in particular an hpRNA or an miRNA, targeting the RECQ4 or TOP3A gene or an RNA encoding the mutated TOP3A protein as defined above, placed under the transcriptional control of a promoter that is functional in a plant cell. The mutated TOP3A protein can in particular be expressed from a TOP3A gene promoter, in particular of a plant, such as the TOP3A gene promoter of the transgenic plant in which said C-terminal-mutated TOP3A promoter is expressed.

A wide choice of promoters suitable for the expression of heterologous genes in plant cells or plants is available in the art.

These promoters can be obtained for example from plants, from plant viruses, or from bacteria such as *Agrobacterium*. They include constitutive promoters, namely promoters which are active in most tissues and cells and under most environmental conditions, and also tissue-specific or cell-specific promoters, which are active only or mainly in certain tissues or certain cell types, and inducible promoters which are activated by physical or chemical stimuli.

Examples of constitutive promoters which are commonly used in plant cells are the cauliflower mosaic virus (CaMV) 35S promoter described by Kay et al. (Science, 1987, 236, 4805) or derivatives thereof, the cassava vein mosaic virus (CsVMV) promoter described in international application WO 97/48819, the corn ubiquitin promoter or the rice "Actin-Intron-actin" promoter (McElroy et al., Mol. Gen. Genet., 1991, 231, 150-160; GenBank accession number S 44221). For implementing the present invention, a promoter that is functional in meiocytes will be chosen.

In the context of the present invention, a meiosis-specific promoter (i.e. one that is exclusively or preferentially active in cells undergoing meiosis) may also be used. By way of nonlimiting example, mention may be made of the DMC1 promoter (Klimyuk & Jones, Plant J., 1997, 11, 1-1).

The expression cassettes of the invention generally comprise a transcriptional terminator, for example the nopaline synthase 3'NOS terminator (Depicker et al., J. Mol. Appl. Genet., 1982, 1, 561-573), the 3' CaMV terminator (Franck et al., Cell, 1980, 21, 285-294) or the terminator of a TOP3A gene, in particular of a plant, such as the terminator of the TOP3A gene of the transgenic plant in which said mutated TOP3A protein is expressed. They can also comprise other transcription-regulating elements such as activators.

The recombinant DNA constructs in accordance with the invention can comprise several expression cassettes encoding, respectively, one of the iRNAs targeting the RECQ4 or TOP3A gene and a C-terminated-mutated TOP3A protein, in particular two expression cassettes, one encoding an iRNA targeting the TOP3A gene and the other encoding a C-terminated-mutated TOP3A protein.

The recombinant DNA constructs in accordance with the invention also encompass recombinant vectors containing one or more expression cassettes in accordance with the invention as defined above. These recombinant vectors can also include one or more marker genes, which allow the selection of the transformed cells or plants. The choice of the most suitable vector depends in particular on the intended host and on the method envisioned for the transformation of the host in question. Numerous methods for genetic transformation of plant cells or of plants are available in the art, for numerous dicotyledonous or monocotyledonous plant species. By way of nonlimiting examples, mention may be made of virus-mediated transformation, microinjection-mediated transformation, electroporation-mediated transformation, microprojectile-mediated transformation, *Agrobacterium*-mediated transformation, etc.

A subject of the invention is also a host cell comprising at least one recombinant DNA construct in accordance with the invention. Said cell can comprise two recombinant DNA constructs, one encoding an iRNA targeting the TOP3A gene and the other encoding a C-terminal-mutated TOP3A protein. Said host cell may be a prokaryotic cell, for example an *Agrobacterium* cell, or a eukaryotic cell, for example a plant cell genetically transformed with at least one DNA construct of the invention. The construct can be expressed transiently, it can also be incorporated into a stable extrachromosomal replicon, or integrated into the chromosome.

The invention also provides a process for producing a mutated plant having a meiotic CO rate that is higher than that of the wild-type plant from which it is derived, characterized in that it comprises the following steps:

a) introduction into an allele of the TOP3A gene of a mutation which results in the inhibition of at least one zinc finger domain of the TOP3A protein, and said plant being heterozygous for this mutation;

b) self-pollination of the plant of step a) so as to obtain a plant that is homozygous for said mutation.

The invention also provides a process for producing a transgenic plant having a meiotic CO rate that is higher than that of the wild-type plant from which it is derived, characterized in that it comprises the following steps:

transformation of a plant cell with at least one vector containing at least one expression cassette producing an iRNA that makes it possible to silence the RECQ4 or TOP3A gene in accordance with the invention;

culture of said transformed cell in order to regenerate a plant having, in its genome, a transgene containing said expression cassette.

According to one advantageous embodiment of said process, the transformation step is carried out with two expression cassettes, one encoding an iRNA targeting the TOP3A gene and the other encoding a C-terminal-mutated TOP3A protein, in accordance with the invention; said cassettes being in the same vector or in two different vectors and, in the case where they are in two different vectors, the transformation being carried out simultaneously with the two vectors or successively with one vector and then with the other.

The invention also encompasses the mutant plants comprising a TOP3A mutation which results in the expression of a TOP3A protein mutated in the C-terminal domain, as defined above.

The invention also encompasses plants genetically transformed with at least one DNA construct of the invention. Preferably, said plants are transgenic plants, in which said construct(s) is (are) contained in a transgene integrated into the genome of the plant such that it is transmitted to the successive generations of plants. The expression of the DNA construct of the invention results in a down-regulation of the expression of the RECQ4 and/or TOP3A gene, the down-regulation of the expression of the TOP3A gene being combined with the expression of a C-terminal-mutated TOP3A protein, which confers on said transgenic plants a meiotic CO rate that is higher than that of the wild-type plants (not containing the DNA construct of the invention) from which they are derived. Generally, this meiotic CO rate is at least 50% higher, preferably at least twice as high as that of the wild-type plants from which they are derived.

Particularly advantageously, the meiotic CO rate can also be increased by combining, in the same plant, the inhibition of the RECQ4 and/or TOP3A protein with that of the FANCM and/or FIDG protein. In this case, the meiotic CO rate is at least three times higher, preferably at least five times higher than that of the wild-type plants from which they are derived.

The increase in the meiotic CO rate by inhibiting the FANCM protein is described in PCT application WO 2013/038376, the content of which is incorporated into the present description by way of reference.

The FANCM protein is defined as a protein having at least 30%, and in order of increasing preference, at least 35, 40, 45, 50, 55, 60, 65, 70, 75, 80, 85, 90, 95 or 98% sequence identity, or at least 45%, and in order of increasing preference, at least 50, 55, 60, 65, 70, 75, 80, 85, 90, 95 or 98% sequence similarity with the AtFANCM protein of *Arabidopsis thaliana* (GenBank: NP_001185141; UniProtKB: F4HYE4), and containing a DEXDc helicase domain (cd00046) and a HELICc helicase domain (cd00079). Preferably, the DEXDc helicase domain has at least 65%, and in order of increasing preference, at least 70, 75, 80, 85, 90, 95 or 98% sequence identity, or at least 75%, and in order of increasing preference, at least 80, 85, 90, 95 or 98% sequence similarity with the DEXDc domain (amino acids 129-272) of the AtFANCM protein, and the HELICc helicase domain has at least 60%, and in order of increasing preference, at least 65, 70, 75, 80, 85, 90, 95 or 98% sequence identity, or at least 70%, and in order of increasing preference, at least 75, 80, 85, 90, 95 or 98% sequence similarity with the HELICc domain (amino acids 445-570) of the AtFANCM protein. The polypeptide sequence of the AtFANCM protein is represented in the appended sequence listing under the number SEQ ID NO: 45.

The sequence identity and similarity values indicated for the FANCM protein are calculated using the BLASTP program or the Needle program with the default parameters. The similarity calculations are carried out using the BLOSUM62 matrix. The sequence of the FIDGETIN-LIKE 1 protein of *Arabidopsis thaliana* is represented in the appended sequence listing under the number SEQ ID NO: 46. A search in the sequence databases has made it possible to identify orthologs of AtFIDG in a wide panel of eukaryotes, and it is very probable that this protein is conserved in all terrestrial plants. Nonlimiting examples of AtFIDG orthologs are mentioned in the table below.

TABLE III

AtFIDG ortholog sequences

| Plant | Accession number |
|---|---|
| *Brachypodium distachyon* | Genbank: XM_003576467 |
| *Carica papaya* | Phytozome: evm.model.supercontig_171.22 |
| | PLAZA: CP00171G00260 |
| *Fragaria vesca* | Phytozome: mrna25885.1 |
| | PLAZA: FV6G37220 |
| *Glycin max* | Phytozome: Glyma19g18350.2 and Glyma05g14440.2 |
| | PLAZA: GM19G18350 and GM05G14440 |
| *Oryza sativa* | GenBank: ABA97741 |
| *Populus tricocarpa* | GenBank: POPTR_0001s33870 |
| *Ricinus communis* | Genbank: XM_002509479 |
| *Solanum lycopersicum* | Genbank: XM_004233540.1 |
| *Sorghum bicolor* | Genbank: XM_002442067.1 |
| *Theobroma cacao* | Phytozome: Thecc1EG017182t1 |
| | PLAZA: TC04G003320 |
| *Vitis vinifera* | GenBank: CBI21358 |
| *Zea mays* | GenBank: DAA54951 |
| *Hordeum vulgare* | Genbank: BAK02801. |
| *Triticum urartu* | Genbank: EMS65393.1. |

The FIDG protein has at least 35%, and in order of increasing preference, at least 40, 45, 50, 55, 60, 65, 70, 75, 80, 85, 90, 95 or 98% sequence identity, or at least 50%, and in order of increasing preference, at least 50, 55, 60, 65, 70, 75, 80, 85, 90, 95 or 98% sequence similarity with the AtFIDG protein of sequence SEQ ID NO: 46, and containing an AAA-ATPase domain (PF00004) and a VSP4 domain (PF09336).

Preferably, said FIDG protein has at least 70%, and in order of increasing preference, at least 75, 80, 85, 90, 95 or 98% sequence identity, or at least 80%, and in order of increasing preference, at least 85, 90, 95 or 98% sequence similarity with any one of the AtFIDG orthologs, the list of which is indicated in Table III above.

According to one preferred embodiment of the present invention, the AAA-ATPase domain of said FIDG protein has at least 60%, and in order of increasing preference, at least 65, 70, 75, 80, 85, 90, 95 or 98% sequence identity, or at least 70%, and in order of increasing preference, at least 75, 80, 85, 90, 95 or 98% sequence similarity with the AAA-ATPase domain of the AtFIDG protein (amino acids 431-561 of SEQ ID NO: 46).

According to another preferred embodiment of the present invention, the VSP4 domain of said FIDG protein has at least 60%, and in order of increasing preference, at least 65, 70, 75, 80, 85, 90, 95 or 98% sequence identity, or at least 70%, and in order of increasing preference, at least 75, 80, 85, 90, 95 or 98% sequence similarity with the VSP4 domain of the AtFIDG protein (amino acids 623-672 of SEQ ID NO: 46).

Advantageously, said FIDG protein also contains a RAD51-binding domain, having at least 50%, and in order of increasing preference, at least 55, 60, 65, 70, 75, 80, 85, 90, 95 or 98% sequence identity, or at least 70%, and in order of increasing preference, at least 75, 80, 85, 90, 95 or 98% sequence similarity with amino acids 268-346 of SEQ ID NO: 46.

The sequence identity and similarity values indicated for the FIDG protein are calculated over the whole length of the sequences compared, using the Needleman-Wunsch global alignment algorithm (Needle EMBOSS program with the default parameters). The similarity calculations are carried out using the BLOSUM62 matrix.

A subject of the present invention is thus also:
- a process for increasing the frequency of meiotic COs in a plant, comprising the inhibition, in said plant, of the RECQ4 and/or ATOP3A protein and of the FANCM and/or FIDG protein;
- expression cassettes and vectors comprising a recombinant DNA sequence of which the transcript is an interfering RNA targeting the RECQ4 or ATOP3A gene, and a recombinant DNA sequence of which the transcript is an interfering RNA targeting the FANCM or FIDG gene;
- host cells and transgenic plants co-transformed with a recombinant DNA sequence of which the transcript is an interfering RNA targeting the RECQ4 and/or ATP3a gene, and a recombinant DNA sequence of which the transcript is an interfering RNA targeting the FIDG and/or FANCM gene;
- mutant plants containing, in the RECQ4 and/or ATOP3A gene, a mutation which induces the inhibition of the RECQ4 and/or ATOP3A protein, and in the FANCM and/or FIDG gene a mutation which induces the inhibition of the FANCM and/or FIDG protein; the invention encompasses in particular the triple and quadruple mutants, in particular the RECQ4/FIDG/FANCM triple mutants;
- mutant and transgenic plants containing, in the RECQ4 and/or ATOP3A gene, a mutation which induces the inhibition of the protein, in accordance with the invention, and transformed with a recombinant DNA sequence of which the transcript is an interfering RNA targeting the FANCM and/or FIDG gene, and optionally with a recombinant DNA sequence encoding a C-terminal-mutated TOP3A protein, in accordance with the invention, or else containing, in the FANCM and/or FIDG gene, a mutation which induces the inhibition of the FANCM and/or FIDG protein, and transformed with a recombinant DNA sequence of which the transcript is an interfering RNA targeting the RECQ4 and/or ATOP3A gene, and optionally with a recombinant DNA sequence encoding a C-terminal-mutated TOP3A protein, in accordance with the invention; the invention encompasses in particular the double mutants and transgenics, the mutants and double or triple transgenics, and the double mutants and double or triple transgenics, in particular those in which the RECQ4 and FANCM proteins, and optionally, in addition, the FIDG protein, are inhibited.

The present invention can be applied in particular in the field of plant breeding, in order to accelerate the production of new varieties. It also makes it possible to facilitate recombination between related species, and therefore introgression of characters of interest. It also makes it possible to accelerate the establishment of genetic maps and positional clonings.

The present invention applies to a wide variety of monocotyledonous or dicotyledonous plants of agronomic interest. By way of nonlimiting examples, mention may be made of rapeseed, sunflower, potato, corn, wheat, barley, rye, sorghum, rice, soy, bean, carrot, tomato, zucchini, bell pepper, eggplant, turnip, onion, pea, cucumber, leek, artichoke, beetroot, cabbage, cauliflower, lettuces, endive, melon, watermelon, strawberry plant, apple tree, pear tree, plum tree, poplar tree, vine, cotton, rose, tulip, etc.

Figure 3:
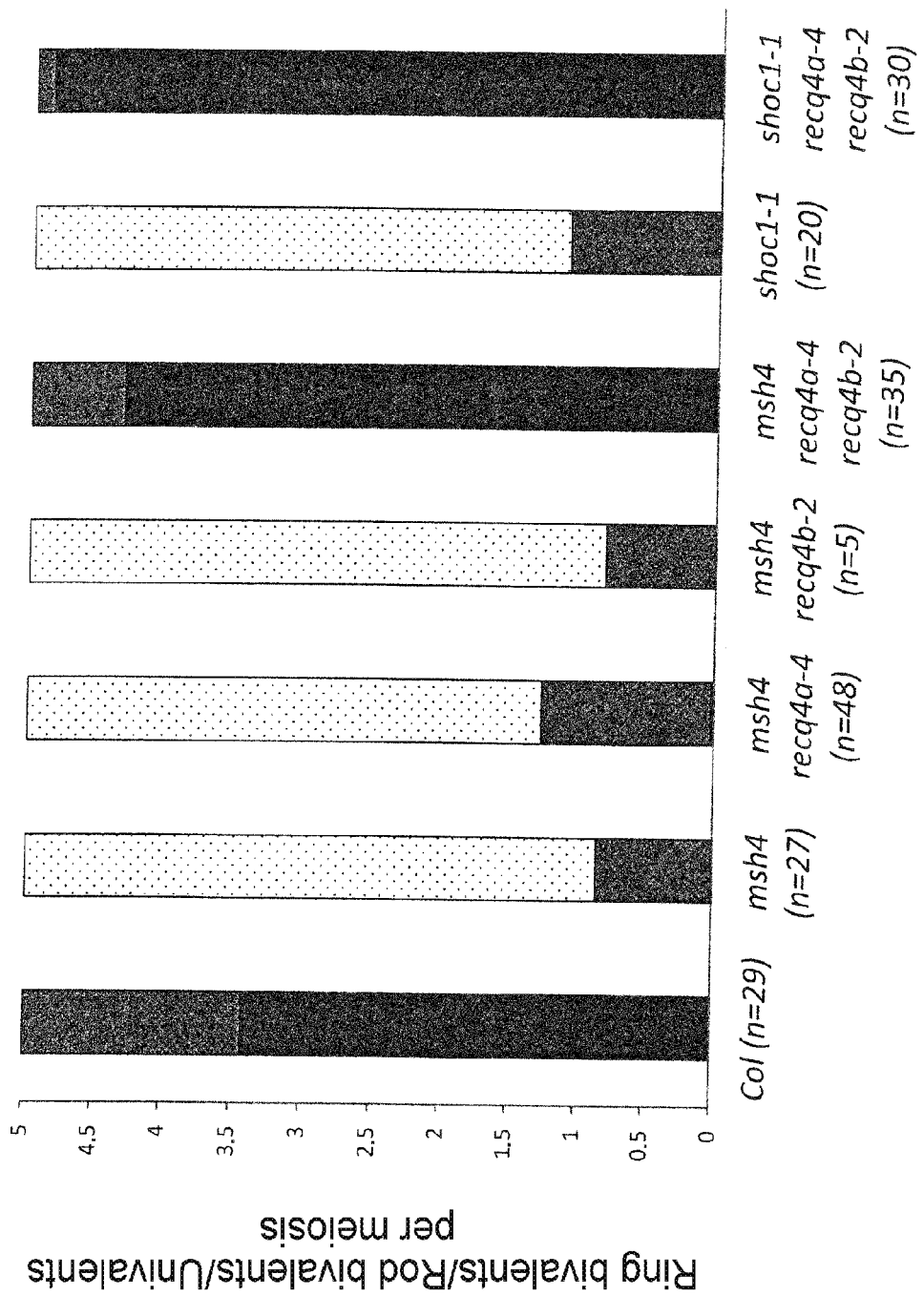
Figure 4:
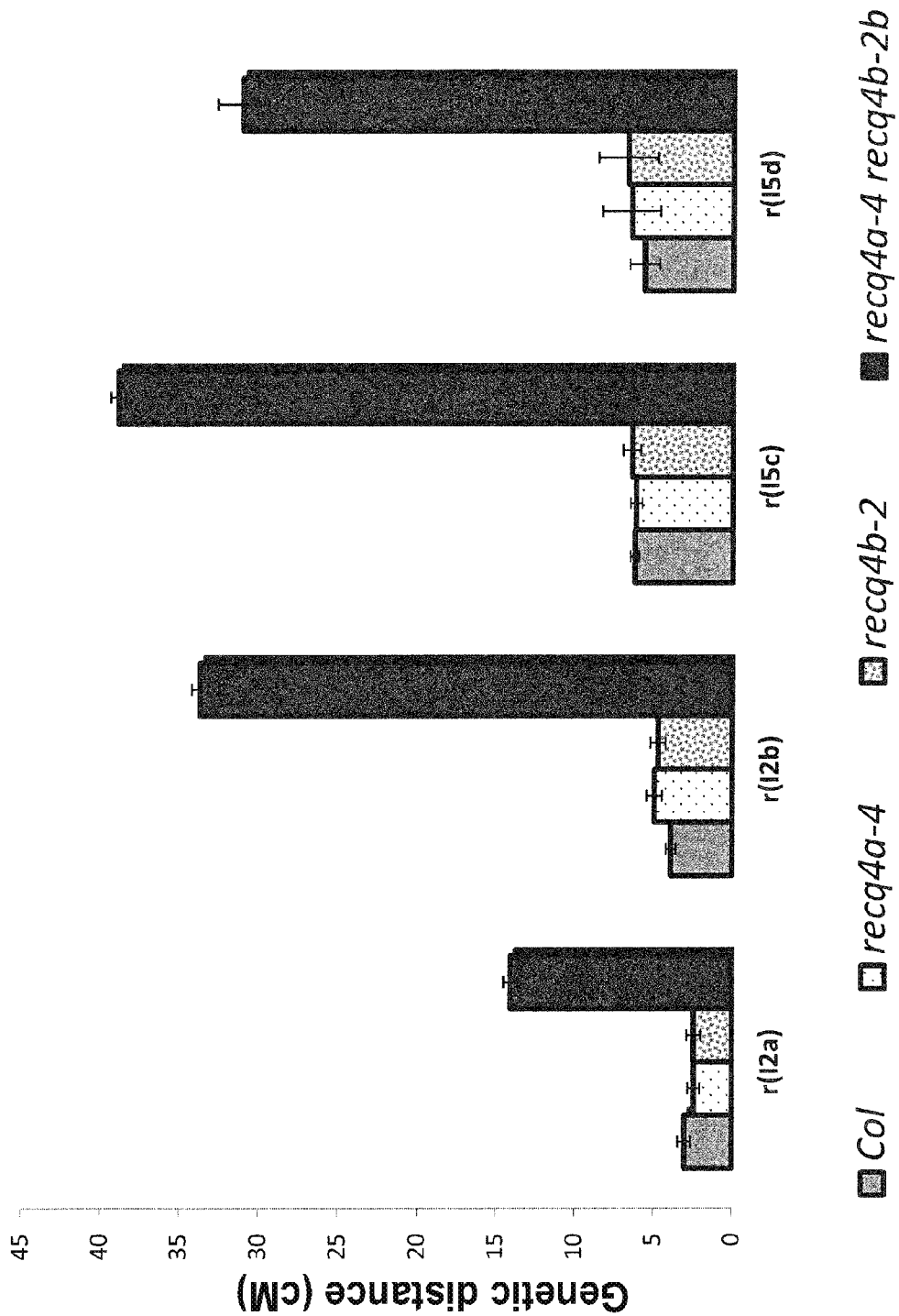
Figure 5:
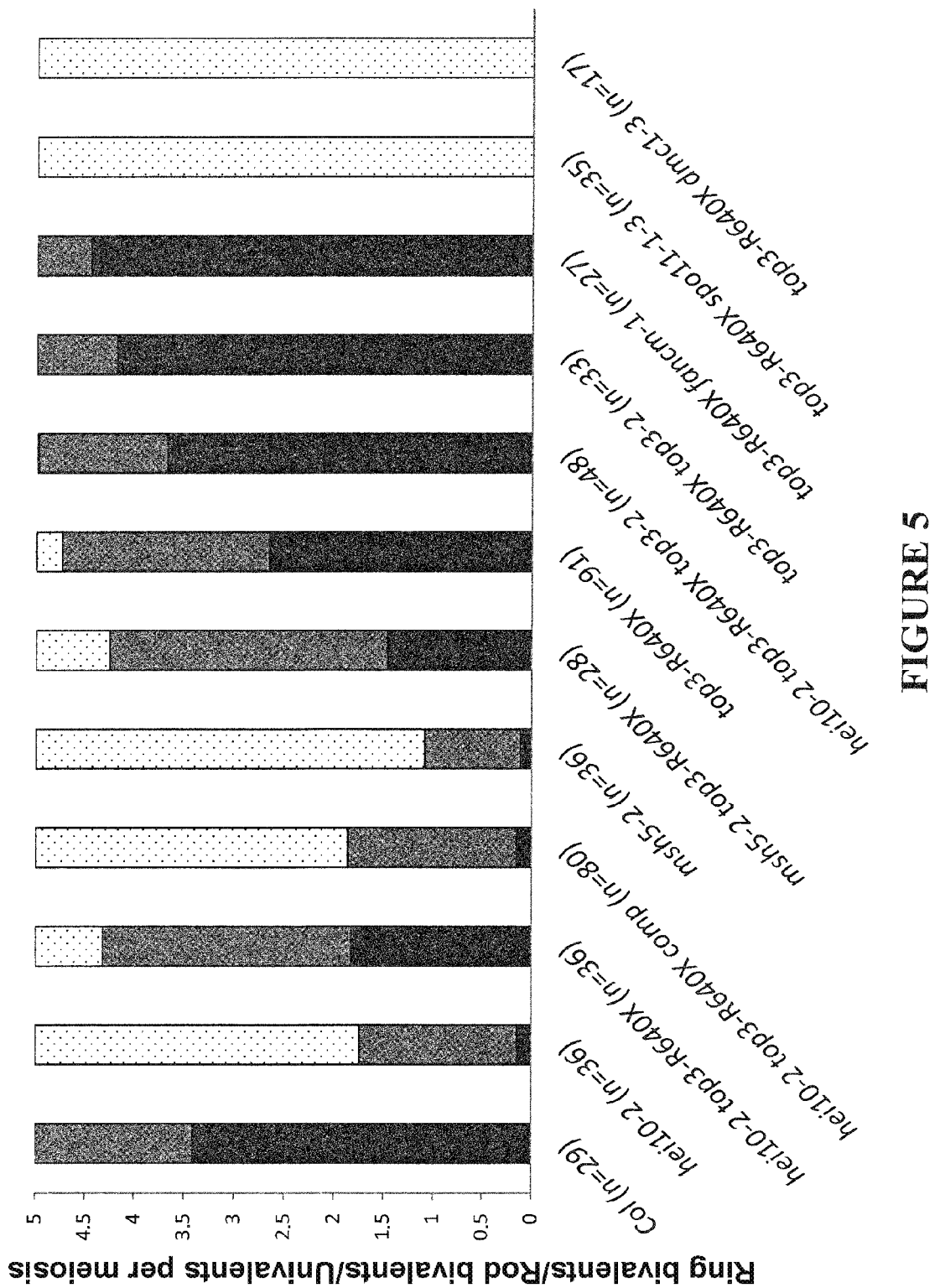
Figure 6:
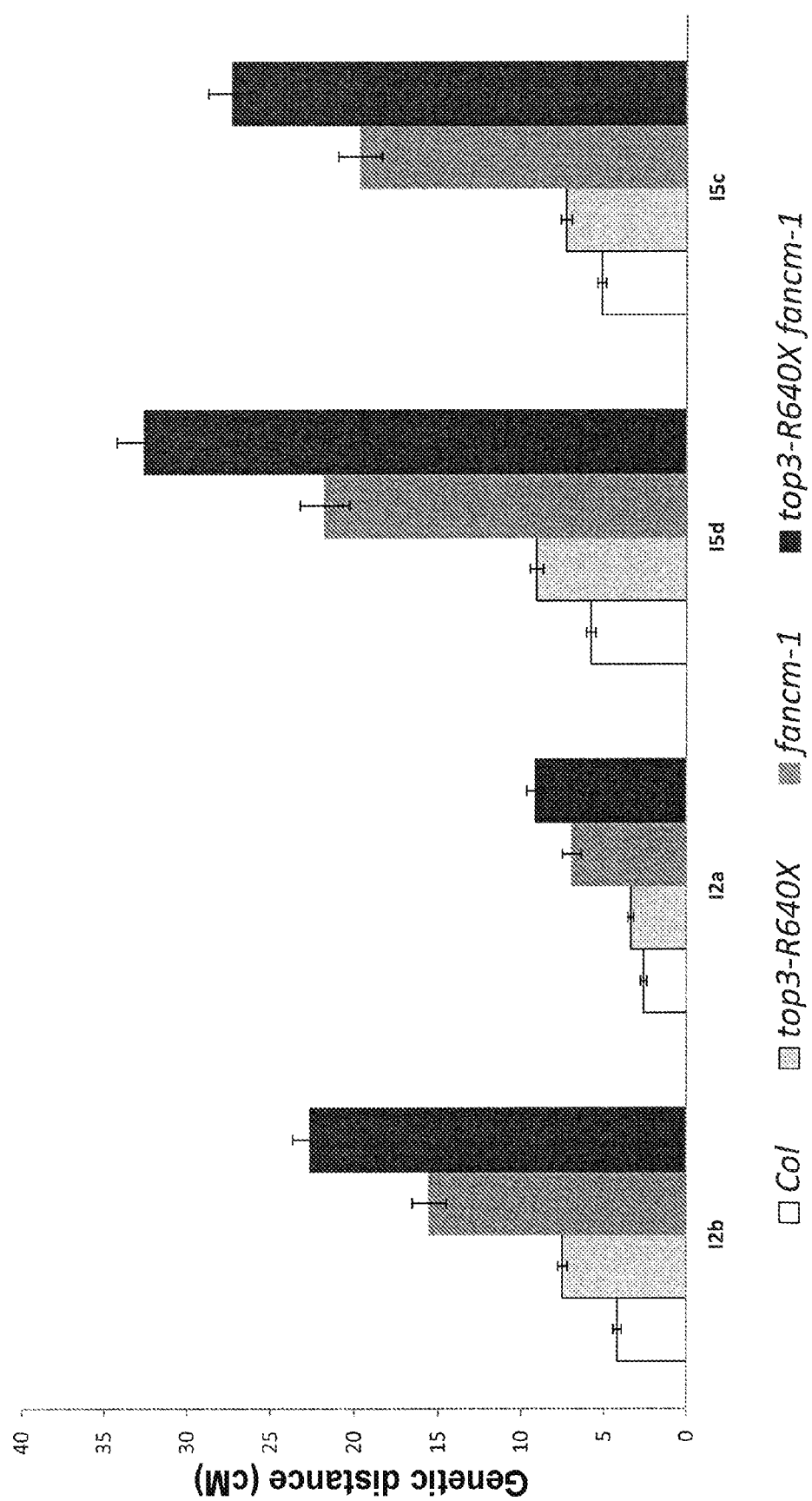

The present invention will be understood more clearly by means of the further description which follows, which refers to nonlimiting examples illustrating the effect of mutations of the AtRECQ4 or AtTOP3A gene, alone or combined with mutations of the FANCM gene, on meiotic recombination and CO rate, with references to the attached drawings in which:

FIG. 1: Phylogenetic tree of the RECQ4 proteins of flowering plants. The analysis was carried out on the Phylogeny.fr platform according to the following steps: the sequences were aligned with T-Coffee (v6.85) using the following methods of alignment in pairs: the ten best local alignments (Lalign_pair), an exact global alignment (slow_pair). After the alignment, the positions with spaces were eliminated from the alignment. The phylogenetic tree was reconstructed using the method of maximum probability, implemented in the PhyML v3.0 aLRT program. The sequences of the proteins were collected in the PLAZA database (http://bioinformatics.psb.ugent.be/plaza/) and the phytozome database (http://www.phytozome.net.): At: *Arabidopsis thaliana*. Al: *Arabidopsis lyrata*. Bra: *Brassica rapa*. Esa: *Thellungiella halophila*. Cp: *Carica papaya*. Tcacao: *Theobroma cacao*. Graimndii: *Gossypium raimondii*. VV: *Vitis vinifera*. Ppersica *Prunus persica*. RC: *Ricinus communis*. ME: *Manihot esculenta*. Solyc: *Solanum lycopersicum*. Eucgr: *Eucalypsus grandis*. Phvul: *Phaseolus vulgaris*. Glyma: *Glycine max*. OS: *Oryza sativa*. BD: *Brachypodium distachyon*. Si: *Setaria italica*. Zmays: *Zea mays*. Sbicolor: *Sorghum bicolor*;

FIG. 2: Alignment of the TOPOISOMERASES 3a of eukaryots using T-Coffee. The conserved domains are indicated by a vertical or horizontal line. At: *Arabidopsis thaliana* (SEQ ID No: 2). Sc: *Saccharomyces* cerevisiea (SEQ ID No: 52). Os: *Oryza sativa* (SEQ ID No: 47). Hs: *Homo sapiens* (SEQ ID No: 48). Dr: *Danio rerio* (SEQ ID No: 49). Ce: *Coenorabditis elegans* (SEQ ID No: 50). Sp: *Schizosaccharomyces pombe* (SEQ ID No: 51). The alignment was carried out using T-Coffee with the default parameters;

FIG. 3: The double mutation of RECQ4A and RECQ4B restores the formation of bivalents in the zmm mutants. Average number of bivalents per male meiocyte. Ring bivalents (black). Rod bivalents (gray). Pairs of univalents (black spots). The number of cells in metaphase I that were analyzed is indicated between parentheses;

FIG. 4: The RECQ4A and RECQ4B helicases redundantly limit CO formation during meiosis. The genetic distances in four intervals, measured using lines carrying fluorescent markers, were calculated with the Perkins equation and are expressed in centiMorgans. I2a and I2b are adjacent intervals on chromosome 2, and I5c and I5d are adjacent intervals on chromosome 5;

FIG. 5: The top3a-R640X mutation restores the formation of bivalents in the zmm mutants. Average number of bivalents per male meiocyte. Ring bivalents (black). Rod bivalents (gray). Pairs of univalents (black spots). The number of cells in metaphase I that were analyzed is indicated between parentheses;

FIG. 6: TOP3A and FANCM independently limit CO formation during meiosis. The genetic distances in four intervals, measured using lines carrying fluorescent markers, were calculated with the Perkins equation and are expressed in centiMorgans. I2a and I2b are adjacent intervals on chromosome 2, and I5c and I5d are adjacent intervals on chromosome 5.

Figure 7:
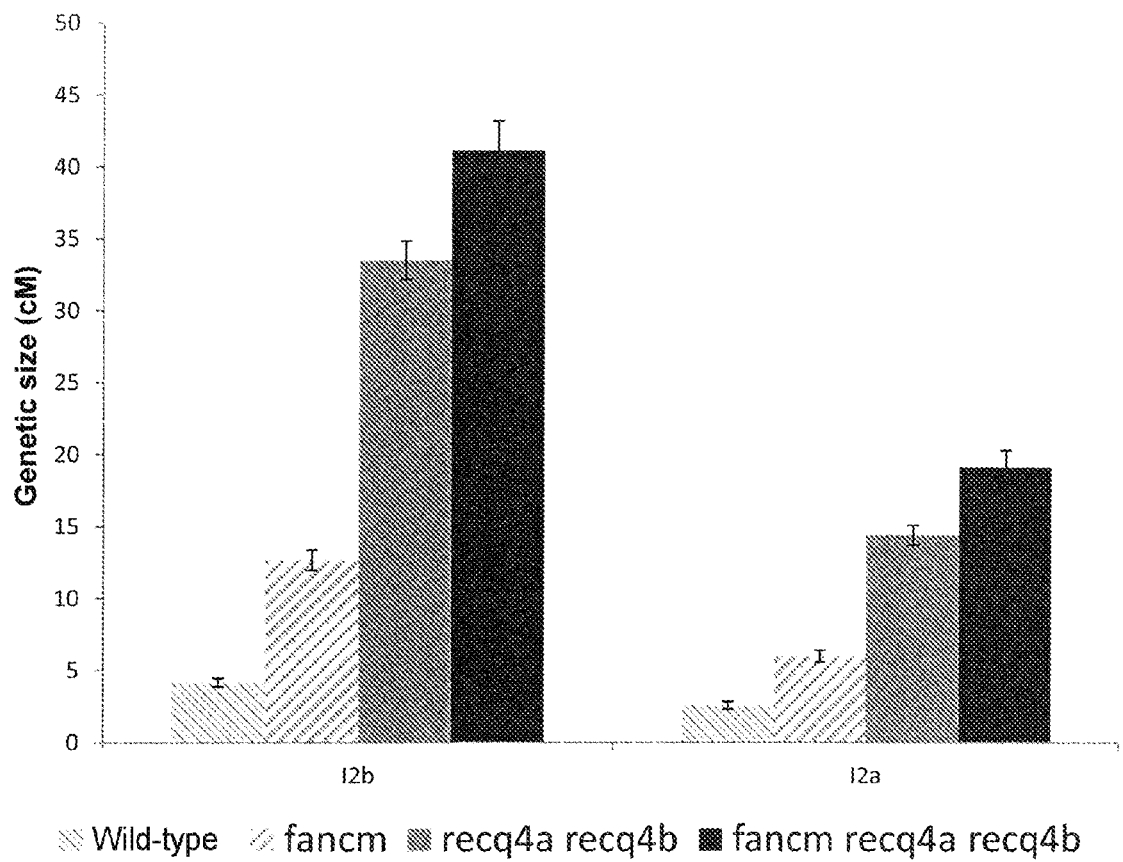

FIG. 7: RECQ4 and FANCM independently limit CO formation during meiosis. The genetic distances in two intervals, measured using lines carrying fluorescent markers, were calculated with the Perkins equation and are expressed in centiMorgans. I2a and I2b are adjacent intervals on chromosome 2.

EXAMPLE 1

Obtaining Mutants of the RECQ4 Gene which are Suppressors of ZMM Gene Mutations

Seeds of the msh4 mutant of *Arabidopsis thaliana* in the Landsberg eracta genetic background (cshl_GT14269; Drouaud et al., PLoS Genet., 2013, 9, e1003922; Higgins et al., Genes Dev., 2004, 18, 2557-2570) were mutated with EMS (ethyl methanesulfonate). The plants derived from the mutated seeds (M1 population, heterozygous for the EMS-induced mutations, and homozygous for the mutation of the ZMM gene) have an identical phenotype, resulting from the inactivation of the ZMM gene, which results in a strong decrease in the frequency of COs, which leads to a strong decrease in the number of bivalents, and a very large drop in fertility ("semi-sterile" plants), resulting in the formation of short siliques which are easily distinguished from those of the wild-type plants. The M1 plants were self-pollinated, so as to produce a population of descendants (M2 population; approximately 1000 families) potentially containing plants homozygous for the EMS-induced mutations. Plants of the M2 population having siliques longer than those of the homozygous zmm plants of the M1 generation were selected and genotyped in order to verify their homozygous status with respect to the msh4 genes. They are suppressors.

Two lines of mutants that are suppressors of the mutation of the AtMSH4 gene, called msh4(s)84 and msh4(s)101, are the subject of this study. The complete sequencing of the genome of these mutants showed that the corresponding mutations were located in the Atlg10930 gene encoding the RECQ4A helicase. The msh4(s)84 mutant comprises the C>T change in position TAIR 10: chr1:3652474 which introduces a stop codon at the W387 codon. The msh4(s)101 mutant comprises the C>T change in position TAIR 10: chr1:3650343 which introduces the G762D substitution. These two suppressors are allelic, demonstrating that the mutations in RECQ4A are the causal mutations of the restoration of fertility.

The comparison of the sequence of the Landsberg ecotype (Gan et al., Nature, 2011, 477, 7365, 419-23) with that of the genome of the Columbia ecotype showed that their RECQ4B loci differed by a series of single-nucleotide and insertion/deletion polymorphisms, including two which introduce a premature stop codon (Q430>STOP) and a reading frame shift (Aa 501) in Landsberg. This strongly suggests that the RECQ4B gene is not functional in Landsberg.

In the light of these results, the hypothesis was put forward that the recq4a mutation in Columbia was not capable of compensating for the effects of that of msh4 because of the redundancy with RECQ4B during meiosis. This would explain why the mutation of RECQ4A alone would be capable of compensating for the effects of that of msh4 in Landsberg but not Columbia.

Consequently, the msh4, recq4a and recq4b mutations were combined in the Columbia genetic background. The number of bivalents in metaphase I of the msh4 recq4a-4 recq4b-2 triple mutant was compared with that of wild-type plants (Col), of zmm (shoc1/Atzip2 or msh4) plants and of msh4 recq4a-4 and msh4 recq4b-2 double mutants.

The results are shown in FIG. 3. Although the wild-type plants systematically show five bivalents per meiosis, the Atmsh4 mutants show a strong decrease in the number of bivalents, and thus the appearance of univalents. In the wild-type plants, normal chromosome segregation is observed, resulting in the formation of equilibrated gametes. On the other hand, in the zmm mutants, poor chromosome segregation is observed which results from a decrease in the number of bivalents, induced by the zmm mutation, and which results in disequilibrated, non-viable gametes.

Furthermore, as has been previously shown (Higgins et al., The Plant Journal, 2011, 65, 492-502), the msh4 recq4a-4 and msh4 recq4b-2 double mutants are virtually sterile, like the msh4 mutant, and have a number of metaphase I bivalents that is similar to that of msh4 (FIG. 3).

Conversely, the msh4 recq4a-4 recq4b-2 triple mutant is fertile and its number of bivalents is reestablished to the level of that of the wild-type (FIG. 3). Similarly, the recq4a recq4b double mutation is also capable of restoring fertility and the formation of bivalents in another zmm mutant, shoc1/Atzip2 (FIG. 3).

These results show that, in Columbia, RECQ4A and RECQ4B have redundant functions which prevent the formation of meiotic COs in the zmm mutants.

EXAMPLE 2

Influence of the Inactivation of the RECQ4 Genes on Meiotic Recombination Frequency The effects of the recq4 mutations on meiotic recombination were then measured in a wild-type plant (Columbia), i.e. in the presence of functional ZMMs. The meiotic recombination frequency was measured by analyzing tetrads using lines labeled with a fluorescent label, as described by Berchowitz & Copenhaver, Nat. Protoc., 2008, 3, 41-50. The genetic distance was measured on four different genetic intervals, two adjacent intervals on chromosome 2 (12a and 12b) and two adjacent intervals on chromosome 5 (intervals 15c and 15d). The results are shown in FIG. 4.

In the recq4a and recq4b single mutants, the genetic distances were not significantly different than the wild-type for all the intervals tested (p>5%). Conversely, the genetic distances were considerably increased in the recq4a recq4b double mutant ($p<10^{-9}$). This increase was by a mean factor of 6.2 with a deviation of 4.6 to 8.6.

These results show that RECQ4A and RECQ4B play a major redundant role in limiting CO formation during meiosis and constitute the most powerful anti-meiotic CO genetic factors identified to date. Furthermore, this demonstrates that having more than six times more COs than the wild-type does not have deleterious effects on the integrity of the chromosomes, the equilibrated segregation of the chromosomes, the completion of meiosis, and fertility.

EXAMPLE 3

Obtaining Mutants of the TOP3A Gene that are Suppressors of ZMM Gene Mutations

A screening similar to that carried out for msh4 (example 1) was carried out in order to search for suppressors of the zmm mutant hei10 (Chelysheva et al., PLoS Genet., 2012, 8, e1002799). Among 1000 mutagenized lines derived from the hei10-2 mutant, a suppressor, hei10(s)61, exhibiting fertility and a number of bivalents greater than the hei10 mutant, was isolated (FIG. 5). The cloning of the mutation on the basis of the genetic map defined an interval of 2.4 Mb on chromosome 5, between the positions Tair10_chr5: 23.819.915 and Tair10_chr5:26.497.664. The complete sequencing of the genome of hei10(s)61 identified a nonsense mutation inside this interval, in the At5g63920 gene which encodes TOPOISOMERASE 3 alpha (TOP3A).

This gene appears to be a good candidate given that TOP3A and Sgs1 belong to the RTR complex, a conserved complex which is essential for maintaining the integrity of the genome (Mankouri and Hickson, Trends Biochem Sci., 2007, 32, 538-46).

In order to test whether this mutation was the cause of the phenotype, hei10(s)61 was transformed with a 10 kb genomic clone containing TOP3A. All the transformants exhibited the phenotype of hei10 (24 independent lines), were sterile and had 1.8 bivalents±0.75 in metaphase I (mean of three independent lines; FIG. 5). This demonstrates that the mutation in TOP3A was in fact the causal mutation that restored the fertility and the formation of bivalents in the hei10(s)61 suppressor. This shows that AtTOP3A prevents the formation of additional COs in the hei10 context. The hei10(s)61 mutation changes Arg640 into a stop codon (hereinafter referred to as top3a-R640X). Consequently, top3a-R640X encodes a protein which has intact TOPRIM and Topoisomerase domains, but which is truncated, removing its final 286 amino acids which contain the two predicted zinc finger domains (FIG. 2).

The increase in the number of bivalents and the restoration of fertility observed in the hei10 top3a-R640X mutant were also observed in an msh5 top3a-R640X double mutant (4.2±0.9 bivalents per meiosis; FIG. 5), showing that the suppression observed was not specific to the hei10 genetic background.

The hei10-2 top3a-2 and hei10-2 top3a-R640X plants differ in terms of both their somatic phenotype and their meiotic phenotype. Like a top3a-2 single mutant, hei10-2 top3a-2 shows stunted growth and complete sterility, contrasting with the normal growth and the fertility of hei10-2 top3a-R640X. In meiosis, the hei10 top3a-2 double mutant was indistinguishable from the top3a-2 single mutant, with aberrant structures in metaphase I and a massive fragmentation in anaphase I. In hei10-2 top3a-R640X, the bivalents observed (4.2 per cell, compared with 1.7 in hei10-2, FIG. 6) segregate in anaphase I without chromosome fragmentation. The top3a-2 phenotype showed that TOP3A is essential for preventing a meiotic catastrophe, whereas top3a-R640X appears to be a separation of function resulting in the restoration of COs in the hei10 genetic background, but keeping its efficient repair activity. This suggests that TOP3A has a double function during meiosis, since it is essential both for resolving meiotic recombination intermediates and also for limiting CO formation.

In the hei10-2 top3a-R640X/top3a-2 plants, no fragmentation was observed, showing that one copy of TOP3AR640X is sufficient to repair the recombination intermediates. The number of bivalents in this genetic background is even higher than in the hei10 top3a-R640X double mutant (4.9±0.1 compared with 4.2±1.1 bivalents, T-test, FIG. 5), suggesting that the TOP3A-R640X protein could conserve the anti-CO activity.

Next, the effect of the top3a-R640X mutation in plants having a functional HERO was analyzed. In agreement with the results obtained in the hei10 context, the top3a-R640X plants show no somatic abnormality and are fertile [seeds per fruit: wild-type=61±4 (n=40), top3a-R640X=61±3 (n=40)]. The meiosis of the top3a-R640X mutant is virtually indistinguishable from that of the wild-type, with no observation of fragmentation.

However, a low frequency of univalents was observed in the top3a-R640X single mutant (0.3 per cell, FIG. 5), whereas univalents are not observed in the wild-type. This suggests that the obligatory CO is slightly affected in the top3a-R640X mutant. The top3a-R640X/top3a-2 plants exhibit no developmental abnormality, are fertile, and no univalent was observed (FIG. 5).

EXAMPLE 4

Influence of the Mutation of the TOP3A Gene on Meiotic Recombination Frequency

The meiotic recombination frequency of the top3a-R640X mutant was then analyzed by analyzing tetrads using lines labeled with a fluorescent label, in four different genetic intervals, as described in example 2 (FIG. 6). In all the intervals tested, the genetic distances were increased in comparison with the wild-type ($P<10^{-5}$). This increase was, on average, by a factor of 1.5, with a deviation of 1.3 to 1.8. This shows that TOP3A has an anti-CO activity not only in an hei10 context, but also in plants that are wild-type for ZMMs.

EXAMPLE 5

Influence of the Combined Inactivation of the TOP3A and FANCM Gene on Meiotic Recombination Frequency The FANCM helicase was the first anti-meiotic CO gene described in *Arabidopsis* (PCT application WO 2013/038376; Crismani et al., Science, 336, 6088, 1588-90). In order to test whether TOP3A and FANCM act in the same path, the recombination frequency was measured in the top3a-R640X fancm-1 double mutant (FIG. 6). In the four intervals tested, it was observed that the genetic distances were significantly greater in the top3a-R640X fancm-1 double mutant than in the two single mutants (p<10-5). The increase in CO in the double mutant, in comparison with the wild-type, was on average by a factor of 4.9, with a deviation of 3.5 to 5.6. The effects of the two mutations on CO formation are cumulative, demonstrating that FANCM and TOP3A act on two parallel pathways to limit CO formation during meiosis. Interestingly, the top3a-R640X fancm-1 double mutant has a normal growth, has wild-type meiosis and is completely fertile [seeds per fruit: wild-type=61±4 (n=40), top3a-R640X fancm-1=65±2 (n=40)]. This confirms that having five times more COs than the wild-type does not have deleterious immediate effects on the integrity of the chromosomes, the equilibrated segregation of the chromosomes, completion of meiosis, and fertility.

EXAMPLE 6

Influence of the Combined Inactivation of the FANCM and RECQ4 Genes on Meiotic Recombination Frequency The FANCM helicase was the first anti-meiotic CO gene described in *Arabidopsis* (PCT application WO 2013/038376; Crismani et al., Science, 336, 6088, 1588-90). In order to test whether RECQ4 and FANCM act on the same pathway, the recombination frequency was measured in the recq4a recq4b fancm-1 triple mutant (FIG. 7). In the two intervals tested, it was observed that the genetic distances were significantly greater in the recq4a recq4b fancm-1 triple mutant than in the recq4a recq4b double mutant (p<0.01) and the fancm-1 single mutant ($p<10^{-6}$). The increase in CO in the triple mutant, in comparison with the wild-type, was on average by a factor of 9. The effects of the mutations of the recq4 and fancm genes on CO formation are cumulative, demonstrating that FANCM and RECQ4 act in parallel to limit CO formation during meiosis. Interestingly, the recq4a recq4b fancm-1 triple mutant has a normal growth, has wild-type meiosis (n=450) and is completely fertile [seeds per fruit: wild-type=53.7±4.8 (n=40), recq4a recq4b fancm-1=49.2±5.3 (n=40)]. This confirms that having nine times more COs than the wild-type has no deleterious immediate effects on the integrity of the chromosomes, the equilibrated segregation of the chromosomes, completion of meiosis, and fertility.

The invention claimed is:

1. A process for increasing the frequency of meiotic crossovers in a plant said process comprising:
    inhibiting in said plant, the expression or the function of:
    a protein of the RTR complex known as RECQ4; or
    both REQ4A and RECQ4B proteins if said plant belongs to the family of Brassicaceae and expresses two functional RECQ4 proteins, said RECQ4 protein having at least 40% sequence identity with the RECQ4 protein of SEQ ID NO: 1, and comprising a region having at least 60% sequence identity with the region which extends from positions 407 to 959 of the sequence SEQ ID NO:1; and
    measuring the frequency of meiotic crossovers in said plant.

2. The process of claim 1, further comprising, inhibiting in said plant, the expression or the function of at least one protein chosen from:
    (i) a protein hereinafter referred to as FIDG, said protein having at least 45% sequence identity with the AtFIDG protein of SEQ ID NO:46 and containing an AAA-ATPase domain and a VSP4 domain, and
    (ii) a protein hereinafter referred to as FANCM, said protein having at least 30% sequence identity with the AtFANCM protein of SEQ ID NO:45, and containing a DEXDc helicase domain and a HELICc helicase domain.

3. The process of claim 1, wherein the inhibition of the RECQ4 is obtained by mutagenesis of the gene encoding said protein or of its promoter.

4. The process of claim 1, wherein the inhibition of the RECQ4 is obtained by silencing the gene encoding said protein by expressing, in said plant, an interfering RNA targeting said gene.

5. The process of claim 1, further comprising, inhibiting in said plant, the expression or the function of a protein known as TOP3A, said TOP3A protein having at least 50% sequence identity with the TOP3A protein of sequence SEQ ID NO: 2.

6. The process of claim 5, wherein the inhibition of the TOP3A protein is obtained by mutagenesis of the gene encoding said protein or of its promoter.

7. The process of claim 6, wherein the mutagenesis of the TOP3A protein comprises the introduction, into an allele of the TOP3A gene, of a mutation which results in the inactivation of at least one zinc finger domain of said TOP3A protein.

8. The process of claim 5, the process further comprising the expression, in said plant, of a recombinant TOP3A protein comprising a TOPRIM domain and a Topoisomerase IA domain which have not been impaired and at least one zinc finger domain which is inactivated.

9. The process of claim 1, wherein said plant is a monocotyledonous or dicotyledonous plant of agronomical interest comprising rapeseed, sunflower, potato, corn, wheat, barley, rye, sorghum, rice, soy, bean, carrot, tomato, zucchini, bell pepper, eggplant, turnip, onion, pea, cucumber, leek, artichoke, beetroot, cabbage, cauliflower, lettuces, endive, melon, watermelon, strawberry plant, apple tree, pear tree, plum tree, poplar tree, vine, cotton, rose, or tulip.

* * * * *

SEQUENCE LISTING

<160> NUMBER OF SEQ ID NOS: 52

<210> SEQ ID NO 1
<211> LENGTH: 1188
<212> TYPE: PRT
<213> ORGANISM: Arabidopsis thaliana

<400> SEQUENCE: 1

```
Met Ile Asn Ser Asn Gln Met Ser Arg Ser His Leu Pro Glu Val Gln
1               5                   10                  15

Lys Pro Arg Gly Pro Gln Thr Asn Trp Ser Glu His Ala Lys Ala Leu
            20                  25                  30

Glu Ser Ser Ser Val Thr Lys Phe Leu Ser Ser Asn Val Leu Tyr
        35                  40                  45

Ala Leu Glu Ser Gln Lys Pro Arg Asp Met Ala Ala Arg Ser Ile Ala
    50                  55                  60

Phe Pro Ser Val Asn Val His Thr Leu Ala His Pro Gln Ile Ser Lys
65                  70                  75                  80

Ala Trp Arg Ala Leu Ser Ser Leu Ser Val Asn Asn Thr Tyr Leu Arg
                85                  90                  95

Pro Gly Val Thr Pro Pro Ile Asp Val Gly Thr Asn Asp Ser Tyr Ser
            100                 105                 110

Ala Arg Glu Arg Ser Thr Ala Lys Val Ile Ser Ser Thr Gly Gly Ser
        115                 120                 125

Val Tyr Ser Ser Thr Arg Pro Asn Leu Ser Ala Met Asn Val Ser Gly
    130                 135                 140

Thr Gly Arg Ser Phe His Ser Phe Pro Ser Ser Val Pro Gly Asp Asp
145                 150                 155                 160

Lys Ile Val Ala Glu Lys Phe Pro Arg Gly Asn Asn Glu Ile Arg Glu
                165                 170                 175

Ser Glu Pro Ser Cys Thr His Leu Asn Gly Val Glu Lys Ser Phe Gly
            180                 185                 190

Asn Ser Ala Phe Pro Ala Glu Gln Phe Glu Ser Arg Lys Ala Cys Leu
        195                 200                 205

Asp Asp Met Asp Asp Asp Ile Leu Glu Asn Ile Asp Val Asp Gln
    210                 215                 220

Ile Val Met Glu His Tyr His Ser Thr Ser Thr Pro Gln Pro Ser Val
225                 230                 235                 240

Ser Asn Phe Ser Leu Arg Thr Pro Pro Val Asp Arg Ser Ala Ser Arg
                245                 250                 255

Leu Glu Glu Glu Cys Asn Leu Pro Pro Glu Leu Cys Ser Asn Cys Ser
            260                 265                 270

His Gly Ile Lys Leu Gly Leu Cys Pro Glu Ala Ser Thr His Val Glu
        275                 280                 285

Gln Met Lys Asp Val Leu Leu Ala Ile Ser Asn Glu Leu Leu Asp Asp
    290                 295                 300

Ala Thr Asp Leu Ser Pro Asp Arg Val Gly Gln Leu Arg Gln Glu Arg
305                 310                 315                 320

Leu Arg Leu Lys Lys Gln Ile Gln Gln Leu Glu Asn His Ile Arg Asp
                325                 330                 335

Lys Glu Ser Gln Lys Ser Gln Phe Leu Ser Ser Thr Ala Thr Arg Ile
            340                 345                 350

Phe Gln Tyr Glu Thr Pro Lys Ser Thr Asn Tyr Lys Met Asp Gln Pro
        355                 360                 365

Gln Thr Asp Phe Arg Ala His Val Ser Asp Gly Arg Tyr Ala Cys
    370                 375                 380

Asp Ser Trp Asn Thr Pro Arg Asp Ser Ser Phe Ser Val Asp Arg Tyr
385                 390                 395                 400

Gly Leu Ser Ser Ala Pro Val Glu Arg Glu Gln Tyr Val Pro Lys Ile
                405                 410                 415
```

```
Ile Asp Val Thr Tyr Thr Glu Gly Ser Asn Asp Lys Lys Trp Ser Ser
            420                 425                 430

Arg Glu Phe Pro Trp Thr Arg Lys Leu Glu Val Asn Asn Lys Lys Val
        435                 440                 445

Phe Gly Asn His Ser Phe Arg Pro Asn Gln Arg Glu Ile Ile Asn Ala
    450                 455                 460

Thr Met Ser Gly Ser Asp Val Phe Val Leu Met Pro Thr Gly Gly Gly
465                 470                 475                 480

Lys Ser Leu Thr Tyr Gln Leu Pro Ala Leu Ile Cys Gly Gly Ile Thr
                485                 490                 495

Leu Val Ile Ser Pro Leu Val Ser Leu Ile Gln Asp Gln Ile Met Asn
            500                 505                 510

Leu Leu Gln Ala Asn Ile Pro Ala Ala Ser Leu Ser Ala Gly Met Glu
        515                 520                 525

Trp Ala Glu Gln Leu Lys Ile Phe Gln Glu Leu Asn Ser Glu His Ser
    530                 535                 540

Lys Tyr Lys Leu Leu Tyr Val Thr Pro Glu Lys Val Ala Lys Ser Asp
545                 550                 555                 560

Ser Leu Leu Arg His Leu Glu Asn Leu Asn Ser Arg Gly Leu Leu Ala
                565                 570                 575

Arg Phe Val Ile Asp Glu Ala His Cys Val Ser Gln Trp Gly His Asp
            580                 585                 590

Phe Arg Pro Asp Tyr Gln Ser Leu Gly Ile Leu Lys Gln Lys Phe Pro
        595                 600                 605

Asn Ile Pro Val Leu Ala Leu Thr Ala Thr Ala Thr Ala Ser Val Lys
    610                 615                 620

Glu Asp Val Val Gln Ala Leu Gly Leu Val Asn Cys Val Val Phe Arg
625                 630                 635                 640

Gln Ser Phe Asn Arg Pro Asn Leu Trp Tyr Ser Val Pro Lys Thr
                645                 650                 655

Lys Lys Cys Leu Glu Asp Ile Asp Lys Phe Ile Lys Glu Asn His Phe
            660                 665                 670

Asp Glu Cys Gly Ile Ile Tyr Cys Leu Ser Arg Met Asp Cys Glu Lys
        675                 680                 685

Val Ser Glu Arg Leu Gln Glu Phe Gly His Lys Ala Ala Phe Tyr His
    690                 695                 700

Gly Ser Met Glu Pro Glu Gln Arg Ala Phe Ile Gln Thr Gln Trp Ser
705                 710                 715                 720

Lys Asp Glu Ile Asn Ile Ile Cys Ala Thr Val Ala Phe Gly Met Gly
                725                 730                 735

Ile Asn Lys Pro Asp Val Arg Phe Val Ile His His Ser Leu Pro Lys
            740                 745                 750

Ser Ile Glu Gly Tyr His Gln Glu Cys Gly Arg Ala Gly Arg Asp Gly
        755                 760                 765

Gln Arg Ser Ser Cys Val Leu Tyr Tyr Gly Tyr Gly Asp Tyr Ile Arg
    770                 775                 780

Val Lys His Met Ile Ser Gln Gly Gly Val Asp Gln Ser Pro Met Ala
785                 790                 795                 800

Thr Gly Tyr Asn Arg Val Ala Ser Ser Gly Arg Leu Leu Glu Thr Asn
                805                 810                 815

Thr Glu Asn Leu Leu Arg Met Val Arg Tyr Cys Glu Asn Glu Val Glu
            820                 825                 830

Cys Arg Arg Phe Leu Gln Leu Val His Leu Gly Glu Lys Phe Asp Ser
```

```
                835                 840                 845
Thr Asn Cys Lys Lys Thr Cys Asp Asn Cys Cys Ser Ser Gln Ser Leu
    850                 855                 860

Ile Asp Lys Asp Val Thr Leu Ile Thr Arg Gln Leu Val Glu Leu Val
865                 870                 875                 880

Lys Gln Thr Gly Glu Arg Phe Ser Ser Ala His Ile Leu Glu Val Tyr
                885                 890                 895

Arg Gly Ser Leu Asn Gln Met Val Lys Lys His Arg His Glu Thr Leu
            900                 905                 910

Gln Phe His Gly Ala Gly Lys His Leu Ser Lys Ile Glu Val Ser Arg
        915                 920                 925

Ile Leu His Tyr Leu Val Thr Glu Asp Ile Leu Val Glu Asp Val Arg
    930                 935                 940

Lys Ser Asp Met Tyr Gly Ser Val Ser Ser Leu Leu Gly Val Asn Asn
945                 950                 955                 960

Ala Lys Ala Thr Ile Leu Phe Ser Gly Ser Gln Thr Ile Val Met Lys
                965                 970                 975

Phe Pro Ser Ser Val Lys Val Leu Lys Pro Ser Lys Gln Gly Ala Thr
            980                 985                 990

Ala Ala Lys Gly Pro Leu Thr Ser Glu Lys Gln Ser Thr Leu Pro Leu
        995                 1000                1005

Thr Thr Glu Asp Ala Pro Pro Lys Asp Val Asn Leu Ser Ala Asn
    1010                1015                1020

Met Tyr Thr Ala Leu Arg Lys Leu Arg Thr Ala Leu Val Lys Glu
    1025                1030                1035

Ala Pro Asp Gly Val Met Ala Tyr His Ile Phe Ile Asn Ser Thr
    1040                1045                1050

Leu Gln Gln Ile Ser Arg Arg Ile Pro Arg Thr Lys Glu Glu Leu
    1055                1060                1065

Leu Glu Ile Asn Gly Leu Gly Lys Ala Lys Val Ser Lys Tyr Gly
    1070                1075                1080

Asp Gln Leu Leu Glu Thr Ile Glu Thr Thr Val Asn Glu Tyr Tyr
    1085                1090                1095

Gly Thr Asn Lys Lys Asp Ser Ile Ile Ser Asn Asp Ser Pro Asp
    1100                1105                1110

Ser Gly Lys Arg Arg Arg Asp Glu Asn Ile Ser Pro Asn Val Ala
    1115                1120                1125

Glu Asp Asp Asp Phe Glu Val Ser Pro Ser Gln Ser Cys Lys Lys
    1130                1135                1140

Thr Val Arg Asn Lys Ser Asn Glu Val Leu His Gly Glu Cys Ile
    1145                1150                1155

Asp Gly Asp Arg Arg Gly Met Glu Leu Asp Phe Asp Phe Lys Asp
    1160                1165                1170

Glu Asp Gly Ser Glu Ile Arg Pro Glu Gly Arg Val Leu Pro Trp
    1175                1180                1185

<210> SEQ ID NO 2
<211> LENGTH: 926
<212> TYPE: PRT
<213> ORGANISM: Arabidopsis thaliana

<400> SEQUENCE: 2

Met Ser Arg Arg Gly Gly Gly Pro Val Thr Val Leu Asn Val Ala Glu
1               5                   10                  15
```

-continued

```
Lys Pro Ser Val Ala Lys Ser Val Ala Gly Ile Leu Ser Arg Gly Thr
                 20                  25                  30
Phe Arg Thr Arg Glu Gly Arg Ser Arg Tyr Asn Lys Ile Phe Glu Phe
             35                  40                  45
Asp Tyr Ala Ile Asn Gly Gln Pro Cys Arg Met Leu Met Thr Ser Val
 50                  55                  60
Ile Gly His Leu Met Glu Leu Glu Phe Ala Asp Arg Tyr Arg Lys Trp
 65                  70                  75                  80
His Ser Cys Asp Pro Ala Asp Leu Tyr Gln Ala Pro Val Met Lys His
                 85                  90                  95
Val Pro Glu Asp Lys Lys Asp Ile Lys Lys Thr Leu Glu Glu Glu Ala
            100                 105                 110
Arg Lys Ser Asp Trp Leu Val Leu Trp Leu Asp Cys Asp Arg Glu Gly
            115                 120                 125
Glu Asn Ile Ala Phe Glu Val Asp Val Cys Arg Ala Val Lys His
            130                 135                 140
Asn Leu Phe Ile Arg Arg Ala His Phe Ser Ala Leu Ile Asp Arg Asp
145                 150                 155                 160
Ile His Glu Ala Val Gln Asn Leu Arg Asp Pro Asn Gln Leu Phe Ala
                165                 170                 175
Glu Ala Val Asp Ala Arg Gln Glu Ile Asp Leu Arg Ile Gly Ala Ser
            180                 185                 190
Phe Thr Arg Phe Gln Thr Met Leu Leu Arg Asp Arg Phe Ala Ile Asp
            195                 200                 205
Ser Thr Gly Glu Glu Arg Ser Arg Val Ile Ser Tyr Gly Pro Cys Gln
210                 215                 220
Phe Pro Thr Leu Gly Phe Ile Val Glu Arg Tyr Trp Glu Ile Gln Ala
225                 230                 235                 240
His Glu Pro Glu Glu Phe Trp Thr Ile Asn Cys Ser His Gln Ser Glu
                245                 250                 255
Glu Gly Leu Ala Thr Phe Asn Trp Met Arg Gly His Leu Phe Asp Tyr
            260                 265                 270
Ala Ser Ala Val Ile Leu Tyr Glu Met Cys Val Glu Glu Pro Thr Ala
            275                 280                 285
Thr Val Met Asn Val Pro His Pro Arg Glu Arg Phe Lys Tyr Pro Pro
290                 295                 300
Tyr Pro Leu Asn Thr Ile Glu Leu Glu Lys Arg Ala Ser Arg Tyr Phe
305                 310                 315                 320
Arg Leu Ser Ser Glu His Thr Met Lys Val Ala Glu Glu Leu Tyr Gln
                325                 330                 335
Ala Gly Phe Ile Ser Tyr Pro Arg Thr Glu Thr Asp Ser Phe Ser Ser
            340                 345                 350
Arg Thr Asp Leu Arg Ala Met Val Glu Glu Gln Thr Arg His Pro Ala
            355                 360                 365
Trp Gly Ser Tyr Ala Gln Arg Leu Leu Glu Pro Glu Gly Gly Leu Trp
            370                 375                 380
Arg Asn Pro Ala Asn Gly Gly His Asp Asp Lys Ala His Pro Pro Ile
385                 390                 395                 400
His Pro Thr Lys Phe Ser Ser Gly Glu Ser Asn Trp Ser Arg Asp His
                405                 410                 415
Leu Asn Val Tyr Glu Leu Val Val Arg His Tyr Leu Ala Cys Val Ser
            420                 425                 430
Gln Pro Ala Val Ala Ala Glu Thr Thr Val Glu Ile Asp Ile Ala Gly
```

```
                435                 440                 445
Glu Arg Phe Ser Ala Ser Gly Arg Ala Ile Leu Ala Lys Asn Tyr Leu
450                 455                 460

Glu Val Tyr Arg Phe Glu Ser Trp Gly Gly Ser Val Ile Pro Val Tyr
465                 470                 475                 480

Glu Lys Gly Gln Gln Phe Ile Pro Thr Thr Leu Thr Leu Asp Ala Ala
                485                 490                 495

Val Thr Arg Pro Pro Leu Leu Cys Glu Ala Asp Leu Leu Ser Cys
                500                 505                 510

Met Asp Lys Ala Gly Ile Gly Thr Asp Ala Thr Met His Asp His Ile
                515                 520                 525

Lys Lys Leu Leu Asp Arg Gly Tyr Ala Thr Lys Asp Ala Asn Thr Arg
530                 535                 540

Phe Ser Pro Thr Asn Leu Gly Glu Ala Leu Val Met Gly Tyr Asp Asp
545                 550                 555                 560

Met Gly Tyr Glu Leu Trp Lys Pro Asn Leu Arg Ala Leu Met Glu His
                565                 570                 575

Asp Met Asn Glu Val Ser Val Gly Arg Lys Thr Lys Ala Glu Val Leu
                580                 585                 590

Glu Thr Cys Leu Gln Gln Met Lys Ala Cys Phe Leu Asp Ala Arg Val
                595                 600                 605

Lys Lys Ser Lys Leu Leu Glu Ala Met Thr Ile Phe Phe Glu Arg Ser
610                 615                 620

Asn Asn Thr Asp Glu Ser Glu Ser Gln Thr Ala Gly Glu Val Val Arg
625                 630                 635                 640

Arg Cys Asn Leu Cys Asn Glu Ser Asp Met Ala Leu Arg Lys Asn Arg
                645                 650                 655

Asp Gly Asn Phe Met Val Gly Cys Met Asn Tyr Pro Gln Cys Arg Asn
                660                 665                 670

Ala Val Trp Leu Pro Gly Pro Thr Leu Glu Ala Ser Val Thr Thr Asn
                675                 680                 685

Val Cys Gln Ser Cys Gly Pro Gly Pro Val Tyr Lys Ile Leu Phe Lys
                690                 695                 700

Phe Arg Gln Ile Gly Ile Pro Pro Gly Phe Asp Val Asn His Leu Gly
705                 710                 715                 720

Cys Val Gly Gly Cys Asp Asp Ile Leu Lys Gln Leu Ile Asp Ile Cys
                725                 730                 735

Gly Thr Gly Ser Arg Ser Gln Ala Arg Arg Thr Pro Gly Thr Ala Pro
                740                 745                 750

Ser Asn Asn Ile Gln Gly Ser Asn Thr Arg Gln Ser Asn Val Cys Ile
                755                 760                 765

His Cys Gln Gln Arg Gly His Ala Ser Thr Asn Cys Pro Ser Arg Val
                770                 775                 780

Pro Ala Ser Arg Asn Ser Arg Pro Thr Ala Thr Asn Pro Arg Asn Asp
785                 790                 795                 800

Glu Ser Thr Val Ser Cys Asn Thr Cys Gly Ser Gln Cys Val Leu Arg
                805                 810                 815

Thr Ala Asn Thr Glu Ala Asn Arg Gly Arg Gln Phe Phe Ser Cys Pro
                820                 825                 830

Thr Gln Gly Cys Ser Phe Phe Ala Trp Glu Asp Ser Ile Asn Asn Ser
                835                 840                 845

Ser Gly Asn Ala Thr Thr Gly Ser Asn Ser Gly Gly Ser Gly Arg Arg
                850                 855                 860
```

Gly Ser Arg Gly Arg Gly Arg Gly Gly Arg Gly Gln Ser Ser Gly
865                 870                 875                 880

Gly Arg Arg Gly Ser Gly Thr Ser Phe Val Ser Ala Thr Gly Glu Pro
                885                 890                 895

Val Ser Gly Ile Arg Cys Phe Ser Cys Gly Asp Pro Ser His Phe Ala
            900                 905                 910

Asn Ala Cys Pro Asn Arg Asn Asn Ser Asn Gly Asn Tyr Phe
        915                 920                 925

<210> SEQ ID NO 3
<211> LENGTH: 1189
<212> TYPE: PRT
<213> ORGANISM: Arabidopsis lyrata

<400> SEQUENCE: 3

Met Ser Trp Ser His Leu Pro Glu Val Gln Lys Pro Arg Gly Pro Gln
1               5                   10                  15

Thr Asn Trp Ser Glu His Ala Lys Ala Leu Glu Ser Ser Ser Ser Val
            20                  25                  30

Thr Lys Phe Leu Ser Ser Asn Val Leu Tyr Ala Leu Glu Ser Gln Lys
        35                  40                  45

Pro Arg Asp Met Ser Ala Arg Ser Ile Ala Phe Pro Ser Val Asn Val
50                  55                  60

His Thr Leu Ala His Pro Gln Ile Ser Lys Ala Trp Arg Ala Leu Ser
65                  70                  75                  80

Ser Leu Ser Ile Asn Asn Ala Tyr Leu Arg Pro Gly Val Thr Pro Pro
                85                  90                  95

Ile Asp Asp Gly Gly Thr Asn Gly Ser Tyr Ser Ala Arg Glu Gly Ser
            100                 105                 110

Thr Val Lys Val Ile Ser Ser Thr Gly Gly Ser Val Tyr Ser Ser Ser
        115                 120                 125

Arg Gln Asn Gln Asn Ala Met Asn Val Ser Gly Thr Gly Arg Ser Phe
130                 135                 140

His Ser Phe Pro Ser Ser Val Leu Gly Ala Asp Lys Met Ile Ala Glu
145                 150                 155                 160

Lys Phe Pro Leu Gly Asn Asp Glu Val Arg Glu Ser Glu Pro Ser Phe
                165                 170                 175

Thr His Leu Asn Gly Val Glu Lys Ser Phe Arg Asn Ser Ala Phe Pro
            180                 185                 190

Pro Glu Gln Phe Glu Ser Gly Lys Ala Cys Leu Gly Asp Met Asp Asp
        195                 200                 205

Asp Asp Ile Leu Lys Asn Ile Asp Val Asp Gln Ile Val Met Glu His
210                 215                 220

Tyr His Ser Thr Ser Thr Pro Gln Pro Ser Val Ser Asn Phe Ser Leu
225                 230                 235                 240

Arg Thr Pro Pro Ala Pro Pro Val Asp Arg Ser Ala Ser Arg Leu Glu
                245                 250                 255

Glu Glu Cys Tyr Leu Pro Pro Glu Leu Cys Ser Asn Cys Ser His Gly
            260                 265                 270

Ile Lys Leu Gly Leu Cys Pro Glu Ala Ser Thr His Val Glu Gln Met
        275                 280                 285

Lys Asp Val Leu Leu Ala Ile Ser Asn Glu Leu Leu Asp Asp Ala Ala
290                 295                 300

Asp Leu Ser Pro Tyr Arg Val Glu Gln Leu Arg Gln Glu Arg Leu Gln

-continued

```
            305                 310                 315                 320
        Leu Lys Lys Gln Ile Gln Gln Leu Glu Asn His Ile Arg Asp Lys Glu
                        325                 330                 335
        Arg Gln Lys Ser Gln Phe Ser Ser Thr Ala Thr Arg Thr Phe Gln
                        340                 345                 350
        Tyr Glu Thr Pro Lys Ser Thr Asn Tyr Lys Met Asp Gln Pro Gln Thr
                        355                 360                 365
        Asp Phe Arg Ala His Leu Ser Asp Gln Gly Arg Tyr Ala Gly Asp Ser
                370                 375                 380
        Trp Asn Thr Pro Arg Asp Ser Ser Phe Ser Val Asp Arg Tyr Gly Leu
        385                 390                 395                 400
        Ser Thr Ala Pro Val Glu Arg Glu Pro Tyr Val Pro Lys Ile Ile Asp
                        405                 410                 415
        Val Thr Tyr Thr Glu Gly Ser Asn Asp Lys Lys Trp Ser Ser Arg Glu
                        420                 425                 430
        Phe Pro Trp Thr Arg Lys Leu Glu Val Asn Asn Lys Lys Val Phe Gly
                        435                 440                 445
        Asn His Ser Phe Arg Pro Asn Gln Arg Glu Ile Ile Asn Ala Thr Met
                450                 455                 460
        Ser Gly Ser Asp Val Phe Val Leu Met Pro Thr Gly Gly Gly Lys Ser
        465                 470                 475                 480
        Leu Thr Tyr Gln Leu Pro Ala Leu Ile Cys Gly Gly Ile Thr Leu Val
                        485                 490                 495
        Ile Ser Pro Leu Val Ser Leu Ile Gln Asp Gln Ile Met Asn Leu Leu
                        500                 505                 510
        Gln Ala Asn Ile Pro Ala Ala Ser Leu Ser Ala Gly Met Glu Trp Ala
                        515                 520                 525
        Glu Gln Leu Lys Ile Phe Gln Glu Leu Asn Ser Glu His Ser Lys Tyr
                        530                 535                 540
        Lys Leu Leu Tyr Val Thr Pro Glu Lys Val Ala Lys Ser Asp Ser Leu
        545                 550                 555                 560
        Leu Arg His Leu Glu Asn Leu Asn Ser Arg Gly Leu Leu Ala Arg Phe
                        565                 570                 575
        Val Ile Asp Glu Ala His Cys Val Ser Gln Trp Gly His Asp Phe Arg
                        580                 585                 590
        Pro Asp Tyr Gln Ser Leu Gly Ile Leu Lys Gln Lys Phe Pro Asn Ile
                        595                 600                 605
        Pro Val Leu Ala Leu Thr Ala Thr Ala Thr Ala Ser Val Lys Glu Asp
                610                 615                 620
        Val Val Gln Ala Leu Gly Leu Val Asn Cys Val Val Phe Arg Gln Ser
        625                 630                 635                 640
        Phe Asn Arg Pro Asn Leu Trp Tyr Ser Val Val Pro Lys Thr Lys Lys
                        645                 650                 655
        Cys Leu Glu Asp Ile Asp Lys Phe Ile Lys Glu Asn His Phe Asp Glu
                        660                 665                 670
        Cys Gly Ile Ile Tyr Cys Leu Ser Arg Met Asp Cys Glu Lys Val Ser
                        675                 680                 685
        Glu Arg Leu Gln Glu Phe Gly His Lys Thr Ala Phe Tyr His Gly Ser
                690                 695                 700
        Met Glu Pro Glu Gln Arg Ala Phe Ile Gln Thr Gln Trp Ser Lys Asp
        705                 710                 715                 720
        Glu Ile Asn Ile Ile Cys Ala Thr Val Ala Phe Gly Met Gly Ile Asn
                        725                 730                 735
```

Lys Pro Asp Val Arg Phe Val Ile His His Ser Leu Pro Lys Ser Ile
            740                 745                 750

Glu Gly Tyr His Gln Glu Cys Gly Arg Ala Gly Arg Asp Gly Gln Arg
            755                 760                 765

Ser Ser Cys Val Leu Tyr Gly Tyr Gly Asp Tyr Ile Arg Val Lys
770                 775                 780

His Met Ile Ser Gln Gly Gly Val Asp Gln Ser Pro Met Ala Thr Gly
785                 790                 795                 800

Tyr Asn Arg Val Ala Ser Leu Gly Arg Ile Leu Glu Thr Asn Thr Glu
                805                 810                 815

Asn Leu Leu Arg Met Val Ser Tyr Cys Glu Asn Glu Val Glu Cys Arg
            820                 825                 830

Arg Phe Leu Gln Leu Val His Phe Gly Glu Lys Phe Asp Ser Thr Asn
            835                 840                 845

Cys Lys Lys Thr Cys Asp Asn Cys Cys Ser Ser Gln Ser Leu Ile Asp
            850                 855                 860

Lys Asp Val Thr Leu Ile Thr Arg Gln Leu Val Glu Leu Val Lys Gln
865                 870                 875                 880

Thr Gly Glu Arg Phe Ser Ser Ala His Ile Leu Glu Val Tyr Arg Gly
                885                 890                 895

Ser Leu Asn Gln Met Val Lys Lys His Arg His Glu Thr Leu Gln Leu
            900                 905                 910

His Gly Val Gly Lys His Leu Ser Lys Ile Glu Val Ser Arg Ile Leu
            915                 920                 925

His Tyr Leu Val Thr Glu Asp Ile Leu Val Glu Asp Val Arg Lys Ser
            930                 935                 940

Asp Met Tyr Gly Ser Val Ser Ser Leu Leu Lys Val Asn Asn Ala Lys
945                 950                 955                 960

Ala Thr Leu Leu Phe Ser Gly Ser Gln Thr Ile Met Met Lys Phe Pro
                965                 970                 975

Ser Ser Val Lys Val Leu Lys Pro Ser Lys Gln Gly Ala Thr Ala Ala
            980                 985                 990

Lys Gly Pro Leu Thr Ser Glu Lys  Gln Ser Thr Leu Pro  Leu Thr Thr
            995                 1000                1005

Glu Asp  Ala Pro Pro Lys Asp  Leu Asn Leu Ser Ala  Asn Met Tyr
1010                1015                1020

Thr Ala  Leu Arg Lys Leu Arg  Thr Ala Leu Val Lys  Glu Ala Pro
1025                1030                1035

Asp Gly  Val Met Ala Tyr His  Ile Phe Ile Asn Ser  Thr Leu Gln
1040                1045                1050

Gln Ile  Ser Arg Arg Ile Pro  Arg Thr Lys Glu Glu  Leu Leu Glu
1055                1060                1065

Ile Asn  Gly Leu Gly Lys Ala  Lys Val Ser Lys Tyr  Gly Asp Arg
1070                1075                1080

Leu Leu  Glu Thr Ile Glu Thr  Thr Val Asn Glu Tyr  Tyr Gly Thr
1085                1090                1095

Asn Lys  Lys Asp Ser Ile Ile  Ser Asn Asp Ser Pro  Asp Ser Gly
1100                1105                1110

Lys Arg  Arg Arg Asp Glu Asn  Ile Ser Pro Asn Val  Ala Glu Asp
1115                1120                1125

Asp Asp  Phe Glu Val Ser Pro  Ser Gln Ser Cys Lys  Lys Thr Val
1130                1135                1140

```
Arg Asn Lys Ser Asn Glu Val Leu His Gly Glu Cys Val Asp Gly
    1145                1150                1155

Asp Arg Arg Gly Met Val Met Glu Lys Leu Asp Phe Asp Phe Arg
    1160                1165                1170

Asp Glu Asp Val Ser Glu Ile Arg Pro Glu Gly Arg Val Leu Pro
    1175                1180                1185

Trp

<210> SEQ ID NO 4
<211> LENGTH: 1172
<212> TYPE: PRT
<213> ORGANISM: Arabidopsis lyrata

<400> SEQUENCE: 4

Met Thr Leu Ile Val Lys Phe Val Val Glu Gln His Cys Ser Phe His
 1               5                  10                  15

Ser Asp Asn Arg Ser Gln Leu Lys Phe Val Asn Gly Gly Asp Lys Arg
            20                  25                  30

Arg Ser Asn Cys Trp Lys Leu Phe Gly Ile Gly Ser His Leu Pro Glu
        35                  40                  45

Val Asn Lys Ser Arg Gly His Phe Leu Gln Thr Asn Trp Ser Lys His
 50                  55                  60

Ala Lys Ala Phe Glu Cys Ile Pro Ser Leu Asn Lys Phe Met Gly Ser
65                  70                  75                  80

Asn Phe Leu Tyr Ser Leu Glu Ser Gln Lys Leu Ala Arg Asp Arg Glu
                85                  90                  95

Met Gly Ala Arg Ser Ile Glu Asn Ile Ala Pro Val Thr Val Gln Thr
            100                 105                 110

Leu Ala Arg Pro Glu Ile Glu Lys Ala Trp Cys Thr Leu Ile Asn Leu
        115                 120                 125

Ser Ile Asn Asn Thr Tyr Leu Arg Pro Gly Ile Thr Pro Ala Ile Asp
    130                 135                 140

Asp Gly Ser Thr Asp Arg Ser Ser Ser Thr Lys Arg Ser Thr Val Lys
145                 150                 155                 160

Val Thr Ser Ser Ala Asp Gly Ser Phe Tyr Ala His Asn His Pro Glu
                165                 170                 175

His Ser Gln Arg Ser Leu Arg Gly Thr Ala Lys Ser Phe Asp Ser Phe
            180                 185                 190

Ser Ser Ser Ser Val Gly Asp Asn Asn Ile Thr Ile Gly Lys Val Pro
        195                 200                 205

Arg Val Asn Asp Glu Val Arg Asp Ser Val Thr Gly Cys Lys Tyr Thr
    210                 215                 220

Asn Gly Met Glu Met Pro Pro Ile Lys Asn Ser Ala His Leu Val Arg
225                 230                 235                 240

Leu Val Glu Pro Arg Glu Ala Ser Leu Gly Glu Ile Asp Tyr Asp Asp
                245                 250                 255

Ile Met Glu Ile Ile Glu Val Asp Gln Ile Val Met Asp His Cys Pro
            260                 265                 270

Ser Arg Cys Pro Lys Gln Pro Ser Val Ser Lys Phe Val Asp Thr Phe
        275                 280                 285

Ala Ser Arg Arg Glu Glu Glu Gln Gly Leu Phe Pro Glu Leu Cys Ser
    290                 295                 300

Asn Cys Ser His Gly Ile Lys Leu Gly Leu Cys Pro Glu Ala Ser Thr
305                 310                 315                 320
```

-continued

His Val Glu Gln Met Lys Asp Thr Leu Leu Ala Ile Ser Asn Glu Phe
               325                 330                 335

Leu Asp Asn Thr Tyr Asp Leu Gly Pro Asp His Val Glu Gln Leu Arg
        340                 345                 350

Gln Lys Arg Leu Leu Lys Lys Gln Ile Gln Gln Leu Glu Ile Leu
    355                 360                 365

Ile Gln Asn Lys Glu Arg Lys Lys Ser Glu Cys Leu Val Ser Thr Pro
370                 375                 380

Ser His Asn Ile Gln Tyr Glu Thr Pro Gln Thr Asn His Val Val
385                 390                 395                 400

Val Tyr Thr Gln Thr Asp Ser Pro Asp Lys Ser Cys Gly Gly Leu Cys
                405                 410                 415

Pro Ala Thr Glu Gly Arg Tyr Val Thr Asp Asn Trp Asn Met Pro Arg
            420                 425                 430

Asp Tyr Leu Val Ser Lys Glu Arg Tyr Asp Ile Ser Ser Gly Ser Val
        435                 440                 445

Glu Arg Glu Gln Ser Val Ser Glu Val Ile Asp Val Thr Asp Thr Glu
    450                 455                 460

Ser Ser Asn Asp Lys Lys Trp Ala Ser Arg Asp Phe Pro Trp Thr Lys
465                 470                 475                 480

Asn Leu Glu Val Tyr Asn Lys Ile Val Phe Gly Asn His Ser Phe Arg
                485                 490                 495

Pro Asn Gln Arg Glu Ile Ile Asn Ala Thr Met Ser Gly Cys Asp Val
            500                 505                 510

Phe Val Leu Met Pro Thr Gly Gly Lys Ser Leu Thr Tyr Gln Leu
        515                 520                 525

Pro Ala Leu Leu Cys Ala Gly Ile Thr Leu Val Ile Ser Pro Leu Val
    530                 535                 540

Ser Leu Ile Gln Asp Gln Ile Met Asn Leu Leu Gln Thr Asn Ile Ser
545                 550                 555                 560

Ala Ala Ser Leu Ser Ala Gly Met Glu Trp Ala Glu Gln Leu Glu Ile
                565                 570                 575

Leu Gln Glu Leu Ser Ser Glu Asn Ser Lys Tyr Lys Leu Leu Tyr Val
            580                 585                 590

Thr Pro Glu Lys Val Ala Lys Ser Glu Ser Leu Ile Arg His Leu Glu
        595                 600                 605

Ile Leu Asn Ser Arg Ser Leu Leu Ala Arg Phe Val Ile Asp Glu Ala
    610                 615                 620

His Cys Val Ser Gln Trp Gly His Asp Phe Arg Pro Asp Tyr Gln Gly
625                 630                 635                 640

Leu Gly Val Leu Lys Gln Lys Phe Pro Asn Ile Pro Met Leu Ala Leu
                645                 650                 655

Thr Ala Thr Ala Thr Thr Ser Val Lys Glu Asp Val Val Gln Ala Leu
            660                 665                 670

Gly Leu Val Asn Cys Val Val Phe Arg Gln Ser Phe Asn Arg Pro Asn
        675                 680                 685

Leu Trp Tyr Ser Val Val Pro Lys Thr Asn Lys Cys Leu Glu Asp Ile
    690                 695                 700

Asp Lys Phe Ile Arg Glu Asn His Phe Asp Glu Cys Gly Ile Ile Tyr
705                 710                 715                 720

Cys Leu Ser Arg Met Asp Cys Glu Lys Val Thr Glu Met Leu Arg Ala
                725                 730                 735

Phe Gly His Lys Ala Ala Phe Tyr His Gly Ser Met Asp Pro Gly Lys

-continued

```
                740                 745                 750
Arg Ala Phe Val Gln Lys Gln Trp Ser Lys Asp Glu Ile Asn Ile Ile
            755                 760                 765
Cys Ala Thr Val Ala Phe Gly Met Gly Ile Asn Lys Pro Asp Val Arg
            770                 775                 780
Phe Val Ile His His Ser Leu Pro Lys Ser Ile Glu Gly Tyr His Gln
785                 790                 795                 800
Glu Cys Gly Arg Ala Gly Arg Asp Gly Gln Arg Ser Ser Cys Val Leu
                805                 810                 815
Tyr Tyr Ser Tyr Thr Asp Tyr Ile Arg Val Lys His Met Ile Ser Gln
                820                 825                 830
Gly Gly Leu Gly Gln Gly Gln Met Lys Met Gly Tyr Asn Cys Lys Ala
                835                 840                 845
Ser Ser Gly Arg Met Leu Glu Thr Asn Thr Glu Asn Leu Leu Arg Met
                850                 855                 860
Val Ser Tyr Cys Glu Asn Glu Val Asp Cys Arg Arg Phe Leu Gln Leu
865                 870                 875                 880
Val His Leu Gly Glu Lys Phe Asp Ser Thr Asn Cys Lys Lys Thr Cys
                885                 890                 895
Asp Asn Cys Ser Ser Lys Ile Leu Ile Asp Lys Asp Val Thr Val
                900                 905                 910
Ile Ala Arg Gln Leu Val Glu Leu Val Lys Leu Thr Gly Glu Arg Phe
                915                 920                 925
Ser Ser Ala His Ile Val Glu Ile Tyr Arg Gly Ser Leu Asn Gln Ser
                930                 935                 940
Val Lys Arg Asn Arg Gln Glu Thr Leu His Leu His Gly Ala Gly Lys
945                 950                 955                 960
His Leu Thr Lys Ser Glu Ala Ser Arg Ile Leu His Tyr Leu Val Thr
                965                 970                 975
Glu Asp Ile Leu Ala Glu Gly Val Arg Lys Ser Asp Leu Tyr Gly Ser
                980                 985                 990
Val Ser Ser Leu Leu Lys Val Asn  Arg Ser Lys Ala Ala  Ser Leu Leu
                995                 1000                1005
Ser Gly Gly Gln Ser Ile Thr Met Arg Phe Pro Ser  Thr Ile Lys
    1010                1015                1020
Ala Ser Lys Pro Ser Lys Ser Thr Ala Lys Val Pro  Leu Lys Gln
    1025                1030                1035
Thr Thr Leu Pro Met Ala Lys Ala Ala Pro Gln Asp  Ser Asn Leu
    1040                1045                1050
Pro His Ile Leu Leu Thr Ala Leu Lys Lys Leu Arg  Ser Asp Ile
    1055                1060                1065
Val Lys Glu Ser Ser Asp Gly Val Met Ala Tyr His  Ile Phe Gly
    1070                1075                1080
Lys Ala Thr Leu Glu Gln Ile Ser Lys Arg Leu Pro  Arg Thr Lys
    1085                1090                1095
Glu Glu Leu Leu Asp Ile Asn Gly Leu Gly Lys Ala  Lys Val Ser
    1100                1105                1110
Lys Tyr Gly Asp Arg Leu Leu Glu Thr Ile Tyr Ser  Thr Ile Asn
    1115                1120                1125
Asp His Tyr Lys Thr Gly Pro Gly Ser Gly Lys Arg  Arg Arg Asp
    1130                1135                1140
Glu Asn Ile Cys Pro Asn Val Ala Asp Asp Asp  Pro Asp Trp
    1145                1150                1155
```

Thr Ala Ser Gln Ser His Lys Lys Ala Val Lys Asn Lys Lys
    1160            1165            1170

<210> SEQ ID NO 5
<211> LENGTH: 1150
<212> TYPE: PRT
<213> ORGANISM: Arabidopsis thaliana

<400> SEQUENCE: 5

Met Val Val Thr Arg Gly Asp Lys Phe Ala Gly Ser Ser Leu Ala Cys
1               5                   10                  15

Lys Ser Met Ile Gly Ala Asn Lys Met Ser Gly Ser His Leu His Glu
            20                  25                  30

Val Asn Asn Ser Arg Ser His Phe Pro Gln Thr Asn Trp Leu Lys Val
        35                  40                  45

Ala Lys Ala Phe Glu Cys Ile Pro Ser Leu Asn Lys Phe Met Gly Ser
    50                  55                  60

Asn Phe Leu Tyr Ser Leu Glu Ser Gln Lys Leu Gly Arg Asp Arg Glu
65                  70                  75                  80

Met Ala Ala Arg Ser Ile Glu Asn Ile Ala Pro Val Thr Val Gln Thr
                85                  90                  95

Leu Ala Arg Pro Gln Ile Glu Lys Ala Trp Cys Thr Leu Ile Asn Leu
            100                 105                 110

Ser Ile Asn Asn Thr Tyr Leu Arg Pro Gly Ile Thr Pro Ala Ile Asp
            115                 120                 125

Asn Asp Ser Thr Ser Arg Thr Ser Ser Thr Lys Gly Ser Thr Phe Lys
130                 135                 140

Val Thr Ser Asn Ala Asp Gly Ser Phe Cys Ala His Asn His Pro Glu
145                 150                 155                 160

His Ser Gln Arg Ser Val Arg Gly Thr Ala Lys Ser Ile Asp Ser Phe
                165                 170                 175

Ser Ser Ser Ser Val Gly Asp Asn Lys Ile Ile Ile Asp Lys Val Pro
            180                 185                 190

Arg Val Asn Tyr Glu Val Arg Asp Ser Val Thr Val Thr Asn Gly Met
        195                 200                 205

Glu Met Pro Pro Ile Lys Asn Ser Ala Gln Leu Ala Arg Pro Val Glu
210                 215                 220

Pro Arg Glu Val Ser Leu Gly Glu Ile Asp Tyr Asp Ile Met Glu
225                 230                 235                 240

Ile Ile Asp Val Asp Gln Ile Ala Met Glu His Cys Pro Ser Thr Cys
                245                 250                 255

Thr Lys Gln Pro Ser Val Ser Lys Phe Val Asp Ile Phe Thr Ser Arg
            260                 265                 270

Arg Glu Glu Glu Gln Gly Leu Pro Pro Glu Ile Cys Ser Asn Cys Ser
        275                 280                 285

His Gly Ile Lys Leu Gly Leu Cys Pro Glu Ala Ser Thr His Val Glu
    290                 295                 300

Gln Met Lys Asp Thr Leu Leu Ala Ile Ser Asn Glu Ile Leu Asp Asn
305                 310                 315                 320

Thr Tyr Asp Leu Gly Pro Asp His Val Glu Leu His Gln Lys Arg
                325                 330                 335

Leu Leu Leu Lys Lys Gln Ile Gln Gln Leu Glu Ile Leu Ile His Asn
            340                 345                 350

Lys Glu Arg Lys Lys Ser Gln Cys Leu Val Ser Ile Pro Ser His Asn

-continued

```
            355                 360                 365
Thr Gln Tyr Glu Thr Pro Gln Thr Thr Asn Leu Glu Val Val Tyr Gly
370                 375                 380
Gln Thr Asp Ser Pro Thr His Val Lys Glu Gln Gly Arg Cys Val Thr
385                 390                 395                 400
Asp Asn Trp Asn Met Pro Arg Asp Tyr Leu Val Ser Lys Glu Arg Tyr
                    405                 410                 415
Asp Ile Ser Ser Gly Ser Glu Arg Glu Gln Ser Val Ser Glu Val
                420                 425                 430
Ile Asp Val Thr Asp Thr Glu Ser Ser Asn Asp Lys Lys Trp Thr Ser
            435                 440                 445
Ser Asp Phe Pro Trp Thr Lys Asn Leu Glu Val Tyr Asn Lys Leu Val
450                 455                 460
Phe Gly Asn His Ser Phe Arg Pro Asn Gln Arg Glu Ile Ile Asn Ala
465                 470                 475                 480
Thr Met Ser Gly Cys Asp Val Phe Val Leu Met Pro Thr Gly Gly Gly
                    485                 490                 495
Lys Ser Leu Thr Tyr Gln Leu Pro Ala Leu Leu Cys Ala Gly Ile Thr
                500                 505                 510
Leu Val Ile Ser Pro Leu Val Ser Leu Ile Gln Asp Gln Ile Met Asn
            515                 520                 525
Leu Leu Gln Thr Asn Ile Ser Ala Ala Ser Leu Ser Ala Gly Met Glu
530                 535                 540
Trp Ala Glu Gln Leu Glu Ile Leu Gln Glu Leu Ser Ser Glu Lys Ser
545                 550                 555                 560
Lys Tyr Lys Leu Leu Tyr Val Thr Pro Glu Lys Val Ala Lys Ser Glu
                    565                 570                 575
Ser Leu Leu Arg His Leu Glu Ile Leu Asn Ser Arg Ser Leu Leu Ala
                580                 585                 590
Arg Phe Val Ile Asp Glu Ala His Cys Val Ser Gln Trp Gly His Asp
            595                 600                 605
Phe Arg Pro Asp Tyr Gln Gly Leu Gly Val Leu Lys Gln Lys Phe Pro
610                 615                 620
Asn Ile Pro Met Leu Ala Leu Thr Ala Thr Ala Thr Ser Val Lys
625                 630                 635                 640
Glu Asp Val Val Gln Ala Leu Gly Leu Val Asn Cys Val Val Phe Arg
                    645                 650                 655
Gln Ser Phe Asn Arg Pro Asn Leu Trp Tyr Ser Val Val Pro Lys Thr
                660                 665                 670
Asn Lys Cys Leu Glu Asp Ile Asp Lys Phe Ile Arg Glu Asn His Phe
            675                 680                 685
Asp Glu Cys Gly Ile Ile Tyr Cys Leu Ser Arg Met Asp Cys Glu Lys
690                 695                 700
Val Thr Glu Ala Leu Arg Val Phe Gly His Lys Ala Ala Phe Tyr His
705                 710                 715                 720
Gly Ser Met Asp Pro Gly Lys Arg Ala Phe Val Gln Lys Gln Trp Ser
                    725                 730                 735
Lys Asp Glu Ile Asn Ile Ile Cys Ala Thr Val Ala Phe Gly Met Gly
                740                 745                 750
Ile Asn Lys Pro Asp Val Arg Phe Val Ile His His Ser Leu Pro Lys
            755                 760                 765
Ser Ile Glu Gly Tyr His Gln Glu Cys Gly Arg Ala Gly Arg Asp Gly
770                 775                 780
```

Gln Arg Ser Ser Cys Val Leu Tyr Tyr Ser Tyr Thr Asp Tyr Ile Arg
785                 790                 795                 800

Val Lys His Met Ile Ser Gln Gly Gly Leu Gly Gly Gln Met Lys
        805                 810                 815

Met Gly Tyr Asn Cys Lys Ala Ser Ser Gly Arg Met Leu Glu Thr Asn
            820                 825                 830

Thr Glu Asn Leu Leu Arg Met Val Ser Tyr Cys Glu Asn Glu Val Asp
        835                 840                 845

Cys Arg Arg Phe Leu Gln Leu Val His Leu Gly Glu Lys Phe Asp Ser
850                 855                 860

Thr Asn Cys Lys Asn Thr Cys Asp Asn Cys Ser Ser Lys Ile Leu
865                 870                 875                 880

Ile Asp Lys Asp Val Thr Val Ile Ala Arg Gln Leu Val Ala Leu Val
                885                 890                 895

Lys Leu Thr Gly Glu Arg Phe Ser Ser Ala His Ile Val Glu Ile Tyr
            900                 905                 910

Arg Gly Ser Leu Asn Gln Ser Val Lys Arg Asn Arg Gln Asp Thr Leu
        915                 920                 925

His Leu His Gly Ala Gly Lys His Leu Thr Lys Ser Glu Ala Ser Arg
    930                 935                 940

Ile Leu His Tyr Leu Val Thr Glu Asp Ile Leu Ala Glu Gly Val Lys
945                 950                 955                 960

Lys Ser Glu Leu Tyr Gly Ser Val Ser Leu Leu Lys Val Asn Arg
            965                 970                 975

Ser Lys Ala Ala Ser Leu Leu Ser Gly Gly Gln Ser Ile Thr Met Arg
        980                 985                 990

Phe Pro Ser Thr Ile Lys Val Ser  Lys Gln Ser Lys Ser  Thr Ala Asn
        995                 1000                1005

Pro Ala  Lys Val Pro Leu Lys  Gln Thr Thr Leu Pro  Met Ala Lys
    1010                1015                1020

Ala Ala  Pro Gln Asp Ser Asn  Leu Ser Gly Ile Leu  Leu Thr Ala
    1025                1030                1035

Leu Lys  Asn Leu Arg Thr Asp  Ile Val Lys Glu Ser  Pro Asp Leu
    1040                1045                1050

Val Met  Ala Tyr His Ile Phe  Gly Asn Ala Thr Leu  Lys Glu Ile
    1055                1060                1065

Ser Lys  Arg Leu Pro Arg Thr  Lys Glu Glu Leu Leu  Asp Ile Asn
    1070                1075                1080

Gly Leu  Gly Lys Ala Lys Val  Ser Lys Tyr Gly Asp  Arg Leu Leu
    1085                1090                1095

Glu Thr  Ile Asp Ser Thr Ile  Asn Asp His Tyr Lys  Thr Arg Pro
    1100                1105                1110

Gly Ser  Gly Lys Arg Arg Arg  Asp Glu Asn Val Asn  Pro Asn Val
    1115                1120                1125

Ala Glu  Asp Asp Asp Pro Asp  Trp Ser Ala Ser Gln  Ser His Lys
    1130                1135                1140

Lys Val  Val Lys Asn Lys Lys
    1145                1150

<210> SEQ ID NO 6
<211> LENGTH: 1222
<212> TYPE: PRT
<213> ORGANISM: Brachypodium distachyon

<400> SEQUENCE: 6

```
Met Gln Gly Ser Asn Lys Leu Asn Ala Gly Ser Ser Cys Asn Asp Lys
1               5                   10                  15

Leu Pro Arg Val Asn Trp Pro His His Ala Ser Ala Ile Gln Ser Ser
            20                  25                  30

Ser Ser Lys Asp Asp Phe Leu Ser Ser Phe Leu Phe Ser Leu Pro
        35                  40                  45

Thr Gln Arg Pro Asn Pro Glu Ala Asn Cys Asn Ser Met Ile Ser Leu
    50                  55                  60

Arg Ser Ala Ala Cys Lys Ile Gln Gly Pro Glu Arg Leu Gln Val Pro
65                  70                  75                  80

Trp Ile Glu Lys Val Trp Thr Leu Leu Trp Gln Ala Trp Arg Ser Val
                85                  90                  95

Cys Asn Thr Gln Val Ala Cys Lys Ser Tyr Leu Arg Pro Gly Leu Ser
            100                 105                 110

Ala Lys Val Glu Asp Cys Ala Lys Asp Tyr Thr His Thr Tyr Ala Thr
        115                 120                 125

Asn Ser Ser Tyr Asn Thr Asn Arg Gln Asp Asn Val Pro Arg Asn Met
    130                 135                 140

Ile Pro Ser Gln Glu Gly Ile His Gln Arg Thr Glu Ser Gly Ile Leu
145                 150                 155                 160

Glu Asn Asn Ser Ser His Gly Pro Thr Gly Ile Asn Ser Cys Thr Arg
                165                 170                 175

Thr Tyr Gln Ser Asn His Val Val Arg Ala Asp Asn Ile Gly Thr Thr
            180                 185                 190

Asn His Cys Gly Phe Ala Arg Thr Asp Ala Lys Ser Cys Gln Asn Val
        195                 200                 205

Pro Val Ala Asp Asn Met Cys Ala Asp Thr Leu Asp Ala Met Asp
    210                 215                 220

Asp Asp Glu Ile Met Ala Ser Ile Asp Val Asp Arg Ile Val Met Glu
225                 230                 235                 240

His Tyr Glu Ala Thr Asn Thr His Arg Gly Leu Ala Ser Trp Gln Met
                245                 250                 255

Ser Thr Pro Ser Gly Asn Lys Cys Asn Leu Thr Gly Leu Asp Glu Asn
            260                 265                 270

Ser Leu Pro Gln Glu Leu Ser Glu Ile Cys Ile His Gly Cys Lys Leu
        275                 280                 285

Ala Phe Cys Pro Glu Ala Lys Tyr His Val Gln Glu Met Lys Asp Gln
    290                 295                 300

Met Leu Ala Ile Cys Ser Glu Leu Ile Asp Gly Ser Gly Glu Leu Ser
305                 310                 315                 320

Pro Gln Asp Ser Glu Ala Leu Arg Lys Gln Arg Ala His Leu Lys Lys
                325                 330                 335

Gln Thr Lys Leu Leu Glu Asp Tyr Met Ala Arg Ser Thr Gln Asp Asp
            340                 345                 350

Glu Arg Gln Arg Ser His Ser Met Ala Thr Ala Ser Gln Gly His His
        355                 360                 365

Pro Pro Met Thr Pro Ser Thr Ser Val Met Asp Asn Asp Arg Phe Gln
    370                 375                 380

Ser Gln Ile Tyr Ser Arg Asn Glu Pro Val Asn Ser Gly Ser Cys Tyr
385                 390                 395                 400

Pro Pro Ala Pro His Pro Tyr Met Asp Ser Leu Asn Thr Pro Leu Thr
                405                 410                 415
```

```
Ser Val Gln Arg Asp Tyr Thr Arg Thr Asn Ile Asp Ile Asn Tyr Thr
            420             425             430

Glu Gly Ser Gly Asp Lys Lys Trp Ser Ser Lys Asp Phe Pro Trp Thr
            435             440             445

Lys Glu Leu Glu Ala His Asn Lys Arg Val Phe Gly Asn His Ser Phe
450             455             460

Arg Pro Asn Gln Arg Glu Ile Ile Asn Ala Thr Met Tyr Gly Ser Asp
465             470             475             480

Val Phe Val Leu Met Pro Thr Gly Gly Lys Ser Leu Thr Tyr Gln
                485             490             495

Leu Pro Ala Leu Ile Asp Glu Gly Ile Thr Leu Val Val Cys Pro Leu
            500             505             510

Val Ser Leu Ile Gln Asp Gln Ile Met His Leu Ala Gln Ala Asn Ile
        515             520             525

Pro Ala Ile Cys Leu Ser Ala Asn Val Glu Trp Thr Glu Gln Gln Arg
530             535             540

Ile Leu Arg Asp Leu Met Ser Pro Ser Ser Thr Cys Thr Tyr Lys Leu
545             550             555             560

Leu Tyr Val Thr Pro Glu Lys Ile Ala Lys Ser Asp Ala Leu Leu Arg
            565             570             575

Gln Leu Glu Ile Leu Tyr Ser Arg Gly His Leu Ser Arg Ile Val Ile
            580             585             590

Asp Glu Ala His Cys Val Ser Gln Trp Gly His Asp Phe Arg Pro Asp
            595             600             605

Tyr Gln His Leu Gly Leu Leu Lys Gln Lys Phe Pro Glu Thr Pro Val
            610             615             620

Leu Ala Leu Thr Ala Thr Ala Thr Ala Ser Val Lys Glu Asp Val Val
625             630             635             640

Gln Ala Leu Gly Leu Ala Asn Cys Val Val Phe Arg Gln Ser Phe Asn
            645             650             655

Arg Pro Asn Leu Arg Tyr Ile Val Met Pro Lys Thr Lys Lys Cys Leu
            660             665             670

Glu Asp Ile Asp Asn Phe Ile Arg Ala Ser His His Lys Glu Cys Gly
            675             680             685

Ile Ile Tyr Cys Leu Ser Arg Met Asp Cys Glu Lys Val Ala Ala Lys
            690             695             700

Leu Arg Glu Tyr Gly His Lys Ala Ser His Tyr His Gly Ser Met Asp
705             710             715             720

Pro Leu Asp Arg Thr Glu Ile Gln Arg Gln Trp Ser Arg Asp Lys Ile
            725             730             735

Asn Ile Ile Cys Ala Thr Val Ala Phe Gly Met Gly Ile Asn Lys Pro
            740             745             750

Asp Val Arg Phe Val Ile His His Ser Leu Pro Lys Ser Ile Glu Gly
            755             760             765

Tyr His Gln Glu Cys Gly Arg Ala Gly Arg Asp Gly Gln Arg Ser Ser
            770             775             780

Cys Val Leu Tyr Tyr Asn Tyr Ser Asp Tyr Ile Arg Val Lys His Met
785             790             795             800

Ile Thr Gln Gly Val Val Glu Gln Glu Thr Ser Met Pro Arg Gly Gly
            805             810             815

Ser Leu Ser Ser His Arg Gln Ala Leu Glu Thr His Lys Glu Asn Leu
            820             825             830
```

```
Leu Cys Met Val Ser Tyr Cys Glu Asn Asp Val Asp Cys Arg Arg Leu
        835                 840                 845

Leu Gln Leu Ile His Phe Gly Glu Thr Phe Asp Pro Ser Cys Cys Ala
    850                 855                 860

Lys Thr Cys Asp Asn Cys Met Lys Glu Met Arg Trp Ile Glu Lys Asp
865                 870                 875                 880

Val Thr Thr Ile Ala Arg Gln Leu Val Glu Leu Val Met Met Thr Arg
                885                 890                 895

Pro Ala Cys Ser Thr Ser His Ile Leu Glu Val Phe Arg Gly Ser Val
                900                 905                 910

Asn Gln Asn Val Lys Lys Asn Arg His Asp Thr Leu Ser Leu His Gly
            915                 920                 925

Gly Gly Lys Asn Leu Ala Lys Gly Glu Ala Ser Arg Val Leu Arg His
    930                 935                 940

Leu Val Thr Glu Gly Ile Leu Ile Glu Asp Val Lys Lys Ser Asp Thr
945                 950                 955                 960

Tyr Gly Leu Val Ser Ser Val Leu Lys Val Asn Gln Met Lys Val Gly
                965                 970                 975

Gly Leu Arg Ser Gly Asn His Thr Ile Val Leu Lys Phe Pro Thr Arg
            980                 985                 990

Glu Ala Pro Leu Met Gly Lys Leu Asp Glu Ser Ser Thr Pro Gln Ile
    995                 1000                    1005

Asn Lys Thr Ala Gln Arg Gln Ser Glu Val Asp Glu Asn Ile Ser
    1010                1015                    1020

Ser Leu Leu Phe Glu Thr Leu Lys Cys Leu Arg Ser Gln Ile Ala
    1025                1030                    1035

Glu Ser Thr Ala Gly Cys Gly Val His His Ile Phe Lys Asn Glu
    1040                1045                    1050

Thr Leu Lys Glu Ile Ser Ser Arg Val Pro Arg Thr Lys Glu Glu
    1055                1060                    1065

Leu Leu Glu Ile Asn Gly Ile Gly Lys Val Lys Leu Asn Lys Tyr
    1070                1075                    1080

Gly Asp Ser Val Leu Ala Thr Ile Glu Asp Phe Leu Ser His Phe
    1085                1090                    1095

Pro Asn Ala Ser Lys Arg Ser Ser Ser Gly Ser Asn Glu Gln
    1100                1105                    1110

Asn Glu Ala Pro Lys Lys Arg Gly Leu Ser Ala Thr Asn Ala
    1115                1120                    1125

Ser Gly Lys Cys Asp Gly Phe Glu Glu Arg Thr Val Gln Ser Lys
    1130                1135                    1140

Lys Cys Ala Ala Lys Thr Lys Asn Thr Lys Gln Gly Ile Ser Asp
    1145                1150                    1155

Ala Ala Ser Met Val Gln Asp Val Arg Tyr Ile Asp Leu Asp Leu
    1160                1165                    1170

Asp Gly Cys Glu Asp Val Asp Glu Leu Cys Ser Ser Ala Gln
    1175                1180                    1185

Gln Pro Val Ala Ser Ser Arg Val Leu Pro Lys Trp Pro Thr Ala
    1190                1195                    1200

Val Thr Lys Gly Asn Ser Pro Val Ala Asn Leu Phe Glu Glu Phe
    1205                1210                    1215

Lys Tyr Thr Lys
    1220
```

<210> SEQ ID NO 7
<211> LENGTH: 1162
<212> TYPE: PRT
<213> ORGANISM: Brassica rapa

<400> SEQUENCE: 7

```
Met Ser Leu Ser Glu Val Gln Lys Pro Lys Ala Pro Gln Thr Asn Trp
1               5                   10                  15

Ser Glu His Val Lys Val Leu Asp Gly Ser Pro Ser Ser Val Thr Lys
            20                  25                  30

His Leu Ser Ser Asn Phe Leu Tyr Ala Leu Glu Ser Gln Lys Pro Gly
        35                  40                  45

Arg Cys Arg Asp Met Ala Ala Arg Ser Ile Ala Phe Pro Ser Val Asn
    50                  55                  60

Val His Thr Leu Ala His Pro Gln Ile Ala Lys Ala Trp Arg Ala Leu
65                  70                  75                  80

Ser Ser Leu Ser Ile Asn Lys Thr Tyr Leu Arg Pro Gly Ile Thr Pro
                85                  90                  95

Pro Val Asp Asp Ser Gly Thr Asn Gly Ser Tyr Ser Ala Arg Glu Ser
            100                 105                 110

Ser Thr Val Lys Val Thr Ser Ser Thr Gly Gly Ser Phe Tyr Ser Asn
        115                 120                 125

Asn Gln Gln Asn Gln Ser Gln Met Gly Val Pro Gly Thr Gly Arg Tyr
    130                 135                 140

Ser His Ser Phe Pro Ser Ser Val Pro Gly Asp Asp Lys Arg Ala Ala
145                 150                 155                 160

Glu Lys Phe Ser Arg Val Asn Asp Glu Val Arg Glu Pro Glu Thr Ser
                165                 170                 175

Cys Ala His Ser Asn Gly Val Glu Lys Pro Phe Arg Lys Ser Ala Leu
            180                 185                 190

Ala Ala Glu Gln Leu Glu Ser Gly Ala Cys Leu Asp Glu Ile Asn
        195                 200                 205

Asp Asp Ile Leu Gln Asn Ile Asp Val Asp Gln Ile Leu Met Glu His
    210                 215                 220

Tyr Gln Ser Thr Ser Thr Pro Gln Pro Ser Val Ser Ser Phe Pro Leu
225                 230                 235                 240

Arg Thr Pro Pro Val Asp Arg Ser Ala Ser Ser Arg Glu Glu Glu Phe
                245                 250                 255

Cys Leu Pro Pro Glu Leu Cys Cys Asn Cys Ser His Gly Ile Lys Leu
            260                 265                 270

Gly Leu Cys Pro Glu Ala Ser Thr His Leu Glu Gln Met Lys Asn Thr
        275                 280                 285

Leu Ile Ala Ile Ser Asn Glu Leu Leu Asp Asp Thr Asp Leu Ser
    290                 295                 300

Pro Asp Arg Ile Gln Glu Leu Arg Gln Glu Arg Leu Gln Leu Lys Lys
305                 310                 315                 320

Gln Ile Gln Gln Leu Glu Asn His Ile Arg Asp Lys Glu Arg Glu Thr
                325                 330                 335

Ser Lys Phe Leu Ser Ser Thr Ala Thr Pro Phe Gln Tyr Glu Thr Pro
            340                 345                 350

Lys Ala Thr Asn Arg Asn Met Asp Asp Pro Gln Thr Asp Ser Arg Ala
        355                 360                 365

Glu Phe Ser Glu Gln Gly Gly Tyr Ala Ser Gly Ser Trp Asn Met Pro
    370                 375                 380
```

-continued

```
Arg Asp Ser Ser Phe Ser Val Asp Arg Tyr Gly Leu Ser Ala Pro
385                 390                 395                 400

Val Glu Arg Glu Gln Tyr Val Pro Arg Ile Ile Asp Val Lys Tyr Thr
            405                 410                 415

Glu Gly Ser Ser Asp Lys Lys Trp Ser Ser Arg Glu Phe Ser Trp Thr
                420                 425                 430

Lys Lys Leu Glu Val Ser Asn Lys Val Phe Gly Asn His Ser Phe
        435                 440                 445

Arg Pro Asn Gln Arg Glu Ile Ile Asn Ala Thr Met Ser Gly Ser Asp
    450                 455                 460

Val Phe Val Leu Met Pro Thr Gly Gly Lys Ser Leu Thr Tyr Gln
465                 470                 475                 480

Leu Pro Ala Leu Ile Cys Gln Gly Ile Thr Leu Val Ile Ser Pro Leu
                485                 490                 495

Val Ser Leu Ile Gln Asp Gln Ile Met Asn Leu Leu Gln Ala Asn Ile
                500                 505                 510

Pro Ala Ala Ser Leu Ser Ala Gly Met Glu Trp Ala Glu Gln Leu Lys
                515                 520                 525

Ile Phe Gln Glu Leu Ser Ser Glu His Ser Lys Tyr Lys Leu Leu Tyr
        530                 535                 540

Val Thr Pro Glu Lys Val Ala Gln Ser Asp Ser Leu Leu Arg His Leu
545                 550                 555                 560

Asp Ser Leu Asn Ser Arg Gly Leu Leu Ala Arg Phe Val Ile Asp Glu
                565                 570                 575

Ala His Cys Val Ser Gln Trp Gly His Asp Phe Arg Pro Asp Tyr Gln
                580                 585                 590

Ser Leu Gly Ile Leu Lys Gln Lys Phe Pro Asn Ile Pro Val Leu Ala
                595                 600                 605

Leu Thr Ala Thr Ala Thr Ala Ser Val Lys Glu Asp Val Val Gln Ala
    610                 615                 620

Leu Gly Leu Val Asn Cys Val Val Phe Arg Gln Ser Phe Asn Arg Pro
625                 630                 635                 640

Asn Leu Trp Tyr Ser Val Val Pro Lys Thr Lys Lys Cys Leu Glu Asp
                645                 650                 655

Ile Asp Lys Phe Ile Arg Glu Asn His Phe Asp Glu Cys Gly Ile Ile
                660                 665                 670

Tyr Cys Leu Ser Arg Met Asp Cys Glu Lys Val Ala Glu Lys Leu Lys
        675                 680                 685

Glu Phe Gly His Lys Ala Ala Phe Tyr His Gly Ser Ile Glu Pro Thr
    690                 695                 700

Gln Arg Ala Leu Val Gln Lys Gln Trp Ser Lys Asp Glu Ile Asn Ile
705                 710                 715                 720

Ile Cys Ala Thr Val Ala Phe Gly Met Gly Ile Asn Lys Pro Asp Val
            725                 730                 735

Arg Phe Val Ile His His Ser Leu Pro Lys Ser Ile Glu Gly Tyr His
                740                 745                 750

Gln Glu Cys Gly Arg Ala Gly Arg Asp Gly Gln Arg Ala Ser Cys Val
        755                 760                 765

Leu Tyr Tyr Gly Tyr Gly Asp Tyr Ile Arg Val Lys His Met Ile Ser
    770                 775                 780

Gln Gly Gly Val Asp Gln Ser Pro Met Ala Gly Gly Tyr Asn Arg Val
785                 790                 795                 800

Ala Ser Ser Ala Arg Leu Leu Glu Thr Asn Ser Glu Asn Leu His Arg
```

```
                805                 810                 815
Met Leu Arg Tyr Cys Glu Asn Glu Val Asp Cys Arg Arg Phe Leu Gln
            820                 825                 830

Leu Val His Phe Gly Glu Lys Phe Asp Ser Thr Asn Cys Lys Asn Thr
            835                 840                 845

Cys Asp Asn Cys Cys Ser Ser Gln Ser Leu Ile Asp Lys Asp Val Thr
        850                 855                 860

Leu Ile Thr Arg Gln Leu Val Glu Leu Val Lys Gln Thr Gly Glu Arg
865                 870                 875                 880

Phe Ser Ser Ser His Ile Leu Glu Val Tyr Arg Gly Ser Leu Asn Gln
                885                 890                 895

Met Val Lys Lys His Arg His Glu Thr Leu Gln Phe His Gly Ala Gly
            900                 905                 910

Lys Gln Leu Ser Lys Ile Glu Val Ser Arg Ile Leu His Tyr Leu Val
            915                 920                 925

Thr Glu Asp Ile Leu Val Glu Asp Val Arg Lys Ser Asp Met Tyr Gly
        930                 935                 940

Ser Val Ser Ser Leu Leu Lys Val Asn Asn Ala Lys Ala Ala Ser Leu
945                 950                 955                 960

Phe Ser Gly Ser Gln Thr Ile Met Met Arg Phe Pro Ser Ser Val Lys
                965                 970                 975

Val Leu Lys Thr Thr Lys Pro Ala Pro Thr Pro Ala Lys Ala Pro Val
            980                 985                 990

Thr Ser Ala Asp Thr Pro Pro Glu Asp Leu Asn Leu Ser Ala Ile Met
            995                1000                1005

Tyr Thr Ala Leu Arg Lys Leu Arg Thr Leu Leu Val Lys Glu Ala
    1010                1015                1020

Pro Asp Gly Val Met Ala Tyr His Ile Phe Gly Asn Ala Thr Leu
    1025                1030                1035

Gln Gln Ile Ser Lys Lys Ile Pro Arg Thr Lys Glu Glu Leu Leu
    1040                1045                1050

Glu Ile Asn Gly Leu Gly Lys Ala Lys Val Thr Lys Tyr Gly Asp
    1055                1060                1065

Arg Leu Leu Glu Thr Ile Glu Ser Thr Val Asn Glu Tyr Tyr Gly
    1070                1075                1080

Thr Ser Asn Lys Asp Ser Met Ile Ser Pro Asp Thr Gly Lys Arg
    1085                1090                1095

Arg Arg Asp Glu Asn Thr Ser Pro Asn Val Ala Asp Asp Asp
    1100                1105                1110

Asp Phe Ala Glu Met Ser Ile Gln Ser Cys Lys Lys Thr Ala Arg
    1115                1120                1125

Asn Lys Ser Asn Glu Ile Gly Met Val Val Glu Lys Leu Asp Phe
    1130                1135                1140

Asp Phe Glu Asp Glu Asp Gly Ser Glu Leu Arg Pro Glu Gly Arg
    1145                1150                1155

Val Leu Pro Trp
    1160

<210> SEQ ID NO 8
<211> LENGTH: 1159
<212> TYPE: PRT
<213> ORGANISM: Brassica rapa

<400> SEQUENCE: 8
```

-continued

```
Met Val Val Val Thr Arg Asp Asp Arg Leu Ala Gly Ala Leu Pro His
1               5                   10                  15

Val Gln Pro Met Ser Ala Ala Asn Lys Met Cys Gly Ser His Leu Pro
            20                  25                  30

Glu Ala Gln Lys Ser Arg Val His Leu Pro Gln Thr Asn Trp Leu Lys
        35                  40                  45

His Ala Asn Ala Phe Glu Cys Ile Pro Ser Ser Asn Asn Phe Leu Ser
    50                  55                  60

Ser Ser Met Leu Tyr Ser Leu Glu Ser Gln Lys Pro Ser Arg Ser Arg
65                  70                  75                  80

Glu Thr Ala Ser Arg Pro Ile Tyr Asn Ile Ile Pro Val Asp Val Gln
                85                  90                  95

Thr Leu Ala His Gln His Ile Ser Lys Ala Trp Cys Ala Leu Ala Asn
            100                 105                 110

Leu Ser Ile Asn Asn Thr Tyr Leu Arg Pro Gly Ile Thr Pro Ala Ile
        115                 120                 125

Asp Asp Ile Asn Thr Asn Cys Ser Phe Ser Thr Arg Gly Arg Ser Thr
    130                 135                 140

Ala Lys Val Thr Ser Asn Thr Asp Gly Ser Phe Phe Ala His Asn His
145                 150                 155                 160

Gln Glu Asp Ser Gln Lys Arg Ile Arg Gly Thr Ala Thr Ser Phe Asp
                165                 170                 175

Arg Phe Ser Ser Ser Pro Gly Asp Gly Lys Leu Ile Ser Gly Lys
            180                 185                 190

Val Pro Arg Val Tyr Asn Glu Val Arg Asp Ser Val Thr Gly Cys Ile
        195                 200                 205

Asn Gly Met Glu Val Pro Pro Ile Arg Asn Leu Ala His Pro Ala Arg
    210                 215                 220

Gln Val Glu Val Ile Glu Ile Asp Asp Asp Ile Leu Lys Ser Ile
225                 230                 235                 240

Asp Val Glu Lys Ile Val Met Glu His Tyr His Ser Thr Cys Thr His
                245                 250                 255

Gln Pro Ser Val Asn Ile Phe Ala Ser Arg Gly Glu Glu Asn Pro Cys
            260                 265                 270

Leu Pro Pro Glu Leu Cys Ser Asn Tyr Ser His Gly Val Lys Leu Gly
        275                 280                 285

Leu Cys Leu Gln Ala Pro Ser His Val Glu Gln Met Lys Asp Ala Leu
    290                 295                 300

Leu Ala Val Ser Asn Glu Leu Leu Asp Asp Ser Thr Asp Leu Ser Pro
305                 310                 315                 320

Gly His Phe Glu Gln Leu Cys Gln Glu Arg Leu Leu Leu Lys Lys Gln
                325                 330                 335

Ile Gln Gln Leu Glu Ile Leu Ile Gln Asp Lys Glu Lys Lys Ser Ser
            340                 345                 350

Gly Cys Leu Ala Ser Arg Pro Thr Arg Asn Ile Gln Tyr Glu Thr Pro
        355                 360                 365

Gln Thr Thr Asn Arg Lys Ala Asp Tyr Ala His Ala Asp Ser Arg Val
    370                 375                 380

His Val Thr Glu Gln Gly Arg Tyr Val Ser Asp Asn Trp Asn Met Pro
385                 390                 395                 400

Arg Asp Tyr Leu Cys Ser Glu Asp Arg Ser Gly Leu Ser Ser Gly Pro
                405                 410                 415

Ile Glu Arg Glu Arg Cys Val Pro Glu Ile Ile Asp Val Thr Tyr Thr
```

```
                420             425             430
Asp Gly Ser Asn Asp Lys Lys Trp Ser Ser Arg Asp Phe Pro Trp Thr
            435             440             445

Lys Asn Leu Glu Val Asn Asn Lys Arg Val Phe Gly Asn His Ser Phe
450             455             460

Arg Pro Asn Gln Arg Glu Ile Ile Asn Ala Thr Met Ser Gly Cys Asp
465             470             475             480

Val Phe Val Leu Met Pro Thr Gly Gly Lys Ser Leu Thr Tyr Gln
                485             490             495

Leu Pro Ala Leu Ile Cys Ala Gly Ile Thr Leu Val Ile Ser Pro Leu
                500             505             510

Val Ser Leu Ile Gln Asp Gln Ile Met Asn Leu Leu Gln Ala Asn Ile
            515             520             525

His Ala Ala Ser Leu Ser Ala Gly Met Asp Trp Thr Gln Gln Leu Asp
            530             535             540

Ile Leu Arg Glu Leu Ser Ser Glu Asn Ser Lys Tyr Arg Leu Leu Tyr
545             550             555             560

Val Thr Pro Glu Lys Val Ala Lys Ser Asp Ser Leu Leu Arg His Leu
                565             570             575

Glu Ser Leu Asn Ser His Ser Leu Leu Ala Arg Phe Val Ile Asp Glu
            580             585             590

Ala His Cys Val Ser Gln Trp Gly His Asp Phe Arg Pro Asp Tyr Gln
            595             600             605

Gly Leu Gly Ile Leu Lys Lys Lys Phe Pro Lys Ile Pro Met Leu Ala
            610             615             620

Leu Thr Ala Thr Ala Thr Ala Ser Val Lys Glu Asp Val Val Gln Ala
625             630             635             640

Leu Gly Leu Val Asn Thr Val Val Phe Arg Gln Ser Phe Asn Arg Pro
                645             650             655

Asn Leu Trp Tyr Ser Val Val Pro Lys Thr Asn Lys Cys Leu Glu Asp
            660             665             670

Ile Asp Gln Phe Ile Lys Lys Asn His Phe Asp Glu Cys Gly Ile Ile
            675             680             685

Tyr Cys Leu Ser Lys Met Asp Cys Glu Lys Val Thr Glu Thr Leu Arg
            690             695             700

Lys Phe Gly His Lys Ala Ala Phe Tyr His Gly Ser Met Asp Pro Gly
705             710             715             720

Lys Arg Ala Phe Val Gln Lys Lys Trp Ser Lys Asp Glu Ile Asn Ile
                725             730             735

Ile Cys Ala Thr Val Ala Phe Gly Met Gly Ile Asn Lys Pro Asp Val
            740             745             750

Arg Phe Val Ile His His Ser Leu Pro Lys Ser Ile Glu Gly Tyr Tyr
            755             760             765

Gln Glu Cys Gly Arg Ala Gly Arg Asp Gly Gln Arg Ser Ser Cys Val
            770             775             780

Leu Tyr Tyr Cys Tyr Ser Asp Tyr Ile Arg Val Lys His Met Ile Ser
785             790             795             800

Gln Gly Gly Pro Gly Gln Ser Thr Met Thr Thr Gly Tyr Asn Arg Ile
                805             810             815

Ala Ser Ser Gly Arg Thr Leu Glu Ser Asn Thr Asp Asn Leu Leu Arg
            820             825             830

Met Val Ser Tyr Cys Glu Asn Glu Val Asp Cys Arg Arg Phe Leu Gln
            835             840             845
```

Leu Val His Leu Gly Glu Asn Phe Asp Ser Thr Asn Cys Lys Asn Thr
    850                 855                 860

Cys Asp Asn Cys Ser Ser Ser Lys Thr Leu Ile Glu Lys Asp Val Thr
865                 870                 875                 880

Leu Ile Gly Arg Gln Leu Val Glu Leu Val Lys Leu Thr Gly Glu Arg
                885                 890                 895

Phe Ser Ser Ala His Ile Val Glu Leu Tyr Arg Gly Ser Leu Asn Gln
                900                 905                 910

Thr Val Lys Lys His Arg His Glu Thr Leu His Leu His Gly Ala Gly
            915                 920                 925

Lys His Leu Ser Lys Ser Glu Ala Ser Arg Ile Leu His Tyr Leu Val
        930                 935                 940

Thr Lys Asp Ile Leu Thr Glu Tyr Val Lys Lys Ser Asp Leu Tyr Gly
945                 950                 955                 960

Ser Val Ser Ser Leu Leu Lys Val Asn Arg Ser Lys Ala Ala Ser Ile
                965                 970                 975

Leu Ser Gly Gly Gln Thr Ile Glu Met Arg Phe Pro Ser Ala Val Lys
            980                 985                 990

Ala Val Lys Pro Ser Lys Gln Gly Pro Thr Pro Ala Arg Val Ala Leu
        995                 1000                1005

Lys Gln Thr Thr Leu Pro Met Ala Pro Ala Pro Gln Asp Ser
    1010                1015                1020

Ile Leu Ser Asp Thr Leu Val Lys Ala Leu Lys Asn Leu Arg Ala
    1025                1030                1035

Asp Ile Val Lys Glu Ser Ser Asp Ala Val Met Ser Tyr His Ile
    1040                1045                1050

Phe Gly Asn Pro Thr Leu Gln Ile Ser Lys Arg Leu Pro Arg
    1055                1060                1065

Thr Lys Glu Glu Leu Leu Asp Ile His Gly Leu Gly Lys Ala Lys
    1070                1075                1080

Val Ser Lys Tyr Gly Asp Arg Leu Leu Glu Thr Ile Glu Ser Thr
    1085                1090                1095

Ile Asn Asn His Tyr Gly Thr Asn Lys Asn Glu Gly Thr Gly Ser
    1100                1105                1110

Gly Lys Arg Arg Arg Asp Glu Asn Thr Asn Pro Ile Val Val Asp
    1115                1120                1125

Asn Asp Asp Asp Pro Asp Trp Thr Pro Ser Gln Gln Ser Tyr
    1130                1135                1140

Lys Lys Ala Tyr Ala Val Arg Gly Gln Thr Ser Glu Glu Ala Ile
    1145                1150                1155

Cys

<210> SEQ ID NO 9
<211> LENGTH: 1196
<212> TYPE: PRT
<213> ORGANISM: Brassica rapa

<400> SEQUENCE: 9

Met Ile Asn Ser Asp Gln Val Ser Arg Ser His Leu Pro Glu Val Gln
1               5                   10                  15

Lys Pro Lys Ala Pro Gln Thr Asn Trp Ser Glu His Ala Asn Ala Phe
            20                  25                  30

Glu Asp Pro Ser Ser Arg Thr Lys His Leu Ser Ser Gly Phe Leu Tyr
        35                  40                  45

```
Ala Leu Glu Ser Gln Lys Pro Arg Lys Ser Ser Asp Met Ala Ala Arg
 50                  55                  60

Ser Ile Ala Phe Pro Ser Val Asn Ala His Thr Leu Ala Pro Pro Gln
 65                  70                  75                  80

Ile Ala Lys Ala Trp Arg Ala Leu Ser Ser Leu Ser Leu Asn Lys Thr
                     85                  90                  95

Tyr Leu Arg Pro Gly Ile Thr Pro Pro Val Asp Asp Gly Gly Thr Asn
                100                 105                 110

Gly Ser Tyr Ser Ala Arg Glu Arg Ser Thr Val Lys Val Thr Cys Ser
            115                 120                 125

Thr Asp Gly Ser Phe Tyr Ser Asn Asn Gln Asn Gln Ser Gln Met
130                 135                 140

Gly Val Pro Gly Thr Gly Arg Ser Phe His Ser Phe Pro Pro Val
145                 150                 155                 160

Pro Gly Asp Gly Lys Asn Phe Ala Glu Lys Phe Arg Arg Ile Asn Asp
                165                 170                 175

Glu Thr Arg Glu Pro Glu Thr Ser Ser Ala His Leu Asn Gly Val Glu
                180                 185                 190

Lys Pro Phe Lys Asn Ser Thr Phe Ala Ala Glu Gln Leu Gly Ser Gly
            195                 200                 205

Glu Ala Cys Leu Asp Glu Ile Asp Asp Ile Leu Gln Asn Ile Asp
210                 215                 220

Val Asp Gln Ile Met Met Glu His Tyr Gln Ser Thr Ser Thr Pro Pro
225                 230                 235                 240

Ser Ser Val Ser Ser Leu Pro Ser Arg Thr Pro Val Asp Arg Ser
                245                 250                 255

Ala Ser Arg Arg Glu Glu Glu Cys Ser Leu Pro Pro Glu Leu Cys Ser
            260                 265                 270

Asn Cys Ser His Gly Ile Lys Leu Gly Leu Cys Pro Glu Ala Ser Thr
            275                 280                 285

His Leu Glu Gln Met Lys Asn Met Leu Ile Ala Ile Ser Asn Glu Leu
290                 295                 300

Leu Asp Asp Asp Thr Asp Leu Ser Pro Asp Arg Ile Gln Glu Leu Arg
305                 310                 315                 320

Gln Glu Arg Leu Leu Leu Lys Lys Gln Ile Gln Gln Leu Glu Asp His
                325                 330                 335

Ile Arg Asp Lys Glu Lys Gln Lys Ser Gln Phe Leu Ser Ser Thr Ala
            340                 345                 350

Thr Arg Ala Ser Gln Tyr Glu Thr Pro Lys Ser Thr Asn Leu Arg Phe
            355                 360                 365

Asp His Pro Gln Thr Asp Ser Arg Ala His Phe Asn Glu Gln Gly Arg
370                 375                 380

Tyr Ala Ser Asp Ser Trp Asn Met Pro Lys Asp Ser Ser Phe Ser Val
385                 390                 395                 400

Asp Arg Tyr Gly Leu Ser Ser Ala Pro Val Glu Arg Glu Gln Tyr Val
                405                 410                 415

Pro Arg Ile Ile Glu Val Thr Tyr Thr Glu Gly Ser Asn Asp Gln Lys
                420                 425                 430

Trp Ser Ser Arg Asp Phe Pro Trp Thr Arg Lys Leu Glu Val Ser Asn
            435                 440                 445

Lys Lys Val Phe Gly Asn His Ser Phe Arg Pro Asn Gln Arg Glu Ile
450                 455                 460
```

-continued

| | | | | | | | | | | | | | | | |
|---|---|---|---|---|---|---|---|---|---|---|---|---|---|---|---|
|Ile|Asn|Ala|Thr|Met|Ser|Gly|Ser|Asp|Val|Phe|Val|Leu|Met|Pro|Thr|
|465| | | | |470| | | | |475| | | | |480|

Gly Gly Gly Lys Ser Leu Thr Tyr Gln Leu Pro Ala Leu Ile Cys Gln
                  485                  490                  495

Gly Ile Thr Leu Val Ile Ser Pro Leu Val Ser Leu Ile Gln Asp Gln
500 505 510

Ile Met Asn Leu Leu Gln Ala Asn Ile Pro Ala Thr Ser Leu Ser Ala
515 520 525

Gly Met Glu Trp Ser Glu Gln Leu Lys Ile Phe Gln Glu Leu Ser Ser
530 535 540

Glu His Ser Lys Tyr Lys Leu Leu Tyr Val Thr Pro Glu Lys Val Ala
545 550 555 560

Gln Ser Asp Ser Leu Leu Arg His Leu Asp Asn Leu Asn Ser Arg Gly
565 570 575

Leu Leu Ala Arg Phe Val Ile Asp Glu Ala His Cys Val Ser Gln Trp
580 585 590

Gly His Asp Phe Arg Pro Asp Tyr Gln Ser Leu Gly Ile Leu Lys Gln
595 600 605

Lys Phe Pro Asn Ile Pro Val Leu Ala Leu Thr Ala Thr Ala Thr Ala
610 615 620

Ser Val Lys Glu Asp Val Val Gln Ala Leu Gly Leu Val Asn Cys Val
625 630 635 640

Val Phe Arg Gln Ser Phe Asn Arg Pro Asn Leu Leu Tyr Ser Val Val
645 650 655

Pro Lys Thr Lys Lys Cys Leu Glu Asp Ile Asp Lys Phe Ile Lys Glu
660 665 670

Asn His Phe Asp Glu Cys Gly Ile Ile Tyr Cys Leu Ser Arg Asn Asp
675 680 685

Cys Glu Lys Val Ala Gln Lys Leu Gln Glu Phe Gly His Lys Ala Ala
690 695 700

Phe Tyr His Gly Ser Ile Glu Pro Thr Gln Arg Ala Leu Val Gln Lys
705 710 715 720

Gln Trp Ser Lys Asp Glu Val Asn Ile Ile Cys Ala Thr Val Ala Phe
725 730 735

Gly Met Gly Ile Asn Lys Pro Asp Val Arg Phe Val Ile His His Ser
740 745 750

Leu Pro Lys Ser Ile Glu Gly Tyr His Gln Glu Cys Gly Arg Ala Gly
755 760 765

Arg Asp Gly Gln Arg Ala Ser Cys Val Leu Tyr Tyr Gly Tyr Gly Asp
770 775 780

Tyr Ile Arg Val Lys His Met Ile Ser Gln Val Gly Val Glu Gln Ser
785 790 795 800

Pro Met Ala Asn Gly Tyr Asn Arg Val Ala Ser Ser Gly Arg Leu Leu
805 810 815

Glu Thr Asn Thr Glu Asn Leu Leu Arg Met Val Arg Tyr Cys Glu Asn
820 825 830

Glu Val Asp Cys Arg Arg Phe Leu Gln Leu Val His Phe Gly Glu Lys
835 840 845

Phe Asp Ser Thr Asn Cys Lys Arg Thr Cys Asp Asn Cys Ser Ser Ser
850 855 860

Gln Ser Leu Ile Asp Lys Asp Val Thr Leu Ile Thr Arg Gln Leu Val
865 870 875 880

Glu Leu Val Lys Gln Thr Gly Glu Arg Phe Ser Ser Ser His Ile Leu 885                 890                 895
Glu Val Tyr Arg Gly Ser Leu Asn Gln Met Val Lys Lys His Arg His
                900                 905                 910
Glu Thr Leu Gln Phe His Gly Ala Gly Lys His Leu Thr Lys Leu Glu
            915                 920                 925
Val Ser Arg Ile Leu His Tyr Leu Val Thr Glu Asp Ile Leu Val Glu
        930                 935                 940
Asp Val Arg Lys Ser Asp Met Tyr Gly Val Ser Ser Leu Leu Lys
945                 950                 955                 960
Val Asn Lys Ser Lys Ala Ala Ser Leu Phe Ser Gly Ser Gln Thr Ile
                965                 970                 975
Met Met Arg Phe Asp Phe Val Leu Glu Ile Tyr Leu Ser Ser Lys Arg
            980                 985                 990
Phe Pro Ser Ser Val Lys Val Leu Lys Pro Cys Lys Ala Ala Pro Thr
        995                 1000                1005
Pro Ala Lys Ala Pro Leu Val Ser Ala Asp Ala Pro Pro Glu Asp
    1010                1015                1020
Val Asn Leu Ser Ala Ile Met Tyr Thr Ala Leu Arg Lys Leu Arg
    1025                1030                1035
Thr Leu Leu Val Lys Glu Ala Pro Asp Gly Val Met Ala Tyr His
    1040                1045                1050
Ile Phe Gly Asn Ala Thr Leu Gln Gln Met Ser Lys Lys Ile Pro
    1055                1060                1065
Arg Thr Lys Glu Glu Leu Leu Glu Ile Asn Gly Leu Gly Lys Ala
    1070                1075                1080
Lys Val Leu Lys Tyr Gly Glu Arg Leu Leu Glu Thr Ile Glu Ser
    1085                1090                1095
Thr Val Asn Glu Tyr Tyr Gly Thr Ser Lys Lys Glu Glu Ser Met
    1100                1105                1110
Ile Ser Pro Asp Ser Gly Lys Arg Arg Arg Asp Glu Asn Ile Ser
    1115                1120                1125
Pro Asn Val Thr Glu Glu Asp Asp Asp Phe Ala Glu Ser Ser Ser
    1130                1135                1140
Gln Ser Cys Lys Lys Thr Val Arg Ser Lys Ser Ser Glu Val Leu
    1145                1150                1155
His Gly Glu Cys Val Ala Gly Asp Gly Val Gly Met Val Met Glu
    1160                1165                1170
Lys Leu Asp Phe Asp Phe Glu Asp Glu Asp Gly Ser Glu Ile Arg
    1175                1180                1185
Pro Glu Gly Arg Val Leu Pro Trp
    1190                1195

<210> SEQ ID NO 10
<211> LENGTH: 963
<212> TYPE: PRT
<213> ORGANISM: Carica papaya

<400> SEQUENCE: 10

Met Thr Asn Phe Leu Lys Val Leu Ser Ser Asn Phe Leu Phe Ser Leu
1               5                   10                  15
Glu Lys Gln Lys Pro Ser Thr Glu Gly Arg Thr Gly Ala Arg Ser Val
            20                  25                  30
Ala Cys Gln Ile Lys Asn Leu Gln Arg Leu Arg Ser Pro Gln Ser Glu
        35                  40                  45

-continued

Lys Ala Trp Gln Ile Leu Ser Asn Pro Pro Thr Gly Arg Thr Tyr Ile
50              55                  60

Lys Pro Gly Leu Thr Ala Ser Leu Lys His Asp Ile Asp Asn Ser Leu
65              70                  75                  80

Asp Gly Ile Arg Lys Thr Ser Leu Gln Thr Thr Tyr Gly Ser Ser Lys
                85                  90                  95

Asn Ser Lys Tyr Thr His Thr Arg Arg Asn Cys Ser Gln Ile Asn Ala
                100                 105                 110

Lys Thr Thr Glu Thr Ala Lys Tyr Met Asp Ser Cys Pro Pro Asp Ile
                115                 120                 125

Val Asp Thr Thr Glu Thr Arg Thr Gly Leu Arg Val His Asn Lys Val
130                 135                 140

Asp Ala Leu Val Ser Asn Gly Thr His Ser Asn Ala Leu Asp Gly Ser
145                 150                 155                 160

Tyr Gly Asp Arg Pro Met His Ala Gly Gln Thr Lys Glu Arg Pro Glu
                165                 170                 175

Val Ser Ala Asp Gly Met Asp Asp Asp Ile Leu Lys Asn Ile Asp
                180                 185                 190

Val Asp Gln Ile Val Met Glu His Tyr Gln Ser Thr Cys Thr Pro Gln
                195                 200                 205

Pro Ser Ile Ser Met Phe Pro Pro Arg Met Pro Asn Val Glu Arg Asn
210                 215                 220

Ser Ser Ala Arg Glu Glu Ser Cys Leu Pro Glu Leu Cys Ser
225                 230                 235                 240

Lys Cys Ile His Gly Phe Lys Val Gly Val Cys Pro Glu Ala Cys Thr
                245                 250                 255

His Val Gln Glu Ile Lys Asp Gln Leu Ile Ala Ile Ser Asn Glu Leu
                260                 265                 270

Leu Asp Asn Ala Ala Glu Leu Thr Lys Glu Gln Leu Glu Glu Leu Arg
                275                 280                 285

Gln Asp Arg Leu Arg Leu Asn Lys Gln Leu Gln Leu Glu Thr Tyr
290                 295                 300

Leu Cys Asp Met Glu Arg Lys Arg Ser His Phe Ser Thr Ser Ala Thr
305                 310                 315                 320

Thr His Ser Ser Gln Tyr Asp Thr Pro Gln Ala Arg Ile Phe Arg Met
                325                 330                 335

Asp His Leu Gly Ser Gly Asp Gln Phe His Leu Asn Glu Ser His Ile
                340                 345                 350

His Met Lys Trp Asn Pro Tyr Ser Glu Ser Ile Ser Ser Glu Gly Arg
                355                 360                 365

Val Ala Ile Ser Ser Gly Asn Val Glu Arg Glu Leu Tyr Ile Pro Lys
370                 375                 380

Val Ile Glu Val Asn Tyr Ile Glu Gly Ser Asn Asp His Lys Trp Ser
385                 390                 395                 400

Ser Arg Asp Phe Leu Trp Thr Lys Lys Leu Glu Ile Asn Asn Lys Lys
                405                 410                 415

Val Phe Gly Asn His Ser Phe Arg Pro Asn Gln Arg Glu Val Ile Asn
                420                 425                 430

Ala Thr Met Ser Gly Tyr Asp Val Phe Val Leu Met Pro Thr Gly Gly
                435                 440                 445

Gly Lys Ser Leu Thr Tyr Gln Leu Pro Ala Leu Ile Cys Pro Gly Ile
450                 455                 460

Thr Leu Val Ile Ser Pro Leu Val Ser Leu Ile Gln Asp Gln Ile Met

```
               465                 470                 475                 480
        Ser Leu Leu Gln Ala Asn Ile Pro Ala Thr Tyr Leu Ser Ala Asn Met
                        485                 490                 495

Glu Trp Ala Glu Gln Leu Glu Ile Leu Lys Glu Leu Ser Ser Asp Tyr
                        500                 505                 510

Cys Lys Phe Lys Leu Leu Tyr Val Thr Pro Glu Lys Val Ala Lys Ser
                        515                 520                 525

Asp Val Leu Leu Arg His Leu Glu Gly Leu Asn Ala Arg Gly Phe Leu
                        530                 535                 540

Ser Arg Ile Val Ile Asp Glu Ala His Cys Val Ser Gln Trp Gly His
        545                 550                 555                 560

Asp Phe Arg Pro Asp Tyr Gln Gly Leu Gly Ile Leu Lys Gln Lys Phe
                        565                 570                 575

Ser Asn Thr Pro Val Leu Ala Leu Thr Ala Thr Ala Thr Ala Ser Val
                        580                 585                 590

Lys Glu Asp Val Val Gln Ala Leu Gly Leu Val Asn Cys Ile Val Phe
                        595                 600                 605

Arg Gln Ser Phe Asn Arg Pro Asn Leu Trp Tyr Ala Val Pro Lys
                        610                 615                 620

Thr Lys Lys Cys Leu Glu Glu Ile Asn Lys Phe Val Lys Glu Asn His
        625                 630                 635                 640

Phe Asp Glu Cys Gly Ile Ile Tyr Cys Leu Ser Arg Met Asp Cys Glu
                        645                 650                 655

Lys Val Ala Glu Lys Met Gln Glu Tyr Gly His Lys Ala Ala Phe Tyr
                        660                 665                 670

His Gly Ser Met Asp Pro Ala Gln Arg Ser Phe Val Gln Glu Gln Trp
                        675                 680                 685

Ser Lys Tyr Glu Ile Asn Ile Ile Cys Ala Thr Val Ala Phe Gly Met
                        690                 695                 700

Gly Ile Asn Lys Pro Asp Val Arg Phe Val Ile His His Ser Leu Pro
        705                 710                 715                 720

Lys Ser Ile Glu Gly Tyr His Gln Glu Cys Gly Arg Ala Gly Arg Asp
                        725                 730                 735

Gly Gln Arg Ser Ser Cys Val Leu Tyr Tyr Ser Tyr Ser Asp Tyr Ile
                        740                 745                 750

Arg Val Lys His Met Ile Ser Gln Gly Val Ala Glu Gln Gly Thr Leu
                        755                 760                 765

Thr Pro Gly Tyr Asn Arg Met Ala Asn Ser Gly Arg Ile Leu Glu Thr
        770                 775                 780

Asn Thr Glu Asn Leu Leu Arg Met Val Ser Tyr Cys Glu Asn Asp Val
        785                 790                 795                 800

Asp Cys Arg Arg Phe Leu Gln Leu Gly His Leu Gly Glu Lys Phe Asp
                        805                 810                 815

His Ala Asn Cys Lys Arg Thr Cys Asp Asn Cys Ser Lys Asn Lys Ser
                        820                 825                 830

Leu Ile Glu Lys Asp Val Thr Lys Thr Ala Lys Gln Leu Val Glu Leu
                        835                 840                 845

Val Lys Leu Thr Gly Gln Gln Phe Ser Ser His Ile Leu Glu Val
                        850                 855                 860

Tyr Arg Gly Ser Leu Ser Lys Tyr Val Lys Lys His Arg His Glu Thr
        865                 870                 875                 880

Leu Ser Leu His Gly Ala Gly Lys Leu Leu Thr Lys Glu Glu Ala Ser
                        885                 890                 895
```

```
Arg Val Leu Arg His Leu Val Thr Asn Asp Ile Leu Val Glu Asp Val
            900                 905                 910

Lys Lys Ser Asp Ile Tyr Gly Ser Leu Ser Ser Val Leu Lys Val Asn
            915                 920                 925

Glu Ser Lys Ala Tyr Asn Leu Phe Ser Asp Gly Gln Thr Ile Thr Leu
            930                 935                 940

Arg Leu Asn Phe Met Leu Lys Leu Leu Leu Ser Asn Leu Ile Met Asn
945                 950                 955                 960

Val Gln His

<210> SEQ ID NO 11
<211> LENGTH: 1170
<212> TYPE: PRT
<213> ORGANISM: Thellungiella halophila

<400> SEQUENCE: 11

Met Ile Asn Ser Asn Gln Ile Arg Ser His Leu Pro Glu Val Gln Lys
1               5                   10                  15

Pro Lys Gly Pro Gln Thr Asn Trp Ser Glu His Ala Lys Ala Leu Glu
            20                  25                  30

Ser Thr Ser Phe Leu Ser Ser Asn Phe Leu Tyr Asp Leu Glu Ser Gln
        35                  40                  45

Lys Pro Arg Arg Asp Arg Asp Met Ala Ala Arg Ala Ile Ala Phe Pro
    50                  55                  60

Asn Val Asn Val His Thr Leu Ala His Pro Gln Ile Ala Lys Ala Trp
65                  70                  75                  80

Arg Ala Leu Ser Ser Leu Ser Val Asn Asn Ser Tyr Leu Arg Pro Gly
                85                  90                  95

Ile Thr Pro Pro Val Asp Asp Gly Ala Thr Asn Gly Ser Tyr Ser Ala
            100                 105                 110

Lys Glu Arg Ser Thr Val Lys Val Thr Cys Ser Thr Asp Gly Ser Phe
        115                 120                 125

Tyr Pro Asn Ser Arg Gln Asn Gln Ser His Met Ser Val Ser Gly Thr
    130                 135                 140

Gly Arg His Phe His Ser Ser Ser Ala Pro Gly Glu Glu Lys Phe Val
145                 150                 155                 160

Ala Glu Lys Phe Ala Arg Val Asn Gly Glu Val Arg Glu Ser Glu Thr
                165                 170                 175

Ser Ser Thr His Leu Asn Gly Leu Glu Asn Pro Phe Arg Asn Ser Ala
            180                 185                 190

Phe Pro Asp Glu Gln Leu Glu Ser Gly Glu Ala Phe Leu Asp Asp Asp
        195                 200                 205

Asp Ile Leu Met Asn Ile Asp Leu Asp Gln Ile Ala Met Glu His Tyr
    210                 215                 220

Gln Ser Thr Ser Thr Gln Pro Ser Val Ser Asn Phe Pro Leu Arg Asn
225                 230                 235                 240

Pro Pro Val Asp Arg Ser Ala Ser Arg Arg Glu Glu Cys Leu Pro
                245                 250                 255

Pro Glu Leu Cys Phe Asn Cys Ser His Gly Ile Lys Leu Gly Leu Cys
            260                 265                 270

Pro Glu Ala Ser Thr His Leu Glu Gln Met Lys Asn Val Leu Ile Ala
        275                 280                 285

Val Ser Asn Glu Leu Leu Asp Asp Thr Asp Leu Ser Pro Asp Arg
    290                 295                 300
```

```
Ala Lys Gln Leu Arg Gln Glu Arg Leu Gln Leu Lys Lys Gln Ile Gln
305                 310                 315                 320

Gln Leu Glu Asn His Ile Arg Asp Lys Glu Arg Gln Lys Pro Gln Ser
            325                 330                 335

Leu Ser Ser Ala Pro Thr Pro Gly Phe Gln Phe Glu Thr Pro Lys Ser
            340                 345                 350

Thr Asn Arg Lys Met Asp Leu Pro Gln Thr Glu Phe Gln Ala His Leu
        355                 360                 365

Ser Glu Gln Gly Arg Tyr Ala Cys Asp Ser Trp Asn Met Pro Arg Asp
370                 375                 380

Ser Ser Phe Ser Val Asp Arg Tyr Gly Leu Ser Ser Ala Pro Val Glu
385                 390                 395                 400

Arg Glu Gln Tyr Val Pro Arg Ile Ile Asp Val Thr Tyr Thr Glu Gly
                405                 410                 415

Ser Asn Asp Lys Lys Trp Ser Ser Asp Phe Pro Trp Thr Arg Lys
            420                 425                 430

Leu Glu Val Ser Asn Lys Lys Val Phe Gly Asn His Ser Phe Arg Pro
            435                 440                 445

Asn Gln Arg Glu Ile Ile Asn Ala Thr Met Ser Gly Ser Asp Val Phe
450                 455                 460

Val Leu Met Pro Thr Gly Gly Gly Lys Ser Leu Thr Tyr Gln Leu Pro
465                 470                 475                 480

Ala Leu Ile Cys Lys Gly Ile Thr Leu Val Ile Ser Pro Leu Val Ser
                485                 490                 495

Leu Ile Gln Asp Gln Ile Met Asn Leu Leu Gln Ala Asn Ile Pro Ala
            500                 505                 510

Ala Ser Leu Ser Ala Gly Met Glu Trp Ala Glu Gln Leu Lys Ile Phe
            515                 520                 525

Gln Glu Leu Ser Ser Glu His Ser Lys Tyr Lys Leu Leu Tyr Val Thr
530                 535                 540

Pro Glu Lys Val Ala Lys Ser Asp Ser Leu Leu Arg His Leu Glu Ser
545                 550                 555                 560

Leu Asn Ser Arg Gly Leu Leu Ala Arg Phe Val Ile Asp Glu Ala His
                565                 570                 575

Cys Val Ser Gln Trp Gly His Asp Phe Arg Pro Asp Tyr Gln Ser Leu
            580                 585                 590

Gly Ile Leu Lys Gln Lys Phe Pro Asn Ile Pro Val Leu Ala Leu Thr
            595                 600                 605

Ala Thr Ala Thr Ala Ser Val Lys Glu Asp Val Val Gln Ala Leu Gly
            610                 615                 620

Leu Val Asn Cys Val Val Phe Arg Gln Ser Phe Asn Arg Pro Asn Leu
625                 630                 635                 640

Trp Tyr Ser Val Val Pro Lys Thr Lys Lys Cys Leu Glu Asp Ile Asp
                645                 650                 655

Lys Phe Ile Lys Glu Asn His Phe Asp Glu Cys Gly Ile Ile Tyr Cys
            660                 665                 670

Leu Ser Arg Met Asp Cys Glu Lys Val Ala Glu Lys Leu Gln Asp Phe
            675                 680                 685

Gly His Lys Ala Ala Phe Tyr His Gly Ser Ile Glu Pro Ala Gln Arg
            690                 695                 700

Ala Leu Val Gln Lys Gln Trp Ser Lys Asp Glu Ile Asn Ile Ile Cys
705                 710                 715                 720
```

-continued

```
Ala Thr Val Ala Phe Gly Met Gly Ile Asn Lys Pro Asp Val Arg Phe
            725                 730                 735

Val Ile His His Ser Leu Pro Lys Ser Ile Glu Gly Tyr His Gln Glu
            740                 745                 750

Cys Gly Arg Ala Gly Arg Asp Gly Gln Arg Ser Ser Cys Val Leu Tyr
            755                 760             765

Tyr Gly Tyr Gly Asp Tyr Ile Arg Val Lys His Met Ile Ser Gln Gly
            770             775                 780

Gly Val Asp Gln Ser Pro Met Ala Ser Gly Tyr Asn Arg Val Ala Ser
785             790                 795                 800

Ser Gly Arg Ile Leu Glu Thr Asn Thr Glu Asn Leu Leu Arg Met Val
                805                 810                 815

Ser Tyr Cys Glu Asn Glu Val Asp Cys Arg Arg Phe Leu Gln Leu Val
            820                 825                 830

His Phe Gly Glu Lys Phe Asp Ser Thr Asn Cys Lys Lys Thr Cys Asp
            835                 840                 845

Asn Cys Cys Ser Ser Gln Ser Leu Ile Asp Lys Asp Val Thr Leu Ile
850                 855                 860

Thr Lys Gln Leu Val Glu Leu Val Lys Gln Thr Gly Glu Arg Phe Ser
865                 870                 875                 880

Ser Ser His Ile Leu Glu Val Tyr Arg Gly Ser Leu Asn Gln Met Val
                885                 890                 895

Lys Lys His Arg His Glu Thr Leu Gln Leu His Gly Ala Gly Lys His
                900                 905                 910

Leu Ser Lys Ile Glu Val Ser Arg Ile Met His Tyr Leu Val Thr Glu
            915                 920                 925

Asp Ile Leu Val Glu Asp Val Arg Lys Ser Asp Met Tyr Gly Thr Val
            930                 935                 940

Ser Ser Leu Leu Lys Val Asn His Ser Lys Ala Ala Ser Leu Phe Ser
945                 950                 955                 960

Gly Ser Gln Thr Ile Met Met Arg Phe Pro Ser Ser Gly Lys Val Leu
                965                 970                 975

Lys Pro Ser Lys Pro Ala Ala Thr Pro Ala Lys Gly Pro Ile Thr Ser
            980                 985                 990

Ala Ala Asp Ala Pro Pro Glu Asp Leu Asn Leu Ser Val Arg Met Tyr
            995                 1000                1005

Thr Ala Leu Arg Lys Leu Arg Thr Leu Leu Val Lys Glu Ala Pro
        1010                1015                1020

Asp Gly Val Met Ala Tyr His Ile Phe Gly Asn Ala Thr Leu Gln
        1025                1030                1035

Gln Met Ser Lys Lys Ile Pro Arg Thr Lys Glu Glu Leu Leu Glu
        1040                1045                1050

Ile Ser Gly Leu Gly Lys Ala Lys Val Ser Lys Tyr Gly Asp Arg
        1055                1060                1065

Leu Leu Glu Thr Ile Glu Ser Thr Val Ser Glu Tyr Tyr Gly Thr
        1070                1075                1080

Asn Lys Lys Asp Ser Val Ile Asn Asn Asp Ser Pro Asp Ser Gly
        1085                1090                1095

Lys Arg Arg Arg Asp Glu Asn Ile Ser Pro Asn Val Ala Gly Asp
        1100                1105                1110

Asp Asp Phe Ala Glu Ser Ser Thr Gln Ala Cys Lys Lys Ala Val
        1115                1120                1125

Arg Asn Lys Ser Asn Glu Ala Arg Arg Gly Glu Asn Val Asp Gly
```

-continued

```
          1130              1135              1140
Tyr Gly Val Gly Met Val Met Asp Lys Leu Asp Phe Asp Phe Glu
          1145              1150              1155
Asp Glu Asp Gly Ser Glu Ile Arg Pro Glu Gly Arg
          1160              1165              1170

<210> SEQ ID NO 12
<211> LENGTH: 1148
<212> TYPE: PRT
<213> ORGANISM: Thellungiella halophila

<400> SEQUENCE: 12

Met Val Val Thr Arg Glu Asp Lys Phe Ala Gly Ser Tyr Leu Gly Val
1               5                   10                  15
Lys Pro Met Ile Gly Pro Tyr Lys Leu Arg Gln Asn Cys Gly Ser Tyr
            20                  25                  30
Leu Pro Glu Val Glu Asn Ser Arg Gly His Phe Pro Gln Thr Asn Trp
        35                  40                  45
Ser Glu His Ala Lys Ala Phe Glu Cys Ile Pro Ser Val Asn Lys Ser
    50                  55                  60
Leu Ser Ser Asn Leu Leu Tyr Ser Leu Glu Ser Gln Lys His Arg Arg
65                  70                  75                  80
Ser Arg Asp Ser Ala Ser Arg Pro Ile Glu Asn Val Ile Pro Val Asn
                85                  90                  95
Met Gln Asn Leu Thr Arg Gln Gln Ile Glu Lys Ala Trp Cys Ala Leu
            100                 105                 110
Thr Asn Leu Ser Ile Asn His Thr Tyr Leu Arg Pro Gly Ile Thr Pro
        115                 120                 125
Ala Val Asp Asp Ser Ser Thr Asn Cys Thr Ser Ser Met Arg Gly Arg
    130                 135                 140
Ser Thr Val Lys Val Thr Ser Asn Ala Asp Gly Ser Phe Tyr Ala His
145                 150                 155                 160
Asn His Pro Glu Gln Ser Gln Glu Ser Val Arg Gly Thr Ala Arg Ser
                165                 170                 175
Phe Asp Arg Phe Ser Ser Ser Phe Pro Gly Asp Gly Lys Leu Thr Ala
            180                 185                 190
Gly Lys Val Pro Arg Val Asn Asn Glu Val Arg Asp Ser Val Thr Gly
        195                 200                 205
Cys Lys Tyr Ile Asn Gly Met Asp Ile Gln Pro Ile Arg Asn Phe Ala
    210                 215                 220
Leu Pro Ala Arg Gln Val Glu Ala Ser Leu Ile Glu Ile Asp Asp Asp
225                 230                 235                 240
Asp Ile Leu Glu Ile Ile Asp Val Asp Gln Ile Val Met Glu Asn Tyr
                245                 250                 255
His Leu Thr Tyr Thr Pro Gln Pro Ser Val Asn Ile Phe Ala Ser Arg
            260                 265                 270
Gly Glu Glu Val Pro Cys Leu Pro Glu Leu Cys Ser Asn Cys Ser
        275                 280                 285
His Gly Val Lys Leu Gly Leu Cys Leu Glu Ala Ser Thr His Val Glu
    290                 295                 300
Gln Met Lys Asp Ala Leu Leu Ala Ile Ser Asn Lys Leu Leu Asp Asp
305                 310                 315                 320
Ser Thr Asp Leu Ser Arg Asp His Ser Glu Gln Leu Cys Gln Glu Arg
                325                 330                 335
```

Leu Leu Leu Lys Asn Gln Ile Gln Gln Leu Glu Ile Leu Ile Gln Asn
            340                 345                 350
Lys Glu Arg Lys Lys Ser Ser Thr Pro Thr His Asn Phe Gln Tyr Gly
            355                 360                 365
Thr Pro Gln Ile Thr Asn Cys Lys Val Asp Tyr Ala Gln Thr Asp Ser
        370                 375                 380
Arg Glu Glu Gln Gly Arg Tyr Val Ser Asp Asn Trp Asn Met Pro Arg
385                 390                 395                 400
Asp Tyr Leu Leu Ser Glu Asp Arg Tyr Gly Leu Ser Ser Gly Pro Val
                405                 410                 415
Glu Arg Glu Arg His Val Pro Glu Ile Ile Asp Val Thr Tyr Thr Asp
            420                 425                 430
Gly Ser Asn Asp Thr Lys Trp Cys Ser Arg Asp Phe Pro Trp Thr Lys
            435                 440                 445
Asn Leu Glu Ile Asn Asn Lys Arg Val Phe Gly Asn His Ser Phe Arg
        450                 455                 460
Pro Asn Gln Arg Glu Ile Ile Asn Ala Thr Met Ser Gly Cys Asp Val
465                 470                 475                 480
Phe Val Leu Met Pro Thr Gly Gly Lys Ser Leu Thr Tyr Gln Leu
                485                 490                 495
Pro Ala Leu Ile Cys Ala Gly Ile Thr Leu Val Ile Ser Pro Leu Val
            500                 505                 510
Ser Leu Ile Gln Asp Gln Ile Met Asn Leu Leu Gln Thr Asn Ile Pro
        515                 520                 525
Ala Ala Ser Leu Ser Ala Gly Met Glu Trp Gly Glu Gln Gln Glu Ile
        530                 535                 540
Leu Arg Glu Leu Ser Ser Gly Asn Ser Lys Tyr Lys Phe Leu Tyr Val
545                 550                 555                 560
Thr Pro Glu Lys Val Ala Lys Ser Asp Ser Leu Leu Arg His Leu Glu
                565                 570                 575
Ser Leu Asn Ser His Ser Leu Leu Ala Arg Phe Val Ile Asp Glu Ala
            580                 585                 590
His Cys Val Ser Gln Trp Gly His Asp Phe Arg Pro Asp Tyr Gln Gly
            595                 600                 605
Leu Gly Val Leu Lys Lys Lys Phe Pro Asn Ile Pro Met Leu Ala Leu
        610                 615                 620
Thr Ala Thr Ala Thr Ala Ser Val Lys Glu Asp Val Val Gln Ala Leu
625                 630                 635                 640
Gly Leu Val Asn Cys Val Val Phe Arg Gln Ser Phe Asn Arg Pro Asn
                645                 650                 655
Leu Trp Tyr Ser Val Val Pro Lys Thr Asn Lys Cys Leu Glu Asp Ile
            660                 665                 670
Asp Lys Phe Ile Arg Glu Asn His Phe Asp Glu Ser Gly Ile Ile Tyr
        675                 680                 685
Cys Leu Ser Arg Met Asp Cys Glu Lys Val Thr Glu Ala Leu Gln Lys
        690                 695                 700
Phe Gly His Lys Ala Ala Phe Tyr His Gly Ser Met Asp Pro Ala Gln
705                 710                 715                 720
Arg Ala Phe Val Gln Lys Gln Trp Ser Lys Asp Glu Ile Asn Ile Ile
                725                 730                 735
Cys Ala Thr Val Ala Phe Gly Met Gly Ile Asn Lys Pro Asp Val Arg
            740                 745                 750
Phe Val Ile His His Ser Leu Pro Lys Ser Ile Glu Gly Tyr His Gln

```
            755                 760                 765
Glu Cys Gly Arg Ala Gly Arg Asp Gly Gln Ser Ser Cys Val Leu
770                 775                 780

Tyr Tyr Ser Tyr Ser Asp Tyr Ile Arg Val Lys His Met Ile Ser Gln
785                 790                 795                 800

Gly Gly Pro Gly Gln Gly Pro Thr Thr Met Gly Tyr Asn Arg Leu Ala
                805                 810                 815

Ser Ala Gly Arg Ile Leu Glu Thr Asn Thr Glu Asn Leu Leu Arg Met
                820                 825                 830

Val Ser Tyr Cys Glu Asn Glu Val Asp Cys Arg Arg Phe Leu Gln Leu
                835                 840                 845

Val His Leu Gly Glu Thr Phe Asp Ser Thr Asn Cys Lys Lys Thr Cys
850                 855                 860

Asp Asn Cys Ser Ser Arg Ser Leu Ile Asp Lys Asp Val Thr Leu
865                 870                 875                 880

Ile Ala Arg Gln Leu Val Ala Leu Val Lys Leu Thr Gly Glu Arg Phe
                885                 890                 895

Ser Ser Ala His Ile Ile Glu Ile Tyr Arg Gly Ser Leu Asn Gln Thr
                900                 905                 910

Val Lys Lys His Arg His Glu Thr Leu His Leu His Gly Ala Gly Lys
                915                 920                 925

His Leu Ala Lys Ser Glu Ala Ser Arg Ile Leu His Tyr Leu Val Thr
930                 935                 940

Lys Asp Ile Leu Ala Glu Tyr Val Lys Ser Tyr Leu Tyr Gly Ser
945                 950                 955                 960

Val Ser Ser Leu Leu Lys Val Asn Arg Ser Lys Ala Asp Ala Ile Leu
                965                 970                 975

Ser Gly Gly Gln Thr Ile Ile Met Arg Phe Pro Ser Ala Val Lys Val
                980                 985                 990

Ser Lys Thr Ser Lys Ser Gly Ala  Ile Pro Ala Lys Ala  Pro Leu Lys
                995                 1000                1005

Gln Thr  Thr Phe Thr Pro Leu  Met Thr His Ala Pro  Ser Gln Asp
    1010                1015                1020

Ser Ile  Leu Ser Val Thr Leu  Tyr Thr Ala Leu Lys  Lys Leu Arg
    1025                1030                1035

Thr Asp  Ile Val Lys Glu Ser  Ser Asp Ala Val Met  Ala His His
    1040                1045                1050

Ile Phe  Gly Asn Gly Thr Leu  Arg Gln Ile Ser Lys  Arg Leu Pro
    1055                1060                1065

Arg Thr  Lys Glu Glu Leu Leu  Asp Ile Thr Gly Leu  Gly Lys Ala
    1070                1075                1080

Lys Val  Asn Lys His Gly Asp  Arg Leu Leu Glu Ile  Ile Glu Ser
    1085                1090                1095

Thr Ile  Asn Glu His Tyr Arg  Thr Glu Lys Ser Glu  Gly Pro Gly
    1100                1105                1110

Ser Gly  Lys Arg Arg Arg Asn  Glu Asn Ile Ser Pro  Asn Val Ala
    1115                1120                1125

Asp Asp  Asp Asp Pro Asp Trp  Thr Pro Thr His Ser  His Lys Lys
    1130                1135                1140

Ala Val  Lys Asn Lys
    1145

<210> SEQ ID NO 13
```

<211> LENGTH: 1202
<212> TYPE: PRT
<213> ORGANISM: Eucalyptus grandis

<400> SEQUENCE: 13

```
Met Gln Thr Arg Arg Arg Glu Gly Gly Asp Asp Arg Leu Pro Arg Val
1               5                   10                  15

Asn Trp Ser Asp His Ala Ser Ala His Asp Asp Phe Ser Asn Gln Ser
            20                  25                  30

Lys Phe Leu Ser Ser Asn Phe Leu Tyr Ser Leu Pro Asn Gln Arg Pro
        35                  40                  45

Pro Val Gln Glu Ser Met Gly Ser Arg Ser Met Val Phe Ser Met Val
    50                  55                  60

Asn Pro Gln Arg Leu Pro Thr Asn Gln Ile Asp Lys Ala Trp His Ala
65                  70                  75                  80

Leu Ser Ser Leu Arg Ile Ser Ser Arg Thr Tyr Ile Thr Pro Gly Lys
                85                  90                  95

Thr Leu Pro Val Lys Asp Asp Asn Ala Gly His Ser Asn Lys Val Ser
            100                 105                 110

Arg Thr Val Ser Ser Ser Gly Lys Glu His Gly His Ser Trp Glu Ser
        115                 120                 125

Asn Lys Lys Leu Asn Lys Ser Thr Ala Arg Ile Asp Ala Ser Asn Asn
    130                 135                 140

Tyr Val Ser Asn Pro Val Leu Ala His Tyr Glu Ala Ala Glu Gly
145                 150                 155                 160

Gly Cys Pro Ala Arg Gln Ser Gly Asn Gly Ile Leu Gly Ala Asn Lys
                165                 170                 175

Ala His Ser Glu Gly Phe Ala Ala Ala Met Asn Arg Asp Ser Met Pro
            180                 185                 190

Asn Ala Gln Thr Lys Ser Ser Gly Gly Val Leu Ala Asp Glu Leu Asp
        195                 200                 205

Asp Asp Asp Ile Leu Glu Ser Ile Asp Val Asp Gln Ile Val Met Glu
    210                 215                 220

His Tyr Gln Ser Thr Ser Thr Pro Gln Pro Ser Ile Gln Lys Leu Pro
225                 230                 235                 240

Pro Ile Thr Pro Asp Val Glu Arg Asn Ser Leu Gln Gln Asp Glu Ser
                245                 250                 255

Cys Leu Pro Glu Glu Leu Arg Ser Asn Cys Ser His Gly Leu Lys Leu
            260                 265                 270

Gly Leu Cys Pro Asp Ala Ala Arg His Leu Gln Glu Met Lys Asp Asn
        275                 280                 285

Leu Ile Ala Ile Ser Asn Glu Leu Leu Asp Asn Val Thr Glu Leu Thr
    290                 295                 300

Pro Glu Ala Val Glu Lys Leu Arg His Asp Arg Ser His Leu Asn Arg
305                 310                 315                 320

Gln Ile Gln Gln Leu Glu Asn His Leu Arg Ser Leu Thr Val Asp Glu
                325                 330                 335

Glu Arg Arg Lys Ser His Phe Ser Ala Ser Ala Pro Pro Thr Ser
            340                 345                 350

Ser Leu Tyr Glu Thr Pro Arg Ala Phe Gly Ser Arg Val Glu Pro Phe
        355                 360                 365

Arg Leu Glu Ala His Val His Pro Gln Asn Glu Pro Gly Gly Tyr Asp
    370                 375                 380

Arg Trp Asn Ser Pro Ser Val Ser Phe Thr Ser Asp Arg Phe Pro Val
```

```
                385                 390                 395                 400
        Ser Ser Gly Pro Val Asp Arg Asp Ser Cys Ile Gln Lys Pro Val Glu
                            405                 410                 415

Val Asn Tyr Thr Glu Gly Ser Ile Asp Lys Lys Trp Ser Ser Trp Ser
                            420                 425                 430

Phe Pro Trp Thr Lys Ser Leu Glu Asp His Asn Lys Lys Val Phe Gly
                            435                 440                 445

Asn His Ser Phe Arg Pro Asn Gln Arg Glu Ile Ile Asn Ala Thr Met
                    450                 455                 460

Ser Arg Tyr Asp Val Phe Val Leu Met Pro Thr Gly Gly Lys Ser
        465                 470                 475                 480

Leu Thr Tyr Gln Leu Pro Ala Leu Ile Cys Pro Gly Val Thr Leu Val
                            485                 490                 495

Ile Ser Pro Leu Val Ser Leu Ile Gln Asp Gln Ile Met His Leu Leu
                    500                 505                 510

Gln Ala Asn Ile Pro Ala Thr Tyr Leu Ser Ala Asn Met Asp Trp Ser
                    515                 520                 525

Glu Gln Gln Glu Ile Leu Arg Glu Leu Asn Ser Asp Tyr Cys Lys Phe
                    530                 535                 540

Lys Leu Leu Tyr Val Thr Pro Glu Lys Val Ala Lys Ser Asp Val Leu
        545                 550                 555                 560

Leu Arg Gln Leu Glu Ser Leu His Ala Arg Glu Leu Leu Ala Arg Ile
                    565                 570                 575

Val Ile Asp Glu Ala His Cys Val Ser Gln Trp Gly His Asp Phe Arg
                    580                 585                 590

Pro Asp Tyr Gln Gly Leu Gly Ile Leu Lys Gln Lys Phe Pro Ser Thr
                    595                 600                 605

Pro Val Leu Ala Leu Thr Ala Thr Ala Thr Ala Ser Val Lys Glu Asp
                    610                 615                 620

Val Val Arg Ala Leu Ala Leu Val Asn Cys Ile Ile Phe Arg Gln Ser
        625                 630                 635                 640

Phe Asn Arg Pro Asn Leu Arg Tyr Ser Val Ile Pro Lys Thr Lys Lys
                            645                 650                 655

Cys Leu Glu Asp Ile Asp Lys Phe Ile Lys Glu Asn His Phe Asp Glu
                    660                 665                 670

Cys Gly Ile Ile Tyr Cys Leu Ser Arg Met Asp Cys Glu Lys Val Ala
                    675                 680                 685

Glu Lys Leu Gln Glu Tyr Gly His Lys Ala Ala Phe Tyr His Gly Ser
                    690                 695                 700

Met Asp Pro Ala Gln Arg Ala Phe Val Gln Lys Gln Trp Ser Lys Asp
        705                 710                 715                 720

Glu Ile Asn Ile Ile Cys Ala Thr Val Ala Phe Gly Met Gly Ile Asn
                            725                 730                 735

Lys Pro Asp Val Arg Phe Val Ile His His Ser Leu Pro Lys Ser Ile
                            740                 745                 750

Glu Gly Tyr His Gln Glu Cys Gly Arg Ala Gly Arg Asp Gly Gln His
                    755                 760                 765

Ser Ser Cys Val Leu Tyr Tyr Ser Asp Tyr Ile Arg Val Lys
        770                 775                 780

His Met Ile Ser Gln Gly Ala Val Glu Gln Ser Pro Phe Ser Asn Gly
        785                 790                 795                 800

Tyr Asn Arg Ile Asn Met Ala Asn Ser Gly Arg Val Leu Glu Thr Asn
                            805                 810                 815
```

Thr Asp Asn Leu Leu Arg Met Val Ser Tyr Cys Glu Asn Asp Val Asp
            820                 825                 830

Cys Arg Arg Leu Leu Gln Leu Val His Phe Gly Lys Phe Asp Ser
            835                 840                 845

Asn Asn Cys Gly Lys Thr Cys Asp Asn Cys Leu Lys Ile Lys Ser Phe
            850                 855                 860

Val Glu Lys Asp Val Thr Glu Ile Ala Lys Gln Leu Val Glu Leu Val
865                 870                 875                 880

Lys Leu Ala Gly Gln Gln Phe Ser Ser Ala His Leu Leu Gly Val Tyr
            885                 890                 895

Arg Gly Ser Leu Asn Gln Phe Val Lys Lys His Arg His Glu Lys Leu
            900                 905                 910

Asn Leu His Gly Ala Gly Lys His Leu Ala Lys Gly Glu Ala Ser Arg
            915                 920                 925

Val Leu Arg His Leu Val Thr Glu Asp Phe Leu Val Glu Asp Val Arg
            930                 935                 940

Lys Ser Asp Leu Tyr Gly Ser Leu Ser Ser Ile Leu Lys Val Asn Glu
945                 950                 955                 960

Ser Lys Ala Tyr Asn Leu Cys Ser Gly Arg Gln Ser Val Ile Leu Arg
            965                 970                 975

Phe Pro Ser Val Ala Lys Ile Ser Lys Ser Ser Lys Ser Asp Val Thr
            980                 985                 990

Pro Ala Lys Gly Leu Ser Thr Phe Gly Lys Leu Met Pro Gln Ile Asp
            995                 1000                1005

Gly Pro Ala Gln Thr Glu Ala Gln Gly Asp Leu Ile Leu Ser Ala
            1010                1015                1020

Lys Leu Tyr Thr Ser Leu Arg Met Leu Arg Thr Ile Leu Val Lys
            1025                1030                1035

Glu Ala Gly Asp Gly Val Met Ala Tyr His Ile Phe Gly Asn Ala
            1040                1045                1050

Thr Leu Gln His Ile Ser Lys Arg Ile Pro Arg Thr Lys Glu Glu
            1055                1060                1065

Leu Leu Glu Ile Asn Gly Ile Gly Lys Ala Lys Val Ser Lys Tyr
            1070                1075                1080

Gly Asp Arg Leu Leu Glu Thr Ile Glu Thr Thr Ile Arg Glu Tyr
            1085                1090                1095

Gln Gly Thr Asp Asn Arg Asn Ser Ser Ser Ser Asn Asp Ser Met
            1100                1105                1110

Asp Ser Met Lys Arg Arg Arg Glu Ala Asn Gly Gly Thr Lys Pro
            1115                1120                1125

Asn Tyr Glu Glu Asp Asp Asp Phe Thr Arg Ser Thr Gly Arg Ser
            1130                1135                1140

Lys Lys Arg Ala Thr Val Ile Glu Ala Gln Asn Tyr Asn Asn Gln
            1145                1150                1155

Ala Val Asn Glu Pro Gly Asp Asp Ile Thr Cys Ile Asp Asp Leu
            1160                1165                1170

Asp Phe Glu Asp Tyr Asp Phe Asp Val Asp Val Asp Ala Ser Asn
            1175                1180                1185

Val Asn Ser Gly Gly Arg Val Leu Pro Ser Trp Ser Lys Ser
            1190                1195                1200

<210> SEQ ID NO 14
<211> LENGTH: 1152

<212> TYPE: PRT
<213> ORGANISM: Glycine max

<400> SEQUENCE: 14

```
Met Arg His Gly Glu Ala Asn Ser Gly Gln Gly Pro Lys Val Asn Leu
1               5                   10                  15

Leu Gln His Ala Asn Ala Leu Glu Asn Phe Ser Ser Gln Ala Lys Phe
            20                  25                  30

Leu Ser Ser Thr Phe Leu Phe Ser Val Pro Pro Lys Lys Pro His His
        35                  40                  45

Glu Gln Pro Asn Pro Gly Phe Val Phe Arg Arg Ser Glu Thr Ile Gln
    50                  55                  60

Gly Ser Gln Arg Val Gln Val Glu Lys Ala Leu Ala Ala His Ser Ser
65                  70                  75                  80

Leu Gln Asn Ser Ser Arg Asn Tyr Val Gln Pro Gly Lys Thr Gln Val
                85                  90                  95

Thr Pro Gln Leu His Glu Asp Arg Arg Thr Thr Ser Phe His Gly Gly
            100                 105                 110

Tyr Glu Asn Gly Asn His Arg Cys Pro Asp Val Ala Ala Thr Pro Ile
        115                 120                 125

Val Asn Asn His Asn Ser Arg Gly Leu Asp Gly Ser Val Asn Asn His
    130                 135                 140

Thr Asn Tyr Thr Gly Gln Ile Asn Lys Ser Ser Asn Cys Met Ala Val
145                 150                 155                 160

Asp Ile Asp Asp Asp Ser Leu Phe Lys Asn Ile Asp Val Asp Gln
            165                 170                 175

Ile Val Glu Asp Tyr Cys Thr Pro Lys Pro Ser Ile Ser Lys Leu Pro
        180                 185                 190

Pro Ile Thr Pro Thr Ala Asp Lys Asp Asn Phe Ala Arg Gln Gly Asp
    195                 200                 205

Asp Val Leu Pro Pro Glu Leu Cys Leu Asp Cys Val His Gly Tyr Met
210                 215                 220

Leu Gly Phe Cys Pro Glu Ala Ala Ser His Leu Gln Asp Met Lys Asp
225                 230                 235                 240

Asn Leu Ile Ala Ile Phe Asn Glu Leu Leu Asp Asn Gly Glu Asn Leu
                245                 250                 255

Asn Ser Thr Gln Ile Ala Lys Leu Arg His Asp Arg Ser Gln Leu Asn
            260                 265                 270

Lys Gln Ile Gln Gln Leu Glu Lys Tyr Ile His Ser Gly Asn Leu Asn
        275                 280                 285

Glu Glu Arg Gln Lys Ser His Phe Ser Ala Ser Thr Ala Pro Pro Thr
    290                 295                 300

Ser Phe Val Tyr Glu Thr Pro Gln Gln Thr Val Leu Cys Asn Gly Ser
305                 310                 315                 320

Lys Arg Tyr Asp Thr Glu Ala Tyr Met Gly Asn Gly Thr Tyr Gly Ser
                325                 330                 335

Ser Phe Gln Ser Leu Pro Pro Phe Ser Val Asp Asn Cys Ser Met Pro
            340                 345                 350

Ser Gly Ser Val Gly Arg Glu Val Phe Ile Pro Lys Ile Ile Glu Val
        355                 360                 365

Asn Tyr Ile Glu Gly Ser Gly Asp Lys Arg Trp Ser Ser Tyr Asp Phe
    370                 375                 380

Ser Trp Thr Lys Glu Leu Glu Val Asn Asn Lys Lys Val Phe Gly Asn
385                 390                 395                 400
```

```
His Ser Phe Arg Pro Asn Gln Arg Glu Ile Ile Asn Ala Ser Met Ser
                405                 410                 415

Gly Cys Asp Val Phe Val Leu Met Pro Thr Gly Gly Lys Ser Leu
            420                 425                 430

Thr Tyr Gln Leu Pro Ala Leu Ile His Pro Gly Ile Thr Leu Val Ile
        435                 440                 445

Ser Pro Leu Val Ser Leu Ile Gln Asp Gln Ile Met His Leu Leu Gln
450                 455                 460

Ala Asn Ile Pro Ala Ala Tyr Leu Ser Ala Asn Met Glu Trp Thr Glu
465                 470                 475                 480

Gln Gln Asp Ile Leu Arg Glu Leu Asn Ser Asp Tyr Cys Lys Tyr Lys
                485                 490                 495

Leu Leu Tyr Val Thr Pro Glu Lys Val Ala Arg Ser Asp Asn Leu Leu
            500                 505                 510

Arg His Leu Asp Asn Leu His Phe Arg Glu Leu Leu Ala Arg Ile Val
        515                 520                 525

Ile Asp Glu Ala His Cys Val Ser Gln Trp Gly His Asp Phe Arg Pro
530                 535                 540

Asp Tyr Gln Gly Leu Gly Ile Leu Lys Gln Lys Phe Pro Asn Thr Pro
545                 550                 555                 560

Val Leu Ala Leu Thr Ala Thr Ala Thr Ala Ser Val Lys Glu Asp Val
                565                 570                 575

Val Gln Ala Leu Gly Leu Val Asn Cys Ile Ile Phe Arg Gln Ser Phe
            580                 585                 590

Asn Arg Pro Asn Leu Arg Tyr Ser Val Ile Pro Lys Thr Lys Lys Cys
        595                 600                 605

Leu Glu Asp Ile Asp Lys Phe Ile Arg Glu Asn His Phe Asp Glu Cys
610                 615                 620

Gly Ile Val Tyr Cys Leu Ser Arg Met Asp Cys Glu Lys Val Ala Glu
625                 630                 635                 640

Lys Leu Gln Glu Cys Gly His Lys Cys Ala Phe Tyr His Gly Ser Met
                645                 650                 655

Asp Pro Val Gln Arg Ala Ser Val Gln Lys Gln Trp Ser Lys Asp Glu
            660                 665                 670

Ile Asn Ile Ile Cys Ala Thr Val Ala Phe Gly Met Gly Ile Asn Lys
        675                 680                 685

Pro Asp Val Arg Phe Val Ile His His Ser Leu Pro Lys Ser Ile Glu
690                 695                 700

Gly Tyr His Gln Glu Cys Gly Arg Ala Gly Arg Asp Gly Gln His Ser
705                 710                 715                 720

Ser Cys Val Leu Tyr Tyr Thr Tyr Ser Asp Tyr Ile Arg Val Lys His
                725                 730                 735

Met Leu Ser Gln Gly Ala Ile Glu Gln Ser Met Thr Ser Gly Tyr
            740                 745                 750

Asn Arg Ser Asn Met Ile Asn Ser Gly Arg Ile Leu Glu Thr Asn Thr
        755                 760                 765

Glu Asn Leu Val Arg Met Val Ser Tyr Cys Glu Asn Asp Val Asp Cys
770                 775                 780

Arg Arg Leu Leu Gln Leu Ala His Phe Gly Glu Lys Phe Asn Ser Ser
785                 790                 795                 800

Thr Cys Leu Lys Thr Cys Asp Asn Cys Leu Lys Ile Thr Ser Phe Ile
                805                 810                 815
```

Glu Lys Asp Val Thr Glu Ile Ala Lys Gln Leu Val Glu Leu Val Lys
               820                 825                 830

Leu Thr Gly Gln Arg Phe Ser Ser His Ile Leu Val Tyr Arg
        835                 840                 845

Gly Ser Leu Ser Gln Met Val Lys Lys His Arg His Glu Ser Val Ser
    850                 855                 860

Leu His Gly Ala Gly Lys His Leu Ala Lys Gly Glu Ala Ser Arg Ile
865                 870                 875                 880

Leu His His Leu Val Glu Asp Phe Leu Trp Glu Val Lys Lys
                885                 890                 895

Ser Asp Phe Tyr Gly Ser Val Ser Ser Ile Leu Lys Val Asn Glu Pro
                900                 905                 910

Lys Ile His Asn Leu Phe Ala Gly Gln Arg Ile Ile Leu Arg Phe Pro
            915                 920                 925

Ser Leu Val Lys Ala Ser Lys Pro Gly Lys Ser Asp Ala Thr Pro Ala
        930                 935                 940

Lys Gly Ser Leu Thr Ser Gly Lys Leu Asn Val Met Gln Ile Asp Pro
945                 950                 955                 960

Pro Ser Pro Gln Thr Glu Val Asp Asp Ile Leu Ser Ala Lys Leu Tyr
                965                 970                 975

Asn Ala Leu Arg Leu Leu Arg Lys Ser Leu Val Thr Glu Ala Gly Asp
            980                 985                 990

Gly Val Met Pro His His Ile Phe Gly Asn Ala Thr Leu Leu Leu Ile
        995                 1000                1005

Ser Lys Arg Val Pro Arg Arg Lys Glu Glu Leu Leu Asp Ile Asn
    1010                1015                1020

Gly Ile Gly Lys Ala Lys Val Ser Lys Tyr Gly Asp Gln Leu Leu
    1025                1030                1035

Glu Ser Ile Glu Lys Thr Ile Asn Glu His Tyr Lys Leu Asp Lys
    1040                1045                1050

Val Ser Ser Gly Ser Lys Gly Ser Ser Asp Ser Thr Lys Lys Arg
    1055                1060                1065

Arg Leu Ser Asn Gly Asn Pro Asp Ala Asn Ala Glu Asp Asp Asp
    1070                1075                1080

Ala Pro Thr Lys Ser Thr Gly Arg Ser Lys Lys Arg Met Val Lys
    1085                1090                1095

Arg Gln Asn Arg Lys Ala Val Ile Tyr Asp Ser Pro Glu Glu Asp
    1100                1105                1110

Tyr Phe Gln Gly Cys Pro Asp Glu Asp Leu Asp Phe Asp Ile Ile
    1115                1120                1125

Glu Ile Asp Ala Leu Asp Gln Val Thr Cys Lys Asn Ala Ala Gly
    1130                1135                1140

Arg Val Leu Pro Gln Trp Thr Ala Ser
    1145                1150

<210> SEQ ID NO 15
<211> LENGTH: 1160
<212> TYPE: PRT
<213> ORGANISM: Glycine max

<400> SEQUENCE: 15

Met Arg Gln Gly Glu Ala Asn Ser Thr Gln Gly Pro Lys Val Asn Leu
1               5                   10                  15

Leu Gln His Ala Asn Ala Leu Glu Asn Phe Ser Ser Gln Ala Lys Phe
            20                  25                  30

```
Leu Ser Ser Thr Phe Leu Phe Ser Val Pro Pro Lys Lys Pro Pro His
            35                  40                  45

His Ala Glu Pro Asn Pro Gly Thr Ala Gly Phe Val Phe Arg Arg Ser
 50                  55                  60

Glu Thr Ile Gln Gly Ser His Arg Val Gln Val Glu Lys Ala Leu Thr
 65                  70                  75                  80

Ala His Ser Ser Leu Gln Asn Ser Ser Arg Ile Tyr Val Gln Leu Gly
                 85                  90                  95

Lys Thr Gln Val Thr Pro Gln Leu His Glu Asp Arg Arg Thr Thr Ser
             100                 105                 110

Phe His Gly Arg Tyr Glu Asn Asp Ser Arg Ile Cys Pro Asp Val Thr
             115                 120                 125

Val Thr Pro Ile Val Asn Asn His Ser Ser Arg Gly Leu Asp Gly Leu
         130                 135                 140

Val Asn Asn His Thr Asn Tyr Thr Gly Gln Ile Ile Lys Ser Ser Asn
145                 150                 155                 160

Cys Met Ala Val Asp Ile Asp Asp Asp Ala Ile Leu Ala Asn
                 165                 170                 175

Ile Asp Val Asp Gln Ile Val Glu Glu His Gln Ser Thr Cys Thr Pro
             180                 185                 190

Lys Pro Ser Ile Ser Lys Phe Pro Pro Ile Thr Pro Thr Ala Asp Lys
         195                 200                 205

Asp Asn Phe Ala Arg Gln Gly Asp Asn Val Leu Pro Pro Glu Leu Cys
     210                 215                 220

Leu Asp Cys Ile His Gly Tyr Lys Leu Gly Phe Cys Pro Glu Ala Ala
225                 230                 235                 240

Ser His Leu Gln Glu Met Lys Asp Asn Leu Ile Ala Ile Ser Asn Glu
                 245                 250                 255

Leu Leu Asp Asn Gly Glu Asn Leu Asn Ser Thr Gln Ile Ala Lys Leu
             260                 265                 270

Arg His Asp Arg Ser Gln Leu Asn Lys Gln Ile Gln Gln Leu Glu Lys
         275                 280                 285

Tyr Ile His Ser Gly Asn Leu Asn Glu Glu Arg Gln Lys Ser His Phe
     290                 295                 300

Ser Ala Ser Thr Ala Pro Pro Thr Ser Phe Val Tyr Glu Thr Pro Gln
305                 310                 315                 320

Gln Thr Val Leu Cys Asn Gly Ser Lys Arg Tyr Asp Thr Gln Ala Tyr
                 325                 330                 335

Met Gly Asn Glu Thr Tyr Gly Ser Ser Phe Gln Ser Leu Pro Ser Phe
             340                 345                 350

Ser Val Asp Asn Cys Asn Met Pro Leu Gly Ser Val Gly Arg Glu Ala
         355                 360                 365

Phe Ile Pro Lys Ile Ile Glu Val Asn Tyr Ile Glu Gly Ser Gly Asp
     370                 375                 380

Lys Arg Trp Ser Ser Tyr Asp Phe Pro Trp Thr Lys Glu Leu Glu Val
385                 390                 395                 400

Asn Asn Lys Lys Val Phe Gly Asn His Ser Phe Arg Pro Asn Gln Arg
                 405                 410                 415

Glu Ile Ile Asn Ala Ser Met Ser Gly Cys Asp Val Phe Val Leu Met
             420                 425                 430

Pro Thr Gly Gly Gly Lys Ser Leu Thr Tyr Gln Leu Pro Ala Leu Ile
         435                 440                 445
```

```
Arg Pro Gly Ile Thr Leu Val Ile Ser Pro Leu Val Ser Leu Ile Gln
    450                 455                 460

Asp Gln Ile Met His Leu Leu Gln Ala Asn Ile Pro Ala Ala Tyr Leu
465                 470                 475                 480

Ser Ala Asn Met Glu Trp Ala Glu Gln Gln Glu Ile Leu Arg Glu Leu
                485                 490                 495

Asn Ser Asp Tyr Cys Lys Tyr Lys Leu Leu Tyr Val Thr Pro Glu Lys
                500                 505                 510

Val Ala Arg Ser Asp Asn Leu Leu Arg His Leu Asp Asn Leu His Phe
        515                 520                 525

Arg Glu Leu Leu Ala Arg Ile Val Ile Asp Glu Ala His Cys Val Ser
530                 535                 540

Gln Trp Gly His Asp Phe Arg Pro Asp Tyr Gln Gly Leu Gly Ile Leu
545                 550                 555                 560

Lys Gln Lys Phe Pro Asn Thr Pro Val Leu Ala Leu Thr Ala Thr Ala
                565                 570                 575

Thr Ala Ser Val Lys Glu Asp Val Gln Ala Leu Gly Leu Val Asn
            580                 585                 590

Cys Ile Ile Phe Arg Gln Ser Phe Asn Arg Pro Asn Leu Trp Tyr Ser
        595                 600                 605

Val Val Pro Lys Thr Lys Lys Cys Leu Glu Asp Ile Asp Lys Phe Ile
610                 615                 620

Arg Val Asn His Phe Asp Glu Cys Gly Ile Ile Tyr Cys Leu Ser Arg
625                 630                 635                 640

Met Asp Cys Glu Lys Val Ala Glu Lys Leu Gln Glu Cys Gly His Lys
                645                 650                 655

Cys Ala Phe Tyr His Gly Ser Met Asp Pro Ala Gln Arg Ala Ser Val
                660                 665                 670

Gln Lys Gln Trp Ser Lys Asp Glu Ile Asn Ile Ile Cys Ala Thr Val
        675                 680                 685

Ala Phe Gly Met Gly Ile Asn Lys Pro Asp Val Arg Phe Val Ile His
690                 695                 700

His Ser Leu Pro Lys Ser Ile Glu Gly Tyr His Gln Glu Cys Gly Arg
705                 710                 715                 720

Ala Gly Arg Asp Gly Gln Arg Ser Ser Cys Ile Leu Tyr Tyr Asn Tyr
                725                 730                 735

Ser Asp Tyr Ile Arg Val Lys His Met Leu Ser Gln Gly Ala Ile Glu
                740                 745                 750

Gln Ser Ser Met Thr Ser Gly Tyr Asn Arg Ser Asn Met Ile Asn Ser
        755                 760                 765

Gly Arg Ile Leu Glu Thr Asn Thr Glu Asn Leu Val Arg Met Val Ser
770                 775                 780

Tyr Cys Glu Asn Asp Val Asp Cys Arg Arg Leu Leu Gln Leu Ala His
785                 790                 795                 800

Phe Gly Glu Lys Phe Asn Ser Ser Thr Cys Gln Lys Thr Cys Asp Asn
                805                 810                 815

Cys Leu Lys Ile Thr Ser Phe Ile Glu Lys Asp Val Thr Glu Ile Ala
                820                 825                 830

Asn Gln Leu Val Glu Leu Val Lys Leu Thr Gly Gln Arg Phe Ser Ser
        835                 840                 845

Ser His Ile Leu Glu Val Tyr Arg Gly Ser Leu Ser Gln Met Val Lys
850                 855                 860

Lys His Arg His Glu Thr Val Ser Leu His Gly Ala Gly Lys His Leu
```

-continued

Ala Lys Gly Glu Ala Ser Arg Ile Leu His His Leu Val Val Glu Asp
865                 870                 875                 880

Phe Leu Gly Glu Glu Val Lys Lys Ser Asp Phe Tyr Gly Ser Val Ser
            885                 890                 895

Ser Ile Leu Lys Val Asn Glu Pro Lys Val Arg Asn Leu Phe Ala Gly
        900                 905                 910

Gln Arg Ile Ile Leu Arg Phe Pro Ser Val Lys Ala Ser Lys Pro
    915                 920                 925

Gly Lys Ser Asp Ala Thr Pro Ala Lys Gly Ser Leu Thr Ser Glu Lys
930                 935                 940

Leu Asn Val Met Gln Ile Asp Pro Pro Ser Pro Gln Thr Glu Val Asp
945                 950                 955                 960

His Ile Leu Ser Ala Lys Leu Tyr Asn Ala Leu Arg Leu Leu Arg Lys
            965                 970                 975

Ser Leu Val Thr Glu Ala Gly Glu Gly Val Met Pro His His Ile Phe
        980                 985                 990

Gly Asn Ala Thr Leu Leu Leu Ile Ser Lys Arg Val Pro Arg Thr
    995                 1000                1005

Lys Glu Glu Leu Leu Asp Ile Asn Gly Ile Gly Lys Ala Lys Val
1010                1015                1020

Ser Lys Tyr Gly Asp Gln Leu Leu Glu Thr Ile Glu Lys Thr Val
1025                1030                1035

Asn Glu His Tyr Lys Leu Asp Asn Ile Gly Ser Gly Ser Lys Gly
1040                1045                1050

Ser Ala Asp Ser Thr Lys Lys Arg Arg Val Pro Asn Gly Asn Ser
1055                1060                1065

Asp Thr Asn Val Glu Asp Asp Ala Pro Thr Lys Ser Thr Gly
1070                1075                1080

Arg Ser Lys Lys Arg Thr Val Lys Arg Gln Asn Arg Lys Gly Val
1085                1090                1095

Ile Tyr Asp Ser Pro Glu Glu Asp Tyr Phe Gln Gly Cys Pro Asp
1100                1105                1110

Glu Asp Leu Asp Phe Asp Ile Ile Glu Ile Asp Ala Leu Asp Gln
1115                1120                1125

Val Thr Cys Lys Asn Thr Ala Gly Arg Val Leu Pro Gln Trp Thr
1130                1135                1140

Ala Ser
1145                1150                1155

Ala Ser
1160

<210> SEQ ID NO 16
<211> LENGTH: 1203
<212> TYPE: PRT
<213> ORGANISM: Gossypium raimondii

<400> SEQUENCE: 16

Met Pro Asp Gln Ser Asn Ser Val Glu Ser Gln Lys Cys Tyr Asp Lys
1               5                   10                  15

Leu Pro Asn Val Asn Trp Leu Gln His Phe Asp Ala His Asp Lys Phe
            20                  25                  30

Ala Cys Gln Lys Lys Phe Leu Cys Thr Asn Phe Leu Phe Ser Leu Glu
        35                  40                  45

Gly Gln Lys Pro Gln Gly Thr Met Phe Ala Arg Leu Thr Ser Arg Gln
    50                  55                  60

```
Ile Gln Asn Ser Gln Ile Phe Gln His Thr Gln Val Glu Lys Ala Trp
 65                  70                  75                  80

Gln Ile Leu Ser Ser Leu Pro Ala Ser Cys Arg Thr Tyr Leu Lys Pro
                 85                  90                  95

Gly Thr Ser Ala Pro Val Lys Thr Ser Thr Asp Glu Ile Ser His Asn
            100                 105                 110

Arg Arg Gly Arg Ser Thr Leu Val Glu Pro Ser Gly Met Lys Arg Ser
            115                 120                 125

Glu His Met Leu Val His Pro Asn Ser Ser Glu Thr Asp Gly Lys Val
            130                 135                 140

Asn Gly Phe Gly Arg Cys Met Thr Ser Ser Phe Pro Ser Asn Asn Ala
145                 150                 155                 160

Asn Thr Met Glu Ser Gly Asn Asn Leu Arg Gly Asn Ser Gly Ile Thr
                165                 170                 175

Thr Ser Met Phe Ser His Ser Asn Ser Lys Val Ser Gly Gly Ser Leu
                180                 185                 190

Lys Asn Gln Thr Phe His Gly Val Gln Gln Gln Ser Ala Glu Val
            195                 200                 205

Leu Ala Asn Glu Ile Asp Asp Asp Leu Leu Lys Asp Ile Asp Val
            210                 215                 220

Asp Gln Ile Val Ser Glu His Tyr Gln Ser Thr Cys Thr Pro Gln Pro
225                 230                 235                 240

Ser Val Ser Lys Phe Pro Pro Ile Thr Pro Ser Val Asp Lys Asn Ala
                245                 250                 255

Phe Ala Gly Gln Glu Thr Cys Leu Pro Pro Glu Leu Cys Ser Asn Cys
            260                 265                 270

Ser His Gly Cys Lys Leu Gly His Cys Pro Glu Ala Ala Ser His Val
            275                 280                 285

Gln Glu Met Lys Asp Met Leu Ile Ala Val Ser Asn Glu Leu Leu Asp
            290                 295                 300

Asn Ala Thr Asn Leu Ser Pro Glu Gln Ile Glu Lys Leu Arg Gln Asp
305                 310                 315                 320

Arg Leu Leu Leu Asn Lys Gln Ile Gln Leu Leu Glu Lys Tyr Ile Ser
                325                 330                 335

Asp Val Glu Arg Gln Lys Ser Asn Phe Ser Ala Ser Thr Ala Thr Leu
            340                 345                 350

Ser Phe Gln Tyr Gly Thr Pro Gln Thr Thr Ser Leu Arg Pro Asn Leu
            355                 360                 365

Ile Gln Phe Asp Thr Gln Val His Ser Arg Asn Glu Pro Asn Gly Tyr
            370                 375                 380

Asp Asn Trp Asn Ser Pro Thr Val Pro Phe Ser Ser Val Asn Ser Phe
385                 390                 395                 400

Gly Val Pro Ser Gly Pro Ile Glu Arg Glu Pro Tyr Ile Pro Gln Ile
                405                 410                 415

Ile Asp Val Asn Tyr Ile Glu Gly Ser Asn Asp Gln Lys Trp Ser Ser
            420                 425                 430

Arg Asp Phe Pro Trp Thr Arg Lys Leu Glu Ala Asn Lys Lys Val
            435                 440                 445

Phe Gly Asn His Ser Phe Arg Pro Asn Gln Arg Glu Val Ile Asn Ala
            450                 455                 460

Thr Met Ser Gly Tyr Asp Val Phe Val Leu Met Pro Thr Gly Gly
465                 470                 475                 480

Lys Ser Leu Thr Tyr Gln Leu Pro Ala Leu Ile Cys Pro Gly Ile Thr
```

```
                485                 490                 495
Leu Val Ile Ser Pro Leu Val Ser Leu Ile Gln Asp Gln Ile Met His
                500                 505                 510
Leu Leu Gln Ala Asn Ile Pro Ala Ala Tyr Leu Ser Ala Asn Met Asp
                515                 520                 525
Trp Ser Glu Gln Gln Glu Ile Leu Arg Glu Leu Thr Ser Asp Tyr Cys
                530                 535                 540
Lys Tyr Lys Leu Leu Tyr Val Thr Pro Glu Lys Val Ala Arg Ser Asp
545                 550                 555                 560
Val Leu Leu Arg His Leu Asn Ile Leu Asn Ser Arg Asp Leu Leu Ala
                565                 570                 575
Arg Ile Val Ile Asp Glu Ala His Cys Val Ser Gln Trp Gly His Asp
                580                 585                 590
Phe Arg Pro Asp Tyr Gln Gly Leu Gly Ile Leu Lys Gln Lys Phe Pro
                595                 600                 605
Lys Thr Pro Val Leu Ala Leu Thr Ala Thr Ala Thr Ala Ser Val Lys
                610                 615                 620
Glu Asp Val Val Gln Ala Leu Gly Leu Ile Asn Cys Ile Ile Phe Arg
625                 630                 635                 640
Gln Ser Phe Asn Arg Pro Asn Leu Trp Tyr Ser Val Ile Pro Lys Thr
                645                 650                 655
Lys Lys Cys Val Glu Asp Ile Asp Lys Phe Ile Lys Glu Asn His Phe
                660                 665                 670
Asp Glu Cys Gly Ile Ile Tyr Cys Leu Ser Arg Met Asp Cys Glu Lys
                675                 680                 685
Val Ala Glu Lys Leu Gln Glu Tyr Gly His Lys Ala Ala Phe Tyr His
690                 695                 700
Gly Asn Met Asp Pro Ala Gln Arg Ala Phe Ile Gln Lys Gln Trp Ser
705                 710                 715                 720
Lys Asp Glu Ile Asn Ile Ile Cys Ala Thr Val Ala Phe Gly Met Gly
                725                 730                 735
Ile Asn Lys Pro Asp Val Arg Phe Val Ile His His Ser Leu Pro Lys
                740                 745                 750
Ser Ile Glu Gly Tyr His Gln Glu Cys Gly Arg Ala Gly Arg Asp Gly
                755                 760                 765
Gln Arg Ser Ser Cys Leu Leu Tyr Tyr Ser Tyr Ser Asp Tyr Ile Arg
                770                 775                 780
Val Lys His Met Ile Ser Gln Gly Ala Ala Glu Gln Ser Pro Leu Ile
785                 790                 795                 800
Thr Gly His Ser Arg Phe Asn Asn Ser Gly Arg Ile Leu Glu Thr Asn
                805                 810                 815
Thr Glu Asn Leu Leu Arg Met Val Ser Tyr Cys Glu Asn Asp Val Asp
                820                 825                 830
Cys Arg Arg Leu Leu Gln Leu Leu His Phe Gly Glu Lys Phe Asp Ser
                835                 840                 845
Thr His Cys Gln Lys Thr Cys Asp Asn Cys Cys Lys Thr Ser Cys Ser
                850                 855                 860
Val Asp Lys Asp Val Thr Asn Ile Ala Lys Gln Leu Val Glu Leu Val
865                 870                 875                 880
Lys Leu Thr Gly Gln Gln Phe Ser Ser His Ile Leu Glu Val Tyr
                885                 890                 895
Arg Gly Ser Leu Ser Gln Phe Val Lys Lys His Arg His Glu Thr Leu
                900                 905                 910
```

```
Ser Leu His Gly Val Gly Lys His Leu Ala Lys Gly Glu Ala Ser Arg
        915                 920                 925

Ile Ile His His Leu Val Val Glu Glu Tyr Leu Leu Glu Asp Val Lys
        930                 935                 940

Lys Ser Asp Ile Tyr Gly Ser Val Ser Val Leu Lys Val Asn Glu
945                 950                 955                 960

Ser Lys Val Lys Asn Leu Phe Ser Gly Arg Gln Ala Ile Ile Arg
        965                 970                 975

Phe Pro Ser Thr Val Lys Val Gly Lys Leu Ser Lys Pro Glu Val Thr
            980                 985                 990

Pro Ala Lys Gly Ser Leu Thr Thr Ser Gly Lys Leu Ser Pro Pro Arg
        995                 1000                1005

Val Asp Thr Pro Ala Gln Phe Gln Ser Ile Val Asp Leu Asn Leu
    1010                1015                1020

Ser Ala Lys Leu Tyr Ser Ala Leu Arg Met Leu Arg Thr Ile Leu
    1025                1030                1035

Val Lys Glu Ala Gly Glu Gly Val Met Ala Tyr His Ile Phe Gly
    1040                1045                1050

Asn Ala Thr Leu Gln His Ile Ser Lys Arg Val Pro Arg Thr Lys
    1055                1060                1065

Glu Glu Leu Leu Glu Ile Asn Gly Ile Gly Lys Ala Lys Ile Leu
    1070                1075                1080

Lys Tyr Gly Asp Arg Leu Leu Glu Thr Ile Glu Ala Thr Ile Lys
    1085                1090                1095

Glu His Tyr Lys Thr Asp Lys Ile Asn Ser Gly Ser Ser Asn Asp
    1100                1105                1110

Ser Asn Asp Ser Ala Lys Arg Arg Arg Asn Thr Asn Ala Asn Ile
    1115                1120                1125

Asp Asn Asp Asp Asp Phe Ser Arg Ser Thr Gly Arg Ser Lys Arg
    1130                1135                1140

Arg Thr Val Glu Arg Gln Asp Lys Asp Gly Asn Gly Asp Asn Asn
    1145                1150                1155

His Gln Tyr Pro Ala Asp Glu Asn Asp Leu Asp Phe Asp Asp Leu
    1160                1165                1170

Asp Tyr Val Tyr Asp Val Glu Ser Lys Glu Asn Arg Pro Gln Val
    1175                1180                1185

Glu Val Asn Ile Asn Gly Arg Met Leu Pro Ser Trp Pro Arg Thr
    1190                1195                1200

<210> SEQ ID NO 17
<211> LENGTH: 1230
<212> TYPE: PRT
<213> ORGANISM: Manihot esculenta

<400> SEQUENCE: 17

Met Arg Lys Asn Leu Ser Asn Ser Gly Gln Asp Asn Lys Cys Asn Glu
1               5                   10                  15

Lys Leu Pro Glu Val Asn Trp Ser Gln His Ala Asn Ala His Asp Asn
            20                  25                  30

Phe Ser Ser Gln Lys Lys Phe Leu Ser Ser Asn Phe Leu Phe Ser Leu
        35                  40                  45

Glu Gly Gln Lys Pro Cys Ile Glu Gly Ser Met Ala Met Arg Leu Thr
    50                  55                  60

Cys Cys Gln Ile Gln Ser Leu Gln Arg Leu Gln Ser Gln Glu Val Glu
```

```
                65                  70                  75                  80
Lys Ala Trp His Thr Leu Cys Thr Leu Gln Ile Ser Cys Arg Asn Tyr
                    85                  90                  95
Leu Gln Pro Gly Lys Thr Gly Pro Leu Lys Asn Ala Arg Asn Asp Ser
                100                 105                 110
Leu Gln Asp Val Gly Lys Pro Thr Leu His Ser Ser Ser Asn Arg Arg
                115                 120                 125
Lys Asp Ser Glu Asp Met His Ala Asn Gln Asn Phe Arg Asp Ser Ser
130                 135                 140
Leu Arg Asn Asn Glu Ser Thr Arg Tyr Thr Gly Asn Val Phe Pro Gln
145                 150                 155                 160
Asp Asn Ala Arg Ala Ala Glu Ala Gly Ser Asp Met Gly Arg Gln Asn
                165                 170                 175
Asn Ile Lys Gly Ser Ala Ile Asn Asn Thr Gln Ser Lys Ala Phe Val
                180                 185                 190
Gly Leu Met Ser Asn His Ile Val His Thr Lys Gln Ser Lys Glu Ser
                195                 200                 205
Pro Glu Ala Leu Ala Asp Phe Ile Asp Asp Asp Leu Leu Gly Asn
                210                 215                 220
Ile Asp Val Asp Gln Ile Val Met Glu His Tyr Gln Ser Thr Ser Thr
225                 230                 235                 240
Pro Gln Pro Ser Val Ser Lys Phe Pro Pro Ile Thr Pro Thr Ala Asp
                245                 250                 255
Lys Asn Asn Phe Met Arg Ser Glu Glu Thr Phe Leu Pro Ser Glu Leu
                260                 265                 270
Cys Gln Asn Cys Asn His Gly Phe Lys Leu Gly Leu Cys Pro Glu Ala
                275                 280                 285
Ala Asn His Leu Gln Glu Met Lys Asp Met Leu Ile Ser Val Ser Asn
                290                 295                 300
Glu Leu Leu Asp Asn Thr Ala Asn Leu Ser Pro Ala Gln Ile Glu Lys
305                 310                 315                 320
Leu Arg Gln Asp Arg Leu Gln Leu Asn Lys Gln Ile Gln Gln Leu Glu
                325                 330                 335
Lys Tyr Leu Cys Asp Gly Glu Arg Gln Asn Ser His Phe Ser Ala Ser
                340                 345                 350
Thr Ala Thr Arg Asn Phe Gln Tyr Glu Thr Pro Gln Ser Ala Ala Cys
                355                 360                 365
Arg Ile Asp Pro Pro Arg Phe Asn Ala Gln Phe Gln Leu Pro Asn Gly
                370                 375                 380
Pro Gly Gly His Glu Asn Trp Asn Leu Pro Ser Val Ser Phe Ser Ser
385                 390                 395                 400
Val Asp Arg Phe Gly Leu Ser Ser Gly Pro Val Asp Arg Glu Pro Tyr
                405                 410                 415
Ile Pro Lys Phe Ile Glu Val Asn Tyr Ile Glu Gly Ser Asn Asp Pro
                420                 425                 430
Lys Trp Ser Ser Thr Asn Phe Ser Trp Thr Lys Lys Leu Glu Ala Tyr
                435                 440                 445
Asn Lys Lys Val Phe Gly Asn His Ser Phe Arg Pro Asn Gln Arg Glu
                450                 455                 460
Val Ile Asn Ala Ser Met Ser Gly Phe Asp Val Phe Leu Met Pro
465                 470                 475                 480
Thr Gly Gly Gly Lys Ser Leu Thr Tyr Gln Leu Pro Ala Leu Ile Ser
                485                 490                 495
```

```
Pro Gly Ile Thr Leu Val Ile Ser Pro Leu Val Ser Leu Ile Gln Asp
            500                 505                 510

Gln Ile Met His Leu Leu Gln Ala Asn Ile Ser Ala Thr Tyr Leu Ser
            515                 520                 525

Ala Asn Met Asp Trp Thr Glu Gln Glu Ile Leu Arg Glu Leu Cys
            530                 535                 540

Ser Asp Tyr Cys Lys Tyr Lys Leu Leu Tyr Val Thr Pro Glu Lys Val
545                 550                 555                 560

Ala Lys Ser Asp Val Leu Leu Arg His Leu Asp Ser Leu Asn Ala Arg
            565                 570                 575

Gly Leu Leu Ala Arg Ile Val Ile Asp Glu Ala His Cys Val Ser Gln
            580                 585                 590

Trp Gly His Asp Phe Arg Pro Asp Tyr Lys Glu Leu Gly Ile Leu Lys
            595                 600                 605

Lys Lys Phe Gly Lys Thr Pro Val Leu Ala Leu Thr Ala Thr Ala Thr
            610                 615                 620

Ala Ser Val Lys Glu Asp Val Val Gln Ala Leu Gly Leu Val Asp Cys
625                 630                 635                 640

Ile Val Phe Arg Gln Ser Phe Asn Arg Pro Asn Leu Trp Tyr Ser Val
            645                 650                 655

Ile Pro Lys Thr Lys Lys Cys Leu Asp Asp Ile Asp Gln Phe Ile Lys
            660                 665                 670

Gly Asn His Phe Asp Glu Cys Gly Ile Ile Tyr Cys Leu Ser Arg Met
            675                 680                 685

Asp Cys Glu Lys Val Ala Lys Lys Leu Gln Glu Cys Gly His Lys Ala
            690                 695                 700

Ala Phe Tyr His Gly Asn Met Asp Ser Ala Gln Arg Ala Tyr Ile Gln
705                 710                 715                 720

Lys Gln Trp Ser Lys Asp Glu Ile Asn Ile Ile Cys Ala Thr Val Ala
            725                 730                 735

Phe Gly Met Gly Ile Asn Lys Pro Asp Val Arg Phe Val Ile His His
            740                 745                 750

Ser Leu Pro Lys Ser Ile Glu Gly Tyr His Gln Glu Cys Gly Arg Ala
            755                 760                 765

Gly Arg Asp Gly Gln Arg Ser Ser Cys Val Leu Tyr Tyr Ser Tyr Ser
            770                 775                 780

Asp Tyr Ile Arg Val Lys His Met Ile Ile Gln Gly Gln Ile Glu Gln
785                 790                 795                 800

Asn Pro Trp Thr Pro Gly Tyr Asn Arg Thr Asn Met Thr Asn Ser Glu
            805                 810                 815

Arg Val Leu Glu Lys Asn Thr Glu Asn Val Leu Arg Met Val Ser Tyr
            820                 825                 830

Cys Glu Asn Asp Val Asp Cys Arg Arg Leu Leu Gln Leu Leu His Phe
            835                 840                 845

Gly Glu Lys Phe Asp Ser Gly Asn Cys Lys Lys Thr Cys Asp Asn Cys
            850                 855                 860

Ser Lys Ile Lys Thr Leu Val Glu Lys Asp Val Thr Glu Ile Ala Lys
865                 870                 875                 880

Gln Leu Val Glu Leu Val Lys Leu Thr Gly Gln Gln Phe Ser Ser Ser
            885                 890                 895

His Ile Leu Glu Val Tyr Arg Gly Ser Leu Asn Gln Tyr Val Lys Arg
            900                 905                 910
```

```
Tyr Lys His Glu Thr Leu Ser Leu His Gly Ala Gly Lys His Leu Ala
            915                 920                 925

Lys Gly Glu Ala Ser Arg Ile Leu Arg His Leu Val Thr Glu Asp Phe
    930                 935                 940

Leu Val Glu Asp Val Lys Lys Ser Asp Ile Tyr Gly Ser Val Ser Ser
945                 950                 955                 960

Val Leu Lys Val Asn Glu Ser Lys Ala Tyr Asn Leu Cys Ser Ser Gly
                965                 970                 975

Gln Thr Ile Val Leu Arg Phe Pro Ala Val Lys Val Ser Lys Leu
            980                 985                 990

Ser Lys Tyr Asp Ala Thr Pro Ala Lys Gly Thr Leu Thr Tyr Gly Glu
        995                 1000                1005

Gln Ser Pro Leu Val Asp Ala Pro Ala Gln Pro Gln Ser Glu Val
        1010                1015                1020

Asp Leu Ser Leu Ser Ala Lys Leu Tyr Ser Ala Leu Arg Met Leu
        1025                1030                1035

Arg Thr Ile Leu Val Lys Glu Ala Gly Asp Gly Val Met Ala Tyr
        1040                1045                1050

His Ile Phe Gly Asn Ala Thr Leu Gln His Leu Cys Lys Arg Ile
        1055                1060                1065

Pro Arg Thr Lys Glu Glu Leu Leu Glu Ile Asn Gly Ile Gly Lys
        1070                1075                1080

Ala Lys Val Ser Lys Tyr Gly Asp Arg Leu Leu Glu Thr Ile Glu
        1085                1090                1095

Ser Thr Ile Arg Glu His His Asn Thr Asp Lys Asn Ser Ser Gly
        1100                1105                1110

Ser Asn Asp Ser Thr Asp Ser Ile Lys Arg Arg Arg Asp Ala Thr
        1115                1120                1125

Arg Ala Ala Lys Leu Asn Val Glu Glu Glu Asp Phe Thr Lys
        1130                1135                1140

Ser Thr Gly Arg Ser Lys Lys Arg Ala Ala Lys Leu Gln Asn Lys
        1145                1150                1155

Asp Thr Glu Val Tyr Asn Ala Arg Glu Thr Asp Gln Asn Gln Cys
        1160                1165                1170

Leu Asp Asp Asp Leu Asp Phe Glu Asp Ser Cys Tyr Asp His Glu
        1175                1180                1185

Thr Asn Gly Ser Ala Val Glu Ala Asp Lys Asn Gly Thr Gly Arg
        1190                1195                1200

Val Leu Pro Ser Trp Ser Thr Pro Gly Asn Lys Ile Lys Ser Ser
        1205                1210                1215

Asn His Asn Leu Phe Gln Glu Tyr Ala Met Asn Ser
        1220                1225                1230

<210> SEQ ID NO 18
<211> LENGTH: 1174
<212> TYPE: PRT
<213> ORGANISM: Oryza sativa

<400> SEQUENCE: 18

Met Ile Lys Pro Arg Val Asn Trp Ser Asp His Ala Asn Ala Val Gln
1               5                   10                  15

Ser Ser Cys Ile Lys Asp Glu Phe Leu Ser Ser Phe Leu Phe Ser
                20                  25                  30

Leu Pro Thr Gln Arg Pro Asn Gln Glu Ala Asp Cys Thr Gly Met Leu
            35                  40                  45
```

```
Pro Leu Arg Ser Ala Ala Cys Arg Ile Gln Gly Leu Glu Arg Leu Gln
    50                  55                  60

Ala Pro Ser Ile Glu Lys Ala Trp Arg Ser Leu Arg Asn Thr Gln Val
65                  70                  75                  80

Ala Arg Lys Asn Tyr Leu Arg Pro Gly Leu Ser Gly Lys Val Lys Asp
                85                  90                  95

Cys Asp Ser Asp His Ala His Thr Tyr Gly Thr Ser Ser Tyr Asn
                100                 105                 110

Val Asn Lys Met Asp Ser Val Ser Arg Asn Arg Asn Pro Thr Gln Glu
            115                 120                 125

Ser Met His Gln Thr Thr Glu Ser Gly Thr Met Glu Lys Asn Ser Ser
        130                 135                 140

His Leu Pro Ala Gly Thr Lys Ser Cys Thr Arg Thr Tyr Leu Asn Asn
145                 150                 155                 160

His Val Val Gln Ala Asp Thr Ile Thr Thr Asn Gln Ser Leu Ala
                    165                 170                 175

Arg Thr Gly Pro Glu Leu Phe Lys Thr Ala Pro Phe Ile Asp Asn Met
            180                 185                 190

Cys Asp Asp Ala Lys Leu Asp Ala Met Asp Glu Asp Leu Leu Ala
                195                 200                 205

Ser Ile Asp Val Asp Arg Ile Val Met Glu His Tyr Gln Ala Thr Asn
    210                 215                 220

Thr Pro Arg Gly Ser Ser Lys Ser Pro Leu Glu Lys Cys Asn Phe Asn
225                 230                 235                 240

Gly Phe Asp Glu Asn Asn Leu Pro Gln Glu Leu Ser Ile Met Cys Asp
                245                 250                 255

His Gly Ser Lys Leu Ala Phe Cys Pro Glu Ala Lys Ser His Leu Leu
            260                 265                 270

Glu Met Lys Asp Asn Leu Leu Ala Ile Ser His Glu Leu Ile Asp Gly
        275                 280                 285

Gln Leu Ser Pro Gln Gln Ser Asp Asp Leu His Gln Lys Arg Ala Leu
    290                 295                 300

Leu Lys Lys Gln Ile Glu Leu Leu Gly Glu Tyr Thr Ala Arg Leu Thr
305                 310                 315                 320

Gln Asp Glu Glu Arg Gln Gln Ser His Ser Met Ala Ser Thr Thr Ala
                325                 330                 335

His Gln Gly His His Pro Thr Ser Ile Leu Ser Ser Ser Phe Val Lys
            340                 345                 350

Asp Thr Asn Ile Phe Gln Ser Pro Ile Tyr Thr Arg Asn Glu Pro Gly
        355                 360                 365

Glu Ser Gly Leu Cys Phe Ser Ser Ala Pro Tyr Ser Tyr Met Asp Gly
    370                 375                 380

Leu Ser Met Pro Leu Pro Ser Val Gln Arg Asp Tyr Thr Pro Arg Ala
385                 390                 395                 400

Ile Asp Ile Ser Tyr Thr Glu Gly Ser Gly Asp Lys Gln Trp Ser Ser
                405                 410                 415

Thr His Phe Ala Trp Thr Lys Glu Leu Glu Ala Asn Asn Lys Arg Val
            420                 425                 430

Phe Gly Asn Arg Ser Phe Arg Pro Asn Gln Arg Glu Ile Ile Asn Ala
        435                 440                 445

Thr Met Ser Gly Asn Asp Val Phe Val Leu Met Pro Thr Gly Gly Gly
    450                 455                 460
```

```
Lys Ser Leu Thr Tyr Gln Leu Pro Ala Leu Ile Cys Asn Gly Val Thr
465                 470                 475                 480

Leu Val Val Ser Pro Leu Val Ser Leu Ile Gln Asp Gln Ile Met His
            485                 490                 495

Leu Leu Gln Ala Asn Ile Ser Ala Ala Tyr Leu Ser Ala Ser Met Glu
            500                 505                 510

Trp Ser Glu Gln Gln Glu Ile Leu Arg Glu Leu Met Ser Pro Thr Cys
            515                 520                 525

Thr Tyr Lys Leu Leu Tyr Val Thr Pro Glu Lys Ile Ala Lys Ser Asp
530                 535                 540

Ala Leu Leu Arg Gln Leu Glu Asn Leu Tyr Ser Arg Gly His Leu Ser
545                 550                 555                 560

Arg Ile Val Ile Asp Glu Ala His Cys Val Ser Gln Trp Gly His Asp
                565                 570                 575

Phe Arg Pro Asp Tyr Gln His Leu Gly Ile Leu Lys Gln Lys Phe Pro
                580                 585                 590

Gln Thr Pro Val Leu Ala Leu Thr Ala Thr Ala Thr Ala Ser Val Lys
            595                 600                 605

Glu Asp Val Val Gln Val Leu Gly Leu Ala Asn Cys Ile Ile Phe Arg
            610                 615                 620

Gln Ser Phe Asn Arg Pro Asn Leu Arg Tyr Phe Val Trp Pro Lys Thr
625                 630                 635                 640

Lys Lys Cys Leu Glu Asp Ile His Asn Phe Ile His Ala Asn His Asn
                645                 650                 655

Lys Glu Cys Gly Ile Ile Tyr Cys Leu Ser Arg Met Asp Cys Glu Lys
                660                 665                 670

Val Ala Ala Lys Leu Arg Glu Tyr Gly His Thr Ala Ser His Tyr His
675                 680                 685

Gly Ser Met Asp Pro Glu Asp Arg Ala Asn Ile Gln Lys Gln Trp Ser
            690                 695                 700

Lys Asp Arg Ile Asn Ile Ile Cys Ala Thr Val Ala Phe Gly Met Gly
705                 710                 715                 720

Ile Asn Lys Pro Asp Val Arg Phe Val Ile His His Ser Leu Pro Lys
                725                 730                 735

Ser Ile Glu Gly Tyr His Gln Glu Cys Gly Arg Ala Gly Arg Asp Ser
            740                 745                 750

Gln Leu Ser Thr Cys Val Leu Phe Tyr Asn Tyr Ser Asp Tyr Ile Arg
            755                 760                 765

Leu Lys His Met Val Thr Gln Gly Phe Ala Glu Gln Gly Thr Ser Ala
            770                 775                 780

Pro Arg Gly Gly Ser Ser Gln Glu Gln Ala Leu Glu Thr His Lys Glu
785                 790                 795                 800

Asn Leu Leu Arg Met Val Ser Tyr Cys Glu Asn Asp Val Asp Cys Arg
                805                 810                 815

Arg Leu Leu Gln Leu Ile His Phe Gly Glu Met Phe Asn Pro Ser Cys
            820                 825                 830

Cys Ala Lys Thr Cys Asp Asn Cys Leu Lys Glu Leu Arg Trp Val Glu
            835                 840                 845

Lys Asp Val Thr Asn Ile Ala Arg Gln Leu Val Asp Leu Val Met Met
850                 855                 860

Thr Lys Gln Thr Tyr Ser Thr His Ile Leu Glu Val Tyr Arg Gly
865                 870                 875                 880

Ser Val Asn Gln Asn Val Lys Lys His Arg His Asp Thr Leu Ser Leu
```

His Gly Ala Gly Lys His Leu Ala Lys Gly Glu Ala Ala Arg Ile Leu
            885                 890                 895

Arg His Leu Val Ile Glu Glu Ile Leu Ile Glu Asp Val Lys Lys Ser
            900                 905                 910

Glu Asn Tyr Gly Ser Val Ser Ser Val Leu Lys Thr Asn His Lys Lys
            915                 920                 925

Ser Gly Asp Leu Leu Ser Gly Lys His Asn Val Val Leu Lys Phe Pro
930                 935                 940

Thr Pro Glu Lys Ala Pro Lys Met Gly Val Leu Asp Glu Ser Ser Val
945                 950                 955                 960

Pro Arg Ile Asn Lys Thr Asn Gln Gln Ser Gln Val Asp Gly Ser Leu
            965                 970                 975

Ala Ala Glu Leu Tyr Glu Ala Leu Gln Cys Leu Arg Thr Gln Ile Met
            980                 985                 990

Asp Glu Asn Pro Gln Leu Leu Ala Tyr His Ile Phe Lys Asn Glu
            995                 1000                1005

Thr Leu Lys Glu Ile Ser Asn Arg Met Pro Arg Thr Lys Glu Glu
        1010                1015                1020

Leu Val Glu Ile Asn Gly Ile Gly Lys Asn Lys Leu Asn Lys Tyr
        1025                1030                1035

Gly Asp Arg Val Leu Ala Thr Ile Glu Asp Phe Leu Ala Arg Tyr
        1040                1045                1050

Pro Asn Ala Thr Arg Lys Ser Ser Gly Gly Ser Asn Glu His
        1055                1060                1065

Ser Glu Ala Val Lys Lys Arg Arg Gly Phe Ser Val Thr Asn Thr
        1070                1075                1080

Ser Thr Asn Cys Asp Asp Phe Glu Glu Arg Thr Val Gln Ser Lys
        1085                1090                1095

Lys Arg Ala Ala Lys Thr Arg Thr Arg Gln Glu Ile Ser Asp Ala
        1100                1105                1110

Ala Ser Ile Val Gln Asp Val Arg Tyr Ile Asp Leu Glu Leu Asp
        1115                1120                1125

Gly Cys Glu Gln Val Asn Glu Val Pro Tyr Ser Val Gln Lys Pro
        1130                1135                1140

Val Ala Ser Gly Arg Val Leu Pro Ala Trp Gln Ser Ala Arg Ile
        1145                1150                1155

Ala
        1160                1165                1170

<210> SEQ ID NO 19
<211> LENGTH: 1167
<212> TYPE: PRT
<213> ORGANISM: Phaseolus vulgaris

<400> SEQUENCE: 19

Met Cys Cys Leu Val Gly Thr Gln Met Arg Gln Gly Glu Ala Asn Ser
1               5                   10                  15

Val Arg Val Val Lys Glu Asn Asn Lys Asn Trp Leu Gln His Ala Asn
            20                  25                  30

Ala His Glu Asn Phe Ser Ser Gln Lys Phe Leu Ser Asn Phe
            35                  40                  45

Leu Leu Ser Val Pro Pro Lys Lys Pro Arg His Gln Glu Pro Asn Pro
50                  55                  60

Gly Thr Ser Gly Phe Val Phe Gln Arg Ser Glu Asn Ile Gln Val Ser

-continued

```
             65                  70                  75                  80
Gln Arg Val Gln Phe Asp Lys Ala Trp Asp Val Leu Ser Ser Leu Gln
                     85                  90                  95

Asn Ser Ser Arg Thr Tyr Ile Gln Pro Gly Lys Thr Val Lys Val Thr
                100                 105                 110

Arg Gln Ile His Glu Asn Thr Arg Thr Thr Pro Phe His Gly Gly Tyr
                115                 120                 125

Glu Asn Asp Asn Arg Thr Cys Pro Asp Val Thr Ala Ala Pro Val Val
130                 135                 140

Ser Ser His Ser Ser Arg Gly Leu Asp Gly Ser Val Asn Asn His Asn
145                 150                 155                 160

Lys Tyr Thr Gly Gln Ile Asn Glu Ser Ser Asn Cys Met Ser Gly Asp
                165                 170                 175

Ile Asp Asp Asp Asn Ile Leu Glu Asn Ile Asp Val Asp Gln Ile Val
                180                 185                 190

Glu Lys Tyr Gln Ser Thr Cys Thr Pro Lys Pro Ser Ile Ser Lys Leu
                195                 200                 205

Pro Pro Ile Thr Pro Ile Ala Asp Lys Asp Asp Phe Ala Arg Glu Gly
    210                 215                 220

Asp Asn Ala Leu Pro Pro Asp Leu Cys Leu Asp Cys Ile His Gly Tyr
225                 230                 235                 240

Lys Leu Gly Leu Cys Pro Glu Ala Ala Ile His Leu Gln Glu Leu Lys
                245                 250                 255

Asp Asn Leu Ile Ala Ile Ser Asn Glu Leu Leu Asp Asn Gly Glu Asn
                260                 265                 270

Leu Asn Ser Thr Gln Ile Ser Lys Leu Arg His Asp Arg Ser Gln Leu
                275                 280                 285

Asn Lys Gln Ile Gln Gln Leu Glu Lys Tyr Ile Gln Ser Gly Asn Leu
                290                 295                 300

Asn Glu Glu Arg Gln Lys Ser His Phe Ser Ala Ser Thr Ala Pro Ser
305                 310                 315                 320

Thr Ser Tyr Val Tyr Gly Thr Pro Gln Gln Thr Ala Pro Cys Asn Gly
                325                 330                 335

Ser Lys Arg Tyr Asp Ala Gln Ala Tyr Met Gly Asp Gly Thr Phe Gly
                340                 345                 350

Ser Ser Phe Gln Ser Leu Pro Ser Phe Ser Ile Asp Lys Tyr Ser Thr
                355                 360                 365

Leu Ser Gly Pro Val Glu Arg Glu Ala Phe Ile Pro Lys Ile Ile Glu
                370                 375                 380

Val Asn Tyr Ile Glu Gly Ser Gly Asp Lys Arg Trp Ser Ser His Asp
385                 390                 395                 400

Phe Ser Trp Thr Lys Glu Leu Glu Val Asn Asn Lys Lys Val Phe Gly
                405                 410                 415

Asn His Ser Phe Arg Pro Asn Gln Arg Glu Val Ile Asn Ala Thr Met
                420                 425                 430

Ser Gly Cys Asp Val Phe Val Leu Met Pro Thr Gly Gly Gly Lys Ser
                435                 440                 445

Leu Thr Tyr Gln Leu Pro Ala Leu Ile Cys Gln Gly Ile Thr Leu Val
                450                 455                 460

Ile Ser Pro Leu Val Ser Leu Ile Gln Asp Gln Ile Met His Leu Leu
465                 470                 475                 480

Gln Ala Asn Ile Pro Ala Thr Tyr Leu Ser Ala Asn Met Glu Trp Thr
                485                 490                 495
```

```
Glu Gln Gln Glu Ile Leu Arg Glu Leu Thr Ser Asp Tyr Cys Lys Tyr
            500                 505                 510

Lys Leu Leu Tyr Val Thr Pro Glu Lys Val Lys Ser Asp Asn Leu
        515                 520                 525

Leu Arg His Leu Glu Asn Leu His Phe Arg Glu Leu Ala Arg Ile
        530                 535                 540

Val Ile Asp Glu Ala His Cys Val Ser Gln Trp Gly His Asp Phe Arg
545                 550                 555                 560

Pro Asp Tyr Gln Gly Leu Gly Ile Leu Lys Gln Lys Phe Pro Asn Thr
                565                 570                 575

Pro Val Leu Ala Leu Thr Ala Thr Ala Ser Val Lys Glu Asp
            580                 585                 590

Val Val Gln Ala Leu Gly Leu Val Asn Cys Val Ile Phe Arg Gln Ser
        595                 600                 605

Phe Asn Arg Pro Asn Leu Trp Tyr Ser Val Val Pro Lys Thr Lys Lys
        610                 615                 620

Cys Leu Glu Asp Ile Asp Lys Phe Ile Arg Glu Asn His Phe Asp Glu
625                 630                 635                 640

Cys Gly Ile Ile Tyr Cys Leu Ser Arg Met Asp Cys Glu Lys Val Ala
                645                 650                 655

Gly Asn Leu Gln Glu Cys Gly His Lys Cys Ala Phe Tyr His Gly Ser
                660                 665                 670

Met Asp Pro Pro Gln Arg Ala Phe Val Gln Asn Gln Trp Ser Lys Asp
            675                 680                 685

Glu Ile Asn Ile Ile Cys Ala Thr Val Ala Phe Gly Met Gly Ile Asn
        690                 695                 700

Lys Pro Asp Val Arg Phe Val Ile His His Ser Leu Pro Lys Ser Ile
705                 710                 715                 720

Glu Gly Tyr His Gln Glu Cys Gly Arg Ala Gly Arg Asp Gly Gln Arg
                725                 730                 735

Ser Ser Cys Val Leu Tyr Tyr Ser Tyr Ser Asp Tyr Ile Arg Val Lys
            740                 745                 750

His Met Ile Ser Gln Gly Gly Ala Ile Glu Gln Ser Pro Leu Thr Ser
        755                 760                 765

Gly Tyr Asn Arg Ser Asn Met Ile Asn Pro Gly Ser Ile Leu Glu Thr
        770                 775                 780

Asn Thr Glu Asn Leu Met Arg Met Val Ser Tyr Cys Glu Asn Asp Val
785                 790                 795                 800

Asp Cys Arg Arg Leu Leu Gln Leu Val His Phe Gly Glu Lys Phe Asn
                805                 810                 815

Ser Ser Thr Cys His Lys Thr Cys Asp Asn Cys Leu Lys Ile Thr Asn
            820                 825                 830

Phe Ile Glu Lys Asp Val Thr Glu Ile Ala Lys Gln Leu Val Glu Leu
        835                 840                 845

Val Lys Leu Thr Gly Gln Arg Phe Ser Ser His Ile Leu Glu Val
        850                 855                 860

Tyr Arg Gly Ser Phe Ser Gln Met Val Lys Lys Asn Arg His Glu Thr
865                 870                 875                 880

Val Ser Leu His Ala Ala Gly Lys His Leu Ala Lys Gly Glu Ala Ser
                885                 890                 895

Arg Ile Leu His His Leu Val Val Glu Asp Ile Leu Val Glu Glu Val
                900                 905                 910
```

```
Lys Lys Ser Asp Phe Tyr Gly Ser Ile Ser Ile Leu Lys Val Asn
            915                 920                 925

Glu Pro Lys Val Cys Asn Leu Phe Ala Gly His Arg Ile Ile Leu Arg
        930                 935                 940

Phe Pro Ser Ser Val Lys Ala Thr Lys Pro Gly Lys Ser Asp Ala Thr
945                 950                 955                 960

Pro Ala Lys Gly Ser Leu Thr Ser Gly Lys Gln Asn Val Phe Pro Ile
            965                 970                 975

Asp Thr Pro Gln Pro Gln Thr Glu Val Asp Leu Asn Leu Ser Ala Lys
            980                 985                 990

Leu Tyr Thr Ala Leu Arg Met Leu Arg Thr Thr Leu Val Lys Glu Ala
            995                 1000                1005

Gly Asp Ser Val Phe Ala Tyr His Ile Phe Gly Asn Ala Thr Leu
    1010                1015                1020

Gln Gln Ile Ser Lys Arg Val Pro Arg Thr Lys Glu Glu Leu Leu
    1025                1030                1035

Asp Ile Asn Gly Ile Gly Lys Ala Lys Val Ser Lys Tyr Gly Asp
    1040                1045                1050

Lys Ile Leu Glu Thr Ile Glu Asn Thr Ile Asn Glu Tyr Tyr Lys
    1055                1060                1065

Leu Asp Lys Gly Ser Ser Gly Ser Lys Gly Ser Ala Asp Ser Ala
    1070                1075                1080

Lys Arg Arg Arg Asp Gly Asp Pro Asp Ala Asp Ala Asp Glu Glu
    1085                1090                1095

Ala Leu Thr Asn Ser Thr Gly Arg Ser Lys Lys Arg Thr Ile Lys
    1100                1105                1110

Arg Gln Asn Arg Lys Ala Val Ile Tyr Asp Ser Ala Asp Glu Asp
    1115                1120                1125

Tyr Phe His Gly Cys His Asp Glu Asp Leu Asp Phe Asp Leu Ile
    1130                1135                1140

Glu Ile Asp Ala Ile Asp Gln Val Thr Cys Lys Asn Gly Asp Gly
    1145                1150                1155

Arg Val Leu Pro Gln Trp Thr Thr Ser
    1160                1165

<210> SEQ ID NO 20
<211> LENGTH: 1198
<212> TYPE: PRT
<213> ORGANISM: Prunus persica

<400> SEQUENCE: 20

Met Ser Ser Met Ala Cys Arg Ile Gln Asn Ile Gly Arg Leu Pro Ser
1               5                   10                  15

Ala Gln Val Gln Lys Ala Trp His Ala Leu Ser Asn Leu Gln Ile Ser
            20                  25                  30

His Arg Asn Tyr Thr Lys Pro Gly Lys Thr Val Leu Val Lys Asp Ala
        35                  40                  45

Ser Ser Arg Tyr Cys Arg Asp Val Gly Arg Thr Ala Thr Pro Ser Ser
    50                  55                  60

Cys Asp Ile Asp Lys Ser His Thr His Met Gln Thr His Gln Tyr Ile
65                  70                  75                  80

Asn Gly Thr Asn Ser Arg Asn Ser Glu Ala Ala Thr Cys Leu Gly Asn
                85                  90                  95

Arg Phe Pro Ser Ser Asn Val Asn Val Ala Asp Val Gly Asn Phe Phe
            100                 105                 110
```

```
Gly Gly Gln Ser Gln Val Arg Ala Ser Met Val Asn Phe Asp Ser
        115                 120                 125

Arg Val Pro Gly Gly Ser Phe Ser Asn Asn Ser Val His Thr Ser Gln
130                 135                 140

Ile Lys His Ser Ala Lys Val Leu Val Asn Asp Ile Asp Asp Asp
145                 150                 155                 160

Glu Ile Leu Glu Asn Ile Asp Val Asp Gln Ile Val Glu Gln Tyr Gln
                    165                 170                 175

Ser Asn Cys Thr Pro Gln Pro Leu Ile Ser Lys Leu Pro Pro Ile Thr
            180                 185                 190

Pro Ser Ile Asp Lys Asp Ser Ile Ala Arg Gln Glu Val Thr Ser Leu
        195                 200                 205

Pro Pro Asp Leu Cys Ser Asn Cys Ile His Gly Leu Lys Ile Gly Leu
        210                 215                 220

Cys Pro Glu Ala Ala Ser His Leu Gln Glu Met Lys Asp Thr Leu Ile
225                 230                 235                 240

Thr Ile Ser Asn Glu Leu Leu Asp Asp Val Asn Asp Leu Ser Pro Thr
                245                 250                 255

Arg Ile Glu Lys Leu Arg Gln Asp Arg Leu Gln Leu Asn Lys Lys Ile
            260                 265                 270

Gln Gln Leu Glu Arg His Leu Cys Asn Asn Ser Leu Asp Glu Glu Arg
        275                 280                 285

Arg Lys Ser His Phe Ser Ala Ser Thr Ala Thr Pro Arg Pro Phe Gln
        290                 295                 300

Tyr Glu Thr Pro Gln Ala Ala Phe Arg Thr Asp Thr Met Ile Phe
305                 310                 315                 320

Asp Ser Gln Val Gln Ser His Asn Val Pro Gly Asp Tyr Glu Arg Cys
                325                 330                 335

Asn Ser Ser Ser Val Ser Phe Ser Ser Val Asp Gly Phe Gly Phe Ser
            340                 345                 350

Ser Cys Pro Val Glu Arg Glu Pro Tyr Ile Pro Lys Phe Val Glu Val
        355                 360                 365

Asn Tyr Ile Glu Gly Ser Asn Asp Asn Lys Trp Ser Ser Asn Asn Phe
        370                 375                 380

Pro Trp Thr Lys Lys Leu Glu Ala Asn Asn Lys Lys Val Phe Gly Asn
385                 390                 395                 400

His Ser Phe Arg Leu Asn Gln Arg Glu Val Ile Asn Ala Thr Met Ser
                405                 410                 415

Gly Tyr Asp Val Phe Val Leu Met Pro Thr Gly Gly Lys Ser Leu
            420                 425                 430

Thr Tyr Gln Leu Pro Ala Leu Ile Cys Pro Gly Val Thr Leu Val Ile
        435                 440                 445

Ser Pro Leu Val Ser Leu Ile Gln Asp Gln Ile Met His Leu Leu Gln
450                 455                 460

Ala Asn Ile Pro Ala Ala Tyr Leu Ser Ala Asn Met Glu Trp Thr Glu
465                 470                 475                 480

Gln Gln Glu Ile Phe Arg Glu Leu Asn Ser Glu Tyr Cys Lys Tyr Lys
                485                 490                 495

Leu Leu Tyr Val Thr Pro Glu Lys Val Ala Lys Ser Asp Val Leu Leu
            500                 505                 510

Arg Gln Leu Glu Asn Leu Asn Ala Arg Gln Leu Leu Ala Arg Ile Val
        515                 520                 525
```

```
Ile Asp Glu Ala His Cys Val Ser Gln Trp Gly His Asp Phe Arg Pro
    530                 535                 540

Asp Tyr Gln Ala Leu Gly Ile Leu Lys Gln Lys Phe Pro Asn Thr Pro
545                 550                 555                 560

Val Leu Ala Leu Thr Ala Thr Ala Thr Ala Ser Val Lys Glu Asp Val
                565                 570                 575

Val Gln Ala Leu Gly Leu Val Asn Cys Ile Val Phe Arg Gln Ser Phe
                580                 585                 590

Asn Arg Pro Asn Leu Trp Tyr Ser Val Ile Pro Lys Thr Lys Lys Cys
        595                 600                 605

Leu Asp Asp Ile Asp Lys Phe Ile Lys Glu Asn His His Asp Glu Ser
        610                 615                 620

Gly Ile Ile Tyr Cys Leu Ser Arg Met Asp Cys Glu Lys Val Ala Glu
625                 630                 635                 640

Arg Leu Gln Glu Cys Gly His Lys Ala Ala Phe Tyr His Gly Ser Met
                645                 650                 655

Asp Pro Ala Gln Arg Ala Phe Val Gln Lys Gln Trp Ser Lys Asp Glu
                660                 665                 670

Ile Asn Ile Ile Cys Ala Thr Val Ala Phe Gly Met Gly Ile Asn Lys
                675                 680                 685

Pro Asp Val Arg Phe Val Ile His His Ser Leu Pro Lys Ser Ile Glu
690                 695                 700

Gly Tyr His Gln Glu Cys Gly Arg Ala Gly Arg Asp Gly Gln Arg Ser
705                 710                 715                 720

Ser Cys Val Leu Tyr Tyr Ser Tyr Ser Asp Tyr Ile Arg Val Lys His
                725                 730                 735

Met Ile Ser Gln Gly Val Ile Glu Gln Ser Pro Leu Ala Ser Gly Tyr
                740                 745                 750

Asn Arg Thr Asn Thr Ala Asn Ser Gly Arg Val Leu Glu Thr Asn Thr
        755                 760                 765

Glu Asn Leu Leu Arg Met Val Ser Tyr Cys Glu Asn Asp Val Asp Cys
        770                 775                 780

Arg Arg Ile Leu Gln Leu Ile His Leu Gly Glu Lys Phe Asp Cys Thr
785                 790                 795                 800

Thr Cys Lys Lys Thr Cys Asp Asn Cys Leu Lys Ile Lys Ser Phe Val
                805                 810                 815

Glu Lys Asp Val Thr Gly Ile Ala Lys Gln Leu Val Glu Leu Val Lys
                820                 825                 830

Leu Thr Gly Gln Gln Phe Ser Ser His Ile Leu Glu Val Tyr Arg
        835                 840                 845

Gly Ser Phe Ser Gln Phe Val Lys Lys His Arg His Gln Thr Val Ser
850                 855                 860

Leu His Gly Val Gly Lys His Leu Ala Lys Gly Glu Ala Ser Arg Val
865                 870                 875                 880

Leu Arg His Leu Val Thr Glu Asp Leu Leu Ser Glu Glu Val Lys Lys
                885                 890                 895

Ser Asp Val Tyr Gly Ser Val Ser Ser Ile Leu Lys Arg Cys Met Gln
                900                 905                 910

Tyr Trp Gly Arg Phe Cys Ser Phe Phe Asn Thr Asn Ile Ile His
        915                 920                 925

Phe Ala Ala Asp Gly Thr Leu Asp Val Phe Tyr Val Val Phe Trp Leu
930                 935                 940

Leu Gly Ser Ser Gln Val Cys His Arg Pro Tyr Asp Cys Asp Glu His
```

```
                    945                 950                 955                 960
        Ala Cys Leu Cys Arg Ile Ile Arg Phe Pro Ser Ser Val Lys Ala Ser
                        965                 970                 975
        Lys Gln Lys Asn Ser Glu Val Ile Ser Ala Lys Gly Ser Leu Thr Ser
                        980                 985                 990
        Gly Lys Gln Ser Pro Pro His Ile Gly Thr Glu Gln Pro Gln Ser Lys
                        995                 1000                1005
        Ala Asn Leu Asp Leu Ser Thr Lys Ile Phe Thr Ser Leu Lys Met
                1010                1015                1020
        Leu Arg Thr Asn Leu Val Arg Glu Ser Asp Asp Gly Val Met Ala
                1025                1030                1035
        Tyr His Ile Phe Ala Asn Thr Thr Leu Gln Asn Met Ser Ser Arg
                1040                1045                1050
        Ile Pro Arg Thr Lys Glu Glu Leu Leu Glu Ile Asn Gly Ile Gly
                1055                1060                1065
        Lys Gly Lys Leu Ala Lys Tyr Gly Asp Arg Ile Leu Glu Thr Ile
                1070                1075                1080
        Glu Ala Ala Ile Lys Glu Tyr Tyr Lys Thr Asp Lys Asn Ser Thr
                1085                1090                1095
        Ser Ser Asn Asp Ser Asn Asp Met Lys Arg Lys Arg Asp Gly Asn
                1100                1105                1110
        Asn Asn Gly Asn Glu Asn Phe Asp Asp Asn Asp Phe Thr Lys Ser
                1115                1120                1125
        Thr Asp Arg Ser Lys Lys Lys Ala Pro Lys Arg Gln Asn Lys Thr
                1130                1135                1140
        Ile Glu Ala Tyr Ser Tyr Ala Glu Pro Asp Tyr Pro Gln Leu Ile
                1145                1150                1155
        Asp Asp Glu Leu Asp Leu Tyr Cys Tyr Asp Phe Glu Val Asn Ala
                1160                1165                1170
        Ser Asp Met Lys Thr Asn Gln Asn Ala Gly Gly Arg Val Leu Pro
                1175                1180                1185
        Gln Trp Ser Thr Pro Gly Asn Gly Arg Gln
                1190                1195

<210> SEQ ID NO 21
<211> LENGTH: 1233
<212> TYPE: PRT
<213> ORGANISM: Ricinus communis

<400> SEQUENCE: 21

Met Thr Arg Glu Asn His Met Arg Gln Asn Leu Ser Ile Ser Ala Glu
1               5                   10                  15

Gly Phe Lys Cys Asp Glu Lys Leu Pro Lys Ile Asn Trp Ser Gln His
                20                  25                  30

Asp Lys Ala His Asp Asn Phe Ser Cys Gln Lys Lys Phe Leu Ser Ser
            35                  40                  45

Asn Phe Leu Tyr Ser Leu Glu Asn Gln Lys Pro His Ser Glu Gly Val
        50                  55                  60

Met Ala Met Arg Leu Thr Cys Gln Ile Gln Ser Phe Gln Arg Leu Gln
65                  70                  75                  80

Ser Pro Gln Val Glu Lys Ala Trp His Ala Leu Ser Cys Leu Gln Ile
                85                  90                  95

Ser Cys Arg Asn Tyr Leu Gln Pro Gly Lys Thr Gly Pro Leu Lys Asn
                100                 105                 110
```

```
Ala Asn Leu Leu Gln Asp Val Gly Gln Arg Pro Thr Phe Cys Ser Ser
            115                 120                 125

Ser Asp Gly Gly Lys Tyr Ser Glu Cys Leu His Val His Gln Asn Phe
130                 135                 140

Ser Glu Ser Gly Ala Lys Asn Asn Lys Ser Glu Arg Tyr Met Gly Asn
145                 150                 155                 160

Tyr Val Pro Gln Asp Asn Ala Thr Ala Ala Glu Thr Gly Asn Gly Leu
                165                 170                 175

Gln Arg Gln Ser Gln Ile Lys Ala Ser Ala Ala Asn Asn Thr Glu Ser
            180                 185                 190

Lys Thr Phe Ser Gly Ser Phe Ser Asp His Ser Val Tyr Thr Ser His
            195                 200                 205

Asn Lys Glu Ser Ala Glu Ala Ser Thr Asp Phe Ile Asp Asp Asp Asp
210                 215                 220

Leu Leu Gly Asn Ile Asp Val Asp Gln Ile Val Met Glu His Asn Gln
225                 230                 235                 240

Ser Asn Cys Thr Pro Pro Asn Ser Lys Phe Pro Ser Ile Thr Pro Thr
                245                 250                 255

Ala Asp Lys His Asn Phe Ala Arg Ser Asp Glu Met Phe Leu Pro Thr
            260                 265                 270

Glu Leu Cys Gln Asn Cys Asn His Gly Phe Lys Leu Gly Leu Cys Pro
            275                 280                 285

Glu Ala Gly Asn His Leu Gln Glu Met Lys Asp Met Leu Ile Ala Val
            290                 295                 300

Ser Asn Glu Leu Leu Asp Asn Ser Thr Asn Leu Ser Ser Val Gln Ile
305                 310                 315                 320

Glu Lys Leu Arg Gln Asp Arg Leu Gln Leu Asn Lys Gln Ile Gln Gln
                325                 330                 335

Leu Glu Ser Tyr Leu Arg Asp Lys Glu Arg Gln Lys Ser His Phe Ser
            340                 345                 350

Ala Ser Thr Ala Asn Gln Asn Phe Gln Tyr Glu Thr Pro Gln Cys Ala
            355                 360                 365

Ala Asn Lys Ile Asp Pro Met Arg Phe Asp Ala Gln Val Tyr Leu Arg
370                 375                 380

Asn Glu Ser Gly Gly Tyr Glu Ser Trp Asn Thr Pro Ser Ile Ser Phe
385                 390                 395                 400

Ser Ser Val Asp Arg Phe Gly Ile Ser Ser Gly Pro Ile Glu Arg Glu
                405                 410                 415

Pro Tyr Ile Pro Lys Phe Val Glu Val Asn Tyr Ile Glu Gly Ser Asn
            420                 425                 430

Asp Pro Lys Trp Ser Ser Thr Asn Phe Pro Trp Thr Thr Lys Leu Glu
            435                 440                 445

Ala Tyr Asn Lys Lys Val Phe Gly Asn His Ser Phe Arg Pro Asn Gln
450                 455                 460

Arg Glu Val Ile Asn Ala Thr Met Ser Gly Phe Asp Val Phe Val Leu
465                 470                 475                 480

Met Pro Thr Gly Gly Gly Lys Ser Leu Thr Tyr Gln Leu Pro Ala Leu
                485                 490                 495

Val Cys Pro Gly Ile Thr Leu Val Ile Ser Pro Leu Val Ser Leu Ile
            500                 505                 510

Gln Asp Gln Ile Met His Leu Leu Gln Ala Asn Ile Ser Ala Ala Tyr
            515                 520                 525

Leu Ser Ala Asn Met Glu Trp Ala Glu Gln Gln Glu Ile Leu Arg Glu
```

```
            530                 535                 540
Leu Ser Ser Asp Tyr Cys Lys Tyr Lys Leu Leu Tyr Val Thr Pro Glu
545                 550                 555                 560

Lys Val Ala Lys Ser Asp Val Leu Leu Arg Asn Leu Glu Ser Leu Asn
                565                 570                 575

Ala Arg Gly Leu Leu Ala Arg Ile Val Ile Asp Glu Ala His Cys Val
            580                 585                 590

Ser Gln Trp Gly His Asp Phe Arg Pro Asp Tyr Lys Glu Leu Gly Ile
        595                 600                 605

Leu Lys Lys Lys Phe Glu Lys Thr Pro Val Leu Ala Leu Thr Ala Thr
    610                 615                 620

Ala Thr Ala Ser Val Lys Glu Asp Val Val Gln Ala Leu Gly Leu Val
625                 630                 635                 640

Asp Cys Ile Ile Phe Arg Gln Ser Phe Asn Arg Pro Asn Leu Trp Tyr
                645                 650                 655

Ser Val Val Pro Lys Thr Lys Lys Cys Leu Asp Asp Ile Asp Lys Phe
            660                 665                 670

Ile Lys Glu Asn His Phe Asp Glu Cys Gly Ile Ile Tyr Cys Leu Ser
        675                 680                 685

Arg Met Asp Cys Glu Lys Val Ala Glu Lys Leu Gln Glu Cys Gly His
    690                 695                 700

Lys Ala Ala Phe Tyr His Gly Asn Met Asp Ala Ala Gln Arg Ala Phe
705                 710                 715                 720

Val Gln Lys Gln Trp Ser Lys Asp Glu Ile Asn Ile Ile Cys Ala Thr
                725                 730                 735

Val Ala Phe Gly Met Gly Ile Asn Lys Pro Asp Val Arg Phe Val Ile
            740                 745                 750

His His Ser Leu Pro Lys Ser Ile Glu Gly Tyr His Gln Glu Cys Gly
        755                 760                 765

Arg Ala Gly Arg Asp Gly Leu Arg Ser Cys Val Leu Tyr Tyr Ser
    770                 775                 780

Tyr Ser Asp Tyr Ile Arg Val Lys His Met Ile Val Gln Gly Gln Ile
785                 790                 795                 800

Glu Gln Ser Pro Trp Thr Pro Gly Tyr Asn Arg Ile Asn Asn Thr Asn
                805                 810                 815

Ser Asp Arg Ile Leu Glu Lys Asn Thr Glu Asn Leu Leu Arg Met Val
            820                 825                 830

Ser Tyr Cys Glu Asn Asp Val Asp Cys Arg Arg Ile Leu Gln Leu Leu
        835                 840                 845

His Phe Gly Glu Lys Phe Asn Ser Gly Asn Cys Lys Lys Thr Cys Asp
    850                 855                 860

Asn Cys Ser Gln Ile Lys Ala Leu Val Glu Lys Asp Val Thr Glu Thr
865                 870                 875                 880

Ala Lys Gln Leu Val Gln Leu Val Lys Leu Thr Gly Gln Gln Phe Ser
                885                 890                 895

Ser Ser His Ile Leu Glu Val Tyr Arg Gly Ser Leu Asn Gln Tyr Val
            900                 905                 910

Lys Lys Tyr Arg His Glu Thr Leu Ser Leu His Gly Ala Gly Lys His
        915                 920                 925

Leu Ser Lys Gly Glu Ala Ser Arg Ile Leu Arg His Leu Val Thr Asp
    930                 935                 940

Asp Phe Leu Gln Glu Asp Val Lys Lys Ser Asp Val Tyr Gly Ser Val
945                 950                 955                 960
```

```
Ser Ser Ile Leu Lys Val Asn Glu Ser Lys Ala Tyr Asn Leu Cys Ser
            965                 970                 975

Gly Gly Gln Thr Ile Ile Leu Arg Phe Pro Ser Thr Met Lys Ala Ser
        980                 985                 990

Lys Pro Ser Lys Phe Asp Ala Thr Pro Ala Lys Gly Ser Leu Thr Ser
        995                 1000                1005

Gly Lys Gln Ser Pro Pro Glu Val Asp Ser Pro Ala Gln Ala Gln
    1010                1015                1020

Pro Glu Val Asp Leu His Leu Ser Ala Ile Leu Tyr Ser Ala Leu
    1025                1030                1035

Arg Met Leu Arg Thr Leu Leu Val Lys Glu Ala Gly Glu Gly Val
    1040                1045                1050

Met Ala Tyr His Ile Phe Gly Asn Ala Thr Leu Gln His Leu Ser
    1055                1060                1065

Lys Arg Ile Pro Arg Thr Lys Glu Glu Leu Leu Glu Ile Asn Gly
    1070                1075                1080

Ile Gly Lys Ala Lys Val Ser Lys Tyr Gly Asp Arg Leu Leu Glu
    1085                1090                1095

Thr Ile Glu Ser Thr Ile Lys Glu Tyr Tyr Lys Thr Asp Lys Asn
    1100                1105                1110

Ser Ser Ser Ser Asn Gly Ser Asn Asp Ser Val Lys Arg Arg Arg
    1115                1120                1125

Asp Ala Ser Arg Ala Pro Asn Gly Asn Ala Glu Glu Ala Asp Asp
    1130                1135                1140

Phe Thr Lys Ser Thr Gly Arg Ser Lys Lys Arg Val Ala Lys Leu
    1145                1150                1155

Gln Asn Lys Asp Thr Asp Ile Tyr Thr Ser Arg Glu Thr Asn Asn
    1160                1165                1170

Ser Gln Cys Leu Asp Asp Asp Leu Asp Phe Glu Asp Ser Cys His
    1175                1180                1185

Asp Phe Glu Thr Asn Gly Ser Ala Ile Glu Ala Gly Lys Asn Asp
    1190                1195                1200

Ala Gly Arg Val Leu Pro Ser Trp Ser Thr Pro Gly Asn Lys Val
    1205                1210                1215

Lys Ser Ser Ile Pro Asn Leu Tyr Gln Gln Tyr Ala Thr Lys Ser
    1220                1225                1230

<210> SEQ ID NO 22
<211> LENGTH: 1154
<212> TYPE: PRT
<213> ORGANISM: Sorghum bicolor

<400> SEQUENCE: 22

Met Gln Ala Asn Lys Ser Pro Arg Val Asn Trp Pro Gln His Glu Asn
1               5                   10                  15

Ala Val Gln Gly Phe Ser Ser Arg Asp Gly Phe Leu Ser Ser Phe
            20                  25                  30

Leu Phe Ser Leu Pro Thr Gln Lys Pro Ser Pro Glu Ala Pro Glu Ser
        35                  40                  45

Met Leu Ser Leu Arg Ser Ser Ala Cys Lys Ile Gln Gly Ser Glu Arg
    50                  55                  60

Phe His Ala Pro Leu Ile Glu Lys Ala Trp Arg Ser Leu Cys Asn Thr
65                  70                  75                  80

Gln Ala Ala Arg Lys Ser Tyr Leu Arg Pro Gly Leu Ser Ala Lys Val
```

```
                      85                  90                  95
Lys Asp Cys Asp Arg Gly His Ala Arg Thr Cys Gly Glu Gly Ser Tyr
            100                 105                 110

Asn Thr Asn Lys Met Ala Thr Val Ser Gly Asn Arg Met Pro Ser Val
            115                 120                 125

Glu Ser Thr Ser Gln Pro Thr Glu Arg Ile Ser Leu Gln Asn Asn Ser
            130                 135                 140

Ser His Gln Pro Val Gly Ile Ser Ser Met Arg Ser Tyr Gln Ser
145                 150                 155                 160

Asn His Val Ala Gln Glu Asp Thr Arg Ala Thr Asn Gln Tyr Asn Phe
            165                 170                 175

Ala Arg Thr Asp Ala Ala Leu His Gln Ser Ala Pro Val Ala Asp Asn
            180                 185                 190

Met Cys Thr Tyr Asp Asn Tyr Asp Ala Met Asp Asp Ile Leu Ala
            195                 200                 205

Ser Ile Asp Val Asp Arg Ile Val Met Glu His Tyr Gln Ala Thr Pro
            210                 215                 220

Arg Gly Ser Ser His Asn Met Ser Thr Pro Pro Gly Asn Lys Cys Ser
225                 230                 235                 240

Phe Asn Gly Met Asp Glu Ala Asn Leu Pro Arg Glu Leu Ser Glu Leu
            245                 250                 255

Cys Ser His Gln Cys Lys Leu Ala Phe Cys Arg Glu Ala Met Thr His
            260                 265                 270

Leu Gln Glu Met Lys Asp Glu Leu Leu Ala Val Ala Asn Glu Leu Leu
            275                 280                 285

Asp Asp Asp Gly Glu Leu Asn Pro Gln His Ser Gln Glu Leu His Gln
            290                 295                 300

Arg Arg Leu His Leu Lys Lys Leu Val Gln Leu Leu Glu Asp His Met
305                 310                 315                 320

Thr Arg Ser Ala Gln Asp Glu Glu Arg Gln Ile Ser His Ser Met Ala
            325                 330                 335

Ser Thr Lys Ala Thr Gln Gln His Leu Pro Pro Met Thr Pro Gly Ser
            340                 345                 350

Thr Phe Ile Thr Asp Ser Asn Arg Phe Gln Ser Gln Val Tyr Ile Gly
            355                 360                 365

Asn Gly Pro Arg Asp Ser Asp Leu Cys Tyr Ser Ser Ala Pro Tyr Ser
            370                 375                 380

Cys Ser Asp Asn Leu Ser Thr Pro Leu Asn Ser Val Trp Lys Ser Tyr
385                 390                 395                 400

Thr Pro Lys Val Ile Asp Ile Asn Tyr Thr Glu Gly Ser Gly Asp Arg
            405                 410                 415

Lys Trp Ser Ser Thr Asn Phe Pro Trp Thr Lys Asp Leu Glu Ala Lys
            420                 425                 430

Asn Arg Asn Lys Phe Gly Asn Arg Ser Phe Arg Pro Asn Gln Arg Glu
            435                 440                 445

Ile Ile Asn Ala Thr Met Ser Gly Tyr Asp Val Phe Val Leu Met Pro
450                 455                 460

Thr Gly Gly Gly Lys Ser Leu Thr Tyr Gln Leu Pro Ala Leu Ile Ser
465                 470                 475                 480

Val Gly Leu Thr Leu Val Val Cys Pro Leu Val Ser Leu Ile Gln Asp
            485                 490                 495

Gln Ile Met His Leu Ser Gln Ala Asn Ile Pro Ala Thr Tyr Leu Ser
            500                 505                 510
```

-continued

```
Gly Asn Leu Asp Trp Ser Glu Gln Glu Ile Met Arg Asp Leu Lys
            515                 520                 525

Ser Cys Arg Tyr Lys Leu Leu Tyr Val Thr Pro Glu Lys Ile Ala Arg
    530                 535                 540

Ser Gly Ala Leu Ser Gly Leu Leu Arg Asp Leu Asp Ser Gln Gly His
545                 550                 555                 560

Leu Ser Arg Ile Val Ile Asp Glu Ala His Cys Val Ser Gln Trp Gly
                565                 570                 575

His Asp Phe Arg Pro Asp Tyr Lys Glu Leu Gly Val Leu Lys Gln Asn
            580                 585                 590

Phe Pro Lys Thr Pro Val Leu Ala Leu Thr Ala Thr Ala Thr Ala Arg
        595                 600                 605

Val Lys Glu Asp Val Val Gln Ala Leu Ala Leu Glu Asn Cys Ile Val
    610                 615                 620

Phe Lys Gln Ser Phe Asn Arg Pro Asn Leu Arg Tyr Tyr Leu Arg Pro
625                 630                 635                 640

Lys Thr Lys Lys Cys Val Glu Asp Ile Asp Met Phe Ile Arg Glu Asn
                645                 650                 655

His Tyr Lys Glu Cys Gly Ile Ile Tyr Cys Leu Ser Arg Met Asp Cys
            660                 665                 670

Glu Lys Val Ser Glu Lys Leu Arg Glu Cys Gly His Thr Val Ala His
        675                 680                 685

Tyr His Gly Ser Met Asp Pro Val Asn Arg Thr Arg Ile Gln Glu Asp
    690                 695                 700

Trp Ser Lys Asp Lys Ile Asn Ile Ile Cys Ala Thr Ile Ala Phe Gly
705                 710                 715                 720

Met Gly Asn Leu Ile Phe Gln Thr Pro Val Tyr Val Thr Ser Ile Ile
                725                 730                 735

Gly Cys Ser Ile Leu Ile Gly Gln Thr Val Gly Ile Asn Lys Pro Asp
            740                 745                 750

Val Arg Phe Val Ile His His Ser Leu Pro Lys Ser Ile Glu Gly Tyr
        755                 760                 765

His Gln Glu Cys Gly Arg Ala Gly Arg Asp Gly Gln Pro Ser Ser Cys
    770                 775                 780

Leu Leu Tyr Tyr Gln Tyr Ser Asp Tyr Val Ser Tyr Cys Glu Asn Asp
785                 790                 795                 800

Val Asp Cys Arg Arg Leu Leu Gln Leu Ile His Phe Gly Glu Arg Phe
                805                 810                 815

Asp Pro Ser Leu Cys Ala Lys Thr Cys Asp Asn Cys Leu Lys Glu Ser
            820                 825                 830

Gly Trp Val Glu Lys Asp Val Thr Asn Ile Ala Arg Gln Leu Val Asp
        835                 840                 845

Leu Val Thr Met Thr Gly His Ser Asn Ser Ser Thr His Ile Leu Glu
    850                 855                 860

Val Tyr Arg Gly Ser Val Ser Gln Asn Val Lys Lys Gln Arg His Asp
865                 870                 875                 880

Ala Leu Pro Leu His Gly Ala Gly Lys His Leu Ala Lys Gly Glu Ala
                885                 890                 895

Ala Arg Ile Met Arg His Leu Val Thr Glu Glu Ile Leu Ile Glu Asp
            900                 905                 910

Val Lys Lys Ser Asp Met Phe Pro Ala Pro Gly Lys Ala Ser Lys Met
        915                 920                 925
```

```
Gly Asn Leu Asp Thr Ser Leu Phe Pro Gln Ile Asn Lys Thr Val Gln
            930                 935                 940

Gln Gln Ser Glu Val Asp Glu Lys Leu Ala Ser Ile Leu Tyr Glu Ala
945                 950                 955                 960

Leu Leu Thr Leu Arg Arg Gln Ile Met Glu Glu Cys Ser Glu Gly Cys
                965                 970                 975

His Ala Tyr His Ile Phe Lys Thr Asp Thr Leu Lys Glu Met Ser Ile
            980                 985                 990

Arg Val Pro Arg Thr Lys Glu Leu Leu Asp Ile Asn Gly Ile Gly
        995                 1000                1005

Lys Thr Lys Leu Lys Lys Tyr Gly Asp Arg Val Leu Ala Thr Ile
    1010                1015                1020

Glu Asp Phe Leu Ser Lys His Pro Asn Pro Arg Arg Asn Ile Ser
    1025                1030                1035

Gly Ser Gly Gly Lys Glu His Ser Glu Ala Ala Lys Lys Arg Arg
    1040                1045                1050

Gly Ser Thr Ala Ser Ser Ala Val Ser Cys Gly Asp Asp Asp Phe
    1055                1060                1065

Glu Glu Pro Thr Gly Gln Ser Lys Lys Arg Ala Ala Lys Thr Arg
    1070                1075                1080

Thr Val Ser Asp Ala Ala Ser Met Val His Gly Ala Arg Cys Ile
    1085                1090                1095

Asp Ala Asp Leu Asp Gly Pro Glu Val Val Asp Val Asp Glu His
    1100                1105                1110

Cys Ser Val Pro Lys Pro Val Ala Ser Gly Arg Val Leu Pro Lys
    1115                1120                1125

Trp Ala Pro Ala Lys Ala Lys Ser Lys Gly Ser Ser Val Pro Pro
    1130                1135                1140

Ser Asn Leu Phe His Glu Phe Gly Tyr Ala Lys
    1145                1150

<210> SEQ ID NO 23
<211> LENGTH: 1166
<212> TYPE: PRT
<213> ORGANISM: Setaria italica

<400> SEQUENCE: 23

Met Gln Ala Asn Asn Pro Pro Arg Val Asn Trp Gln His His Ala
1               5                   10                  15

Asn Ala Ile Glu Gly Ser Ser Ser Lys Asp Asp Phe Leu Ser Ser Ser
            20                  25                  30

Phe Leu Phe Ser Leu Pro Thr Gln Arg Pro Asn Pro Glu Ala Asn Arg
        35                  40                  45

Glu Gly Met Leu Ser Leu Arg Ser Ser Ala Cys Lys Ile Gln Gly Thr
    50                  55                  60

Glu Arg Leu Gln Val Pro Trp Ile Glu Lys Ala Trp Arg Ser Leu Cys
65                  70                  75                  80

Asn Thr Gln Val Ala Cys Arg Ser Tyr Leu Arg Pro Gly Leu Ser Ala
                85                  90                  95

Lys Val Lys Asp Cys Asp Lys Gly His Ala Arg Ile Tyr Gly Glu Gly
            100                 105                 110

Ser Tyr Asn Ile Asn Lys Met Glu Thr Val Pro Gly Asn Arg Ile Leu
        115                 120                 125

Ser Gln Glu Ser Thr His Arg Pro Cys Glu Ser Gly Ser Val Glu Asn
    130                 135                 140
```

-continued

```
Asn Ser Ile His Gln Pro Thr Gly Ile Asp Ser Ser Thr Arg Thr Tyr
145                 150                 155                 160

Gln Ser Asn His Val Val Gln Thr Asp Ile Met Arg Ala Arg Asn Gln
            165                 170                 175

Tyr Asn Tyr Val Arg Thr Asp Ala Gly Leu His Gln Ala Ala Pro Val
        180                 185                 190

Ala Asp Ser Met Cys Thr Asp Lys Leu Asp Ala Met Asp Asp Asp
    195                 200                 205

Asp Ile Leu Ala Ser Ile Asp Val Asp Arg Ile Val Met Glu His Tyr
        210                 215                 220

Gln Ala Met Asn Thr Pro Arg Gly Ser Ala Ser Gln Asn Thr Ser Thr
225                 230                 235                 240

Pro Pro Gly Asn Lys Cys Asn Phe Asn Gly Ile Asp Glu Thr Asn Leu
            245                 250                 255

Pro Gln Glu Leu Ser Glu Leu Cys Asn His Gln Cys Lys Leu Ala Phe
        260                 265                 270

Cys Pro Lys Ala Met Asp His Leu Gln Glu Met Lys Asn Glu Met Ile
    275                 280                 285

Ala Val Ala Asp Glu Leu Leu Asp Asp Asp Gly Lys Leu Asn Leu Gln
        290                 295                 300

Arg Ser Glu Glu Leu Arg Lys Lys Arg Leu His Leu Lys Lys Gln Ile
305                 310                 315                 320

Gln Leu Leu Glu Glu Tyr Met Ala Arg Ser Ser Gln Asp Glu Glu Arg
            325                 330                 335

Gln Arg Ser His Ser Met Ala Ser Thr Ala Ala Ile Gln Gly His Leu
        340                 345                 350

Pro Pro Met Thr Pro Gly Ser Thr Phe Met Met Asp Ser Ser Arg Phe
    355                 360                 365

Gln Ser Gln Val Tyr Ile Arg Asn Gly Pro Gly Asn Ser Asp Leu Cys
        370                 375                 380

Tyr Ser Pro Ala Pro Tyr Ser Cys Ser Asp Asn Leu Ser Met Pro Leu
385                 390                 395                 400

His Ser Val Trp Arg Glu Tyr Thr Pro Lys Val Ile Asp Thr Asn Tyr
            405                 410                 415

Thr Glu Gly Ser Ala Asp Lys Arg Trp Ser Ser Thr Asn Phe Pro Trp
        420                 425                 430

Thr Lys Glu Leu Glu Ala Lys Asn Arg Asn Lys Phe Gly Asn Arg Ser
    435                 440                 445

Phe Arg Pro Asn Gln Arg Glu Val Ile Asn Ala Thr Met Ser Gly Asn
        450                 455                 460

Asp Val Phe Val Leu Met Pro Thr Gly Gly Lys Ser Leu Thr Tyr
465                 470                 475                 480

Gln Leu Pro Ala Leu Ile Ser Glu Gly Leu Thr Leu Val Val Cys Pro
            485                 490                 495

Leu Val Ser Leu Ile Gln Asp Gln Ile Met His Leu Ser Gln Ala Asn
        500                 505                 510

Ile Pro Ala Thr Tyr Leu Ser Ala Ser Met Glu Trp Pro Glu Gln Gln
    515                 520                 525

Glu Ile Leu Arg Gly Leu Met Ser Cys His Tyr Lys Leu Leu Tyr Val
        530                 535                 540

Thr Pro Glu Lys Ile Ala Lys Ser Asn Ser Leu Thr Gly Leu Leu Asp
545                 550                 555                 560
```

```
Asn Leu Tyr Ser Gln Gly His Leu Ser Arg Ile Val Ile Asp Glu Ala
                565                 570                 575
His Cys Val Ser Gln Trp Gly His Asp Phe Arg Pro Asp Tyr Lys Asn
            580                 585                 590
Leu Gly Val Leu Lys Gln Asn Phe Pro Lys Thr Pro Val Leu Ala Leu
        595                 600                 605
Thr Ala Thr Ala Thr Ala Arg Val Lys Glu Asp Val Gln Ala Leu
610                 615                 620
Gly Leu Ala Asn Cys Ile Val Phe Arg Gln Ser Phe Asn Arg Pro Asn
625                 630                 635                 640
Leu Arg Tyr Leu Leu Arg Pro Lys Thr Lys Lys Cys Leu Glu Asp Ile
                645                 650                 655
Asp Asn Phe Ile Arg Thr Asn His Phe Lys Glu Cys Gly Ile Ile Tyr
            660                 665                 670
Cys Leu Ser Arg Met Asp Cys Glu Lys Val Ala Glu Lys Leu Arg Glu
        675                 680                 685
Cys Gly His Ser Val Ser His Tyr His Gly Ser Met Asp Pro Val Asp
    690                 695                 700
Arg Thr Arg Val Gln Lys Gln Trp Ser Lys Asp Lys Ile Asn Ile Ile
705                 710                 715                 720
Cys Ala Thr Val Ala Phe Gly Met Gly Asn Leu Ile Phe Gln Thr Ser
                725                 730                 735
Val Cys Ile Thr Ser Ile Val Gly Cys Pro Met Leu Met Glu Cys Gly
            740                 745                 750
Arg Ala Gly Arg Asp Gly Leu Pro Ser Ser Cys Leu Leu Tyr Tyr Gln
        755                 760                 765
Tyr Ser Asp Tyr Val Ser Tyr Cys Glu Asn Asp Val Asp Cys Arg Arg
    770                 775                 780
Leu Leu Gln Leu Ile His Phe Gly Glu Met Phe Asp Pro Ser Arg Cys
785                 790                 795                 800
Ala Lys Thr Cys Asp Asn Cys Leu Lys Glu Leu Thr Trp Val Glu Lys
                805                 810                 815
Asp Val Thr Asn Ile Ala Arg Gln Met Val Glu Leu Val Thr Met Thr
            820                 825                 830
Gly Gln Ser His Ser Ser His Ile Leu Glu Val Tyr Arg Gly Ser
        835                 840                 845
Val Ser Gln Asn Val Lys Lys Gln Arg His Asp Ala Leu Pro Leu His
    850                 855                 860
Gly Ala Gly Lys His Leu Ala Lys Gly Asp Ala Arg Ile Met Arg
865                 870                 875                 880
His Leu Val Thr Glu Gly Ile Leu Ile Glu Asp Val Lys Lys Ile Asp
                885                 890                 895
Arg His Ile Phe Leu Ser Glu Asn Asp Leu Leu Val Leu Phe Phe
            900                 905                 910
Leu Tyr Leu Gly Ile His Leu Phe Leu Ile Cys Tyr Leu Leu Phe Asn
        915                 920                 925
Glu Lys Phe Pro Ala Pro Asp Lys Ala Ser Lys Met Gly Lys Leu Asp
    930                 935                 940
Ala Ser Leu Phe Pro Gln Ile Asn Lys Thr Val Gln Gln Ser Glu
945                 950                 955                 960
Val Asp Glu Asn Leu Ser Ser Met Leu Phe Asp Ala Leu Leu Ser Leu
                965                 970                 975
Arg Glu Gln Ile Met Asp Glu Cys Asn Glu Gly Tyr His Ala Tyr His
```

```
                      980                 985                  990
Ile Phe Lys Lys Asp Ser Leu Lys  Glu Met Ser Ile Arg  Val Pro Arg
            995                 1000                 1005

Thr Lys Glu Glu Leu Leu Glu  Ile Asn Gly Ile Gly  Lys Ala Lys
        1010                 1015                 1020

Val Lys Lys Tyr Gly Asp Arg  Val Leu Ala Thr Ile  Glu Asp Phe
        1025                 1030                 1035

Leu Ser Lys His Pro Asn Pro  Arg Arg Asn Ser Ser  Gly Ser Gly
        1040                 1045                 1050

Ser Asn Glu His Thr Glu Ala  Lys Lys Arg Arg Gly  Phe Thr Ala
        1055                 1060                 1065

Ser Tyr Ala Gly Ser Ile Ala  Asp Asp Phe Glu  Glu Arg Thr
        1070                 1075                 1080

Ala Gln Ser Lys Lys Arg Ala  Ala Lys Thr Arg Ser  Thr Lys Gln
        1085                 1090                 1095

Gly Val Ser Asp Ala Thr Ser  Met Val His Gly Ala  Arg Cys Met
        1100                 1105                 1110

Asp Ala Asp Leu Asp Gly Val  Glu Val Leu Asp  Glu Leu Cys
        1115                 1120                 1125

Ser Ile Gln Lys Pro Val Ala  Ser Gly Arg Val Leu  Pro Lys Trp
        1130                 1135                 1140

Ala Pro Ala Lys Ala Lys Gly  Ser Ser Val Pro Pro  Ser Asn Leu
        1145                 1150                 1155

Phe Gln Glu Phe Gly Tyr Val  Lys
        1160                 1165

<210> SEQ ID NO 24
<211> LENGTH: 1180
<212> TYPE: PRT
<213> ORGANISM: Solanum lycopersicum

<400> SEQUENCE: 24

Met Ser Lys Asp Lys Leu Pro Lys Ala Asn Trp Thr Gln His Ala Ile
1               5                   10                  15

Ala His Asp Asn Phe Ser Cys Gln Asp Lys Phe Leu Ser Ser Asn Ile
            20                  25                  30

Leu Phe Ser Leu Pro Thr Gln Arg His Cys Ala Arg Asp Glu Met Asn
        35                  40                  45

Ala Arg Ser Val Thr Cys His Ile Arg Ser Val Ser Lys Leu Glu Ala
    50                  55                  60

Glu Lys Ala Trp Lys Leu Leu Thr Ser Leu Lys Leu Ser Pro Lys Ser
65                  70                  75                  80

Tyr Thr Arg Pro Gly Lys Thr Pro Gln Leu Thr Lys Asp Thr Asn Ala
                85                  90                  95

Phe Ser Gln His Ser Asn His Thr Gln Phe Pro Arg Ala Ser Asp Gly
            100                 105                 110

Asn Cys Ala Pro Ala Arg Cys Arg Pro Val His Gln Val Gly Asp
        115                 120                 125

Asp Gly Glu Asn Ser Asp Ser Arg Arg Tyr Ala Gly Asn Cys Phe Pro
    130                 135                 140

Pro His Ser Ser Gly Val Ala Glu Thr Gly Asn Val Asn Arg Gln
145                 150                 155                 160

Ser Gly Val Asp Asn Ser His Ala Arg Gly Val Gly Glu Ile Ser Ser
                165                 170                 175
```

-continued

```
Ser His Ala Asn Gly Ala Ser Lys Lys Thr Arg Glu Val Tyr Thr Thr
                180                 185                 190

Cys Ala Asp Glu Thr Glu Glu Asp Ile Leu Leu Asn Ile Asp Val
        195                 200                 205

Asp Gln Ile Val Glu His Tyr Gln Thr Asn Cys Thr Pro Gln Pro Ser
        210                 215                 220

Val Ser Arg Phe Pro Ser Thr Thr Pro Val Thr Lys Ser Gln Ser Leu
225                 230                 235                 240

Ala Gly His Glu Glu Thr Asn Leu Pro Pro Glu Leu Ser Ile Asn Cys
                245                 250                 255

Asn His Gly Leu Gln Leu Gly Leu Cys Pro Gly Ala Leu Asp His Leu
                260                 265                 270

Gln Glu Met Lys Asp Lys Leu Ile Glu Ile Ser Asn Asp Leu Leu Asp
                275                 280                 285

Asn Val Ser Asp Leu Ser Ser Glu Gln Ile Glu Met Leu Arg Gln Glu
                290                 295                 300

Arg Ser Gln Leu Lys Leu Gln Ile Gln His Leu Glu Lys Phe Leu Gln
305                 310                 315                 320

Thr Val Ser Gly Asn Glu Glu Arg Lys Met Ser Gln Cys Ser Ala Ser
                325                 330                 335

Thr Leu Thr Ser Ala Phe Gln Tyr Glu Thr Pro Ser Ala Phe Gln Tyr
                340                 345                 350

Ala Thr Pro Ser Ser Phe Pro Ser Arg Ile Asn Pro Thr Arg Leu Asp
                355                 360                 365

Thr Gln Phe Ser Gly Tyr Asn Glu Ser Ser His Phe Asp Asn Trp Asn
                370                 375                 380

Ser Ser Ser Leu Ser Phe Asp Val Thr Gly Gly Asn Gly Leu Ser Thr
385                 390                 395                 400

Ala Pro Val Glu Arg Glu Pro Tyr Ile Pro Lys Tyr Leu Glu Val Asn
                405                 410                 415

Tyr Ile Asp Gly Ser Asn Asp Lys Lys Trp Ser Cys Arg Asp Phe Pro
                420                 425                 430

Trp Thr Lys Lys Leu Glu Ala Asn Asn Lys Lys Val Phe Gly Asn His
                435                 440                 445

Ser Phe Arg Pro Asn Gln Arg Glu Val Ile Asn Ala Thr Met Ser Gly
                450                 455                 460

Asn Asp Val Phe Val Leu Met Pro Thr Gly Gly Lys Ser Leu Thr
465                 470                 475                 480

Tyr Gln Leu Pro Gly Leu Ile Cys Pro Gly Ile Thr Leu Val Ile Ser
                485                 490                 495

Pro Leu Val Ser Leu Ile Gln Asp Gln Ile Met His Leu Leu Gln Val
                500                 505                 510

Asn Ile Pro Ala Ala Tyr Leu Ser Ser Asn Met Glu Trp Thr Glu Gln
                515                 520                 525

Gln Glu Ile Leu Arg Glu Leu Asn Ser Asp Gly Cys Lys Tyr Lys Phe
                530                 535                 540

Leu Tyr Val Thr Pro Glu Lys Val Ala Lys Ser Asp Val Leu Leu Arg
545                 550                 555                 560

His Leu Glu Ser Leu His Thr Arg Asp Thr Leu Ala Arg Ile Val Ile
                565                 570                 575

Asp Glu Ala His Cys Val Ser Gln Trp Gly His Asp Phe Arg Pro Asp
                580                 585                 590

Tyr Gln Cys Leu Gly Ile Leu Lys Gln Lys Phe Pro Thr Val Pro Val
```

```
                    595                 600                 605
Leu Ala Leu Thr Ala Thr Ala Thr Ile Ser Val Lys Glu Asp Val Val
610                 615                 620

Gln Ala Leu Gly Leu Ala Asn Cys Ile Ile Phe Arg Gln Ser Phe Asn
625                 630                 635                 640

Arg Pro Asn Leu Arg Tyr Thr Val Ile Pro Lys Thr Lys Lys Cys Leu
                    645                 650                 655

Glu Asp Ile Gly Thr Phe Ile Lys Asn Asn His Phe Asp Gln Cys Gly
                    660                 665                 670

Ile Ile Tyr Cys Leu Ser Arg Met Asp Cys Glu Arg Val Ala Glu Lys
                    675                 680                 685

Leu Gln Glu Tyr Gly His Lys Ala Ala Phe Tyr His Gly Ser Met Asp
690                 695                 700

Gly Ala Gln Arg Ala Asn Ile Gln Lys Gln Trp Ser Lys Asp Glu Ile
705                 710                 715                 720

Asn Ile Ile Cys Ala Thr Ile Ala Phe Gly Met Gly Ile Asn Lys Pro
                    725                 730                 735

Asn Val Arg Phe Val Ile His His Ser Leu Pro Lys Ser Ile Glu Gly
                    740                 745                 750

Tyr His Gln Glu Cys Gly Arg Ala Gly Arg Asp Gly Leu Pro Ser Ser
                    755                 760                 765

Cys Val Leu Tyr Tyr Ser Tyr Ser Asp Tyr Ile Arg Val Lys His Met
770                 775                 780

Ile Ser Gln Gly Thr Val Glu Gln Ser Pro Phe Gly Ser Gly Tyr Gly
785                 790                 795                 800

Arg Ser Asn Val Ala Ala Ser Gly Arg Asn Leu Glu Thr Asn Val Glu
                    805                 810                 815

Asn Leu Leu Arg Met Val Ser Tyr Cys Glu Asn Glu Val Asp Cys Arg
                    820                 825                 830

Arg Leu Leu Gln Leu Ile His Phe Gly Glu Lys Phe Glu Ser Thr Asn
                    835                 840                 845

Cys Arg Lys Thr Cys Asp Asn Cys Cys Lys Thr Gln Asn Cys Ile Glu
850                 855                 860

Lys Asp Val Thr Glu Val Ala Lys Gln Leu Val Glu Leu Val Lys Thr
865                 870                 875                 880

Thr Gly Gln Lys Phe Ser Ser Ala His Val Leu Glu Val Phe Arg Gly
                    885                 890                 895

Ser Leu Ser Gln Tyr Val Lys Lys His Arg His Glu Ser Leu His Leu
                    900                 905                 910

His Gly Ala Gly Lys Lys Leu Ala Lys Gly Glu Ala Ser Arg Val Leu
                    915                 920                 925

Arg His Leu Val Thr Glu Asp Ile Leu Val Glu Asp Val Lys Lys Ser
930                 935                 940

Asp Leu Tyr Gly Ser Val Ser Ser Val Leu Lys Val Asn Glu Ser Lys
945                 950                 955                 960

Ala Tyr Asn Leu Phe Ala Gly Gly Gln Thr Leu Arg Leu Arg Phe Pro
                    965                 970                 975

Ser Phe Val Lys Ala Ser Lys Leu Gly Lys Tyr Glu Ala Thr Pro Ala
                    980                 985                 990

Lys Gly Ser Leu Thr Ser Gly Lys  Gln Ser Pro Pro Arg  Thr Asp Pro
                    995                1000                1005

Ser Gly  Val Pro Gln Ser Thr  Phe Asp Pro Ser Leu  Ser Ala Ile
        1010                1015                1020
```

-continued

```
Leu Tyr Ser Ala Leu Arg Lys Leu Arg Thr Asn Ile Val Arg Glu
    1025                1030                1035

Ser Gly Asp Gly Val Met Ala His His Ile Phe Gly Asp Asp Thr
    1040                1045                1050

Leu Gln Leu Ile Gly Gln Lys Val Pro Arg Thr Lys Asn Glu Leu
    1055                1060                1065

Leu Asp Ile Asn Gly Ile Gly Lys Val Lys Ile Asn Lys Tyr Gly
    1070                1075                1080

Asp Asn Val Leu Gln Thr Ile Glu Ala Thr Val Arg Asp Tyr Tyr
    1085                1090                1095

Lys Ser Asp Lys Thr Ser Ser Ser Gly Asn Asp Asn Thr Asp Ser
    1100                1105                1110

Gly Lys Lys Arg Arg Asn Ser Ile Asn Val Gln Asn Gly Asn Ser
    1115                1120                1125

Lys Asp Glu Glu Phe Phe Thr Glu Ser Thr Gly Cys Thr Lys Lys
    1130                1135                1140

Arg Val Leu Lys Lys Gln Asn Lys His Ala Glu Val Ile Asp Tyr
    1145                1150                1155

Arg Asp Leu Gly Tyr Phe Asp Glu Cys Ile Asp Gly Asp Leu Asp
    1160                1165                1170

Phe Asp Glu Thr Met Met Pro
    1175                1180

<210> SEQ ID NO 25
<211> LENGTH: 1250
<212> TYPE: PRT
<213> ORGANISM: Theobroma cacao

<400> SEQUENCE: 25

Met Ser Leu Phe Val Leu Lys Leu Ala Arg Thr Val Tyr Ser Arg Leu
1               5                   10                  15

Leu His Gly Glu Val Leu Glu Gln Trp Asn Phe Tyr Gln Gln Phe Arg
                20                  25                  30

Ile Tyr Val Ser Gln Trp Pro Arg Lys Asn Ile Arg Val Lys Ala Ile
        35                  40                  45

Gln Val Lys Val Thr Lys Met Asn Asp Lys Leu Pro Lys Ile Asn Trp
    50                  55                  60

Leu Ser His Val Asp Ala His Asp Asn Phe Ser Cys Gln Lys Lys Phe
65                  70                  75                  80

Leu Ser Ser Asn Phe Leu Cys Ser Leu Glu Thr Gln Lys Pro Cys Thr
                85                  90                  95

Glu Glu Glu Ile Arg Ala Arg Leu Arg Val Cys Gln Ile Gln Asn Ser
            100                 105                 110

Gln Lys Val Gln His Pro Gln Val Glu Lys Ala Trp Gln Ile Leu Ser
        115                 120                 125

Ser Leu Pro Thr Ser Cys Arg Thr Tyr Leu Arg Pro Gly Thr Thr Ala
    130                 135                 140

Pro Val Lys Asn Ser Asn Asp Glu Ile Ser His Asn Trp Arg Gly Arg
145                 150                 155                 160

Ser Thr Leu Thr Asn Ser Ser Asp Met Lys Trp Ser Lys His Met His
                165                 170                 175

Val Ser Arg Asn Val Asn Glu Thr Asp Gly Lys Ile Asn Glu Val Gly
            180                 185                 190

Arg Cys Met Ala Ser Ser Phe Pro Ser Ser Asn Ala Asn Ala Val Glu
```

```
                195                 200                 205
Asp Gly Asn His Leu Gln Arg His Ser Glu Ile Lys Ala Ser Met Ser
210                 215                 220

Asn Arg Ser Asn Ser Lys Val Leu Gly Gly Ser Leu Trp Asn His Ile
225                 230                 235                 240

Val His Ala Ser Gln Leu Glu Gln Ser Ala Glu Val Leu Ala Asp Glu
            245                 250                 255

Ile Asp Asp Asp Leu Leu Lys Asp Ile Asp Val Asp Gln Ile Val
        260                 265                 270

Ser Lys His Tyr Gln Ser Thr Cys Thr Pro Gln Pro Ser Val Ser Lys
            275                 280                 285

Phe Pro Pro Ile Ala Gln Met Asp Lys Arg Ala Phe Ala Gly Glu Glu
290                 295                 300

Glu Ala Cys Leu Pro Thr Glu Leu Cys Ser Asn Cys Ser His Gly Cys
305                 310                 315                 320

Lys Leu Gly Leu Cys Pro Glu Ala Ala Ser His Val Gln Glu Met Lys
            325                 330                 335

Asp Lys Leu Ile Ala Val Ser Asn Glu Leu Leu Asp Asn Ala Ser Asn
            340                 345                 350

Leu Ser Pro Glu Gln Ile Glu Lys Leu Arg Glu Asp Arg Leu Gln Leu
            355                 360                 365

Asn Lys Gln Ile Gln Gln Leu Glu Arg Tyr Ile Cys Asp Met Glu Arg
370                 375                 380

Gln Lys Ser His Phe Ser Ala Ser Thr Ala Thr Arg Thr Phe Leu Tyr
385                 390                 395                 400

Gly Thr Pro Gln Thr Ala Ser Phe Ser Ile Asp Pro Ile Arg Phe Asp
            405                 410                 415

Ala Gln Val His Leu Cys Asn Glu Pro Asn Gly Tyr Glu Asn Trp Asn
            420                 425                 430

Ser Ser Ser Val Ser Phe Ser Val Asn Asn Phe Gly Val Ser Ser
            435                 440                 445

Gly Pro Met Glu Arg Glu Pro Tyr Val Pro Lys Ile Ile Glu Val Asn
450                 455                 460

Tyr Ile Glu Gly Ser Asn Asp Gln Lys Trp Ser Ser Arg Asp Phe Pro
465                 470                 475                 480

Trp Thr Lys Lys Leu Glu Ala Asn Asn Lys Lys Val Phe Gly Asn His
            485                 490                 495

Ser Phe Arg Pro Asn Gln Arg Glu Val Ile Asn Ala Thr Met Ser Gly
            500                 505                 510

Cys Asp Val Phe Val Leu Met Pro Thr Gly Gly Gly Lys Ser Leu Thr
            515                 520                 525

Tyr Gln Leu Pro Ala Leu Ile Cys Pro Gly Ile Thr Leu Val Ile Ser
            530                 535                 540

Pro Leu Val Ser Leu Ile Gln Asp Gln Ile Met His Leu Leu Gln Ala
545                 550                 555                 560

Asn Ile Pro Ala Ala Tyr Leu Ser Ala Asn Met Glu Trp Thr Glu Gln
            565                 570                 575

Gln Glu Ile Leu Arg Glu Leu Thr Ser Asp Tyr Cys Lys Tyr Lys Leu
            580                 585                 590

Leu Tyr Val Thr Pro Glu Lys Val Ala Lys Ser Asp Val Leu Leu Arg
            595                 600                 605

His Leu Asp Ser Leu Asn Ala Arg Asp Leu Ile Ala Arg Ile Val Ile
610                 615                 620
```

```
Asp Glu Ala His Cys Val Ser Gln Trp Gly His Asp Phe Arg Pro Asp
625                 630                 635                 640

Tyr Gln Gly Leu Gly Ile Leu Lys Gln Lys Phe Pro Lys Thr Pro Val
            645                 650                 655

Leu Ala Leu Thr Ala Thr Ala Thr Ala Ser Val Lys Glu Asp Val Val
        660                 665                 670

Gln Ala Leu Gly Leu Asn Asn Cys Ile Ile Phe Arg Gln Ser Phe Asn
    675                 680                 685

Arg Pro Asn Leu Trp Tyr Ser Val Ile Pro Lys Thr Lys Lys Cys Val
690                 695                 700

Asp Asp Ile Asp Lys Phe Ile Lys Glu Asn His Phe Asp Glu Cys Gly
705                 710                 715                 720

Ile Ile Tyr Cys Leu Ser Arg Met Asp Cys Glu Lys Val Ala Glu Lys
                725                 730                 735

Leu Gln Glu Cys Gly His Lys Ala Ala Phe Tyr His Gly Asn Met Asp
            740                 745                 750

Pro Ala Gln Arg Ala Ala Ile Gln Lys Gln Trp Ser Lys Asp Glu Ile
        755                 760                 765

Asn Ile Ile Cys Ala Thr Val Ala Phe Gly Met Gly Ile Asn Lys Pro
770                 775                 780

Asp Val Arg Phe Val Ile His His Ser Leu Pro Lys Ser Ile Glu Gly
785                 790                 795                 800

Tyr His Gln Glu Cys Gly Arg Ala Gly Arg Asp Gly Gln Arg Ser Ser
                805                 810                 815

Cys Leu Leu Tyr Tyr Ser Tyr Ser Asp Tyr Ile Arg Val Lys His Met
            820                 825                 830

Ile Ser Gln Gly Ala Ala Glu Gln Ser Pro Phe Val Ser Gly Tyr Ser
        835                 840                 845

Arg Phe Asn Asn Ser Gly Arg Ile Leu Glu Thr Asn Thr Glu Asn Leu
850                 855                 860

Leu Arg Met Val Ser Tyr Cys Glu Asn Asp Val Asp Cys Arg Arg Leu
865                 870                 875                 880

Leu Gln Leu Leu His Phe Gly Glu Lys Phe Asp Ser Gly Asn Cys Lys
                885                 890                 895

Lys Thr Cys Asp Asn Cys Cys Arg Val Lys Gly Phe Val Asp Lys Asp
            900                 905                 910

Val Thr Asn Ile Ala Lys Gln Leu Val Glu Leu Val Lys Leu Thr Gly
        915                 920                 925

Gln Gln Phe Ser Ser Ser His Ile Leu Glu Val Tyr Arg Gly Ser Leu
    930                 935                 940

Ser Gln Phe Val Lys His Arg His Glu Thr Leu Ser Leu His Gly
945                 950                 955                 960

Ala Gly Lys His Val Ala Lys Gly Glu Ala Ser Arg Ile Leu Arg His
                965                 970                 975

Leu Val Ile Glu Glu Phe Leu Val Glu Asp Val Lys Lys Ser Asp Ile
            980                 985                 990

Tyr Gly Ser Val Ser Ser Val Leu Lys Val Asn Glu Ser Lys Val Gln
        995                 1000                1005

Asn Leu Cys Val Gly Gly Gln Thr Ile Ile Leu Arg Phe Pro Ser
    1010                1015                1020

Thr Val Lys Ala Thr Lys Leu Ser Lys Ser Glu Val Thr Pro Ala
    1025                1030                1035
```

```
Lys Gly Ser Leu Thr Ser Gly Lys Leu Ser Pro Pro Arg Val Asp
    1040                1045                1050

Thr Pro Ala Gln Ser Gln Ser Lys Val Asp Leu Asn Leu Ser Ala
    1055                1060                1065

Lys Leu Tyr Ser Ala Leu Arg Met Leu Arg Thr Val Leu Val Lys
    1070                1075                1080

Glu Ala Gly Asp Gly Val Met Ala Tyr His Ile Phe Gly Asn Ala
    1085                1090                1095

Thr Leu Gln His Ile Ser Lys Arg Val Pro Arg Thr Glu Glu Glu
    1100                1105                1110

Leu Leu Glu Ile Asn Gly Ile Gly Lys Ala Lys Ile Ser Lys Tyr
    1115                1120                1125

Gly Asp Arg Ile Leu Glu Thr Ile Glu Val Thr Ile Lys Glu His
    1130                1135                1140

Tyr Lys Thr Asp Arg Asn Ser Ser Ser Asn Asp Ser Asn Asp
    1145                1150                1155

Ser Thr Lys Arg Arg Arg Asp Ala Asn Gly Ala Pro Lys Ala Asn
    1160                1165                1170

Val Asp Asp Asp Phe Thr Arg Ser Thr Ser Arg Ser Lys Lys
    1175                1180                1185

Arg Thr Val Lys Met Gln Asn Asn Asp Gly Gly Ala His Ser Ser
    1190                1195                1200

Lys Asp Pro Asp Tyr Asn Asn Gln Cys Thr Gly Asn Asp Leu Asp
    1205                1210                1215

Phe Asp Asp Tyr Asp Asp Tyr Gly Val Glu Ser Lys Cys Pro Glu
    1220                1225                1230

Met Lys Val His Val Asp Gly Thr Gly Arg Val Leu Pro Ser Trp
    1235                1240                1245

Ser Thr
    1250

<210> SEQ ID NO 26
<211> LENGTH: 1235
<212> TYPE: PRT
<213> ORGANISM: Vitis vinifera

<400> SEQUENCE: 26

Met His Ile Asp Gln Asn Asp Met Ile Phe Ile Ser Ile Lys Val His
1               5                   10                  15

Ile Ala Gln Asn Gly Met Ile Phe Glu Ser Ile Gln Met Cys Ser Asn
                20                  25                  30

Ile Val Ala Asn Phe Phe Arg Pro Met Ile Cys Gln Ile Gln His Ile
            35                  40                  45

Gln Arg Leu Gln Ser Leu Gln Val Glu Lys Ala Trp Gly Ala Leu Ser
        50                  55                  60

Ser Leu Lys Leu Ser Ser Arg Asn Tyr Ser Lys Pro Gly Lys Met Ala
65                  70                  75                  80

Pro Leu Leu Lys Asp Ala Ser Val Glu Phe Pro Arg Asp Val Arg Lys
                85                  90                  95

Cys Asn Leu Gln Ser Ser His Asn Thr Asn Asn Gln Tyr Leu Glu His
            100                 105                 110

Asn Leu Pro His Gln Asn Leu Gly Glu Thr Asn Ser Ser Tyr Ser Glu
        115                 120                 125

Thr Ala Ser Cys Arg Gly Asn Ser Phe Arg Ser Gly Ser Ala Cys Ala
    130                 135                 140
```

```
Glu Asn Ala Gly Arg Glu Gly Gln Asn Glu Thr Lys Pro Ser Met
145                 150                 155                 160

Leu Tyr Asn Ser His Ile Gln Val Val Gly Gln Ser Gly Thr Cys
            165                 170                 175

Asn Val His Thr Gly Gln Val Lys Glu Leu Val Gly Ala Phe Pro Asn
        180                 185                 190

Gly Thr Asp Asp Asp Ile Leu Glu Asp Ile Asp Val Asp Gln Ile
        195                 200                 205

Val Met Glu His Tyr Gln Ser Thr Cys Thr Pro Gln Pro Ser Ile Ser
210                 215                 220

Lys Leu Pro Pro Val Thr Pro Thr Leu Ser Thr Val Asn Ile Ala Lys
225                 230                 235                 240

His Glu Glu Thr Phe Leu Pro Leu Glu Leu Cys Ser Asn Cys Ser His
                245                 250                 255

Gly Phe Lys Leu Gly Leu Cys Pro Glu Ala Ala Asn His Leu Gln Glu
            260                 265                 270

Leu Lys Asp Met Leu Ile Val Ile Ser Asn Glu Leu Leu Asp Asn Val
        275                 280                 285

Asp Leu Thr Ser Val Gln Val Glu Lys Leu Arg Gln Asp Arg Leu Tyr
    290                 295                 300

Leu Asn Lys Gln Ile Gln Gln Leu Glu Ile His Leu His Ser Val Ser
305                 310                 315                 320

Val Asp Glu Glu Arg Lys Asn Ser Asn Phe Ser Ala Ser Thr Thr Thr
                325                 330                 335

Pro Trp Ala Gln Phe Gln Thr Pro Ala Thr Ala Val Gly Ile Asp
            340                 345                 350

Pro Met Arg Phe Asp Ala Gln Val His Leu Arg Asn Glu Pro Gly Asn
        355                 360                 365

Tyr Glu Lys Trp Asn Thr Ser Ser Val Ser Phe Ser Ser Ile Asp Arg
370                 375                 380

Phe Gly Val Thr Pro Tyr Pro Leu Glu Arg Glu Pro Tyr Ile Pro Lys
385                 390                 395                 400

Leu Ile Glu Val Asn Tyr Ile Glu Gly Ser Ser Asp Lys Lys Trp Ser
                405                 410                 415

Ser Gly Asn Phe Pro Trp Thr Lys Lys Leu Glu Ala Asn Asn Lys Lys
            420                 425                 430

Val Phe Gly Asn His Ser Phe Arg Pro Asn Gln Arg Glu Val Ile Asn
        435                 440                 445

Ala Thr Met Ser Gly Tyr Asp Val Phe Val Leu Met Pro Thr Gly Gly
    450                 455                 460

Gly Lys Ser Leu Thr Tyr Gln Leu Pro Ala Leu Ile Ser Pro Gly Ile
465                 470                 475                 480

Thr Leu Val Ile Ser Pro Leu Val Ser Leu Ile Gln Asp Gln Ile Met
                485                 490                 495

His Leu Leu Gln Ala Asn Ile Pro Ala Ala Tyr Leu Ser Ala Ser Met
            500                 505                 510

Glu Trp Asn Glu Gln Gln Glu Ile Leu Arg Glu Leu Ser Ser Cys Lys
        515                 520                 525

Tyr Lys Leu Leu Tyr Ala Thr Pro Glu Lys Val Ala Lys Ser Asp Val
    530                 535                 540

Leu Met Arg Asn Leu Asp Asn Leu His Ala Arg Glu Leu Leu Ser Arg
545                 550                 555                 560
```

```
Ile Val Ile Asp Glu Ala His Cys Val Ser Gln Trp Gly His Asp Phe
            565                 570                 575
Arg Pro Asp Tyr Gln Gly Leu Gly Ile Leu Lys Gln Lys Phe Pro Asn
            580                 585                 590
Thr Pro Val Leu Ala Leu Thr Ala Thr Ala Thr Ala Ser Val Lys Glu
            595                 600                 605
Asp Val Val Gln Ala Leu Gly Leu Val Asn Cys Ile Ile Phe Arg Gln
            610                 615                 620
Ser Phe Asn Arg Pro Asn Leu Trp Tyr Ser Val Leu Pro Lys Thr Arg
625                 630                 635                 640
Lys Cys Leu Asp Asp Ile Asp Lys Phe Ile Arg Glu Asn His Phe Asp
            645                 650                 655
Glu Cys Gly Ile Ile Tyr Cys Leu Ser Arg Leu Asp Cys Glu Lys Val
            660                 665                 670
Ala Glu Arg Leu Gln Glu Cys Gly His Lys Ala Ala Phe Tyr His Gly
            675                 680                 685
Ser Met Asp Pro Ala Arg Arg Ala Phe Val Gln Lys Gln Trp Ser Lys
            690                 695                 700
Asp Glu Ile Asn Ile Ile Cys Ala Thr Val Ala Phe Gly Met Gly Ile
705                 710                 715                 720
Asn Lys Pro Asp Val Arg Phe Val Ile His His Ser Leu Pro Lys Ser
            725                 730                 735
Ile Glu Gly Tyr His Gln Glu Cys Gly Arg Ala Gly Arg Asp Gly Gln
            740                 745                 750
Arg Ser Ser Cys Val Leu Tyr Tyr Ser Tyr Ser Asp Tyr Ile Arg Val
            755                 760                 765
Lys His Met Ile Thr Gln Gly Val Val Glu Gln Ser Pro Leu Ala Ser
            770                 775                 780
Gly Gln Asn Arg Ser Asn Met Ala Ser Ser Gly Arg Ile Leu Glu Thr
785                 790                 795                 800
Asn Thr Glu Asn Leu Leu Arg Met Val Ser Tyr Cys Glu Asn Asp Val
            805                 810                 815
Asp Cys Arg Arg Leu Leu Gln Leu Val His Phe Gly Glu Lys Phe Asp
            820                 825                 830
Ser Ala His Cys Lys Lys Thr Cys Asp Asn Cys Leu Lys Ile Lys Ser
            835                 840                 845
Phe Val Glu Lys Asp Val Thr Glu Ile Ala Lys Gln Leu Val Glu Leu
            850                 855                 860
Val Lys Leu Thr Arg Glu Gln Phe Ser Ser His Ile Leu Glu Val
865                 870                 875                 880
Tyr Arg Gly Ser Leu Ser Gln Tyr Val Lys Lys His Arg His Glu Thr
            885                 890                 895
Leu Gly Leu His Ala Ala Gly Lys His Leu Ala Lys Gly Glu Ala Ser
            900                 905                 910
Arg Ile Leu Arg His Leu Val Thr Glu Asp Phe Leu Met Glu Asp Val
            915                 920                 925
Lys Lys Ser Asp Ile Tyr Gly Ser Val Ser Val Leu Lys Val Asn
930                 935                 940
Glu Ser Lys Val Tyr Lys Leu Phe Ser Gly Gln Lys Ile Ile Leu
945                 950                 955                 960
Arg Phe Pro Ser Ser Ala Lys Ser Ser Lys Leu Ser Asn Phe Glu Ala
            965                 970                 975
Thr Pro Ala Lys Gly Ser Leu Thr Ser Gly Lys Leu Ser Pro Pro Arg
```

```
                 980             985             990
Ile Glu Thr Pro Ala His Leu Pro Glu Val Asp Leu Asn Leu Ser Ala
             995            1000           1005

Lys Leu Tyr Ser Ala Leu Arg Ile Leu Arg Thr Val Leu Val Lys
        1010           1015           1020

Glu Ala Gly Glu Gly Val Met Ala Tyr His Ile Phe Gly Asn Ala
    1025           1030           1035

Thr Leu Gln Gln Ile Ser Lys Arg Ile Pro Arg Thr Lys Glu Glu
    1040           1045           1050

Leu Leu Glu Val Asn Gly Ile Gly Lys Ala Lys Ile Ser Lys Tyr
    1055           1060           1065

Gly Asp Arg Val Leu Glu Thr Ile Glu Ser Thr Ile Lys Glu Tyr
    1070           1075           1080

Tyr Lys Thr Asp Lys Asn Ser Ser Ser Asn Asp Ser Thr Asp
    1085           1090           1095

Thr Ile Lys Arg Arg Arg Glu Ser Ala Lys Val Leu Asp Ala Asn
    1100           1105           1110

Pro Glu Asp Asp Asp Phe Thr Lys Ser Thr Asp Arg Ser Arg Gly
    1115           1120           1125

Arg Ala Met Lys Arg His Asn Lys Gly Gly Glu Ala Asn Asn Thr
    1130           1135           1140

Arg Glu Thr Asp Tyr Tyr Asn Gln Cys Ile Asp Asp Leu Asp
    1145           1150           1155

Phe Asp Asp Ala Asn Cys Asp Val Ala Ile Asn Gly Ser Ala Pro
    1160           1165           1170

Lys Val Asp Arg Asp Gly Ala Arg Arg Thr Leu Pro Ser Trp Ser
    1175           1180           1185

Thr Pro Ser Asn Lys Gly His Asp Gln His Leu Asn Met Phe Gln
    1190           1195           1200

Glu Tyr Ser Phe Lys Gly Thr His Ile Lys Ala Gly Lys Met Lys
    1205           1210           1215

Asp Val Gly Gln Phe Ala Val Ala Ile Glu Phe Val Leu Val Phe
    1220           1225           1230

Leu Leu
    1235

<210> SEQ ID NO 27
<211> LENGTH: 923
<212> TYPE: PRT
<213> ORGANISM: Arabidopsis lyrata

<400> SEQUENCE: 27

Met Ser Arg Arg Gly Gly Gly Pro Val Thr Val Leu Asn Val Ala Glu
1               5                   10                  15

Lys Pro Ser Val Ala Lys Ser Val Ala Gly Ile Leu Ser Arg Gly Thr
            20                  25                  30

Phe Arg Thr Arg Glu Gly Arg Ser Arg Tyr Asn Lys Ile Phe Glu Phe
        35                  40                  45

Asp Tyr Ala Ile Asn Gly Gln Pro Cys Arg Met Leu Met Thr Ser Val
    50                  55                  60

Ile Gly His Leu Met Glu Leu Glu Phe Ala Asn Arg Tyr Arg Lys Trp
65                  70                  75                  80

His Ser Cys Asp Pro Ala Asp Leu Tyr Gln Ala Pro Val Met Lys His
                85                  90                  95
```

```
Val Pro Glu Asp Lys Lys Asp Ile Lys Lys Thr Leu Glu Glu Ala
            100                 105                 110
Arg Lys Ser Asp Trp Leu Val Leu Trp Leu Asp Cys Asp Arg Glu Gly
        115                 120                 125
Glu Asn Ile Ala Phe Glu Val Asp Val Cys Arg Ala Val Lys His
        130                 135                 140
Asn Leu Phe Ile Arg Arg Ala His Phe Ser Ala Leu Ile Asp Arg Asp
145                 150                 155                 160
Ile His Glu Ala Val Gln Asn Leu Arg Asp Pro Asn Gln Leu Phe Ala
                165                 170                 175
Glu Ala Val Asp Ala Arg Gln Glu Ile Asp Leu Arg Ile Gly Ala Ser
            180                 185                 190
Phe Thr Arg Phe Gln Thr Met Leu Leu Arg Asp Arg Phe Ala Ile Asp
        195                 200                 205
Ser Thr Gly Glu Glu Arg Ser Arg Val Ile Ser Tyr Gly Pro Cys Gln
        210                 215                 220
Phe Pro Thr Leu Gly Phe Ile Val Glu Arg Tyr Trp Glu Ile Gln Ala
225                 230                 235                 240
His Glu Pro Glu Glu Phe Trp Thr Ile Asn Cys Ser His Gln Ser Glu
                245                 250                 255
Glu Gly Leu Ala Thr Phe Asn Trp Met Arg Gly His Leu Phe Asp Tyr
            260                 265                 270
Ala Ser Ala Val Ile Leu Tyr Glu Met Cys Val Glu Glu Pro Thr Ala
        275                 280                 285
Thr Val Met Asn Val Pro His Pro Arg Glu Arg Phe Lys Tyr Pro Pro
        290                 295                 300
Tyr Pro Leu Asn Thr Ile Glu Leu Glu Lys Arg Ala Ser Arg Tyr Phe
305                 310                 315                 320
Arg Leu Ser Ser Glu His Thr Met Lys Val Ala Glu Glu Leu Tyr Gln
                325                 330                 335
Ala Gly Phe Ile Ser Tyr Pro Arg Thr Glu Thr Asp Ser Phe Ser Ser
            340                 345                 350
Arg Thr Asp Leu Cys Ala Met Val Glu Glu Gln Arg His Pro Ala
        355                 360                 365
Trp Gly Ser Tyr Ala Gln Arg Leu Leu Glu Pro Glu Gly Gly Leu Trp
        370                 375                 380
Arg Asn Pro Gly Asn Gly Gly His Asp Asp Lys Ala His Pro Pro Ile
385                 390                 395                 400
His Pro Thr Lys Phe Ser Ser Gly Glu Ser Asn Trp Ser Arg Asp His
                405                 410                 415
Leu Asn Val Tyr Glu Leu Val Val Arg His Tyr Leu Ala Cys Val Ser
            420                 425                 430
Gln Pro Ala Lys Ala Ala Glu Thr Thr Val Glu Ile Asp Ile Ala Gly
        435                 440                 445
Glu Arg Phe Ser Ala Ser Gly Arg Ala Ile Leu Ala Lys Asn Tyr Leu
        450                 455                 460
Glu Val Tyr Arg Phe Glu Ser Trp Gly Gly Ser Val Ile Pro Val Tyr
465                 470                 475                 480
Glu Lys Gly Gln Gln Phe Ile Pro Thr Thr Leu Thr Leu Asp Ser Ala
                485                 490                 495
Val Thr Arg Pro Pro Leu Leu Cys Glu Ala Asp Leu Leu Ser Cys
            500                 505                 510
Met Asp Lys Ala Gly Ile Gly Thr Asp Ala Thr Met His Asp His Ile
```

```
            515                 520                 525
Lys Lys Leu Leu Asp Arg Gly Tyr Ala Thr Lys Asp Ala Asn Thr Arg
            530                 535                 540

Phe Ser Pro Thr Asn Leu Gly Glu Ala Leu Val Met Gly Tyr Asp Asp
545                 550                 555                 560

Met Gly Tyr Glu Leu Trp Lys Pro Asn Leu Arg Ala Leu Met Glu Arg
                565                 570                 575

Asp Met Asn Glu Val Ser Val Gly Arg Lys Thr Lys Ala Glu Val Leu
            580                 585                 590

Glu Thr Cys Leu Gln Gln Met Lys Ala Cys Phe Leu Asp Ala Arg Val
            595                 600                 605

Lys Lys Ser Lys Leu Leu Glu Ala Met Thr Ile Phe Phe Glu Arg Ser
            610                 615                 620

Asn Asn Thr Asp Glu Ser Glu Ser Gln Thr Ala Gly Glu Val Ile Arg
625                 630                 635                 640

Arg Cys Asn Leu Cys Asn Glu Ser Asp Met Ala Leu Arg Lys Asn Arg
                645                 650                 655

Asp Gly Asn Phe Met Val Gly Cys Met Asn Tyr Pro Gln Cys Arg Asn
            660                 665                 670

Ala Val Trp Leu Pro Gly Pro Thr Leu Glu Ala Ser Val Thr Thr Asp
            675                 680                 685

Val Cys Gln Thr Cys Gly Pro Gly Pro Val Tyr Lys Ile Leu Phe Lys
            690                 695                 700

Phe Arg Gln Ile Gly Ile Pro Pro Gly Phe Asp Val Asn His Leu Gly
705                 710                 715                 720

Cys Ile Gly Gly Cys Asp Asp Ile Leu Lys Gln Leu Ile Asp Ile Cys
                725                 730                 735

Gly Thr Gly Ser Arg Ser Gln Ala Arg Arg Ala Pro Gly Thr Val Pro
            740                 745                 750

Ser Asn Asn Ile Gln Gly Ser Asn Thr Arg Gln Gly Asn Phe Cys Ile
            755                 760                 765

His Cys Gln Gln Arg Gly His Ala Ser Ala Asn Cys Pro Ser Arg Ala
            770                 775                 780

Thr Ala Phe Arg Asn Ser Arg Leu Thr Ala Thr Asn Pro Arg Asn Asp
785                 790                 795                 800

Glu Ser Thr Val Ser Cys Asn Thr Cys Gly Thr Gln Cys Val Leu Arg
                805                 810                 815

Thr Ala Asn Thr Glu Ala Asn Arg Gly Arg Gln Phe Phe Ser Cys Pro
            820                 825                 830

Thr Gln Gly Cys Ser Phe Phe Ala Trp Glu Asp Ser Ile Asn Asn Ser
            835                 840                 845

Ser Gly Asn Ala Thr Thr Gly Ser Asn Ser Gly Ser Gly Arg Arg
            850                 855                 860

Gly Arg Gly Arg Gly Gly Arg Gly Gln Ser Gly Gly Arg Arg
865                 870                 875                 880

Asn Ser Gly Thr Ser Phe Val Ser Ala Thr Gly Glu Pro Val Ser Gly
                885                 890                 895

Ile Arg Cys Phe Ser Cys Gly Asp Pro Ser His Phe Ala Asn Val Cys
            900                 905                 910

Pro Asn Arg Asn Asn Ser Asn Gly Asn Tyr Tyr
            915                 920

<210> SEQ ID NO 28
```

<211> LENGTH: 924
<212> TYPE: PRT
<213> ORGANISM: Brachypodium distachyon

<400> SEQUENCE: 28

```
Met His Pro Ser Gly Gly Gly Gly Ala Ile Arg Val Leu Asn Val
1               5                   10                  15

Ala Glu Lys Pro Ser Val Ala Lys Ser Val Ala Glu Ile Leu Ser Arg
            20                  25                  30

Arg Ala Met Gln Ser Arg Pro Gly Arg Ser Arg Tyr Asn Arg Ile Phe
        35                  40                  45

Glu Phe Asn Tyr Ala Ile Gly Gly Gln Ala Cys His Met Leu Val Thr
50                  55                  60

Ser Val Thr Gly His Leu Met Glu Leu Asp Phe Asp Asp Arg Tyr Arg
65                  70                  75                  80

Arg Trp Tyr Ser Cys Asp Pro Val Glu Leu Phe His Ala Pro Val Arg
                85                  90                  95

Lys Ala Val Pro Gln Asp Lys Leu Asp Ile Lys Arg Thr Leu Glu Glu
            100                 105                 110

Glu Ala Arg Thr Cys Gln Trp Leu Val Leu Trp Leu Asp Cys Asp Arg
        115                 120                 125

Glu Gly Glu Asn Ile Ala Tyr Glu Val Val Glu Ile Cys Ala Gly Val
130                 135                 140

Asn His Cys Leu Asn Ile Trp Arg Ala Arg Phe Ser Ala Leu Ile Asp
145                 150                 155                 160

Arg Glu Ile His Glu Ala Val Gln His Leu Gly Arg Pro Asn Lys Leu
                165                 170                 175

Phe Ala Asp Ala Val Asp Ala Arg Gln Glu Ile Asp Leu Arg Ile Gly
            180                 185                 190

Ala Ser Phe Thr Arg Phe Gln Thr Met Leu Leu Lys Asp Ala Phe Val
        195                 200                 205

Leu Asp Val Ser Gly Glu Glu Arg Asn Met Val Leu Ser Tyr Gly Pro
210                 215                 220

Cys Gln Phe Pro Thr Leu Gly Phe Ile Val Glu Arg Phe Trp Glu Ile
225                 230                 235                 240

Gln Ala His Glu Pro Glu Glu Phe Trp Thr Ile Asn Cys Ser His Thr
                245                 250                 255

Ser Asp Glu Gly Thr Ala Ser Phe Gly Trp Ile Arg Gly His Leu Phe
            260                 265                 270

Asp Tyr Ser Ser Ala Ile Val Ile Tyr Glu Met Cys Val Gln Glu Pro
        275                 280                 285

Met Ala Thr Val Gln Asn Val Arg Asn Gln Glu Lys Leu Lys Tyr Pro
290                 295                 300

Pro Tyr Pro Leu Ser Thr Leu Glu Leu Gln Lys Arg Ala Ser Arg Cys
305                 310                 315                 320

Cys Arg Met Ser Ser Glu His Thr Met Lys Val Ala Glu Glu Leu Tyr
                325                 330                 335

Gln Ala Gly Phe Ile Ser Tyr Pro Arg Thr Glu Thr Asp Asn Phe Ser
            340                 345                 350

Pro Asn Thr Asp Leu His Ala Ile Ala His Glu Gln Val Pro His Pro
        355                 360                 365

Val Trp Gly Ser Tyr Ala Gln Arg Leu Leu Asn Pro Glu Glu Arg Leu
370                 375                 380

Trp Arg Asn Pro Ser Asn Gly Gly His Asp Asp Lys Ala His Pro Pro
```

-continued

```
            385                 390                 395                 400
        Ile His Pro Thr Lys Phe Thr Ala Gly Glu Ser Asn Trp Ser Gln Asp
                        405                 410                 415

His His Lys Val Tyr Glu Leu Val Val Arg His Phe Leu Ala Cys Cys
                        420                 425                 430

Ser Gln Pro Ala Val Gly Ala Glu Thr Thr Val Glu Ile Asp Ile Ala
                        435                 440                 445

Gly Glu Gln Phe Asn Ala Ser Gly Arg Val Val Leu Ala Lys Asn Tyr
                        450                 455                 460

Leu Asp Val Tyr Arg Tyr Asp Ser Trp Gly Gly Ser Leu Leu Pro Thr
        465                 470                 475                 480

Tyr Thr Ile Gly Gln Gln Phe Val Pro Thr Thr Leu Thr Leu Asp Ser
                        485                 490                 495

Gly Val Thr Arg Pro Pro Leu Leu Ala Glu Ala Asp Leu Leu Ser
                        500                 505                 510

Cys Met Asp Lys Ala Gly Ile Gly Thr Asp Ala Thr Met His Glu His
                        515                 520                 525

Ile Lys Lys Leu Leu Asp Arg Cys Tyr Ala Thr Lys Asp Ala Asn Ser
                        530                 535                 540

Arg Phe Ser Pro Thr Asn Leu Gly Glu Ala Leu Val Met Gly Tyr Asp
        545                 550                 555                 560

Glu Met Gly Tyr Glu Leu Trp Lys Pro Tyr Leu Arg Ala Met Met Glu
                        565                 570                 575

Ala Asp Met Lys Ala Val Ser Ile Gly Thr Lys Ser Lys Leu Glu Val
                        580                 585                 590

Leu Glu Gly Cys Leu Gln Gln Met Lys Ala Cys Phe Leu Asp Ala Arg
                        595                 600                 605

Ser Asn Lys Val Lys Leu Leu Asp Ala Met Gly Thr Phe Phe Ala Arg
                        610                 615                 620

Ser Asn Arg Pro Leu Asn Glu Thr Gln Asn Pro Met Glu Val Val Arg
        625                 630                 635                 640

Pro Cys Gly Ala Cys Asn Asp Ser Glu Met Leu Leu Lys Arg Lys Pro
                        645                 650                 655

Asn Gly Gly Phe Met Val Gly Cys Arg Ser Phe Pro Gln Cys Arg Asn
                        660                 665                 670

Val Val Trp Leu Pro Gly Ser Leu Ser Glu Ala Ala Val Thr Glu Gln
                        675                 680                 685

Ile Cys Pro Thr Cys Val Pro Gly Pro Val Tyr Lys Ile Gln Phe Lys
                        690                 695                 700

Phe Asn Arg Arg Asp Ile Pro Pro Asn Phe Asp Val Asp His Leu Gly
        705                 710                 715                 720

Cys Ile Gly Gly Cys Asp Asp Val Leu Lys Glu Leu Ile Glu Ile Thr
                        725                 730                 735

Arg Phe Val Asn His Asn Gln Thr Thr Thr Pro Ala Arg Gly Gln Ser
                        740                 745                 750

Gln Thr Pro Ser Gly Val Arg Gln Gly Ala Pro Arg Gln Asp Leu His
                        755                 760                 765

Pro Gly Phe Arg Pro Ala Gly Gln Phe Ala Asn Gly His Thr Pro Val
                        770                 775                 780

Val Asn Pro Gln Gly Phe Arg Ser Thr His Thr Gln Asn Ser Arg Asn
        785                 790                 795                 800

Ala Ser Gly Gln Val Leu Cys Thr Thr Cys Gly Glu Ala Cys Ile Ser
                        805                 810                 815
```

```
Arg Thr Ala Asn Thr Glu Ala Asn Arg Gly Arg Lys Phe Tyr Lys Cys
            820                 825                 830

Gln Asp Ser Gly Cys Gly Phe Phe Ala Trp Glu Asp Glu Leu Glu Asn
            835                 840                 845

Val Val Pro Arg Gly Arg Gly Arg Gly Arg Gly Gly Gly Arg Gln
850                 855                 860

Ala Ser Ala Ser Ala Gly Arg Arg Gly Gly Thr Gln Gly Arg Gly Arg
865                 870                 875                 880

Arg Gly Arg Gly Arg Asn Ala Asp Ala Asn Gly Met Thr Phe Val Ser
                885                 890                 895

Ala Thr Gly Asp Thr Val His Gly Cys Cys Phe Ala Cys Gly Asp Pro
            900                 905                 910

Ser His Phe Ala Asn Ala Cys Pro Asn Arg Gly Arg
            915                 920

<210> SEQ ID NO 29
<211> LENGTH: 915
<212> TYPE: PRT
<213> ORGANISM: Fragaria vesca

<400> SEQUENCE: 29

Met Leu Thr Glu Phe Gly Ala Glu Leu Gly Trp Gly Trp Leu Ser Val
1               5                   10                  15

Asp Gly Gly Trp Leu Pro Lys Ala Glu Ala Val Val Trp Asn Lys Gln
            20                  25                  30

Ala Ala Val Glu Asp Trp Ala Cys Leu Cys Trp Arg Glu Met Val Arg
        35                  40                  45

Val Leu Asn Val Ala Glu Lys Pro Ser Val Ala Lys Ser Val Ala Asn
    50                  55                  60

Ile Leu Ser Arg Gly Gln Gly Leu Arg Met Arg Glu Gly Arg Ser Arg
65                  70                  75                  80

Tyr Asn Lys Ile Tyr Glu Phe Asn Tyr Ser Ile Asn Gly Cys His Cys
                85                  90                  95

Gln Met Leu Phe Thr Ser Val Thr Gly His Leu Met Glu Leu Glu Phe
            100                 105                 110

Glu Asp Arg Phe Arg Lys Trp His Ser Cys Asp Pro Ala Leu Leu Phe
        115                 120                 125

Gln Ala Pro Val Arg Lys Phe Val Pro Glu Asp Lys Leu Asp Ile Lys
    130                 135                 140

Arg Thr Leu Glu Glu Ala Arg Asn Cys Gln Trp Leu Val Leu Trp
145                 150                 155                 160

Leu Asp Cys Asp Arg Glu Gly Glu Asn Ile Ala Phe Glu Val Ile Asp
                165                 170                 175

Val Cys Thr Ser Val Asn Arg His Leu Thr Ile Lys Arg Ala Arg Phe
            180                 185                 190

Ser Ala Leu Ile Asp Arg Asp Ile His His Ala Val Gln Asn Leu Asp
        195                 200                 205

Asn Ala Asn Lys Tyr Phe Ala Asp Ala Val Asp Ala Arg Gln Glu Ile
    210                 215                 220

Asp Leu Arg Ile Gly Ala Ser Phe Thr Arg Phe Gln Thr Met Leu Leu
225                 230                 235                 240

Arg Asp Ala Phe Val Ile Asp Ser Ala Thr Asp Asp Arg Asn Leu Val
                245                 250                 255

Leu Ser Tyr Gly Pro Cys Gln Phe Pro Thr Leu Gly Phe Ile Val Glu
```

-continued

```
            260                 265                 270
Arg Tyr Trp Glu Ile Gln Ser His Glu Pro Glu Phe Trp Thr Ile
        275                 280                 285
Asn Cys Ser His Arg Ser Asp Glu Gly Thr Ala Thr Phe Gly Trp Met
    290                 295                 300
Arg Gly His Leu Phe Asp His Ala Cys Ala Val Ile Ile Tyr Glu Met
305                 310                 315                 320
Cys Val Glu Asp Pro Ile Ala Thr Val Thr Lys Val Arg Gln Gln Glu
                325                 330                 335
Lys Pro Lys Tyr Pro Pro Tyr Pro Leu Asn Thr Ile Glu Leu Glu Lys
                340                 345                 350
Arg Ala Ser Arg Tyr Phe Arg Met Ser Ser Glu His Thr Met Lys Val
            355                 360                 365
Gly Thr Val Gly Val Ala Glu Glu Leu Tyr Gln Ala Gly Phe Ile Ser
        370                 375                 380
Tyr Pro Arg Thr Glu Thr Asp Gly Phe Ser Pro Arg Thr Asp Leu His
385                 390                 395                 400
Ala Ile Val Gln Glu Gln Gln Gly His Pro Gly Trp Gly Ser Tyr Ala
                405                 410                 415
Gln Arg Leu Leu Asp Pro Ala Ser Gly Leu Trp Arg Asn Pro Ser Ser
                420                 425                 430
Gly Gly His Asp Asp Lys Ala His Pro Pro Ile His Pro Thr Lys Phe
            435                 440                 445
Ser Ala Gly Glu Ser Asn Trp Ser Gln Asp His Asn Arg Leu Tyr Glu
        450                 455                 460
Leu Val Val Arg His Phe Leu Ala Cys Val Ser Gln Pro Ala Val Gly
465                 470                 475                 480
Ala Glu Thr Thr Val Glu Ile Asp Ile Ala Gly Glu Met Phe Ser Ala
                485                 490                 495
Ser Gly Arg Val Ile Leu Ala Lys Asn Tyr Leu Asp Val Tyr Arg Phe
                500                 505                 510
Glu Ser Trp Gly Gly Ser Leu Leu Pro Thr Tyr Ala Val Gly Gln Gln
            515                 520                 525
Phe Met Pro Thr Thr Leu Thr Leu Asp Ser Gly Val Thr Arg Pro Pro
        530                 535                 540
Pro Leu Leu Ser Glu Ala Asp Leu Leu Gly Cys Met Asp Lys Glu Gly
545                 550                 555                 560
Ile Gly Thr Asp Ala Thr Met His Asp His Ile Lys Lys Leu Leu Asp
                565                 570                 575
Arg Phe Tyr Ala Thr Lys Asp Ala Asn Thr Arg Phe Ser Pro Thr Asn
                580                 585                 590
Leu Gly Glu Ala Leu Val Met Gly Tyr Asp Asp Met Gly Ala Val Met
            595                 600                 605
Glu Arg Asp Met Lys Ala Val Ser Glu Gly Asn Lys Ser Lys Ala Glu
        610                 615                 620
Val Leu Glu Thr Cys Leu Gln Gln Met Lys Gly Cys Phe Leu Asp Ala
625                 630                 635                 640
Arg Gln Asn Lys Val Lys Leu Phe Glu Ala Met Ala Val Phe Phe Glu
                645                 650                 655
Arg Ser Asn Arg Pro Gly Gly Asp Asp Gln His Thr Ser Gly Glu Phe
                660                 665                 670
Ile Arg Arg Cys Gly Leu Cys Gln Glu Ala Asp Met Val Leu Arg Lys
            675                 680                 685
```

Asn Arg Asp Gly Asn Phe Met Val Gly Cys Met Gly Tyr Pro Gln Cys
    690                 695                 700

Arg Asn Ala Ile Trp Leu Pro Gly Ser Val Ser Glu Ala Val Ala Thr
705                 710                 715                 720

Thr Asn Ile Cys Asn Ser Cys Thr Pro Gly Glu Asp Asn Gln Leu Glu
            725                 730                 735

Cys Ala Ser Pro Ser Phe Val Gly Ile Gly Leu Asp Ser Ser Ser Ser
        740                 745                 750

Ser Arg Cys Ile Gly Gly Cys Asp Glu Ile Leu Arg Gln Leu Thr Glu
    755                 760                 765

Ile Cys Gly Thr Gly Ser Arg Ser Ala Ala Arg Gly Arg Gly Pro Thr
770                 775                 780

Thr Ser Ser Asn Val Gln Gln Asn Asn Thr Arg Gln Gly Ala Cys Ile
785                 790                 795                 800

Tyr Cys His Gln Ser Gly His Ser Ser Gly Asp Cys Pro Ser Gln Ser
            805                 810                 815

Ser Gly Pro Arg Ser Val Arg Pro Arg Thr Met Asn Ala Gln Ser Gly
        820                 825                 830

Met Thr Ala Gln Leu Ile Trp Glu Asp Asn Val Ser Asn Gly Asn Gly
    835                 840                 845

Gly Arg Gly Phe Gln Arg Ala Asn Val Ser Ala Gly Arg Gly Ala Gly
850                 855                 860

Gly Arg Gly Ser Gly Gly Arg Gly Ala Gln Gly Ala Gly His Ala Thr
865                 870                 875                 880

Gly Gly Thr Phe Val Ser Ala Thr Gly Asp Pro Asn Ser Gly Arg Arg
            885                 890                 895

Cys Phe Val Cys Gly Asp Pro Ser His Phe Ala Asn Val Cys Pro Asn
        900                 905                 910

Arg Gly Asn
        915

<210> SEQ ID NO 30
<211> LENGTH: 814
<212> TYPE: PRT
<213> ORGANISM: Oryza sativa

<400> SEQUENCE: 30

Met His His Gly Gly Gly Gly Ala Ile Arg Val Leu Asn Val Ala
1               5                   10                  15

Glu Lys Pro Ser Val Ala Lys Ser Val Ala Glu Ile Leu Ser Arg Pro
            20                  25                  30

Ser Gly Gly Met Arg Ser Arg Glu Gly Arg Ser Arg Tyr Asn Arg Val
        35                  40                  45

Phe Glu Phe Asp Tyr Ser Ile Gly Gly Arg Ala Cys His Met Leu Val
    50                  55                  60

Thr Ser Val Thr Gly His Leu Met Glu Leu Glu Phe Asp Asp Arg Phe
65                  70                  75                  80

Arg Arg Trp His Ser Cys Asp Pro Ala Asp Leu Phe His Ala Pro Val
                85                  90                  95

Arg Lys Ser Val Pro Gln Asp Lys Gln Asp Ile Lys Arg Thr Leu Glu
            100                 105                 110

Glu Glu Ala Arg Lys Cys Gln Trp Leu Val Leu Trp Leu Asp Cys Asp
        115                 120                 125

Arg Glu Gly Glu Asn Ile Ala Tyr Glu Val Ile Asp Ile Cys Ala Gly

```
            130                 135                 140
Ala Asn Ser Arg Leu Asn Ile Trp Arg Ala Arg Phe Ser Ala Leu Ile
145                 150                 155                 160

Asp Arg Glu Ile His Glu Ala Val Gln His Leu Asp Arg Pro Asn Lys
                    165                 170                 175

Leu Phe Ala Asp Ala Val Asp Ala Arg Gln Glu Ile Asp Leu Arg Ile
                180                 185                 190

Gly Ala Ser Phe Thr Arg Phe Gln Thr Met Leu Leu Lys Asp Ala Phe
            195                 200                 205

Val Leu Asp Asp Thr Gly Asp Asp Arg Asn Ile Ile Leu Ser Tyr Gly
        210                 215                 220

Pro Cys Gln Phe Pro Thr Leu Gly Phe Ile Val Glu Arg Phe Trp Glu
225                 230                 235                 240

Ile Gln Ala His Glu Pro Glu Glu Phe Trp Thr Ile Asn Cys Ser His
                    245                 250                 255

Thr Ser Asp Glu Gly Thr Ala Ser Phe Gly Trp Ile Arg Gly His Leu
                260                 265                 270

Phe Asp Tyr Ser Ser Ala Val Val Ile Tyr Glu Met Cys Val Glu Glu
            275                 280                 285

Pro Met Ala Thr Val Gln Asn Val Arg Asn Gln Glu Lys Leu Lys Tyr
        290                 295                 300

Pro Pro Tyr Pro Leu Ser Thr Ile Glu Leu Gln Lys Arg Ala Ser Arg
305                 310                 315                 320

Tyr Phe Arg Met Ser Ser Glu His Thr Met Lys Val Ala Glu Glu Leu
                    325                 330                 335

Tyr Gln Ala Gly Phe Ile Ser Tyr Pro Arg Thr Glu Thr Asp Asn Phe
                340                 345                 350

Ser Pro Asn Thr Asp Leu His Ser Ile Val His Glu Gln Val Ala His
            355                 360                 365

Pro Asn Trp Gly Thr Tyr Ala Gln Arg Leu Leu Asp Pro Glu Ala Arg
        370                 375                 380

Leu Trp Arg Asn Pro Ser Asn Gly Gly His Asp Asp Lys Ala His Pro
385                 390                 395                 400

Pro Ile His Pro Thr Lys Phe Ser Ala Gly Glu Thr Asn Trp Thr Asp
                    405                 410                 415

Asn His Lys Lys Leu Tyr Glu Leu Val Val Arg His Phe Leu Ala Cys
                420                 425                 430

Cys Ser Gln Pro Ala Val Gly Ala Glu Thr Thr Val Glu Ile Asp Ile
            435                 440                 445

Ala Gly Glu Gln Phe Asn Ala Ser Gly Arg Val Val Leu Ala Lys Asn
        450                 455                 460

Tyr Leu Asp Val Tyr Arg Phe Asp Ser Trp Gly Gly Thr Leu Leu Pro
465                 470                 475                 480

Thr Tyr Ile Ile Gly Gln Gln Ala Gly Ile Gly Thr Asp Ala Thr Met
                    485                 490                 495

His Asp His Ile Lys Lys Leu Leu Asp Arg Cys Tyr Ala Thr Lys Asp
                500                 505                 510

Ala Asn Thr Arg Phe Ser Pro Thr Asn Leu Gly Glu Ala Leu Val Met
            515                 520                 525

Gly Tyr Asp Glu Met Gly Tyr Glu Leu Trp Lys Pro Tyr Leu Arg Ser
        530                 535                 540

Met Met Glu Ala Asp Met Lys Ser Val Ser Ile Gly Thr Lys Ser Lys
545                 550                 555                 560
```

```
Ser Glu Val Leu Glu Asn Cys Leu Gln Gln Met Lys Ala Cys Phe Leu
                565                 570                 575

Asp Ala Arg Ala Asn Lys Val Lys Leu Phe Asp Ala Met Gly Thr Phe
            580                 585                 590

Phe Ala Arg Ser Ser Arg Pro Val Asn Glu Thr Gln Asn Ser Ile Glu
            595                 600                 605

Thr Val Arg Pro Cys Ala Ala Cys Asn Glu Ser Glu Met Phe Leu Lys
        610                 615                 620

Gln Arg Pro Cys Arg Asn Val Val Trp Leu Pro Arg Ser Leu Ser Gly
625                 630                 635                 640

Ala Ala Val Thr Asp Gln Val Cys Pro Thr Cys Ala Pro Gly Pro Val
                645                 650                 655

Tyr Lys Ile Gln Phe Lys Phe Arg Arg Asp Ile Pro Pro Asn Phe
                660                 665                 670

Asp Val Asp His Leu Gly Cys Ile Gly Gly Cys Asp Asp Ile Leu Lys
            675                 680                 685

Glu Leu Met Glu Leu Ser Arg Phe Gly Ser His Ser Gln Thr Ala Thr
        690                 695                 700

Pro Ala Arg Asn Gln Ser Gln Thr Ala Ser Gly Val Arg Gln Gly Ser
705                 710                 715                 720

Ser Arg Gln Asp Leu His Thr Ser Phe His Pro Ala Val Gln Phe Thr
                725                 730                 735

Asn Gly Gln Thr Pro Val Val Asn Pro Gln Gly Phe Arg Ser Thr His
            740                 745                 750

Thr Gln Ser Ser Gly Asn Ala Ser Asp Gly Lys Thr Met Trp Arg Thr
        755                 760                 765

Leu Arg Arg Gly Ala Val Ala Gly Val Gly Gly Ala Gly Ala Val Ala
770                 775                 780

Ala Gly Asn His Leu His Leu His Leu Gln Gly Gly Glu Ala Ala Pro
                785                 790                 795                 800

Lys Gly Glu Ala Gly Gly Ala Glu Asp Gly Met Leu Met Ala
            805                 810
```

<210> SEQ ID NO 31
<211> LENGTH: 910
<212> TYPE: PRT
<213> ORGANISM: Populus trichocarpa

<400> SEQUENCE: 31

```
Met Ile Lys Val Leu Asn Val Ala Glu Lys Pro Ser Val Ala Lys Ser
1               5                   10                  15

Val Ala Thr Ile Leu Ser Arg Asn Gln Leu Arg Val Arg Asp Gly Arg
            20                  25                  30

Ser Arg Tyr Asn Lys Ile Phe Glu Phe Asn Tyr Ser Ile Asn Gly Gln
        35                  40                  45

Gln Cys His Met Leu Val Thr Ser Val Thr Gly His Leu Met Glu Val
    50                  55                  60

Glu Phe Glu Asp Arg Phe Arg Lys Trp His Ser Cys Asp Pro Ala Asp
65                  70                  75                  80

Leu Tyr Thr Ala Pro Val Arg Lys Tyr Val Pro Glu Asp Lys Leu Asp
                85                  90                  95

Ile Lys Arg Thr Leu Glu Glu Glu Ala Arg Arg Cys His Trp Leu Val
            100                 105                 110

Leu Trp Leu Asp Cys Asp Arg Glu Gly Glu Asn Ile Ala Phe Glu Val
```

```
            115                 120                 125
Met Glu Val Cys Lys Gly Val Asn Arg Asn Leu Thr Ile Arg Arg Ala
    130                 135                 140

Arg Phe Ser Ala Leu Ile Glu Arg Asp Ile His Glu Ala Ala Gln Asn
145                 150                 155                 160

Leu Ile Ala Pro Asn Gln Trp Phe Ser Asp Ala Val Asp Ala Arg Gln
                165                 170                 175

Glu Ile Asp Leu Arg Ile Gly Ala Ser Phe Thr Arg Phe Gln Thr Met
            180                 185                 190

Leu Leu Arg Asp Arg Phe Val Ile Asp Ser Ala Gln Asp Asp Arg Asn
            195                 200                 205

Leu Val Leu Ser Tyr Gly Pro Cys Gln Phe Pro Thr Leu Gly Phe Val
    210                 215                 220

Val Glu Arg Tyr Trp Glu Ile Gln Ser His Pro Glu Glu Phe Trp
225                 230                 235                 240

Thr Ile Asn Cys Thr His Arg Ser Asp Glu Gly Leu Ala Ser Phe Asn
                245                 250                 255

Trp Met Arg Gly His Leu Phe Asp Tyr Thr Ser Ser Val Ile Leu Tyr
            260                 265                 270

Glu Met Cys Val Glu Glu Pro Thr Ala Thr Val Ser Asn Arg Asn His
    275                 280                 285

Gln Gln Glu Lys Leu Lys Tyr Pro Pro Tyr Pro Leu Ser Thr Ile Glu
290                 295                 300

Leu Glu Lys Arg Ala Ser Arg Tyr Phe Arg Met Ser Ser Glu Gln Thr
305                 310                 315                 320

Met Lys Val Ala Glu Asp Leu Tyr Gln Ala Gly Phe Ile Ser Tyr Pro
                325                 330                 335

Arg Thr Glu Thr Asp Ser Phe Ser Ser Arg Thr Asp Leu His Thr Ile
            340                 345                 350

Val Gln Glu His Gln Glu His Pro Val Trp Gly Ser Tyr Ala Gln Arg
            355                 360                 365

Leu Leu Asp Pro Gly Ala Gly Leu Trp Arg Asn Pro Ser Asn Gly Gly
    370                 375                 380

His Asp Asp Lys Ala His Pro Pro Ile His Pro Thr Lys Phe Ser Ala
385                 390                 395                 400

Gly Glu Ser Arg Trp Ser Gln Asp His His Arg Leu Tyr Glu Leu Val
                405                 410                 415

Val Arg His Phe Leu Ala Cys Val Ser Gln Pro Ala Val Gly Ala Glu
            420                 425                 430

Thr Val Val Glu Ile Asp Ile Ala Gly Glu Arg Phe Ser Ala Ser Gly
            435                 440                 445

Arg Val Ile Leu Ala Lys Asn Tyr Leu Asp Val Tyr Arg Phe Glu Ser
    450                 455                 460

Trp Gly Asp Ser Met Ile Pro Thr Tyr Leu Gln Gly Gln Gln Phe Ile
465                 470                 475                 480

Pro Ala Thr Leu Thr Leu Asp Ser Gly Val Thr Arg Pro Pro Leu
                485                 490                 495

Leu Ser Glu Ala Asp Leu Leu Ser Cys Met Asp Lys Ala Gly Ile Gly
            500                 505                 510

Thr Asp Ala Thr Met His Asp His Ile Lys Lys Leu Leu Asp Arg Phe
            515                 520                 525

Tyr Val Thr Lys Asp Ala Asn Thr Arg Phe Ser Pro Thr Asn Leu Gly
    530                 535                 540
```

Glu Ala Leu Val Met Gly Tyr Asp Asp Met Gly Tyr Glu Leu Trp Lys
545                 550                 555                 560

Pro Asn Leu Arg Ser Leu Met Glu Cys Asp Met Lys Glu Val Ser Val
                565                 570                 575

Gly Asn Lys Ser Lys Ala Glu Val Leu Ala Thr Cys Leu Gln Gln Met
            580                 585                 590

Lys Ala Cys Phe Leu Asp Ala Lys Val Asn Lys Val Lys Leu Leu Glu
        595                 600                 605

Ala Met Ala Ile Phe Phe Asn Arg Ser Asp Arg Ser Asn Gly Asp Asp
610                 615                 620

Ser Ser Ala Leu Gly Glu Asn Val Arg Pro Cys Gly Leu Cys Gln Glu
625                 630                 635                 640

Ala Asn Met Val Leu Lys Lys Asn Arg Asp Gly Asn Phe Met Val Gly
                645                 650                 655

Cys Ser Gly Phe Pro Gln Cys Arg Asn Ala Val Trp Leu Pro Gly Pro
            660                 665                 670

Val Leu Glu Ala Thr Ile Thr Asn Asn Ile Cys Asn Ser Cys Thr Pro
        675                 680                 685

Gly Pro Val Tyr Leu Ile Gln Phe Lys Phe Arg Gln Leu Glu Ile Pro
690                 695                 700

Pro Gly Phe Asn Val Asn His Leu Gly Cys Ile Gly Gly Cys Asp Glu
705                 710                 715                 720

Thr Leu Arg Gln Leu Ile Glu Ile Cys Gly Thr Gly Ser Arg Val Gln
                725                 730                 735

Gly Gly Asn Gly Pro Pro Thr Thr Pro Ser Asn Pro Gln Arg Ser
            740                 745                 750

Asn Ser Arg Gln Ala Pro Cys Ile Tyr Cys Tyr Gln Thr Gly His Ala
        755                 760                 765

Ser Thr Asp Cys Pro Ser Arg Ile Ser Ala Thr Arg His Val Gln Ser
770                 775                 780

His Gly Met Asn Gln Gln Asn Gly Glu Ser Ser Ile Pro Cys Ser Thr
785                 790                 795                 800

Cys Gly Thr Pro Cys Val Leu Arg Thr Ala Asn Thr Ala Asn Asn Arg
                805                 810                 815

Gly Arg Lys Phe Tyr Ser Cys Ser Ser Gln Ala Cys Asn Phe Phe Val
            820                 825                 830

Trp Glu Asp Asn Leu Asn Asn Gly Ser Ala Pro Arg Ser Ala Pro Arg
        835                 840                 845

Pro Asn Met Ser Asn Ser Ala Ser Asn Pro Ser Arg Arg Gly Gly Arg
        850                 855                 860

Gly Arg Gly Val Gln Asn Ala Gly Arg Ala Ala Asp Val Thr Phe Val
865                 870                 875                 880

Ser Ala Thr Gly Glu Pro Ile Ser Gly Arg Arg Cys Phe Val Cys Gly
                885                 890                 895

Asp Pro Ser His Phe Ala Asn Ala Cys Pro Ser Arg Gly Ser
            900                 905                 910

<210> SEQ ID NO 32
<211> LENGTH: 833
<212> TYPE: PRT
<213> ORGANISM: Ricinus communis

<400> SEQUENCE: 32

Met Ile Asn Val Leu Asn Val Ala Glu Lys Pro Ser Val Ala Lys Ser

-continued

```
1               5                   10                  15
Val Ala Thr Ile Leu Ser Arg Asn Gln Gln His Gly Leu Arg Val Arg
                20                  25                  30
Glu Gly Gln Ser Arg Tyr Asn Lys Ile Phe Glu Phe Asn Tyr Val Ile
                35                  40                  45
Asn Gly Gln Asn Cys His Met Leu Val Thr Ser Val Thr Gly His Leu
            50                  55                  60
Met Glu Leu Glu Phe Asp Asp Arg Phe Arg Lys Trp His Ser Cys Asp
65                  70                  75                  80
Pro Ala Asp Leu Tyr His Ala Pro Val Arg Lys Phe Val Pro Glu Asp
                85                  90                  95
Lys Thr Asn Ile Lys Arg Thr Leu Glu Glu Ala Arg Arg Cys Gln
                100                 105                 110
Trp Leu Ile Leu Trp Leu Asp Cys Asp Arg Glu Gly Glu Asn Ile Ala
                115                 120                 125
Phe Glu Val Val Asp Val Cys Arg Ser Ala Asn Arg Tyr Leu Thr Val
                130                 135                 140
Arg Arg Ala Arg Phe Ser Ala Leu Ile Asp Arg Glu Ile His Glu Ala
145                 150                 155                 160
Ala Gln Asn Leu Val Ser Pro Asn Gln Trp Phe Ser Asp Ala Val Asp
                165                 170                 175
Ala Arg Gln Glu Ile Asp Leu Arg Ile Gly Ala Ser Phe Thr Arg Phe
                180                 185                 190
Gln Thr Leu Leu Leu Arg Asp Lys Phe Val Ile Asp Ser Ala Gln Asp
                195                 200                 205
Asp Arg Asn Leu Val Leu Ser Tyr Gly Pro Cys Gln Phe Pro Thr Leu
                210                 215                 220
Gly Phe Ile Val Glu Arg Tyr Trp Glu Ile Gln Ser His Glu Ser Glu
225                 230                 235                 240
Glu Phe Trp Thr Ile Asn Cys Ser His Thr Ser Val Glu Gly Ile Ala
                245                 250                 255
Asn Phe Ser Trp Met Arg Gly His Leu Phe Asp Tyr Thr Ser Ala Val
                260                 265                 270
Ile Leu Tyr Glu Leu Cys Val Leu Glu Pro Thr Ala Thr Val Thr Lys
                275                 280                 285
Val Gln Gln Lys Glu Lys Gln Lys Tyr Pro Pro Tyr Pro Leu Ser Thr
                290                 295                 300
Ile Glu Leu Glu Lys Arg Ala Ser Arg Tyr Phe His Met Ser Ser Glu
305                 310                 315                 320
Gln Thr Met Lys Val Ala Glu Asp Leu Tyr Gln Ser Gly Phe Ile Ser
                325                 330                 335
Tyr Pro Arg Thr Glu Thr Asp Gly Phe Ser Ser Arg Thr Asp Leu His
                340                 345                 350
Thr Ile Val Arg Asp Gln Gln Ala His Pro Ile Trp Gly Ser Tyr Ala
                355                 360                 365
Gln Arg Leu Leu Asp Pro Gly Thr Gly Leu Trp Arg Asn Pro Ser Thr
                370                 375                 380
Gly Gly His Asp Asp Lys Ala His Pro Ile His Pro Thr Lys Phe
385                 390                 395                 400
Ser Pro Gly Glu Thr Gly Trp Ser Gln Asp His His Arg Val Tyr Glu
                405                 410                 415
Leu Val Val Arg His Phe Leu Ala Cys Val Ser Gln Pro Ala Val Gly
                420                 425                 430
```

```
Ala Glu Thr Thr Val Glu Ile Asp Ile Ala Gly Glu Gln Phe Ser Ala
        435                 440                 445

Ser Gly Arg Val Ile Leu Ala Lys Asn Tyr Leu Asp Val Tyr Arg Phe
450                 455                 460

Glu Ser Trp Gly Gly Ser Met Ile Pro Thr Tyr Val His Gly Gln Gln
465                 470                 475                 480

Phe Met Pro Thr Leu Thr Leu Asp Ser Gly Val Thr Arg Pro Pro
                485                 490                 495

Pro Leu Leu Ser Glu Ser Asp Leu Leu Ser Cys Met Asp Lys Ala Gly
                500                 505                 510

Ile Gly Thr Asp Ala Thr Met His Asp His Ile Lys Lys Leu Leu Asp
            515                 520                 525

Arg Phe Tyr Ala Thr Lys Asp Ala Asn Thr Arg Phe Ser Pro Thr Asn
        530                 535                 540

Leu Gly Glu Ala Leu Val Met Gly Tyr Asp Asp Met Gly Tyr Glu Leu
545                 550                 555                 560

Trp Lys Pro Asn Leu Arg Ser Met Met Glu Tyr Asp Met Lys Glu Val
                565                 570                 575

Ser Met Gly His Lys Ser Lys Ala Glu Val Leu Glu Thr Cys Leu Gln
            580                 585                 590

Gln Met Lys Thr Cys Phe Leu Asp Ala Arg Ile Asn Lys Val Lys Leu
        595                 600                 605

Leu Glu Ala Met Ala Val Phe Phe Glu Arg Ser Asp Arg Ser Ser Gly
610                 615                 620

Asn Asp Asn His Ala Thr Val Asp Ile Val Arg Gln Cys Gly Leu Cys
625                 630                 635                 640

Arg Glu Thr Asn Met Val Leu Arg Arg Asn Arg Asp Gly Asn Phe Met
                645                 650                 655

Val Gly Cys Met Gly Tyr Pro Gln Cys Arg Asn Ala Ile Trp Leu Pro
            660                 665                 670

Gly Pro Ile Ile Glu Ala Thr Val Thr Thr Ser Val Cys Asn Tyr Cys
        675                 680                 685

Thr Pro Gly Pro Val Tyr Leu Ile Gln Phe Lys Phe Arg Gln Leu Glu
        690                 695                 700

Ile Pro Pro Gly Phe Ser Val Asn His Leu Gly Cys Ile Gly Gly Cys
705                 710                 715                 720

Asp Asp Thr Leu Arg Gln Leu Thr Asp Ile Cys Gly Thr Gly Ser Arg
                725                 730                 735

Val Gln Ala Arg Ala Arg Ala Pro Asn Thr Thr Pro Ser Asn Ser Gln
            740                 745                 750

Gln Ser Asn Thr Arg Phe Ala Thr Cys Val His Cys His Gln Thr Gly
        755                 760                 765

His Ala Ser Ile Asp Cys Pro Leu Gln Leu Ser Gly Ser Arg Arg Val
        770                 775                 780

Gln Ser Arg Gly Thr Asn Glu Gln Met Gly Glu Ser Ser Val Thr Cys
785                 790                 795                 800

Gly Thr Cys Gly Thr Pro Cys Ala Leu Arg Thr Ala Asn Thr Ala Asn
                805                 810                 815

Asn Arg Gly Arg Lys Phe Tyr Ser Cys Pro Ser Gln Ser Cys Asn Phe
            820                 825                 830

Phe
```

```
<210> SEQ ID NO 33
<211> LENGTH: 860
<212> TYPE: PRT
<213> ORGANISM: Sorghum bicolor

<400> SEQUENCE: 33
```

| | | | | | | | | | | | | | | |
|---|---|---|---|---|---|---|---|---|---|---|---|---|---|---|
| Met | Gln | Pro | Gly | Gly | Gly | Ala | Ile | Arg | Val | Leu | Asn | Val | Ala | Glu |
| 1 | | | | 5 | | | | | 10 | | | | | 15 |
| Lys | Pro | Ser | Val | Ala | Lys | Ala | Val | Ala | Glu | Ile | Leu | Ser | Arg | Arg | Ser |
| | | | 20 | | | | | 25 | | | | | 30 | | |
| Met | Gln | Ser | Arg | Ala | Gly | Arg | Ser | Gln | Tyr | Asn | Arg | Ile | Phe | Glu | Phe |
| | | 35 | | | | | 40 | | | | | 45 | | | |
| Asn | Tyr | Ala | Ile | Asn | Gly | Arg | Ala | Cys | His | Met | Leu | Val | Thr | Ser | Val |
| 50 | | | | | 55 | | | | | 60 | | | | | |
| Thr | Gly | His | Leu | Met | Glu | Leu | Glu | Phe | Asp | Glu | Arg | Phe | Arg | Arg | Trp |
| 65 | | | | 70 | | | | | 75 | | | | | 80 | |
| His | Ser | Cys | Asp | Pro | Ala | Glu | Leu | Phe | His | Ala | Pro | Val | Arg | Lys | Ser |
| | | | 85 | | | | | 90 | | | | | 95 | | |
| Val | Pro | Gln | Asp | Lys | Gln | Ala | Ile | Lys | Gln | Thr | Leu | Glu | Glu | Glu | Ala |
| | | | 100 | | | | | 105 | | | | | 110 | | |
| Arg | Arg | Cys | Gln | Trp | Leu | Val | Leu | Trp | Leu | Asp | Cys | Asp | Arg | Glu | Gly |
| | | | 115 | | | | | 120 | | | | | 125 | | |
| Glu | Asn | Ile | Ala | Tyr | Glu | Val | Ile | Asp | Val | Cys | Thr | Gly | Ala | Asn | Ser |
| | 130 | | | | | 135 | | | | | 140 | | | | |
| His | Leu | Asn | Ile | Trp | Arg | Ala | Arg | Phe | Ser | Ala | Leu | Ile | Asp | Arg | Glu |
| 145 | | | | | 150 | | | | | 155 | | | | | 160 |
| Ile | His | Glu | Ser | Val | Gln | His | Leu | Gly | Arg | Pro | Asn | Lys | Leu | Phe | Ala |
| | | | | 165 | | | | | 170 | | | | | 175 | |
| Asp | Ala | Val | Asp | Ala | Arg | Gln | Glu | Ile | Asp | Leu | Arg | Ile | Gly | Ala | Ser |
| | | | 180 | | | | | 185 | | | | | 190 | | |
| Phe | Thr | Arg | Phe | Gln | Thr | Met | Leu | Leu | Lys | Asp | Ala | Phe | Val | Ile | Asn |
| | | 195 | | | | | 200 | | | | | 205 | | | |
| Val | Thr | Gly | Asp | Asp | Arg | Asn | Leu | Val | Leu | Ser | Tyr | Gly | Pro | Cys | Gln |
| | 210 | | | | | 215 | | | | | 220 | | | | |
| Phe | Pro | Thr | Leu | Gly | Phe | Ile | Val | Glu | Arg | Phe | Trp | Glu | Ile | Gln | Ala |
| 225 | | | | | 230 | | | | | 235 | | | | | 240 |
| His | Glu | Pro | Glu | Glu | Phe | Trp | Thr | Ile | Asn | Cys | Thr | His | Thr | Ser | Asp |
| | | | | 245 | | | | | 250 | | | | | 255 | |
| Glu | Gly | Thr | Ala | Ser | Phe | Gly | Trp | Ile | Arg | Gly | His | Leu | Phe | Asp | Tyr |
| | | | 260 | | | | | 265 | | | | | 270 | | |
| Ser | Cys | Ala | Ile | Ser | Ile | Tyr | Glu | Met | Cys | Val | Ser | Glu | Pro | Met | Ala |
| | | 275 | | | | | 280 | | | | | 285 | | | |
| Thr | Val | Gln | Asn | Val | Arg | Asn | Gln | Glu | Lys | Leu | Lys | Tyr | Pro | Pro | Tyr |
| | 290 | | | | | 295 | | | | | 300 | | | | |
| Pro | Leu | Ser | Thr | Val | Glu | Leu | Gln | Lys | Arg | Ala | Ser | Arg | Tyr | Phe | Arg |
| 305 | | | | | 310 | | | | | 315 | | | | | 320 |
| Met | Ser | Ser | Glu | His | Thr | Met | Lys | Val | Ala | Glu | Leu | Tyr | Gln | Ala |
| | | | | 325 | | | | | 330 | | | | | 335 |
| Gly | Phe | Ile | Ser | Tyr | Pro | Arg | Thr | Glu | Thr | Asp | Asn | Phe | Ser | Pro | Asn |
| | | | 340 | | | | | 345 | | | | | 350 | | |
| Thr | Asp | Leu | His | Ala | Ile | Val | Arg | Glu | Gln | Val | Asn | His | Pro | Val | Trp |
| | | | 355 | | | | | 360 | | | | | 365 | | |
| Gly | Ala | Tyr | Ala | Gln | Arg | Leu | Leu | Asn | Pro | Glu | Ala | Arg | Leu | Trp | Arg |
| | 370 | | | | | 375 | | | | | 380 | | | | |

```
Asn Pro Ser Asn Gly Gly His Asp Asp Lys Ala His Pro Pro Ile His
385                 390                 395                 400

Pro Thr Lys Phe Ser Glu Gly Glu Arg Asn Trp Ser Pro Asp His Ile
            405                 410                 415

Arg Leu Tyr Glu Leu Val Val Arg His Phe Leu Ala Cys Cys Ser Gln
        420                 425                 430

Pro Ala Val Gly Ala Glu Thr Thr Val Glu Ile Asp Ile Ala Gly Glu
    435                 440                 445

Gln Phe Asn Ala Ser Gly Arg Val Ile Leu Ala Lys Asn Tyr Leu Asp
450                 455                 460

Val Tyr Arg Phe Asp Ser Trp Gly Gly Thr Leu Leu Pro Thr Tyr Asn
465                 470                 475                 480

Ile Gly Gln Gln Phe Val Pro Thr Thr Leu Thr Leu Asp Ser Gly Val
                485                 490                 495

Thr Arg Pro Pro Pro Leu Leu Ala Glu Ala Asp Leu Leu Ser Cys Met
            500                 505                 510

Asp Lys Ala Gly Ile Gly Thr Asp Ala Thr Met His Asp His Ile Lys
        515                 520                 525

Lys Leu Leu Asp Arg Cys Tyr Ala Thr Lys Asp Glu Asn Thr Arg Phe
    530                 535                 540

Ser Pro Thr Asn Leu Gly Glu Ala Leu Val Met Gly Tyr Asp Glu Met
545                 550                 555                 560

Gly Tyr Glu Leu Trp Lys Pro Tyr Leu Arg Ser Met Met Glu Ala Asp
                565                 570                 575

Met Lys Ser Val Ser Met Gly Thr Lys Ser Lys Ser Glu Val Leu Glu
            580                 585                 590

Ser Cys Leu Gln Gln Met Lys Ala Cys Phe Leu Asp Ala Arg Val Asn
        595                 600                 605

Lys Ala Lys Leu Leu Asp Ala Met Gly Thr Phe Phe Ala Arg Ser Asn
    610                 615                 620

Arg Pro Ile Asn Glu Thr Gln Asn Pro Val Gly Val Val Arg Pro Cys
625                 630                 635                 640

Gly Ala Cys Asn Gly Ser Glu Met Val Leu Lys Arg Arg Val Thr Gly
                645                 650                 655

Glu Phe Met Val Gly Cys Arg Ser Tyr Pro Gln Cys Arg Asn Val Val
            660                 665                 670

Trp Leu Pro Gly Ser Leu Ser Glu Ala Ala Val Thr Asn Gln Val Cys
        675                 680                 685

Pro Ile Cys Ala Pro Gly Pro Val Tyr Lys Ile Gln Phe Lys Phe Arg
    690                 695                 700

Arg Arg Asp Ile Pro Pro Asn Phe Asp Val Asp His Leu Gly Cys Val
705                 710                 715                 720

Gly Gly Cys Asp Asp Ile Leu Lys Glu Leu Met Glu Leu Ser Arg Phe
                725                 730                 735

Gly Ser Arg Ser Gln Ala Ala Thr Pro Gly Gln Val Leu Cys Thr Ser
            740                 745                 750

Cys Gly Ala Ala Cys Ile Ser Leu Thr Ala Asn Thr Glu Ala Asn Arg
        755                 760                 765

Gly Arg Lys Phe Tyr Lys Cys Gln Asp Pro Gly Cys Gly Phe Phe Lys
    770                 775                 780

Trp Glu Asp Glu Leu Asp Asn Gly Thr Gly Arg Gly Arg Arg Gly Arg
785                 790                 795                 800

Gly Ser Ser Arg Gln Ala Thr Ala Ser Ala Ser Ala Gly Arg Arg Gly
```

```
                     805                 810                 815
Gly Gly Arg Arg Gly Arg Gly Arg Asn Ala Asp Gly Gly Met Phe Val
                820                 825                 830

Ser Ala Thr Gly Asp Thr Val Pro Gly Cys Cys Phe Thr Cys Gly Asp
                835                 840                 845

Pro Ser His Phe Ala Asn Ala Cys Pro Asn Arg Arg
                850                 855                 860

<210> SEQ ID NO 34
<211> LENGTH: 915
<212> TYPE: PRT
<213> ORGANISM: Zea mays

<400> SEQUENCE: 34

Met Gln Pro Asp Gly Gly Ala Ile Arg Val Leu Asn Val Ala Glu
1               5                   10                  15

Lys Pro Ser Val Ala Lys Ala Val Ala Glu Ile Leu Ser Arg Arg Ser
                20                  25                  30

Ala Gln Ser Arg Ala Gly Arg Ser Gln Tyr Asn Arg Ile Phe Glu Phe
            35                  40                  45

Asn Tyr Ala Ile Asn Gly Arg Ala Cys His Met Leu Val Thr Ser Val
50                  55                  60

Thr Gly His Leu Met Glu Leu Glu Phe Asp Asp Arg Phe Arg Arg Trp
65                  70                  75                  80

His Ser Cys Asp Pro Ala Glu Leu Phe His Ala Pro Val Arg Lys Ser
                85                  90                  95

Val Pro Gln Asp Lys Gln Ala Ile Lys Gln Thr Leu Glu Glu Glu Ala
                100                 105                 110

Arg Arg Cys Gln Trp Leu Val Leu Trp Leu Asp Cys Asp Arg Glu Gly
            115                 120                 125

Glu Asn Ile Ala Tyr Glu Val Ile Asp Val Cys Thr Arg Ala Asn Ser
130                 135                 140

His Leu Asn Ile Trp Arg Ala Arg Phe Ser Ala Leu Ile Asp Arg Glu
145                 150                 155                 160

Ile His Glu Ser Val Gln His Leu Gly Arg Pro Asn Lys Leu Phe Ala
                165                 170                 175

Asp Ala Val Asp Ala Arg Gln Glu Ile Asp Leu Arg Ile Gly Ala Ser
            180                 185                 190

Phe Thr Arg Phe Gln Thr Met Leu Leu Lys Asp Ala Phe Val Ile Asp
        195                 200                 205

Val Thr Gly Asp Glu Arg Ser Leu Val Leu Ser Tyr Gly Pro Cys Gln
210                 215                 220

Phe Pro Thr Leu Gly Phe Ile Val Glu Arg Phe Trp Glu Ile Gln Ala
225                 230                 235                 240

His Glu Pro Glu Glu Phe Trp Thr Ile Asn Cys Thr His Thr Ser Asp
                245                 250                 255

Glu Gly Thr Ala Ser Phe Gly Trp Ile Arg Gly His Leu Phe Asp Tyr
            260                 265                 270

Ser Cys Ala Ile Ser Ile Tyr Glu Met Cys Val Ser Glu Pro Met Ala
        275                 280                 285

Thr Val Gln Asn Val Arg Asn Gln Glu Lys Leu Lys Tyr Pro Pro Tyr
    290                 295                 300

Pro Leu Ser Thr Val Glu Leu Gln Lys Arg Ala Ser Arg Tyr Phe Arg
305                 310                 315                 320
```

```
Met Ser Ser Glu His Thr Met Lys Val Ala Glu Leu Tyr Gln Ala
                325                 330                 335

Gly Phe Ile Ser Tyr Pro Arg Thr Glu Thr Asp Asn Phe Ser Pro Asn
            340                 345                 350

Thr Asp Leu His Ala Ile Val Arg Glu Gln Val Asn His Pro Val Trp
            355                 360                 365

Gly Ala Tyr Ala Gln Arg Leu Leu Asn Pro Glu Ala Arg Leu Trp Arg
            370                 375                 380

Asn Pro Ser Asn Gly Gly His Asp Asp Lys Ala His Pro Pro Ile His
385                 390                 395                 400

Pro Thr Lys Phe Ser Glu Gly Glu Arg Asn Trp Ser Pro Asp His Thr
            405                 410                 415

Arg Leu Tyr Glu Phe Val Val Arg His Phe Leu Ala Cys Cys Ser Gln
            420                 425                 430

Pro Ala Val Gly Ala Glu Thr Thr Val Glu Ile Asp Ile Ala Gly Glu
            435                 440                 445

Gln Phe Asn Ala Ser Gly Arg Val Ile Leu Ala Lys Asn Tyr Leu Asp
            450                 455                 460

Val Tyr Arg Phe Asp Ser Trp Gly Gly Thr Leu Leu Pro Thr Tyr Asn
465                 470                 475                 480

Ile Gly Gln Gln Phe Val Pro Thr Thr Leu Thr Leu Asp Ser Gly Val
                485                 490                 495

Thr Arg Pro Pro Pro Leu Leu Ala Glu Ala Asp Leu Leu Ser Cys Met
            500                 505                 510

Asp Lys Ala Gly Ile Gly Thr Asp Ala Thr Met His Asp His Ile Lys
            515                 520                 525

Lys Leu Leu Asp Arg Cys Tyr Ala Thr Lys Asp Glu Asn Thr Arg Phe
530                 535                 540

Ser Pro Thr Asn Leu Gly Glu Ala Leu Val Met Gly Tyr Asp Glu Met
545                 550                 555                 560

Gly Tyr Glu Leu Trp Lys Pro Tyr Leu Arg Ser Met Met Glu Ala Asp
                565                 570                 575

Met Lys Ser Val Ser Val Gly Thr Lys Ser Lys Ser Glu Val Leu Glu
            580                 585                 590

Ser Cys Leu Gln Gln Met Lys Ala Cys Phe Leu Asp Ala Arg Val Lys
            595                 600                 605

Lys Ala Lys Leu Leu Asp Ala Met Gly Thr Phe Phe Ala Arg Ser Asn
            610                 615                 620

Arg Pro Ile Asn Glu Thr Gln Asn Pro Val Glu Val Arg Pro Cys
625                 630                 635                 640

Gly Ala Cys Asn Gly Ser Glu Met Leu Leu Lys Arg Arg Ala Ser Gly
                645                 650                 655

Glu Phe Met Val Gly Cys Arg Ser Tyr Pro Gln Cys Arg Asn Val Val
            660                 665                 670

Trp Leu Pro Gly Ser Leu Ser Glu Ala Ala Val Thr Asn Gln Val Cys
            675                 680                 685

Pro Ile Cys Ala Pro Gly Pro Val Tyr Lys Ile Gln Phe Lys Phe Arg
            690                 695                 700

Arg Arg Asp Ile Pro Pro Asn Phe Asp Val Asp His Leu Gly Cys Val
705                 710                 715                 720

Gly Gly Cys Asp Asp Ile Leu Lys Asp Leu Met Glu Ile Ser Arg Phe
                725                 730                 735

Gly Ser Arg Ser Gln Ala Ala Thr Pro Ala Arg Gly Pro Thr Pro Asn
```

```
            740                 745                 750
Gly Val Gly Gln Gly Thr Pro Arg Gln Asp Leu His Thr Ile Phe Arg
        755                 760                 765

Pro Ala Ser Gln Leu Asn Asn Asp Asn Pro Ser Val Met His Ser Gln
770                 775                 780

Gly Phe Arg Ser Thr His Thr Gln Asn Pro Ser Asn Ala Ser Asp Ala
785                 790                 795                 800

Gly Gln Val Leu Cys Thr Ser Cys Gly Ala Leu Cys Ile Ser Arg Ile
                805                 810                 815

Ala Asn Thr Glu Ala Asn Arg Gly Arg Arg Phe Tyr Lys Cys Gln Asp
            820                 825                 830

Pro Gly Cys Gly Phe Phe Lys Trp Glu Asp Glu Val Asp Asn Gly Thr
        835                 840                 845

Gly Arg Gly Arg Arg Gly Arg Gly Ser Ser Arg Gln Ala Ser Ala Ser
    850                 855                 860

Ala Ser Ala Gly Arg Arg Gly Gly Arg Arg Gly Arg Gly Arg Gly Asn
865                 870                 875                 880

Ala Asp Gly Gly Met Phe Val Ser Ala Thr Gly Asp Thr Val Leu Gly
                885                 890                 895

Cys Cys Phe Asn Cys Gly Asp Pro Ser His Phe Ala Asn Ala Cys Pro
            900                 905                 910

Asn Arg Arg
        915

<210> SEQ ID NO 35
<211> LENGTH: 930
<212> TYPE: PRT
<213> ORGANISM: Thellungiella halophila

<400> SEQUENCE: 35

Met Ser Arg Arg Gly Gly Gly Pro Val Thr Val Leu Asn Val Ala Glu
1               5                   10                  15

Lys Pro Ser Val Ala Lys Ser Val Ala Gly Ile Leu Ser Arg Gly Ser
            20                  25                  30

Phe Arg Thr Arg Glu Gly Arg Ser Arg Tyr Asn Lys Ile Phe Glu Phe
        35                  40                  45

Asp Tyr Ala Ile Asn Gly Gln Pro Cys Arg Met Leu Met Thr Ser Val
    50                  55                  60

Ile Gly His Leu Met Glu Leu Glu Phe Ser Asp Arg Phe Arg Lys Trp
65                  70                  75                  80

His Ser Cys Asp Pro Ala Asp Leu Tyr Gln Ala Pro Val Met Lys His
                85                  90                  95

Val Pro Glu Asp Lys Lys Asp Ile Lys Lys Thr Leu Glu Glu Glu Ala
            100                 105                 110

Arg Lys Ser Asp Trp Leu Val Leu Trp Leu Asp Cys Asp Arg Glu Gly
        115                 120                 125

Glu Asn Ile Ala Phe Glu Val Val Asp Val Cys Arg Ala Val Lys Gln
    130                 135                 140

Asn Leu Phe Ile Arg Arg Ala His Phe Ser Ala Leu Ile Asp Arg Glu
145                 150                 155                 160

Ile His Glu Ala Ala Gln Asn Leu Arg Glu Pro Asn Gln Leu Phe Ala
                165                 170                 175

Gln Ala Val Asp Ala Arg Gln Glu Ile Asp Leu Arg Ile Gly Ala Ser
            180                 185                 190
```

```
Phe Thr Arg Phe Gln Thr Met Leu Leu Lys Asp Arg Phe Ser Ile Asp
            195                 200                 205

Ser Thr Gly Gly Glu Glu Arg Ser Arg Val Ile Ser Tyr Gly Pro Cys
        210                 215                 220

Gln Phe Pro Thr Leu Gly Phe Ile Val Glu Arg Tyr Trp Glu Ile Gln
225                 230                 235                 240

Ala His Glu Pro Glu Glu Phe Trp Thr Ile Asn Cys Ser His Glu Ser
                245                 250                 255

Glu Glu Gly Leu Ala Thr Phe Asn Trp Met Arg Gly His Leu Phe Asp
            260                 265                 270

Tyr Val Ser Ala Val Ile Leu Tyr Glu Met Cys Val Leu Glu Pro Thr
        275                 280                 285

Ala Thr Val Met Asn Val Pro His Pro Arg Glu Lys Phe Lys Tyr Pro
        290                 295                 300

Pro Tyr Pro Leu Asn Thr Ile Glu Leu Glu Lys Arg Ala Ser Arg Tyr
305                 310                 315                 320

Phe Arg Leu Ser Ser Glu His Thr Met Lys Val Ala Glu Glu Leu Tyr
                325                 330                 335

Gln Ala Gly Phe Ile Ser Tyr Pro Arg Thr Glu Thr Asp Ser Phe Ser
            340                 345                 350

Ser Arg Thr Asp Leu Arg Ala Met Val Glu Glu Gln Thr Arg His Pro
        355                 360                 365

Ala Trp Gly Pro Tyr Ala Gln Arg Leu Leu Glu Pro Glu Gly Gly His
        370                 375                 380

Trp Arg Asn Pro Gly Asn Gly Gly His Asp Asp Lys Ala His Pro Pro
385                 390                 395                 400

Ile His Pro Thr Lys Phe Ser Ser Gly Glu Ser Asn Trp Ser Arg Asp
                405                 410                 415

His Leu Asn Val Tyr Glu Leu Val Val Arg His Tyr Leu Ala Cys Val
            420                 425                 430

Ser Gln Pro Ala Ile Ala Ala Glu Thr Thr Val Glu Ile Asp Ile Ala
        435                 440                 445

Gly Glu Arg Phe Ser Ala Ser Gly Arg Ala Ile Leu Ala Lys Asn Tyr
450                 455                 460

Leu Glu Val Tyr Arg Phe Glu Ser Trp Gly Gly Ser Val Ile Pro Val
465                 470                 475                 480

Tyr Glu Lys Gly Gln Gln Phe Ile Pro Thr Arg Leu Thr Leu Asp Ser
                485                 490                 495

Ala Val Thr Arg Pro Pro Leu Leu Ser Glu Ala Asp Leu Leu Ser
            500                 505                 510

Cys Met Asp Lys Ala Gly Ile Gly Thr Asp Ala Thr Met His Asp His
        515                 520                 525

Ile Lys Lys Leu Leu Asp Arg Gly Tyr Ala Thr Lys Asp Ala Asn Thr
530                 535                 540

Arg Phe Ser Pro Thr Asn Leu Gly Glu Ala Leu Val Met Gly Tyr Asp
545                 550                 555                 560

Asp Met Gly Tyr Glu Leu Trp Lys Pro Asn Leu Arg Ala Ile Met Glu
                565                 570                 575

His Asp Met Asn Glu Val Ser Val Gly Ser Lys Thr Lys Ala Glu Val
            580                 585                 590

Leu Gln Thr Cys Leu Gln Gln Met Lys Ala Cys Phe Leu Asp Ala Arg
        595                 600                 605

Val Lys Lys Ala Lys Leu Leu Glu Thr Met Thr Ile Phe Phe Glu Arg
```

```
                610               615              620
Ser Asn Asn Thr Asp Glu Gly Glu Asn Gln Thr Ala Gly Glu Val Val
625                 630                 635                 640

Arg Arg Cys Asn Leu Cys His Glu Ser Asp Met Ala Leu Arg Lys Asn
                645                 650                 655

Arg Asp Gly Asn Phe Met Val Gly Cys Met Ser Tyr Pro Gln Cys Arg
            660                 665                 670

Asn Ala Val Trp Leu Pro Gly Pro Thr Leu Glu Ala Ser Val Thr Ala
                675                 680                 685

Asp Val Cys Gln Ser Cys Gly Pro Ala Pro Val Tyr Lys Ile Arg Phe
            690                 695                 700

Lys Phe Arg Gln Ile Gly Ile Pro Pro Gly Phe Asp Thr Asn His Leu
705                 710                 715                 720

Gly Cys Val Gly Gly Cys Asp Asp Ile Leu Lys Gln Leu Ile Asp Ile
                725                 730                 735

Cys Gly Thr Gly Ser Arg Ser Gln Ala Arg Thr Ala Pro Gly Ala Ser
            740                 745                 750

Ser Asn Asn Phe Gln Gly Gly Asn Ile Arg Gln Asn Thr Cys Ile
            755                 760                 765

His Cys Gln Gln Arg Gly His Thr Ser Ala Asn Cys Pro Ser Arg Ile
            770                 775                 780

Ser Gly Ser Arg Asn Pro Arg Pro Thr Thr Gly Thr Asn Pro Gly Asn
785                 790                 795                 800

Asp Glu Thr Thr Val Ser Cys Asn Thr Cys Gly Thr Pro Cys Ala Leu
                805                 810                 815

Arg Thr Ala Asn Thr Glu Ala Asn Arg Gly Arg Arg Phe Phe Ser Cys
            820                 825                 830

Pro Ser Gln Gly Cys Asn Phe Ala Trp Glu Asp Ser Ile Ser Asn
            835                 840                 845

Gly Ser Gly Asn Ala Thr Ala Gly Ser Asn Ser Gly Gly Ser Gly Arg
850                 855                 860

Arg Gly Arg Ala Arg Gly Arg Gly Asn Arg Gly Gly Gln Ser Gly Gly
865                 870                 875                 880

Ala Arg Gly Gly Gly Gly Arg Gly Gly Gly Thr Ser Phe Val
            885                 890                 895

Ser Ala Thr Gly Glu Pro Val Ser Gly Arg Arg Cys Phe Ser Cys Gly
                900                 905                 910

Asp Pro Ser His Phe Ala Asn Ala Cys Pro Asn Arg Asn Ser Asn Gly
            915                 920                 925

Asn Phe
930

<210> SEQ ID NO 36
<211> LENGTH: 919
<212> TYPE: PRT
<213> ORGANISM: Capsella rubella

<400> SEQUENCE: 36

Met Ser Arg Arg Gly Gly Gly Pro Val Thr Val Leu Asn Val Ala Glu
1               5                   10                  15

Lys Pro Ser Val Ala Lys Ser Val Ala Gly Ile Leu Ser Arg Gly Ser
                20                  25                  30

Phe Arg Thr Arg Glu Gly Arg Ser Arg Tyr Asn Lys Ile Phe Glu Phe
            35                  40                  45
```

```
Asp Tyr Ala Ile Asn Gly Gln Pro Cys Arg Met Leu Met Thr Ser Val
    50              55                  60

Ile Gly His Leu Met Glu Leu Glu Phe Ser Asp Arg Tyr Arg Lys Trp
65              70                  75                  80

His Ser Cys Asp Pro Ala Asp Leu Tyr Gln Ala Pro Val Met Lys His
                85                  90                  95

Val Pro Glu Asp Lys Arg Asp Ile Lys Lys Thr Leu Glu Glu Glu Ala
            100                 105                 110

Arg Lys Ser Asp Trp Leu Val Leu Trp Leu Asp Cys Asp Arg Glu Gly
        115                 120                 125

Glu Asn Ile Ala Phe Glu Val Val Asp Val Cys Arg Ala Val Lys His
    130                 135                 140

Asn Leu Phe Ile Arg Arg Ala His Phe Ser Ala Leu Ile Asp Arg Glu
145                 150                 155                 160

Ile His Glu Ala Val Gln Asn Leu Arg Asp Pro Asn Gln Leu Phe Ala
                165                 170                 175

Glu Ala Val Asp Ala Arg Gln Glu Ile Asp Leu Arg Ile Gly Ala Ser
            180                 185                 190

Phe Thr Arg Phe Gln Thr Met Leu Leu Arg Asp Arg Phe Ala Ile Asp
        195                 200                 205

Ser Thr Gly Glu Glu Arg Ser Arg Val Ile Ser Tyr Gly Pro Cys Gln
    210                 215                 220

Phe Pro Thr Leu Gly Phe Ile Val Glu Arg Tyr Trp Glu Ile Gln Ala
225                 230                 235                 240

His Glu Pro Glu Glu Phe Trp Thr Ile Asn Cys Ser His Gln Ser Glu
                245                 250                 255

Glu Gly Ile Ala Thr Phe Asn Trp Met Arg Gly His Leu Phe Asp Tyr
            260                 265                 270

Ala Ser Ala Val Ile Leu Tyr Glu Met Cys Val Glu Glu Pro Thr Ala
        275                 280                 285

Thr Val Met Asn Val Pro His Pro Arg Glu Arg Phe Lys Tyr Pro Pro
    290                 295                 300

Tyr Pro Leu Asn Thr Ile Glu Leu Glu Lys Arg Ala Ser Arg Tyr Phe
305                 310                 315                 320

Arg Leu Ser Ser Glu His Thr Met Lys Val Ala Glu Glu Leu Tyr Gln
                325                 330                 335

Ala Gly Phe Ile Ser Tyr Pro Arg Thr Glu Thr Asp Ala Phe Ser Ser
            340                 345                 350

Arg Thr Asp Leu Arg Ala Met Val Glu Glu Gln Thr Arg His Pro Glu
        355                 360                 365

Trp Gly Ala Tyr Ala Gln Arg Leu Leu Glu Pro Glu Gly Gly Leu Trp
    370                 375                 380

Arg Asn Pro Gly Asn Gly Gly His Asp Asp Lys Ala His Pro Pro Ile
385                 390                 395                 400

His Pro Thr Lys Phe Ser Ser Gly Glu Ser Asn Trp Ser Arg Asp His
                405                 410                 415

Leu Asn Val Tyr Glu Leu Val Val Arg His Tyr Leu Ala Cys Val Ser
            420                 425                 430

Gln Pro Ala Val Ala Ala Glu Thr Val Glu Ile Asp Ile Ser Gly
        435                 440                 445

Glu Arg Phe Ser Ala Ser Gly Arg Ala Ile Leu Ala Lys Asn Tyr Leu
450                 455                 460

Glu Val Tyr Arg Phe Glu Ser Trp Gly Gly Ser Val Ile Pro Val Tyr
```

-continued

```
            465                 470                 475                 480
Glu Lys Gly Gln Gln Phe Ile Pro Thr Ser Leu Thr Leu Asp Ser Ala
                        485                 490                 495

Val Thr Arg Pro Pro Leu Leu Cys Glu Ala Asp Leu Leu Ser Cys
                500                 505                 510

Met Asp Lys Ala Gly Ile Gly Thr Asp Ala Thr Met His Asp His Ile
            515                 520                 525

Lys Lys Leu Leu Asp Arg Gly Tyr Ala Thr Lys Asp Ala Asn Thr Arg
        530                 535                 540

Phe Ser Pro Thr Asn Leu Gly Glu Ala Leu Val Met Gly Tyr Asp Asp
545                 550                 555                 560

Met Gly Tyr Glu Leu Trp Lys Pro Asn Leu Arg Ala Ile Met Glu His
                565                 570                 575

Asp Met Asn Glu Val Ser Val Gly Arg Lys Thr Lys Ala Glu Val Leu
                580                 585                 590

Glu Thr Cys Leu Gln Gln Met Lys Ala Cys Phe Leu Asp Ala Arg Val
            595                 600                 605

Lys Lys Ser Lys Leu Leu Glu Ala Met Thr Ile Phe Phe Glu Arg Ser
        610                 615                 620

Asn Asn Thr Asp Glu Gly Glu Asn Gln Thr Ala Gly Glu Val Val Arg
625                 630                 635                 640

Arg Cys Asn Leu Cys Asn Glu Ser Asp Met Ala Leu Arg Lys Asn Arg
                645                 650                 655

Asp Gly Asn Phe Met Val Gly Cys Met Asn Tyr Pro Gln Cys Arg Asn
            660                 665                 670

Ala Val Trp Leu Pro Gly Pro Thr Leu Glu Ala Ser Val Thr Thr Asn
        675                 680                 685

Val Cys Gln Ser Cys Gly Pro Gly Pro Val Tyr Lys Ile Leu Phe Lys
            690                 695                 700

Phe Arg Gln Ile Gly Ile Pro Pro Gly Phe Glu Val Asn His Leu Gly
705                 710                 715                 720

Cys Val Gly Gly Cys Asp Gly Ile Leu Lys Gln Leu Ile Asp Ile Cys
                725                 730                 735

Gly Thr Gly Ser Arg Ser Gln Ala Arg Arg Ala Pro Asp Thr Val Pro
            740                 745                 750

Pro Asn Asn Ile Arg Gly Ser Asn Thr Arg Gln Ser Asn Val Cys Ile
        755                 760                 765

His Cys Gln Gln Arg Gly His Ala Ser Ser Asn Cys Pro Ser Arg Val
        770                 775                 780

Ser Ala Ser Arg Asn Ser Arg Pro Thr Gly Thr Asn Pro Arg Asn Asp
785                 790                 795                 800

Glu Ser Thr Val Ser Cys Asn Thr Cys Gly Thr Gln Cys Val Leu Arg
                805                 810                 815

Thr Ala Asn Thr Glu Ala Asn Arg Gly Arg Gln Phe Phe Ser Cys Pro
            820                 825                 830

Thr Gln Gly Cys Ser Phe Phe Ala Trp Glu Asp Gly Ile Ser Asn Ser
        835                 840                 845

Ser Gly Asn Ala Thr Thr Gly Ser Asn Ser Gly Gly Ser Gly Arg Arg
        850                 855                 860

Gly Asn Arg Gly Arg Gly Arg Gly Arg Gly Gln Ser Gly Gly
865                 870                 875                 880

Arg Arg Gly Ser Gly Thr Ser Phe Val Ser Ala Thr Gly Glu Pro Val
                885                 890                 895
```

-continued

```
Ser Gly Ile Arg Cys Phe Ser Cys Gly Asp Pro Ser His Phe Ala Asn
                900                 905                 910
Ala Cys Pro Asn Arg Asn Ser
        915

<210> SEQ ID NO 37
<211> LENGTH: 921
<212> TYPE: PRT
<213> ORGANISM: Brassica rapa

<400> SEQUENCE: 37

Met Ser Arg Arg Gly Gly Gly Pro Val Thr Val Leu Asn Val Ala Glu
1               5                   10                  15
Lys Pro Ser Val Ala Lys Ser Val Ala Gly Ile Leu Ser Arg Gly Ser
                20                  25                  30
Phe Arg Thr Arg Glu Gly Arg Ser Arg Tyr Asn Lys Ile Phe Glu Phe
            35                  40                  45
Asp Tyr Ala Ile Asn Gly Gln Pro Cys Arg Met Met Met Thr Ser Val
        50                  55                  60
Ile Gly His Leu Met Glu Leu Glu Phe Ala Asp Arg Phe Arg Lys Trp
65                  70                  75                  80
His Ser Cys Asp Pro Ala Asp Leu Tyr Gln Ala Pro Val Met Lys His
                85                  90                  95
Val Pro Glu Asp Lys Lys Asp Ile Lys Lys Thr Leu Glu Glu Glu Ala
                100                 105                 110
Arg Arg Ser Asp Trp Leu Val Leu Trp Leu Asp Cys Asp Arg Glu Gly
            115                 120                 125
Glu Asn Ile Ala Phe Glu Val Val Asp Val Cys Arg Ala Val Lys Gln
        130                 135                 140
Asn Leu Tyr Ile Arg Arg Ala His Phe Ser Ala Leu Ile Asp Arg Glu
145                 150                 155                 160
Ile His Glu Ala Val Gln Asn Leu Arg Glu Pro Asn Gln Leu Phe Ala
                165                 170                 175
Gln Ala Val Asp Ala Arg Gln Glu Ile Asp Leu Arg Ile Gly Ala Ser
                180                 185                 190
Phe Thr Arg Phe Gln Thr Met Leu Leu Lys Asp Arg Phe Val Ile Asp
            195                 200                 205
Ser Thr Gly Asp Glu Glu Arg Ser Arg Val Ile Ser Tyr Gly Pro Cys
        210                 215                 220
Gln Phe Pro Thr Leu Gly Phe Ile Val Glu Arg Tyr Trp Glu Ile Gln
225                 230                 235                 240
Ala His Glu Pro Glu Glu Phe Trp Thr Ile Asn Cys Ser His Glu Ser
                245                 250                 255
Glu Glu Gly Leu Ala Thr Phe Asn Trp Met Arg Gly His Leu Phe Asp
                260                 265                 270
Tyr Ala Ser Ala Ala Ile Leu Tyr Glu Met Cys Val Leu Glu Pro Thr
            275                 280                 285
Ala Thr Val Met Asn Val Pro His Pro Arg Glu Lys Phe Lys Tyr Pro
        290                 295                 300
Pro Tyr Pro Leu Asn Thr Ile Glu Leu Glu Lys Arg Ala Ser Arg Tyr
305                 310                 315                 320
Phe Arg Leu Ser Ser Glu His Thr Met Lys Val Ala Glu Glu Leu Tyr
                325                 330                 335
Gln Ala Gly Phe Ile Ser Tyr Pro Arg Thr Glu Thr Asp Ser Phe Ser
```

-continued

```
                340             345             350
Ser Arg Thr Asp Leu Arg Ala Met Val Glu Glu Gln Thr Arg His Pro
            355             360             365

Ala Trp Gly Pro Tyr Ala Gln Arg Leu Leu Glu Pro Glu Gly Gly Leu
            370             375             380

Trp Arg Asn Pro Gly Asn Gly His Asp Asp Lys Ala His Pro Pro
385             390             395             400

Ile His Pro Thr Lys Phe Ser Ser Gly Glu Ser Asn Trp Ser Arg Asp
            405             410             415

His Leu Asn Val Tyr Glu Leu Val Arg His Tyr Leu Ala Cys Val
            420             425             430

Ser Gln Pro Ala Val Ala Ala Glu Thr Thr Val Glu Ile Asp Ile Ala
            435             440             445

Gly Glu Arg Phe Ser Ala Ser Gly Arg Ala Ile Leu Ala Lys Asn Tyr
            450             455             460

Leu Glu Val Tyr Arg Phe Glu Ser Trp Gly Gly Ser Met Ile Pro Val
465             470             475             480

Tyr Glu Lys Gly Gln Gln Phe Ile Pro Thr Arg Leu Thr Leu Asp Ser
            485             490             495

Ala Val Thr Arg Pro Pro Leu Leu Cys Glu Ala Asp Leu Leu Ser
            500             505             510

Cys Met Asp Lys Ala Gly Ile Gly Thr Asp Ala Thr Met His Asp His
            515             520             525

Ile Lys Lys Leu Leu Asp Arg Gly Tyr Ala Thr Lys Asp Ala Asn Thr
            530             535             540

Arg Phe Ser Pro Thr Asn Leu Gly Glu Ala Leu Val Met Gly Tyr Asp
545             550             555             560

Asp Met Gly Tyr Glu Leu Trp Lys Pro Asn Leu Arg Ala Ile Met Glu
            565             570             575

His Asp Met Asn Glu Val Ser Val Gly Asn Lys Thr Lys Ala Glu Val
            580             585             590

Leu Glu Thr Cys Leu Gln Gln Met Lys Ala Cys Phe Leu Asp Ala Arg
            595             600             605

Val Lys Lys Thr Lys Leu Leu Glu Ala Met Thr Ile Phe Phe Glu Arg
            610             615             620

Ser Asn Asn Ser Asp Glu Gly Glu Asn Gln Thr Ala Gly Glu Val Val
625             630             635             640

Arg Arg Cys Asn Leu Cys His Glu Ser Asp Met Ala Leu Arg Lys Asn
            645             650             655

Gln Asp Gly Asn Phe Met Val Gly Cys Met Ser Tyr Pro Gln Cys Arg
            660             665             670

Asn Ala Val Trp Leu Pro Gly Pro Thr Leu Glu Ala Ser Val Thr Thr
            675             680             685

Asp Thr Cys Gln Ser Cys Gly Pro Gly Val Tyr Lys Ile Arg Phe
            690             695             700

Lys Phe Arg Gln Ile Arg Ile Pro Pro Gly Phe Asp Val Asn His Leu
705             710             715             720

Gly Cys Val Gly Gly Cys Asp Asp Val Leu Lys Gln Leu Ile Asp Ile
            725             730             735

Cys Gly Thr Gly Ser Arg Ser Gln Ala Arg Ala Ala Pro Gly Ala Thr
            740             745             750

Pro Asn Asn Val Arg Gly Ser Asn Ile Arg Gln Asn Asn Val Cys Ile
            755             760             765
```

-continued

```
His Cys Gln Gln Gly Gly His Thr Ser Ala Asn Cys Pro Thr Arg Ala
    770                 775                 780

Ser Gly Tyr Arg Asn Pro Arg Ala Thr Gly Thr Ala Asn Pro Arg Asn
785                 790                 795                 800

Asn Glu Thr Thr Val Ser Cys Thr Thr Cys Gly Thr Pro Cys Ala Ile
                805                 810                 815

Arg Thr Ala Asn Thr Glu Ala Asn Arg Gly Arg Lys Phe Tyr Ser Cys
                820                 825                 830

Pro Ser Gln Gly Cys Asn Phe Phe Thr Trp Glu Asp Ser Ile Ser Asn
            835                 840                 845

Gly Thr Gly Asn Ala Thr Thr Gly Ser Asn Ser Gly Ser Gly Arg
    850                 855                 860

Arg Gly Arg Gly Gly Arg Gly Asn Arg Gly Gly Gln Arg Gly
865                 870                 875                 880

Gly Gly Arg Gly Gly Gly Thr Ser Phe Val Ser Ala Thr Gly Glu
                885                 890                 895

Pro Val Ser Gly Arg Arg Cys Phe Ser Cys Gly Asp Pro Ser His Phe
            900                 905                 910

Ala Asn Ala Cys Pro Asn Arg Asn Ser
            915                 920

<210> SEQ ID NO 38
<211> LENGTH: 909
<212> TYPE: PRT
<213> ORGANISM: Gossypium raimondii

<400> SEQUENCE: 38

Met Ser Gly Thr Ile Lys Val Leu Asn Val Ala Glu Lys Pro Ser Val
1               5                   10                  15

Ala Lys Ser Val Ser Gly Phe Leu Ser Arg Asn Gln Ala Leu Arg Val
                20                  25                  30

Arg Asp Gly Arg Ser Arg Tyr Asn Arg Ile Phe Glu Phe Asn Tyr Ser
            35                  40                  45

Ile Arg Gly Gln Pro Cys His Met Leu Phe Thr Ser Val Thr Gly His
    50                  55                  60

Leu Met Glu Leu Glu Phe Glu Asp Arg Phe Arg Lys Trp His Ser Cys
65              70                  75                  80

Asp Pro Leu Asp Leu Tyr His Ala Pro Val Arg Lys Phe Val Pro Glu
                85                  90                  95

Asp Lys Leu Asp Ile Lys Arg Thr Leu Glu Glu Glu Ala Arg Arg Cys
            100                 105                 110

Gln Trp Leu Val Leu Trp Leu Asp Cys Asp Arg Glu Gly Glu Asn Ile
        115                 120                 125

Ala Phe Glu Val Ile Asn Val Cys Arg Ala Val Asn Arg His Leu Thr
    130                 135                 140

Ile Arg Arg Ala Arg Phe Ser Ala Leu Ile Asp Arg Glu Ile His His
145                 150                 155                 160

Ala Met Gln Asn Leu Ile Asp Pro Asn Pro Trp Phe Ser Asp Ala Val
                165                 170                 175

Asp Ala Arg Gln Glu Ile Asp Leu Arg Ile Gly Ala Ser Phe Thr Arg
            180                 185                 190

Phe Gln Thr Met Leu Leu Arg Asp Lys Phe Val Ile Asp Ser Ala Thr
        195                 200                 205

Asp Asp Arg Asn Leu Val Leu Ser Tyr Gly Pro Cys Gln Phe Pro Thr
```

-continued

```
            210                 215                 220
Leu Gly Phe Val Val Glu Arg Tyr Trp Glu Val Gln Ser His Glu Pro
225                 230                 235                 240

Glu Glu Phe Trp Thr Ile Asn Cys Ser His Arg Ser Asp Glu Gly Val
                245                 250                 255

Ala Thr Phe Asn Trp Met Arg Gly His Leu Phe Asp Tyr Thr Cys Ala
                260                 265                 270

Val Ile Val Tyr Glu Met Cys Val Gln Glu Pro Thr Ala Thr Val Thr
                275                 280                 285

Lys Val Gln His Lys Glu Lys Leu Lys Tyr Pro Pro Tyr Pro Leu Asn
    290                 295                 300

Thr Ile Glu Leu Glu Lys Arg Ala Ser Arg Tyr Phe Arg Met Ser Ser
305                 310                 315                 320

Glu His Thr Met Lys Val Ala Glu Glu Leu Tyr Gln Ala Gly Phe Ile
                325                 330                 335

Ser Tyr Pro Arg Thr Glu Thr Asp Cys Phe Ser Ser Arg Thr Asp Leu
                340                 345                 350

His Ala Ile Val Gln Glu Gln Gln Gly His Pro Asp Trp Gly Ser Tyr
            355                 360                 365

Ala Gln Arg Leu Leu Asp Pro Glu Thr Gly Leu Trp Arg Asn Pro Gly
        370                 375                 380

Ser Gly His Asp Asp Lys Ala His Pro Ile His Pro Thr Lys
385                 390                 395                 400

Phe Ser Thr Gly Glu His Gly Trp Ser Gln Asp His Arg Thr Leu Tyr
                405                 410                 415

Glu Leu Val Val Arg His Phe Leu Ala Cys Val Ser Gln Pro Ala Val
                420                 425                 430

Gly Ala Glu Thr Thr Val Glu Ile Asp Ile Ala Gly Leu Phe Ser
            435                 440                 445

Ala Ser Gly Arg Val Ile Leu Glu Arg Asn Tyr Leu Asp Val Tyr Arg
    450                 455                 460

Tyr Glu Ser Trp Gly Gly Ser Met Ile Pro Thr Tyr Thr Val Gly Gln
465                 470                 475                 480

Gln Phe Val Pro Ala Ser Leu Thr Leu Asp Thr Gly Val Thr Arg Pro
                485                 490                 495

Pro Pro Leu Leu Ser Glu Ala Asp Leu Leu Ser Cys Met Asp Lys Ala
                500                 505                 510

Gly Ile Gly Thr Asp Ala Thr Met His Asp His Ile Lys Lys Leu Leu
            515                 520                 525

Asp Arg Phe Tyr Ala Thr Lys Asp Ser Asn Thr Arg Phe Ser Pro Thr
        530                 535                 540

Asn Leu Gly Glu Ala Leu Val Met Gly Tyr Asp Asp Met Gly Tyr Glu
545                 550                 555                 560

Leu Trp Lys Pro Asn Leu Arg Ser Met Met Glu Phe Asp Met Lys Glu
                565                 570                 575

Val Ser Val Gly Asn Lys Ser Lys Asp Glu Val Leu Ala Thr Cys Leu
                580                 585                 590

Gln Gln Met Lys Ala Cys Phe Phe Asp Ala Arg Leu Asn Lys Val Lys
            595                 600                 605

Leu Leu Glu Ala Met Ala Val Phe Phe Glu Arg Ser Asn Arg Ala Val
        610                 615                 620

Gly Gly Asp Asn Tyr Ala Ala Gly Glu Val Val Arg Gln Cys Asp Leu
625                 630                 635                 640
```

Cys Gln Glu Ser Ser Met Val Leu Lys Lys Asn Arg Asp Gly Asn Phe
            645                 650                 655

Met Val Gly Cys Ser Gly Phe Pro Gln Cys Arg Asn Ala Ile Trp Leu
            660                 665                 670

Pro Gly Ser Ile Leu Glu Ala Ala Val Thr Ser Asn Ile Cys Ser Ser
            675                 680                 685

Cys Asn Pro Gly Pro Val Tyr Leu Ile Gln Phe Lys Phe Arg Gln Ile
            690                 695                 700

Glu Ile Pro Pro Gly Phe Asn Ala Asn His Leu Gly Cys Ile Gly Gly
705                 710                 715                 720

Cys Asp Asp Thr Leu Arg Gln Leu Ile Glu Ile Cys Gly Thr Gly Ser
            725                 730                 735

Arg Met Ser Ala Arg Gly Arg Gly Pro Thr Thr Thr Ser Ser Asn Gly
            740                 745                 750

Gln Arg Ser Ser Asn Arg His Asn Ser Cys Ile His Cys Gln Gln Thr
            755                 760                 765

Gly His Ser Ser Asn Asp Cys Pro Ser Gln Phe Ser Arg Ser Arg Asn
            770                 775                 780

Ser Gln Ser His Thr Asn Ser Glu Asn Gly Asp Pro Ser Val Ser Cys
785                 790                 795                 800

Ser Thr Cys Gly Met Pro Cys Val Leu Arg Thr Ala Asn Thr Ala Asn
            805                 810                 815

Asn Arg Gly Arg Lys Phe Tyr Ser Cys Pro Ser Gln Glu Cys Asn Phe
            820                 825                 830

Phe Ile Trp Glu Asp Gly Val Ser Asn Gly Asn Gly Arg Ser Ile
            835                 840                 845

Pro Ser Thr Asn Cys Ser Ala Ser Asn Ser Gly Arg Arg Gly Gly Arg
            850                 855                 860

Gly Gln Ser Gly Arg Asn Arg Ser His Ala Ala Asp Thr Thr Phe Val
865                 870                 875                 880

Ser Ala Thr Gly Asp Pro Val Ser Asn Arg Cys Tyr Val Cys Gly Asp
            885                 890                 895

Pro Ser His Phe Ala Asn Val Cys Pro Asn Arg Gly Met
            900                 905

<210> SEQ ID NO 39
<211> LENGTH: 914
<212> TYPE: PRT
<213> ORGANISM: Theobroma cacao

<400> SEQUENCE: 39

Met Ser Gly Thr Ile Lys Val Leu Asn Val Ala Glu Lys Pro Ser Val
1               5                   10                  15

Ala Lys Ser Val Ser Gly Ile Leu Ser Arg Asn Gln Gly Leu Arg Val
            20                  25                  30

Arg Asp Gly Arg Ser Arg Phe Asn Arg Ile Phe Glu Phe Asn Tyr Ser
            35                  40                  45

Val Arg Gly Gln Pro Cys His Met Leu Phe Thr Ser Val Thr Gly His
            50                  55                  60

Leu Met Glu Leu Glu Phe Glu Asp Arg Phe Lys Trp His Ser Cys
65                  70                  75                  80

Asp Pro Ala Asp Leu Tyr His Ala Pro Val Arg Lys His Val Pro Glu
            85                  90                  95

Asp Lys Met Asp Ile Lys Arg Thr Leu Glu Glu Glu Ala Arg Arg Cys

```
            100                 105                 110
Gln Trp Leu Val Leu Trp Leu Asp Cys Asp Arg Glu Gly Glu Asn Ile
            115                 120                 125
Ala Phe Glu Val Ile Asp Val Cys Arg Ala Val Asn Cys His Leu Thr
            130                 135                 140
Ile Arg Arg Ala Arg Phe Ser Ala Leu Ile Glu Arg Glu Ile His His
145                 150                 155                 160
Ala Thr Gln Asn Leu Val Asp Pro Asn Pro Trp Phe Ser Asp Ala Val
                165                 170                 175
Asp Ala Arg Gln Glu Ile Asp Leu Arg Ile Gly Ala Ser Phe Thr Arg
            180                 185                 190
Phe Gln Thr Met Met Leu Arg Asp Lys Phe Val Ile Asp Ser Ala Thr
            195                 200                 205
Asp Asp Arg Asn Leu Val Leu Ser Tyr Gly Pro Cys Gln Phe Pro Thr
            210                 215                 220
Leu Gly Phe Val Val Glu Arg Tyr Trp Glu Val Gln Ser His Glu Pro
225                 230                 235                 240
Glu Glu Phe Trp Thr Ile Asn Cys Ser His Lys Leu Asp Glu Gly Val
                245                 250                 255
Ala Thr Phe Asn Trp Met Arg Gly His Leu Phe Asp His Thr Cys Ala
            260                 265                 270
Val Ile Val Tyr Glu Met Cys Val Gln Glu Pro Asn Ala Thr Val Thr
            275                 280                 285
Lys Val Arg His Gln Glu Lys Leu Lys Tyr Pro Pro Tyr Pro Leu Ser
            290                 295                 300
Thr Ile Glu Leu Glu Lys Arg Ala Ser Arg Tyr Phe Arg Met Ser Ser
305                 310                 315                 320
Glu His Thr Met Lys Val Ala Glu Asp Leu Tyr Gln Ala Gly Phe Ile
                325                 330                 335
Ser Tyr Pro Arg Thr Glu Thr Asp Cys Phe Ser Ser Arg Thr Asp Leu
            340                 345                 350
His Ala Ile Val Gln Glu Gln Asp His Pro Glu Trp Gly Ser Tyr
            355                 360                 365
Ala Gln Arg Leu Leu Asp Pro Gly Thr Ser Leu Trp Arg Asn Pro Ser
            370                 375                 380
Ser Gly His Asp Asp Lys Ala His Pro Ile His Pro Thr Lys
385                 390                 395                 400
Phe Ser Ala Gly Glu His Asn Trp Ser Gln Asp His Arg Lys Leu Tyr
                405                 410                 415
Glu Leu Val Val Arg His Phe Leu Ala Cys Val Ser Gln Pro Ala Val
            420                 425                 430
Gly Ala Glu Thr Thr Val Glu Ile Asp Ile Ala Asp Glu Gln Phe Ser
            435                 440                 445
Thr Ser Gly Arg Val Ile Leu Glu Arg Asn Tyr Leu Asp Val Tyr Arg
            450                 455                 460
Tyr Glu Ser Trp Gly Gly Ser Met Ile Pro Thr Tyr Thr Leu Gly Gln
465                 470                 475                 480
Gln Phe Ile Pro Thr Ser Leu Thr Leu Asp Thr Gly Val Thr Arg Pro
                485                 490                 495
Pro Pro Leu Leu Ser Glu Ala Asp Leu Leu Ser Cys Met Asp Lys Ala
            500                 505                 510
Gly Ile Gly Thr Asp Ala Thr Met His Asp His Ile Lys Lys Leu Leu
            515                 520                 525
```

```
Asp Arg Phe Tyr Ala Thr Lys Asp Ser Asn Thr Arg Phe Ser Pro Thr
    530                 535                 540

Lys Leu Gly Glu Ala Leu Val Met Gly Tyr Asp Met Gly Tyr Glu
545                 550                 555                 560

Leu Trp Lys Pro Asn Leu Arg Ser Met Met Glu Phe Asp Met Lys Glu
                565                 570                 575

Val Ser Val Gly Asn Lys Arg Lys Asp Glu Val Leu Ala Thr Cys Leu
                580                 585                 590

Gln Gln Met Lys Ala Cys Phe Leu Asp Ala Arg Leu Asn Lys Val Lys
        595                 600                 605

Leu Leu Glu Ala Met Ala Val Phe Phe Glu Arg Ser Asn Gln Ser Ala
610                 615                 620

Gly Asp Asp Asn His Val Ala Gly Glu Val Val Arg Gln Cys Gly Leu
625                 630                 635                 640

Cys Arg Glu Ser Ser Met Val Leu Lys Lys Asn Arg Asp Gly Asn Phe
                645                 650                 655

Met Val Gly Cys Leu Gly Phe Pro Gln Cys Arg Asn Ala Ile Trp Leu
                660                 665                 670

Pro Gly Ser Val Leu Glu Ala Ala Val Thr Ser Asn Ile Cys Gly Ser
        675                 680                 685

Cys Asn Pro Gly Pro Val Tyr Leu Ile Gln Phe Lys Phe Arg Gln Leu
690                 695                 700

Glu Ile Pro Pro Gly Phe Asn Ala Asn His Leu Gly Cys Ile Gly Gly
705                 710                 715                 720

Cys Asp Asp Ile Leu Arg Gln Leu Ile Glu Ile Cys Gly Thr Gly Ser
                725                 730                 735

Arg Met Ser Ala Arg Gly Arg Gly Pro Thr Thr Thr Ser Ser Asn Val
                740                 745                 750

Gln Arg Asn Ser Ser Arg Gln Gly Ala Cys Leu Tyr Cys Gln Gln Thr
        755                 760                 765

Gly His Ser Ser Asn Asp Cys Pro Ser Gln Phe Ser Gly Ser Arg Asn
770                 775                 780

Ser Arg Ser Arg Thr Ser Ser Gln Asn Gly Glu Pro Ser Val Ser Cys
785                 790                 795                 800

Ser Thr Cys Gly Thr Pro Cys Val Leu Arg Thr Ala Asn Thr Ala Asn
                805                 810                 815

Asn Arg Gly Arg Lys Phe Tyr Ser Cys Pro Ser Gln Glu Cys Asn Phe
                820                 825                 830

Phe Ile Trp Glu Asp Glu His Asn Asn Gly Thr Gly Gly Arg Ser Ile
        835                 840                 845

Pro Arg Ala Gly Ile Asn Gly Ser Ala Ser Asn Ser Arg Gly Gly
850                 855                 860

Gly Arg Gly Arg Gly Arg Phe Gly Gln Asn Gly Ala Arg Ala Ala Asp
865                 870                 875                 880

Val Thr Phe Val Ser Ala Thr Gly Asp Pro Ile Ser Gly Arg Arg Cys
                885                 890                 895

Tyr Val Cys Gly Asp Pro Ser His Phe Ala Asn Val Cys Pro Asn Arg
                900                 905                 910

Gly Met

<210> SEQ ID NO 40
<211> LENGTH: 915
<212> TYPE: PRT
```

<213> ORGANISM: Eucalyptus grandis

<400> SEQUENCE: 40

| | | | | | | | | | | | | | | |
|---|---|---|---|---|---|---|---|---|---|---|---|---|---|---|

Met Ser Gly Gly Gly Arg Ala Ile Asn Val Leu Asn Val Ala Glu Lys
1               5                   10                  15

Pro Ser Val Ala Lys Ser Val Ala Thr Leu Leu Ser Arg Gly Gln Gly
            20                  25                  30

Met Arg Val Arg Glu Gly Arg Ser Arg Tyr Asn Lys Ile Phe Glu Phe
        35                  40                  45

Asp Tyr Gly Ile Arg Gly Gln Arg Cys Arg Met Leu Val Thr Ser Val
    50                  55                  60

Thr Gly His Leu Met Glu Leu Glu Phe Glu Asp Arg Phe Arg Lys Trp
65                  70                  75                  80

His Ser Cys Asp Pro Ala Asp Leu Tyr Ala Ala Pro Val Arg Lys Ser
                85                  90                  95

Val Pro Gln Asp Lys Leu Asp Ile Lys Arg Thr Leu Glu Glu Glu Ala
            100                 105                 110

Arg Arg Cys Gln Trp Leu Val Leu Trp Leu Asp Cys Asp Arg Glu Gly
        115                 120                 125

Glu Asn Ile Ala Phe Glu Val Ile Asp Thr Cys Thr Ala Ala Asn Cys
    130                 135                 140

Asn Leu Thr Ile Lys Arg Ala Arg Phe Ser Ala Leu Ile Glu Arg Glu
145                 150                 155                 160

Ile His Asp Ser Val Gln Asn Leu Val Glu Pro Asn Arg Trp Phe Ala
                165                 170                 175

Asp Ala Val Asp Ala Arg Gln Glu Ile Asp Leu Arg Ile Gly Ala Ser
            180                 185                 190

Phe Thr Arg Phe Gln Thr Met Leu Leu Arg Asp Ala Phe Val Ile Asp
        195                 200                 205

Ser Ala Ala Asp Asp Arg Asn Leu Val Leu Ser Tyr Gly Pro Cys Gln
    210                 215                 220

Phe Pro Thr Leu Gly Phe Val Val Glu Arg Phe Trp Glu Ile Gln Ser
225                 230                 235                 240

His Glu Pro Glu Glu Phe Trp Ile Ile Asn Cys Ser His Lys Ser Glu
                245                 250                 255

Glu Gly Ile Ala Thr Phe Asn Trp Thr Arg Gly His Leu Phe Asp Tyr
            260                 265                 270

Thr Cys Ala Val Ile Ile Tyr Glu Met Cys Val Glu Glu Pro Pro Ala
        275                 280                 285

Thr Val Ala Gly Val Arg Gln Gln Glu Lys Tyr Lys Tyr Pro Pro His
    290                 295                 300

Pro Leu Ser Thr Ile Glu Leu Glu Lys Arg Ala Ser Arg Tyr Phe Arg
305                 310                 315                 320

Met Ser Ser Glu His Thr Met Lys Val Ala Glu Glu Leu Tyr Gln Ala
                325                 330                 335

Gly Phe Ile Ser Tyr Pro Arg Thr Glu Thr Asp Asn Phe Ser Ala Arg
            340                 345                 350

Thr Asp Leu His Ala Ile Val Gln Glu Gln Arg Gly His Pro Val Trp
        355                 360                 365

Gly Ser Tyr Ala Gln Arg Leu Leu Asp Pro Ser Ser Gly Leu Trp Arg
    370                 375                 380

Asn Pro Ser Asn Gly Gly His Asp Asp Lys Ala His Pro Pro Ile His
385                 390                 395                 400

```
Pro Thr Lys Phe Ser Gly Gly Glu Arg Asn Trp Ser Gln Asp His His
            405                 410                 415

Arg Leu Tyr Glu Leu Val Val Arg His Phe Leu Ala Cys Val Ser Gln
            420                 425                 430

Pro Ala Val Gly Ala Glu Thr Thr Val Glu Ile Asp Ile Ala Gly Glu
            435                 440                 445

Gln Phe Ala Ala Ser Gly Arg Val Ile Ile Ala Lys Asn Tyr Leu Asp
            450                 455                 460

Val Tyr Arg Phe Glu Ser Trp Gly Gly Ser Val Ile Pro Thr Tyr Val
465                 470                 475                 480

Pro Gly Gln Gln Phe Ile Pro Thr Thr Leu Thr Leu Asp Ser Gly Val
            485                 490                 495

Thr Arg Pro Pro Pro Leu Leu Ser Glu Ala Asp Leu Leu Asn Cys Met
            500                 505                 510

Asp Lys Ala Gly Ile Gly Thr Asp Ala Thr Met His Asp His Ile Lys
            515                 520                 525

Lys Leu Leu Asp Arg Phe Tyr Ala Thr Lys Asp Gln Asn Met Arg Phe
            530                 535                 540

Ser Pro Thr Asn Leu Gly Glu Ala Leu Val Met Gly Tyr Asp Asp Met
545                 550                 555                 560

Gly Tyr Lys Leu Trp Lys Pro Asn Leu Arg Ser Met Met Glu Phe Asp
            565                 570                 575

Met Arg Ala Val Ser Glu Gly Ala Lys Thr Lys Ala Glu Val Leu Glu
            580                 585                 590

Thr Cys Leu Gln Gln Met Lys Ala Cys Phe Leu Asp Ala Arg Ser Asn
            595                 600                 605

Lys Gln Lys Leu Met Glu Ala Met Ala Val Phe Phe Glu Arg Ala Ala
            610                 615                 620

Arg Thr Ala Arg Asp Glu Gln His Val Val Gly Glu Phe Val Arg Leu
625                 630                 635                 640

Cys Gly Leu Cys His Gln Ser Asn Met Val Leu Lys Arg Asn Arg Asp
            645                 650                 655

Gly Asn Phe Met Val Gly Cys Leu Gly Phe Pro Gln Cys Arg Asn Val
            660                 665                 670

Val Trp Leu Pro Gly Ser Val Ser Glu Ala Val Val Thr Ala Asn Ile
            675                 680                 685

Cys Asn Ser Cys Ser Pro Gly Pro Ile Tyr Met Ile Gln Phe Lys Phe
            690                 695                 700

Arg Arg Leu Glu Ile Pro Pro Ile Phe Ser Val Asp His Leu Gly Cys
705                 710                 715                 720

Ile Gly Gly Cys Asp Asp Thr Leu Gln Gln Leu Thr Glu Ile Cys Gly
            725                 730                 735

Thr Gly Ser Arg Met Ser Ala Ala Arg Gly Gly Pro Thr Pro Leu
            740                 745                 750

Ser Ser Ser Ala Gln Arg Ser Asn Ser Arg Gln Ala Cys Ser Ser
            755                 760                 765

Cys Arg Gln Leu Gly His Ser Ser Thr Asp Cys Pro Ser Val Ile Ser
            770                 775                 780

Gly Thr Arg Asn Ser Arg Ser Arg Arg Ala Asp Gln Asp Gly Gly
785                 790                 795                 800

Leu Ser Val Ser Cys Asp Thr Cys Gly Ala Ser Cys Pro Met Arg Thr
            805                 810                 815

Ala Asn Thr Ala Asn Asn Lys Gly Arg Lys Phe Tyr Ser Cys Gln Ser
```

```
            820                 825                 830
Glu Gly Cys Asn Phe Phe Val Trp Glu Asp Ser Leu Gln Asn Gly Gly
            835                 840                 845

Gly Arg His Gly Ala Asn Gly Ala Ser Asn Ser Arg Ala Arg Ser
        850                 855                 860

Asn Ser Leu Gly Gly Arg Gly Arg Gly Gly Arg Gly Gly Asn Asn Ala
865                 870                 875                 880

Thr Asn Gly Thr Phe Val Ser Ala Thr Gly Asp Pro Val Thr Gly Arg
                885                 890                 895

Cys Tyr Val Cys Gly Asp Pro Ser His Phe Ala Asn Ala Cys Pro Asn
                900                 905                 910

Arg Phe Thr
        915

<210> SEQ ID NO 41
<211> LENGTH: 913
<212> TYPE: PRT
<213> ORGANISM: Glycine max

<400> SEQUENCE: 41

Met Asn Val Leu Asn Val Ala Glu Lys Pro Met Val Ala Arg Thr Val
1               5                   10                  15

Ala Thr Ile Leu Ser Arg Asn Gln Asn Met Arg Met Arg Glu Gly Arg
                20                  25                  30

Ser Arg Tyr Asn Lys Ile Phe Glu Phe Asn Tyr Thr Ile Arg Gly Gln
            35                  40                  45

Pro Cys His Met Ile Phe Thr Ser Val Thr Gly His Leu Met Glu Leu
    50                  55                  60

Glu Phe Asp Asp Arg Tyr Arg Lys Trp His Ser Cys Asp Pro Ala Asp
65                  70                  75                  80

Leu Phe Arg Ala Pro Val His Lys Phe Val Pro Glu Asp Lys Lys Asp
                85                  90                  95

Ile Lys Arg Thr Leu Glu Glu Glu Ala Arg Arg Cys Gln Trp Leu Ile
                100                 105                 110

Leu Trp Leu Asp Cys Asp Val Glu Gly Glu Asn Ile Ala Tyr Glu Val
            115                 120                 125

Ile Asp Val Cys Thr Ala Val Asn Pro His Leu Thr Ile Lys Arg Ala
        130                 135                 140

Trp Phe Ser Thr Leu Ile Asp Arg Asp Ile His Asn Ala Ala Gln Asn
145                 150                 155                 160

Asp Leu Arg Asp Pro Asp Lys Arg Val Ala Asp Ala Val Asp Val Arg
                165                 170                 175

Gln Glu Ile Asp Leu Arg Ile Gly Ala Ser Phe Thr Arg Phe Gln Thr
            180                 185                 190

Met Leu Met Lys Asp Ala Phe Ile Ile Asp Thr Ala Thr Asp Asp Arg
        195                 200                 205

Asn Arg Val Leu Ser Tyr Gly Pro Cys Gln Phe Pro Thr Leu Gly Phe
    210                 215                 220

Val Val Glu Arg Phe Trp Glu Ile Gln Ala His Glu Pro Glu Phe
225                 230                 235                 240

Trp Ser Ile Ile Cys Ser His Glu Ser Lys Glu Gly Thr Ala Glu Phe
                245                 250                 255

Ser Trp Met Arg Gly Arg Leu Phe Asp Tyr Thr Cys Ala Val Ile Ile
            260                 265                 270
```

```
Tyr Glu Met Cys Val Glu Glu Pro Thr Ala Thr Val Thr Asn Ile Arg
            275                 280                 285
Gln Gln Glu Lys Pro Lys Tyr Pro Pro Phe Pro Leu Asn Thr Ile Glu
        290                 295                 300
Leu Gln Lys Arg Ala Ser Arg Tyr Phe Arg Met Ser Ser Asp His Thr
305                 310                 315                 320
Met Lys Val Ala Glu Glu Leu Tyr Gln Ala Gly Phe Ile Ser Tyr Pro
                325                 330                 335
Arg Thr Glu Thr Asp Ser Phe Ser Pro Gly Thr Asp Leu His Thr Ile
            340                 345                 350
Val Gln Glu Gln Gln Gly His Pro Glu Trp Gly Ile Tyr Ala Gln Arg
        355                 360                 365
Leu Met Asp Pro Glu Ala Gly Leu Trp Arg Asn Pro Arg Gly Gly Gly
370                 375                 380
His Asp Asp Lys Ala His Pro Pro Ile Tyr Pro Thr Lys Phe Ser Thr
385                 390                 395                 400
Gly Glu Ser Gly Trp Ser Gln Asp His Arg Lys Leu Tyr Glu Leu Val
                405                 410                 415
Val Arg His Phe Leu Ala Cys Val Ser Lys Pro Ala Leu Gly Ala Glu
            420                 425                 430
Thr Thr Val Glu Ile Asn Ile Ala Gly Glu Leu Phe Ser Ala Cys Gly
        435                 440                 445
Arg Val Ile Leu Glu Lys Asn Tyr Leu Asp Val Tyr Arg Tyr Glu Ser
450                 455                 460
Trp Gly Gly Ser Met Ile Pro Thr Tyr Thr Asn Gly Gln Gln Phe Asn
465                 470                 475                 480
Pro Thr Lys Leu Thr Leu Glu Ser Gly Val Thr Arg Pro Pro Pro Leu
                485                 490                 495
Leu Ser Glu Ala Asp Leu Leu Ser Tyr Met Asp Arg Glu Glu Ala Lys
            500                 505                 510
Ile Gly Thr Asp Ala Thr Met Gln Asp His Ile Lys Lys Met Leu Asp
        515                 520                 525
Arg Ser Tyr Ala Thr Lys Asp Ser Ser Thr Arg Phe Thr Pro Thr Asn
530                 535                 540
Leu Gly Glu Ala Leu Val Leu Gly Tyr Asp Asp Ile Asp Met Thr Tyr
545                 550                 555                 560
Lys Leu Trp Lys Pro Asp Leu Arg Ser Glu Met Lys Lys Met Asp
                565                 570                 575
Asp Val Lys Lys Gly Asp Lys Ser Lys Ala Glu Val Leu Val Thr Ile
            580                 585                 590
Leu Gln Lys Met Glu Ala Cys Phe Leu Glu Ala Arg Leu Asn Lys Val
        595                 600                 605
Lys Leu Leu Glu Ala Met Ala Ile Phe Phe Glu Arg Ser Thr Arg Ser
610                 615                 620
Ser Ser Asp Glu Leu His Ala Thr Gly Glu Val Val Arg Arg Cys Gly
625                 630                 635                 640
Leu Cys Gln Glu Ser Asp Met Leu Leu Arg Lys Asn Arg Asp Gly Asn
                645                 650                 655
Phe Met Val Gly Cys Met Gly Tyr Pro Gln Cys Arg Asn Ala Val Trp
            660                 665                 670
Leu Pro Gly Ser Val Ser Glu Ala Val Val Thr Thr Asn Thr Cys Asn
        675                 680                 685
Phe Cys Thr Pro Gly Pro Val Tyr Leu Ile Gln Phe Lys Phe Arg Arg
```

```
                690             695             700
Leu Glu Ile Pro Pro Asn Tyr Ser Pro Asn His Leu Gly Cys Ile Gly
705                 710             715                 720

Gly Cys Asp Glu Ile Leu Ala Gln Leu Thr Glu Ile Cys Arg Gly
                725             730                 735

Pro Arg Met Pro Ala Arg Pro Arg Gly Pro Thr Ala Pro Thr Ser Asn
            740             745             750

Ala His His Thr Asn Pro Arg Gln Gly Ala Cys Met Asn Cys Arg Glu
        755             760             765

Thr Gly His Ser Ser Thr Asp Cys Pro Leu Arg Tyr Gly Asn Val Gln
    770             775             780

His His Gly Thr Ser Glu His Asn Gly Glu Ala Ser Val Ser Cys Ser
785             790             795                 800

Ser Cys Gly Thr Pro Cys Val Leu Arg Thr Ala Asn Thr Val Asn Asn
                805             810             815

Arg Gly Arg Lys Phe Tyr Ser Cys Gln Ser Gln Glu Cys Asn Phe Phe
                820             825             830

Val Trp Glu Asp Ser Leu Asn Ala Gly Thr Gly Arg Ser Val Thr
            835             840             845

Arg Ser Asn Ser Ile Pro Ala Leu Asn Pro Arg Gln Thr Gly Gly Arg
    850             855             860

Gly Ser Arg Gly Arg Gly Gln Tyr Gly Ser Arg Thr Ala Asn Thr
865             870             875             880

Thr Phe Met Ser Ala Thr Gly Asp Pro Ile Ser Gly Arg Arg Cys Tyr
            885             890             895

Thr Cys Gly Asp Pro Ser His Phe Ala Asn Val Cys Pro His Arg Gly
                900             905             910

Val

<210> SEQ ID NO 42
<211> LENGTH: 923
<212> TYPE: PRT
<213> ORGANISM: Mimulus guttatus

<400> SEQUENCE: 42

Met Ala Gly Gly Gly Arg Pro Leu Arg Ala Leu Asn Val Ala Glu
1               5               10                  15

Lys Pro Ser Val Ala Lys Ala Val Ser Gly Ile Leu Ser Lys Asn Pro
            20              25              30

Ser Ser Gly Gly Leu Arg Val Arg Glu Gly Arg Ser Arg Tyr Asn Lys
        35              40              45

Ile Phe Glu Phe Asn Tyr Ala Ile Gln Asn Gln Gln Phe Gln Met Ser
    50              55              60

Phe Thr Ser Val Thr Gly His Leu Met Glu Leu Glu Phe Glu Asp Arg
65              70              75                  80

Tyr Arg Lys Trp His Ser Cys Asp Pro Val Asp Leu Tyr His Ala Pro
            85              90              95

Val Arg Lys His Val Pro Gln Asp Lys Ser Asp Ile Glu Lys Thr Leu
            100             105             110

Glu Glu Glu Ala Arg Lys Cys Gln Trp Leu Ile Leu Trp Leu Asp Cys
        115             120             125

Asp Arg Glu Gly Glu Asn Ile Ala Phe Glu Val Val Glu Ala Cys Leu
    130             135             140

Arg Thr Asn Arg Asn Leu Asn Ile Trp Arg Ala Arg Phe Ser Ala Leu
```

-continued

```
            145                 150                 155                 160
        Ile Asp Arg Glu Ile His Asp Ala Val Gln His Leu Val Arg Pro Asn
                        165                 170                 175
        Gln Leu Phe Ala Asp Ala Val Asp Val Arg Gln Glu Ile Asp Leu Arg
                        180                 185                 190
        Ile Gly Ala Ser Phe Thr Arg Phe Gln Thr Met Leu Leu Lys Asp Ala
                        195                 200                 205
        Phe Val Leu Asp Phe Ala Thr Glu Glu Arg Asn Val Ile Leu Ser Tyr
            210                 215                 220
        Gly Pro Cys Gln Phe Pro Thr Leu Gly Phe Val Val Glu Arg Phe Trp
        225                 230                 235                 240
        Glu Ile Gln Ser His Glu Pro Glu Glu Phe Trp Thr Ile Asn Cys Thr
                        245                 250                 255
        His Asn Ser Glu Glu Gly Thr Ala Thr Phe Ser Trp Met Arg Gly His
                        260                 265                 270
        Leu Phe Asp Tyr Thr Cys Ala Thr Ile Ile Tyr Glu Met Cys Val Leu
                        275                 280                 285
        Glu Pro Asn Ala Thr Val Thr Asn Val Arg Asn Gln Glu Lys Pro Arg
                        290                 295                 300
        Tyr Pro Pro His Pro Leu Ser Thr Ile Glu Leu Glu Lys Arg Ala Ser
        305                 310                 315                 320
        Arg Tyr Phe Arg Met Ser Ser Glu Gln Thr Met Lys Val Ala Glu Asp
                        325                 330                 335
        Leu Tyr Gln Ala Gly Phe Ile Ser Tyr Pro Arg Thr Glu Thr Asp Ser
                        340                 345                 350
        Phe Ser Val Arg Thr Asp Leu His Thr Ile Val Gln Glu Gln Gln Gly
                        355                 360                 365
        His Pro Thr Trp Gly Ser Tyr Ala Gln Arg Leu Leu Asp Pro Glu Ala
                        370                 375                 380
        Gly Leu Trp Arg Asn Pro Ser Ser Gly Gly His Asp Asp Lys Ala His
        385                 390                 395                 400
        Pro Pro Ile His Pro Thr Lys Phe Ser Ala Gly Glu Ser Gly Trp Ser
                        405                 410                 415
        Gln Asp His His Lys Val Tyr Glu Leu Val Val Arg His Phe Leu Ala
                        420                 425                 430
        Cys Val Ser Gln Pro Ala Ile Gly Ala Val Thr Thr Val Asp Ile Asp
                        435                 440                 445
        Ile Ala Gly Glu Gln Phe Ser Ala Ser Gly Thr Val Ile Leu Ala Lys
        450                 455                 460
        Asn Tyr Leu Asp Val Tyr Arg Phe Glu Thr Trp Gly Gly Ser Met Ile
        465                 470                 475                 480
        Pro Thr Tyr Asn Tyr Gly Gln Gln Phe Thr Pro Thr Leu Thr Leu
                        485                 490                 495
        Asp Ser Gly Val Thr Arg Pro Pro Leu Leu Ser Glu Ala Asp Leu
                        500                 505                 510
        Leu Ser Cys Met Asp Asn Ala Gly Ile Gly Thr Asp Ala Thr Met His
                        515                 520                 525
        Asp His Ile Lys Lys Leu Leu Asp Arg Phe Tyr Ala Thr Lys Asp Ser
                        530                 535                 540
        Asn Met Arg Phe Ser Pro Thr Lys Leu Gly Glu Ala Leu Val Lys Gly
        545                 550                 555                 560
        Tyr Asp Asp Met Gly Tyr Glu Leu Trp Lys Pro Asn Leu Arg Ala Met
                        565                 570                 575
```

```
Met Glu Ser Asp Met Lys Ala Val Ser Met Gly Thr Lys Arg Lys Ser
                580                 585                 590

Glu Val Leu Asp Ser Cys Leu Gln Gln Met Lys Ala Cys Phe Val Asp
            595                 600                 605

Ala Arg Leu Asn Lys Glu Lys Leu Phe Glu Ala Met Asp Val Phe Phe
        610                 615                 620

Glu Arg Ser Asn Arg Ala Asn Gly Asn Glu Gln Gln Ala Ile Gly Glu
625                 630                 635                 640

Val Val Arg Lys Cys Gly Leu Cys Gln Glu Ser Asp Met Val Leu Arg
                645                 650                 655

Lys Lys Pro Asp Gly Asn Phe Met Val Gly Cys Leu Gly Tyr Pro Gln
            660                 665                 670

Cys Arg Asn Val Val Trp Leu Pro Gly Ser Val Ser Glu Ala Thr Val
        675                 680                 685

Thr Thr Thr Ile Cys Ser Thr Cys Ser Pro Gly Pro Val Tyr Met Ile
    690                 695                 700

Gln Phe Lys Phe Arg Arg Leu Glu Ile Pro Pro Asn Tyr Asn Val Asp
705                 710                 715                 720

His Leu Gly Cys Ile Gly Gly Cys Asp Asp Thr Leu Arg Gln Leu Val
                725                 730                 735

Glu Ile Cys Gly Thr Gly Ser Arg Thr Thr Ser Ser Val Pro Gly Arg
            740                 745                 750

Gly Gln Gly His Thr Ser Ser Ser Ser Ala Gln Gln Ser Asn Tyr
        755                 760                 765

Arg Asp Gln Gly Ala Trp Gln Thr Ala Ser Ser Trp Gln Thr Ala
    770                 775                 780

Ser Gly Ser His Pro Ser Gln Ser Ser Arg Gly Arg Ser Ala Arg Ser
785                 790                 795                 800

Gln Arg Ala Gly Gly Ala Pro Asp Gly Glu Ser Ser Ile Pro Cys Thr
                805                 810                 815

Ser Cys Gly Ala Ser Cys Asn Leu Arg Thr Ala Asn Thr Glu Ala Asn
            820                 825                 830

Lys Gly Arg Lys Phe Tyr Ser Cys Gln Ala Gln Gly Cys Ser Phe Phe
        835                 840                 845

Val Trp Glu Asp Asn Ile Asn Ser Gly Gly Thr Ala Ala Arg Gly Gly
    850                 855                 860

Gly Gly Arg Ser Ala Ser Thr Thr Ser Arg Arg Gly Gly Arg Gly Arg
865                 870                 875                 880

Gly Ser Arg Gly Gly Arg Thr Asn Asp Val Ala Phe Val Ser Ala
                885                 890                 895

Thr Gly Glu Pro Ile Ser Gly Arg Cys Phe Val Cys Gly Glu Pro Gly
            900                 905                 910

His Phe Ser Asn Val Cys Pro Cys Arg Gly Arg
        915                 920

<210> SEQ ID NO 43
<211> LENGTH: 936
<212> TYPE: PRT
<213> ORGANISM: Aquilegia caerula

<400> SEQUENCE: 43

Met Ser Arg Pro Ile Arg Val Leu Asn Val Ala Glu Lys Pro Ser Val
1               5                   10                  15

Ala Lys Ser Val Ala Thr Ile Leu Ser Gly Gly Thr Asn Phe Cys Pro
```

-continued

```
                20                  25                  30
Ser Arg Leu Ser His Ser Gln Tyr Asn Arg Ile Phe Glu Phe His Tyr
                35                  40                  45
Thr Ile Arg Asn Gln Pro Cys Glu Met Leu Val Thr Ser Val Thr Gly
            50                  55                  60
His Leu Met Glu Ile Asp Phe Asp Asp Arg Tyr Arg Lys Trp Asn Ser
65                  70                  75                  80
Cys Asp Pro Ala Ile Leu Tyr Glu Ala Pro Val Lys Lys Phe Val Pro
                85                  90                  95
Gln Asp Lys Leu Asn Val Lys Lys Thr Leu Gln Asp Glu Ala Lys His
            100                 105                 110
Cys Gln Trp Leu Val Leu Trp Leu Asp Cys Asp Gln Glu Gly Glu Asn
        115                 120                 125
Ile Ala Phe Glu Val Val Asp Val Cys Cys Ala Val Asn Pro Arg Leu
    130                 135                 140
Asp Val Trp Arg Ala Arg Phe Ser Ala Leu Thr Ser Arg Asp Val Tyr
145                 150                 155                 160
Gln Ala Val Gln Asn Leu Val Arg Pro Asn Lys Trp Leu Ala Asp Ala
                165                 170                 175
Val Asp Val Arg Gln Glu Ser Asp Leu Arg Val Gly Ala Ser Phe Thr
            180                 185                 190
Arg Phe Gln Thr Gln Leu Leu Thr Asn Ala Tyr Leu Ile Asn Leu Asn
        195                 200                 205
Asn Ser Ala Asn Ala His Gln Ala Glu Gly Asp Arg Asn His Val Leu
    210                 215                 220
Ser Tyr Gly Pro Cys Gln Phe Pro Thr Leu Gly Phe Val Val Glu Arg
225                 230                 235                 240
Tyr Trp Glu Ile Gln Ala His Glu Pro Glu Gly Phe Trp Thr Ile Asn
                245                 250                 255
Cys Ser His Thr Ala Glu Glu Gly Thr Ala Thr Phe Ser Trp Met Arg
            260                 265                 270
Gly His Met Phe Asp Tyr Ser Cys Ala Val Met Ile Tyr Glu Met Cys
        275                 280                 285
Val Glu Glu Pro Thr Ala Thr Val Ile Lys Val Leu Asp Gln Gln Lys
    290                 295                 300
Leu Lys Asn Pro Pro Phe Pro Leu Asn Thr Val Glu Leu Asn Lys Arg
305                 310                 315                 320
Ala Ser Trp Tyr Phe Arg Met Ser Ser Glu His Thr Met Lys Val Ala
                325                 330                 335
Glu Asp Leu Tyr Gln Ser Gly Phe Ile Ser Tyr Pro Arg Thr Glu Thr
            340                 345                 350
Asp Ser Phe Ala Gly Asn Thr Asp Leu His Ala Ile Val Gln Glu Gln
        355                 360                 365
Gln Glu His Pro Val Trp Gly Ser Tyr Ala Gln Arg Leu Leu Asp Pro
    370                 375                 380
Glu Ala Gly Leu Trp Lys Asn Pro Arg Ile Gly Thr His Ser Asp Asn
385                 390                 395                 400
Ala His Pro Pro Ile Tyr Pro Thr Lys Phe Ser Ala Gly Glu Ser Arg
                405                 410                 415
Trp Thr Gln Asp His His Arg Leu Tyr Glu Leu Val Val Arg His Phe
            420                 425                 430
Leu Ala Cys Val Ser Gln Pro Ala Ile Gly Ala Glu Thr Lys Ile Glu
        435                 440                 445
```

-continued

```
Ile Asp Ile Ala Gly Glu Leu Phe Ser Val Ser Gly Arg Thr Ile Ile
    450                 455                 460
Ala Lys Asn Tyr Leu Asp Val Tyr Arg Phe Glu Ser Trp Gly Asn Ser
465                 470                 475                 480
Thr Ile Pro Lys Tyr Thr Phe Gly Gln Gln Phe Val Pro Thr Thr Leu
                485                 490                 495
Thr Leu Asp Ser Gly Val Thr Arg Pro Pro Leu Leu Ser Glu Ala
            500                 505                 510
Asp Leu Ile Asn Cys Met Asp Lys Ala Gly Ile Gly Thr Asp Ala Thr
                515                 520                 525
Met His Asp His Ile Lys Lys Leu Leu Asp Arg Leu Tyr Ala Thr Lys
    530                 535                 540
Asp Ala Asn Thr Arg Phe Ala Pro Thr Lys Leu Gly Glu Ala Leu Val
545                 550                 555                 560
Met Gly Tyr Asp Asp Met Gly Tyr Glu Glu Leu Trp Lys Pro Ser Gln
                565                 570                 575
Arg Ser Arg Met Glu Ser Glu Thr Lys Glu Val Ser Val Gly Arg Lys
            580                 585                 590
Ser Lys Ser Glu Val Leu Ala Ser Tyr Leu Gln Asp Met Lys Ala Tyr
    595                 600                 605
Phe Leu Asp Ala Arg Leu Asn Gln Val Lys Leu Lys Glu Ala Met Asp
610                 615                 620
Ile Phe Phe Glu Arg Ser Asn Arg Ser Ala Gly Asp Asp His Arg Ala
625                 630                 635                 640
Val Gly Asp Thr Val Arg Arg Cys Gly Val Cys Asn Asp Ser Asp Met
                645                 650                 655
Val Leu Lys Arg Arg Pro Asp Gly Asn Phe Met Val Gly Cys Leu Gly
            660                 665                 670
Phe Pro Gln Cys Arg Asn Val Val Trp Leu Pro Gly Ser Ile Ser Glu
    675                 680                 685
Ala Thr Val Thr Thr Gln Val Cys Asn Ser Cys Ser Pro Gly Pro Val
690                 695                 700
Tyr Met Ile Gln Phe Lys Phe Arg Met Leu Glu Ile Pro Pro Gly Tyr
705                 710                 715                 720
Asn Val Asn His Leu Gly Cys Ile Gly Gly Cys Asp Glu Ile Leu Arg
                725                 730                 735
His Leu Thr Glu Ile Cys Gly Thr Gly Ser Arg Asn Pro Ser Ser Val
            740                 745                 750
Pro Val Ser Ser Ala Arg Gly Arg Gly Pro Arg Ala Pro Ser Ser Asn
    755                 760                 765
Ala Gln Gln Thr Ser Thr Arg Gln Gly Ala Cys Ile His Cys Arg Gln
770                 775                 780
Thr Gly His Ser Ser Ser Asp Cys Pro Ser Gln Val Val Gln Pro Gln
785                 790                 795                 800
Arg Ala Gln Pro Arg Arg Asn Thr Gln Asn Glu Asn Ala Gly Glu
                805                 810                 815
Ala Ser Ile Pro Cys Thr Thr Cys Gly Glu Ser Cys Val Leu Arg Thr
            820                 825                 830
Ala Asn Thr Asp Asn Asn Arg Gly Arg Lys Phe Tyr Ser Cys Gln Gly
    835                 840                 845
Cys Asn Phe Phe Val Trp Glu Asp Ser Met Asn Asp Ser Ala Gly Gly
850                 855                 860
```

```
Asn Thr Gln Gly Ala Asn Arg Gly Arg Leu Thr Ser Asn Pro Arg Ser
865                 870                 875                 880

Ser Ser Ala Arg Arg Gly Gly Arg Gly Arg Ser Arg Gly Gly Arg
            885                 890                 895

Gln Gly Ala Asn Thr Thr Gly Ala Thr Phe Val Ser Ala Thr Gly Asp
            900                 905                 910

Pro Leu Ser Asn Arg Cys Phe Ser Cys Gly Asp Pro Ser His Phe Ala
            915                 920                 925

Asn Ala Cys Pro Asn Arg Gly Arg
            930             935
```

<210> SEQ ID NO 44
<211> LENGTH: 862
<212> TYPE: PRT
<213> ORGANISM: Setaria italica

<400> SEQUENCE: 44

```
Met Gln Pro Gly Gly Gly Gly Ala Ile Arg Val Leu Asn Val Ala
1               5                   10                  15

Glu Lys Pro Ser Val Ala Lys Ala Val Ala Glu Ile Leu Ser Arg Gly
                20                  25                  30

Ser Met Gln Ser Arg Ala Gly Arg Ser Pro Tyr Asn Arg Val Phe Glu
            35                  40                  45

Phe Asn Tyr Ala Ile Asn Gly Arg Ala Cys Arg Met Leu Val Thr Ser
        50                  55                  60

Val Thr Gly His Leu Met Glu Leu Glu Phe Asp Asp Arg Phe Arg Arg
65                  70                  75                  80

Trp His Ser Cys Asp Pro Ala Asp Leu Phe His Ala Pro Val Arg Lys
                85                  90                  95

Ser Val Pro Gln Asp Lys Gln Ala Ile Lys Gln Thr Leu Glu Glu Glu
                100                 105                 110

Ala Arg Arg Cys Gln Trp Leu Val Leu Trp Leu Asp Cys Asp Arg Glu
            115                 120                 125

Gly Glu Asn Ile Ala Tyr Glu Val Ile Glu Val Cys Thr Gly Ala Asn
130                 135                 140

Ser His Leu Asn Ile Trp Arg Ala Arg Phe Ser Ala Leu Ile Asp Arg
145                 150                 155                 160

Glu Ile His Glu Ser Val Gln His Leu Gly Arg Pro Asn Lys Leu Phe
                165                 170                 175

Ala Asp Ala Val Asp Ala Arg Gln Glu Ile Asp Leu Arg Ile Gly Ala
            180                 185                 190

Ser Phe Thr Arg Phe Gln Thr Met Leu Leu Lys Asp Ala Phe Val Ile
        195                 200                 205

Asp Val Thr Gly Asp Asp Arg Asn Leu Val Leu Ser Tyr Gly Pro Cys
210                 215                 220

Gln Phe Pro Thr Leu Gly Phe Ile Val Glu Arg Phe Trp Glu Ile Gln
225                 230                 235                 240

Ala His Glu Pro Glu Glu Phe Trp Thr Ile Asn Cys Thr His Thr Ser
                245                 250                 255

Asp Glu Gly Thr Ala Ser Phe Gly Trp Ile Arg Gly His Leu Phe Asp
            260                 265                 270

Tyr Pro Ser Ala Val Ile Leu Tyr Glu Met Cys Val Glu Glu Pro Met
        275                 280                 285

Ala Thr Val Gln Asn Val Arg Asn Gln Glu Lys Leu Lys Tyr Pro Pro
290                 295                 300
```

```
Tyr Pro Leu Ser Thr Leu Glu Leu Gln Lys Arg Ala Ser Arg Tyr Phe
305                 310                 315                 320

Arg Met Ser Ser Glu His Thr Met Lys Val Ala Glu Glu Leu Tyr Gln
            325                 330                 335

Ala Gly Phe Ile Ser Tyr Pro Arg Thr Glu Thr Asp Asn Phe Ser Pro
            340                 345                 350

Asn Thr Asp Leu His Ala Ile Val Arg Glu Gln Val Glu His Pro Val
            355                 360                 365

Trp Gly Ala Tyr Ala His Arg Leu Leu Thr Pro Glu Glu Arg Leu Trp
            370                 375                 380

Arg Asn Pro Ser Asn Gly Gly His Asp Asp Lys Ala His Pro Pro Ile
385                 390                 395                 400

His Pro Thr Lys Phe Ser Arg Gly Glu Asn Asn Trp Ser Pro Asp His
            405                 410                 415

Asn Arg Leu Tyr Glu Leu Val Val Arg His Phe Leu Ala Cys Cys Ser
            420                 425                 430

Gln Pro Ala Val Gly Ala Glu Thr Thr Val Glu Ile Asp Ile Ala Gly
            435                 440                 445

Glu Gln Phe Asn Ala Ser Gly Arg Val Val Leu Ala Lys Asn Tyr Leu
450                 455                 460

Asp Val Tyr Arg Phe Asp Ser Trp Gly Gly Thr Leu Leu Pro Thr Tyr
465                 470                 475                 480

Asn Ile Gly Gln Gln Phe Val Pro Thr Thr Leu Thr Leu Asp Ser Gly
            485                 490                 495

Val Thr Arg Pro Pro Leu Leu Ala Glu Ala Asp Leu Leu Ser Cys
            500                 505                 510

Met Asp Lys Ala Gly Ile Gly Thr Asp Ala Thr Met His Asp His Ile
            515                 520                 525

Lys Lys Leu Leu Asp Arg Cys Tyr Ala Thr Lys Asp Glu Asn Thr Arg
530                 535                 540

Phe Ser Pro Thr Asn Leu Gly Glu Ala Leu Val Met Gly Tyr Asp Glu
545                 550                 555                 560

Met Gly Tyr Glu Leu Trp Lys Pro Tyr Leu Arg Ser Met Met Glu Ala
            565                 570                 575

Asp Met Lys Ser Val Ser Ile Gly Thr Lys Ser Lys Ser Gln Val Leu
            580                 585                 590

Glu Ser Cys Leu Gln Gln Met Lys Ala Cys Phe Leu Asp Ala Arg Val
            595                 600                 605

Asn Lys Ala Lys Leu Leu Asp Ala Met Gly Thr Phe Phe Ala Arg Ser
            610                 615                 620

Asn Arg Pro Val Asn Glu Thr Gln Asn Pro Ile Glu Val Val Arg Pro
625                 630                 635                 640

Cys Ala Ala Cys Arg Glu Ser Glu Met Val Leu Lys Gln Lys Gln Asn
            645                 650                 655

Gly Glu Phe Met Val Gly Cys Arg Ser Tyr Pro Gln Cys Arg Asn Val
            660                 665                 670

Val Trp Leu Pro Gly Ser Leu Ser Glu Ala Ser Val Thr Asn Gln Val
            675                 680                 685

Cys Pro Ile Cys Thr Pro Gly Pro Val Tyr Lys Ile Gln Phe Lys Phe
            690                 695                 700

Arg Arg Arg Asp Ile Pro Pro Asn Phe Asp Val Asp His Leu Gly Cys
705                 710                 715                 720
```

```
Ile Gly Gly Cys Asp Asp Ile Leu Lys Glu Leu Thr Glu Ile Ser Arg
                725                 730                 735

Phe Gly Ser Arg Ser Gln Ala Ala Thr Pro Gly Gln Val Leu Cys Thr
            740                 745                 750

Ser Cys Gly Glu Leu Cys Ile Ser Arg Ile Ala Asn Thr Glu Ala Asn
        755                 760                 765

Arg Gly Arg Lys Phe Tyr Lys Cys Glu Asp Pro Gly Cys Gly Phe Phe
    770                 775                 780

Lys Trp Glu Asp Glu Leu Asp Asn Ala Thr Pro Arg Gly Arg Arg Gly
785                 790                 795                 800

Arg Gly Ser Ser Arg Gln Ala Pro Ala Ser Ala Gly Arg Arg Gly Gly
                805                 810                 815

Ala Gln Ala Arg Gly Arg Gly Arg Gly Arg Asn Thr Asp Gly Gly
                820                 825                 830

Met Phe Val Ser Ala Thr Gly Asp Pro Ser Arg Cys Cys Phe Thr Cys
            835                 840                 845

Gly Asp Pro Ser His Phe Ala Asn Ala Cys Pro Asn Arg Arg
        850                 855                 860

<210> SEQ ID NO 45
<211> LENGTH: 1390
<212> TYPE: PRT
<213> ORGANISM: Arabidopsis thaliana
<220> FEATURE:
<221> NAME/KEY: DOMAIN
<222> LOCATION: (129)..(272)
<223> OTHER INFORMATION: Helicase domain DEXDc
<220> FEATURE:
<221> NAME/KEY: DOMAIN
<222> LOCATION: (445)..(570)
<223> OTHER INFORMATION: Helicase domain HELICc

<400> SEQUENCE: 45

Met Gly Ser Arg Val Pro Ile Glu Thr Ile Glu Glu Asp Gly Glu Phe
1               5                   10                  15

Asp Trp Glu Ala Ala Val Lys Glu Ile Asp Leu Ala Cys Leu Lys Thr
            20                  25                  30

Thr Asn Ala Ser Ser Ser Ser Ser His Phe Thr Pro Leu Ala Asn
        35                  40                  45

Pro Pro Ile Thr Ala Asn Leu Thr Lys Pro Pro Ala Lys Arg Gln Ser
    50                  55                  60

Thr Leu Asp Lys Phe Ile Gly Arg Thr Glu His Lys Pro Glu Asn His
65                  70                  75                  80

Gln Val Val Ser Glu Cys Gly Val Asn Asp Asn Asp Asn Ser Pro Leu
                85                  90                  95

Val Gly Ile Asp Pro Glu Ala Ala Lys Thr Trp Ile Tyr Pro Gly Phe
            100                 105                 110

Val Pro Leu Arg Asp Tyr Gln Phe Ala Ile Thr Lys Thr Ala Leu Phe
        115                 120                 125

Ser Asn Thr Leu Val Ala Leu Pro Thr Gly Leu Gly Lys Thr Leu Ile
    130                 135                 140

Ala Ala Val Val Met Tyr Asn Tyr Phe Arg Trp Phe Pro Gln Gly Lys
145                 150                 155                 160

Ile Val Phe Ala Ala Pro Ser Arg Pro Leu Val Met Gln Gln Ile Glu
                165                 170                 175

Ala Cys His Asn Ile Val Gly Ile Pro Gln Glu Trp Thr Ile Asp Leu
            180                 185                 190
```

-continued

```
Thr Gly Gln Thr Cys Pro Ser Lys Arg Ala Phe Leu Trp Lys Ser Lys
        195                 200                 205
Arg Val Phe Phe Val Thr Pro Gln Val Leu Glu Lys Asp Ile Gln Ser
    210                 215                 220
Gly Thr Cys Leu Thr Asn Tyr Leu Val Cys Leu Val Ile Asp Glu Ala
225                 230                 235                 240
His Arg Ala Leu Gly Asn Tyr Ser Tyr Cys Val Val Arg Glu Leu
                245                 250                 255
Met Ala Val Pro Ile Gln Leu Arg Ile Leu Ala Leu Thr Ala Thr Pro
            260                 265                 270
Gly Ser Lys Thr Gln Ala Ile Gln Gly Ile Ile Asp Asn Leu Gln Ile
        275                 280                 285
Ser Thr Leu Glu Tyr Arg Asn Glu Ser Asp His Asp Val Cys Pro Tyr
    290                 295                 300
Val His Asp Arg Lys Leu Glu Val Ile Glu Val Pro Leu Gly Gln Asp
305                 310                 315                 320
Ala Asp Asp Val Ser Lys Arg Leu Phe His Val Ile Arg Pro Tyr Ala
                325                 330                 335
Val Arg Leu Lys Asn Phe Gly Val Asn Leu Asn Arg Asp Ile Gln Thr
            340                 345                 350
Leu Ser Pro His Glu Val Leu Met Ala Arg Asp Lys Phe Arg Gln Ala
        355                 360                 365
Pro Leu Pro Gly Leu Pro His Val Asn His Gly Asp Val Glu Ser Cys
    370                 375                 380
Phe Ala Ala Leu Ile Thr Leu Tyr His Ile Arg Lys Leu Leu Ser Ser
385                 390                 395                 400
His Gly Ile Arg Pro Ala Tyr Glu Met Leu Glu Glu Lys Leu Lys Glu
                405                 410                 415
Gly Pro Phe Ala Arg Leu Met Ser Lys Asn Glu Asp Ile Arg Met Thr
            420                 425                 430
Lys Leu Leu Met Gln Gln Arg Leu Ser His Gly Ala Pro Ser Pro Lys
        435                 440                 445
Leu Ser Lys Met Leu Glu Ile Leu Val Asp His Phe Lys Val Lys Asp
    450                 455                 460
Pro Lys Thr Ser Arg Val Ile Ile Phe Ser Asn Phe Arg Gly Ser Val
465                 470                 475                 480
Arg Asp Ile Met Asn Ala Leu Ser Asn Ile Gly Asp Met Val Lys Ala
                485                 490                 495
Thr Glu Phe Ile Gly Gln Ser Ser Gly Lys Thr Leu Lys Gly Gln Ser
            500                 505                 510
Gln Lys Ile Gln Gln Ala Val Leu Glu Lys Phe Arg Ala Gly Gly Phe
        515                 520                 525
Asn Val Ile Val Ala Thr Ser Ile Gly Glu Glu Gly Leu Asp Ile Met
    530                 535                 540
Glu Val Asp Leu Val Ile Cys Phe Asp Ala Asn Val Ser Pro Leu Arg
545                 550                 555                 560
Met Ile Gln Arg Met Gly Arg Thr Gly Arg Lys Asn Asn Gly Arg Pro
                565                 570                 575
Leu Leu Val Leu Ala Cys Glu Gly Ser Glu Lys Asn Ser Tyr Met Arg
            580                 585                 590
Lys Gln Ala Ser Gly Arg Ala Ile Lys Lys His Met Arg Asn Gly Gly
        595                 600                 605
Thr Asn Ser Phe Asn Phe His Pro Ser Pro Arg Met Ile Pro His Val
```

```
            610                 615                 620
Tyr Lys Pro Glu Val Gln His Val Glu Phe Ser Ile Lys Gln Phe Val
625                 630                 635                 640

Pro Arg Gly Lys Lys Leu Gln Glu Glu Tyr Ala Thr Glu Thr Pro Ala
                645                 650                 655

Phe Gln Lys Lys Leu Thr Pro Ala Glu Thr His Met Leu Ala Lys Tyr
                660                 665                 670

Tyr Asn Asn Pro Asp Glu Glu Lys Leu Arg Val Ser Leu Ile Ala Phe
                675                 680                 685

Pro His Phe Gln Thr Leu Pro Ser Lys Val His Lys Val Met His Ser
690                 695                 700

Arg Gln Thr Gly Met Leu Ile Asp Ala Met Gln His Leu Gln Glu Pro
705                 710                 715                 720

Thr Phe Ser Glu Gln Ser Lys Ser Phe Phe Thr Glu Phe Arg Ala Pro
                725                 730                 735

Leu Gly Glu Arg Glu Glu Leu Asp Thr Gly Leu Arg Val Thr Asn Asp
                740                 745                 750

Pro Lys Asp Leu His Ser Val Arg Asp Leu Glu Val Asn Thr Ser Gln
                755                 760                 765

Arg Lys Ala Lys Gln Val Glu Ser Pro Thr Ser Thr Leu Glu Thr Thr
770                 775                 780

Glu Lys Asp Tyr Glu Ser Ser Pro Thr His Arg Tyr Leu Phe Ser
785                 790                 795                 800

Ser Glu Cys Ala Ser Val Asp Thr Leu Gly Asn Val Phe Val Met Pro
                805                 810                 815

Val Pro Leu Leu Phe Phe Pro Asn Val Leu Glu Ser Asp Asn Thr Pro
                820                 825                 830

Leu Pro Lys Thr Glu Lys Gln His Ser Cys Arg Asn Thr Ser His Ile
                835                 840                 845

Asp Leu Val Pro Val Asp Thr Ser Glu Lys His Arg Gln Asp Asn Ile
                850                 855                 860

Ser Cys Lys Leu Lys Glu Arg Phe Ser Pro Asp Gly Ala Ser Glu Thr
865                 870                 875                 880

Leu Glu Thr His Ser Leu Val Lys Arg Asn Ser Thr Arg Val Gly Glu
                885                 890                 895

Asp Asp Val Ala Asn Ser Val Gly Glu Ile Val Leu Ser Ser Asp Glu
                900                 905                 910

Asp Asp Cys Glu Gly Leu Glu Leu Ser Pro Arg Leu Thr Asn Phe Ile
                915                 920                 925

Lys Ser Gly Ile Val Pro Glu Ser Pro Val Tyr Asp Gln Gly Glu Ala
930                 935                 940

Asn Arg Glu Glu Asp Leu Glu Phe Pro Gln Leu Ser Pro Met Arg
945                 950                 955                 960

Phe Ser Asn Glu Leu Ala Gly Glu Ser Ser Phe Pro Glu Arg Lys Val
                965                 970                 975

Gln His Lys Cys Asn Asp Tyr Asn Ile Val Ser Thr Thr Thr Glu Leu
                980                 985                 990

Arg Thr Pro Gln Lys Glu Val Gly Leu Ala Asn Gly Thr Glu Cys Leu
                995                1000                1005

Ala Val Ser Pro Ile Pro Glu Asp Trp Arg Thr Pro Leu Ala Asn
   1010                1015                1020

Leu Thr Asn Thr Asn Ser Ser Ala Arg Lys Asp Trp Arg Val Ser
   1025                1030                1035
```

-continued

Ser Gly Glu Lys Leu Glu Thr Leu Arg Gln Pro Arg Lys Leu Lys
    1040                1045                1050

Arg Leu Arg Arg Leu Gly Asp Cys Ser Ser Ala Val Lys Glu Asn
    1055                1060                1065

Tyr Pro Gly Ile Thr Glu Ala Asp His Ile Arg Ser Arg Ser Arg
    1070                1075                1080

Gly Lys Lys His Ile Arg Val Lys Trp Lys Ser Ala Glu Ser Trp
    1085                1090                1095

Phe Thr Leu Ser Ser Val Ala Phe Ala Leu Val Thr Lys Lys Lys
    1100                1105                1110

Lys Met Ile Met Asp Asp Val Gln Val Phe Ile Asp Glu Glu
    1115                1120                1125

Ala Glu Val Ser Ser Gly Ala Glu Met Ser Ala Asp Glu Asn Glu
    1130                1135                1140

Asp Val Thr Gly Asp Ser Phe Glu Asp Ser Phe Ile Asp Asp Gly
    1145                1150                1155

Thr Met Pro Thr Ala Asn Thr Gln Ala Glu Ser Gly Lys Val Asp
    1160                1165                1170

Met Met Ala Val Tyr Arg Tyr Ile Gln Pro Lys Ile Ser Phe Phe
    1175                1180                1185

Tyr Cys Glu Val Asn Glu Leu Ile Lys Asn His Lys Val Ser Phe
    1190                1195                1200

His Arg Arg Ser Leu Leu Ser Gln Ser Pro Leu Pro Ala Arg Phe
    1205                1210                1215

Arg Asp Leu Ala Ala Ser Ser Leu Ser Pro Tyr Ser Ala Gly Pro
    1220                1225                1230

Leu Thr Arg Ile Asn Glu Ser Arg Ser Asp Ser Asp Lys Ser Leu
    1235                1240                1245

Ser Ser Leu Arg Thr Pro Lys Thr Thr Asn Ser Glu Ser Asn Gln
    1250                1255                1260

Asp Ala Met Met Ile Gly Asn Leu Ser Val Val Gln Ile Ser Ser
    1265                1270                1275

Asp Ser Arg Lys Arg Lys Phe Ser Leu Cys Asn Ser Ala Asn Ala
    1280                1285                1290

Pro Val Ile Asn Leu Glu Ser Lys Phe Ala Ala His Ala Gln Ala
    1295                1300                1305

Thr Glu Lys Glu Ser His Glu Gly Val Arg Ser Asn Ala Gly Ala
    1310                1315                1320

Leu Glu Tyr Asn Asp Asp Asp Asp Ala Phe Phe Ala Thr Leu
    1325                1330                1335

Asp Phe Asp Ala Met Glu Ala Gln Ala Thr Leu Leu Ser Lys
    1340                1345                1350

Gln Arg Ser Glu Ala Lys Glu Lys Glu Asp Ala Thr Val Ile Pro
    1355                1360                1365

Asn Pro Gly Met Gln Arg Ser Asp Gly Met Glu Lys Asp Ala Pro
    1370                1375                1380

Ser Phe Asp Leu Gly Leu Trp
    1385            1390

<210> SEQ ID NO 46
<211> LENGTH: 672
<212> TYPE: PRT
<213> ORGANISM: Arabidopsis thaliana
<220> FEATURE:

-continued

```
<221> NAME/KEY: DOMAIN
<222> LOCATION: (268)..(346)
<223> OTHER INFORMATION: Binding domain to  RAD51
<220> FEATURE:
<221> NAME/KEY: DOMAIN
<222> LOCATION: (431)..(561)
<223> OTHER INFORMATION: Domain AAA
<220> FEATURE:
<221> NAME/KEY: DOMAIN
<222> LOCATION: (623)..(672)
<223> OTHER INFORMATION: Domain VPS4

<400> SEQUENCE: 46
```

Met Cys Gly Ser Val Val Ser Asp Ser Glu Arg Glu Phe Glu Phe His
1               5                   10                  15

Phe Trp Gly Phe Gly His Leu Gly Lys Glu Glu Arg Ile Met Ala
            20                  25                  30

Gly Lys Arg Ser Ser Pro Phe Ser Pro Leu Leu Arg Pro Pro Pro
        35                  40                  45

Glu Phe Leu Asn Val Lys Glu Glu Gly Glu Thr Glu Thr Pro Cys Trp
    50                  55                  60

Arg Lys Glu Val Asp Glu Asn Leu Lys Arg Leu Gln Ser Leu Leu Phe
65                  70                  75                  80

Gly Ala Asp Lys Phe Leu Glu Lys Ser Asp Phe Ser Ser Ala Gln Ile
                85                  90                  95

Leu Gly Leu Arg Leu Leu Gly Phe Leu Asp Ser Arg Ser Val Thr Asp
            100                 105                 110

Ala Asp Arg Asp Phe Ile Gly Pro Ile Arg Arg Glu Val Ala Ser Lys
        115                 120                 125

Ile Asp Leu Ala Leu Glu Gly Leu Val Ser Asp Ser Asp Arg Lys Ala
130                 135                 140

Phe Glu Leu Ala Asn Thr Ala Pro Gly Ala Ile Phe Gly Ser Lys Gly
145                 150                 155                 160

Gly Phe Asp Val Glu Lys Ile Lys Gln Ser Lys Tyr Phe Gly Phe His
                165                 170                 175

Val Ser Gln Ser Asn Gly Lys Gly Val Lys Glu Met Leu Ile Pro Lys
            180                 185                 190

Ala Pro Lys Ser Met Met Gln Ala Lys Leu Thr Ser Leu Tyr Gly Asn
        195                 200                 205

Ser Ile Gly Lys Pro Asp Asn Gln Arg Lys Thr Ser Val Asn Asn Gln
210                 215                 220

Asp Arg Ala Ser Asp Glu Cys Val Ile Val Glu Arg Ser His Gly Phe
225                 230                 235                 240

Gly Phe Gly Thr Lys Arg Pro His Ala Glu Thr Ser Ser Leu Ala Asn
                245                 250                 255

Asp Gly Glu Val Lys Glu Asp Gly Ala Pro Asn Gly Phe Val Ser Ala
            260                 265                 270

Lys Ile Lys Leu Glu Met Asp Val Arg Gln Lys Arg Gly Ser Thr Glu
        275                 280                 285

Ser Pro Ser Ser Cys Leu Ser Pro Gln Ser Asp Lys Asn Ala Leu Gly
290                 295                 300

Arg Gly Tyr Gly Ser Arg Ser Gly Gly Leu Arg Arg Gly Tyr Arg Ser
305                 310                 315                 320

Asn Phe Val Pro Pro Val Lys Thr Asn Gly Asn Asn Val Gly Asn Leu
                325                 330                 335

Thr Ser Arg Ile Gly Gly Lys Thr Asp Asp Ala Leu Asp Asp Ser Thr
            340                 345                 350

Arg Thr Cys Leu Glu Met Leu Cys Gly Pro Asp Gly Glu Leu Pro Glu
            355                 360                 365

Lys Leu Arg Asn Leu Glu Pro Arg Leu Ile Glu His Val Ser Asn Glu
            370                 375                 380

Ile Met Asp Arg Asp Pro Asn Val Arg Trp Asp Ile Ala Gly Leu
385                 390                 395                 400

Glu His Ala Lys Lys Cys Val Thr Glu Met Val Ile Trp Pro Leu Leu
                405                 410                 415

Arg Pro Asp Ile Phe Lys Gly Cys Arg Ser Pro Gly Lys Gly Leu Leu
            420                 425                 430

Leu Phe Gly Pro Pro Gly Thr Gly Lys Thr Met Ile Gly Lys Ala Ile
            435                 440                 445

Ala Gly Glu Ala Lys Ala Thr Phe Phe Tyr Ile Ser Ala Ser Ser Leu
            450                 455                 460

Thr Ser Lys Trp Ile Gly Glu Gly Glu Lys Leu Val Arg Ala Leu Phe
465                 470                 475                 480

Gly Val Ala Ser Cys Arg Gln Pro Ala Val Ile Phe Val Asp Glu Ile
                485                 490                 495

Asp Ser Leu Leu Ser Gln Arg Lys Ser Asp Gly Glu His Glu Ser Ser
            500                 505                 510

Arg Arg Leu Lys Thr Gln Phe Leu Ile Glu Met Glu Gly Phe Asp Ser
            515                 520                 525

Gly Ser Glu Gln Ile Leu Leu Ile Gly Ala Thr Asn Arg Pro Gln Glu
            530                 535                 540

Leu Asp Glu Ala Ala Arg Arg Leu Thr Lys Arg Leu Tyr Ile Pro
545                 550                 555                 560

Leu Pro Ser Ser Glu Ala Arg Ala Trp Ile Ile Gln Asn Leu Leu Lys
                565                 570                 575

Lys Asp Gly Leu Phe Thr Leu Ser Asp Asp Met Asn Ile Ile Cys
            580                 585                 590

Asn Leu Thr Glu Gly Tyr Ser Gly Ser Asp Met Lys Asn Leu Val Lys
            595                 600                 605

Asp Ala Thr Met Gly Pro Leu Arg Glu Ala Leu Lys Arg Gly Ile Asp
            610                 615                 620

Ile Thr Asn Leu Thr Lys Asp Asp Met Arg Leu Val Thr Leu Gln Asp
625                 630                 635                 640

Phe Lys Asp Ala Leu Gln Glu Val Arg Pro Ser Val Ser Gln Asn Glu
                645                 650                 655

Leu Gly Ile Tyr Glu Asn Trp Asn Asn Gln Phe Gly Ser Leu Ser Leu
            660                 665                 670

```
<210> SEQ ID NO 47
<211> LENGTH: 928
<212> TYPE: PRT
<213> ORGANISM: Oryza sativa

<400> SEQUENCE: 47
```

Met His His Gly Gly Gly Gly Ala Ile Arg Val Leu Asn Val Ala
1                   5                   10                  15

Glu Lys Pro Ser Val Ala Lys Ser Val Ala Glu Ile Leu Ser Arg Pro
                20                  25                  30

Ser Gly Gly Met Arg Ser Arg Glu Gly Arg Ser Arg Tyr Asn Arg Val
            35                  40                  45

Phe Glu Phe Asp Tyr Ser Ile Gly Gly Arg Ala Cys His Met Leu Val

```
            50                  55                  60
Thr Ser Val Thr Gly His Leu Met Glu Leu Glu Phe Asp Asp Arg Phe
65                  70                  75                  80

Arg Arg Trp His Ser Cys Asp Pro Ala Asp Leu Phe His Ala Pro Val
                85                  90                  95

Arg Lys Ser Val Pro Gln Asp Lys Gln Asp Ile Lys Arg Thr Leu Glu
            100                 105                 110

Glu Glu Ala Arg Lys Cys Gln Trp Leu Val Leu Trp Leu Asp Cys Asp
            115                 120                 125

Arg Glu Gly Glu Asn Ile Ala Tyr Glu Val Ile Asp Ile Cys Ala Gly
            130                 135                 140

Ala Asn Ser Arg Leu Asn Ile Trp Arg Ala Arg Phe Ser Ala Leu Ile
145                 150                 155                 160

Asp Arg Glu Ile His Glu Ala Val Gln His Leu Asp Arg Pro Asn Lys
                165                 170                 175

Leu Phe Ala Asp Ala Val Asp Ala Arg Gln Glu Ile Asp Leu Arg Ile
                180                 185                 190

Gly Ala Ser Phe Thr Arg Phe Gln Thr Met Leu Leu Lys Asp Ala Phe
            195                 200                 205

Val Leu Asp Asp Thr Gly Asp Asp Arg Asn Ile Ile Leu Ser Tyr Gly
210                 215                 220

Pro Cys Gln Phe Pro Thr Leu Gly Phe Ile Val Glu Arg Phe Trp Glu
225                 230                 235                 240

Ile Gln Ala His Glu Pro Glu Glu Phe Trp Thr Ile Asn Cys Ser His
                245                 250                 255

Thr Ser Asp Glu Gly Thr Ala Ser Phe Gly Trp Ile Arg Gly His Leu
                260                 265                 270

Phe Asp Tyr Ser Ser Ala Val Val Ile Tyr Glu Met Cys Val Glu Glu
            275                 280                 285

Pro Met Ala Thr Val Gln Asn Val Arg Asn Gln Glu Lys Leu Lys Tyr
            290                 295                 300

Pro Pro Tyr Pro Leu Ser Thr Ile Glu Leu Gln Lys Arg Ala Ser Arg
305                 310                 315                 320

Tyr Phe Arg Met Ser Ser Glu His Thr Met Lys Val Ala Glu Glu Leu
                325                 330                 335

Tyr Gln Ala Gly Phe Ile Ser Tyr Pro Arg Thr Glu Thr Asp Asn Phe
            340                 345                 350

Ser Pro Asn Thr Asp Leu His Ser Ile Val His Glu Gln Val Ala His
            355                 360                 365

Pro Asn Trp Gly Thr Tyr Ala Gln Arg Leu Leu Asp Pro Glu Ala Arg
            370                 375                 380

Leu Trp Arg Asn Pro Ser Asn Gly Gly His Asp Asp Lys Ala His Pro
385                 390                 395                 400

Pro Ile His Pro Thr Lys Phe Ser Ala Gly Glu Thr Asn Trp Thr Asp
                405                 410                 415

Asn His Lys Lys Leu Tyr Glu Leu Val Val Arg His Phe Leu Ala Cys
            420                 425                 430

Cys Ser Gln Pro Ala Val Gly Ala Glu Thr Thr Val Glu Ile Asp Ile
            435                 440                 445

Ala Gly Glu Gln Phe Asn Ala Ser Gly Arg Val Val Leu Ala Lys Asn
            450                 455                 460

Tyr Leu Asp Val Tyr Arg Phe Asp Ser Trp Gly Gly Thr Leu Leu Pro
465                 470                 475                 480
```

```
Thr Tyr Ile Ile Gly Gln Gln Phe Val Pro Thr Thr Leu Thr Leu Asp
                485                 490                 495

Ser Gly Met Thr Arg Pro Pro Leu Leu Ala Glu Ala Asp Leu Leu
            500                 505                 510

Gly Cys Met Asp Lys Ala Gly Ile Gly Thr Asp Ala Thr Met His Asp
            515                 520                 525

His Ile Lys Lys Leu Leu Asp Arg Cys Tyr Ala Thr Lys Asp Ala Asn
    530                 535                 540

Thr Arg Phe Ser Pro Thr Asn Leu Gly Glu Ala Leu Val Met Gly Tyr
545                 550                 555                 560

Asp Glu Met Gly Tyr Glu Leu Trp Lys Pro Tyr Leu Arg Ser Met Met
                565                 570                 575

Glu Ala Asp Met Lys Ser Val Ser Ile Gly Thr Lys Ser Lys Ser Glu
            580                 585                 590

Val Leu Glu Asn Cys Leu Gln Gln Met Lys Ala Cys Phe Leu Asp Ala
            595                 600                 605

Arg Ala Asn Lys Val Lys Leu Phe Asp Ala Met Gly Thr Phe Phe Ala
610                 615                 620

Arg Ser Ser Arg Pro Val Asn Glu Thr Gln Asn Ser Ile Glu Thr Val
625                 630                 635                 640

Arg Pro Cys Ala Ala Cys Asn Glu Ser Glu Met Phe Leu Lys Gln Arg
            645                 650                 655

Pro Thr Gly Glu Phe Met Val Gly Cys Arg Gly Phe Pro Gln Cys Arg
            660                 665                 670

Asn Val Val Trp Leu Pro Arg Ser Leu Ser Gly Ala Ala Val Thr Asp
            675                 680                 685

Gln Val Cys Pro Thr Cys Ala Pro Gly Pro Val Tyr Lys Ile Gln Phe
    690                 695                 700

Lys Phe Arg Arg Arg Asp Ile Pro Pro Asn Phe Asp Val Asp His Leu
705                 710                 715                 720

Gly Cys Ile Gly Gly Cys Asp Asp Ile Leu Lys Glu Leu Met Glu Leu
            725                 730                 735

Ser Arg Phe Gly Ser His Ser Gln Thr Ala Thr Pro Ala Arg Asn Gln
            740                 745                 750

Ser Gln Thr Ala Ser Gly Val Arg Gln Gly Ser Ser Arg Gln Asp Leu
            755                 760                 765

His Thr Ser Phe His Pro Ala Val Gln Phe Thr Asn Gly Gln Thr Pro
    770                 775                 780

Val Val Asn Pro Gln Gly Phe Arg Ser Thr His Thr Gln Ser Ser Gly
785                 790                 795                 800

Asn Ala Ser Gly Gln Val Gln Cys Thr Ser Cys Arg Glu Pro Cys Val
            805                 810                 815

Leu Arg Thr Ala Asn Thr Glu Ala Asn Arg Gly Arg Lys Phe Tyr Lys
            820                 825                 830

Cys Gln Asn Leu Ala Cys Gly Phe Phe Ala Trp Glu Asp Asp Val Glu
            835                 840                 845

Asn Ser Ala Pro Arg Gly Arg Gly Gly Arg Gly Gly Arg Ser
850                 855                 860

Ser Ser Arg Gln Ser Ser Ala Ser Ala Ser Ala Gly Arg Arg Gly Gly
865                 870                 875                 880

Thr Gln Gly Arg Gly Arg Arg Gly Arg Gly Arg Asn Ala Asp Gly Met
            885                 890                 895
```

```
Met Phe Val Ala Ala Thr Gly Glu Pro Val Tyr Gly Ser Cys Phe Ile
                900                 905                 910
Cys Gly Asp Pro Thr His Phe Ala Asn Val Cys Pro Asn Leu Gly Arg
        915                 920                 925

<210> SEQ ID NO 48
<211> LENGTH: 1001
<212> TYPE: PRT
<213> ORGANISM: Homo sapiens

<400> SEQUENCE: 48

Met Ile Phe Pro Val Ala Arg Tyr Ala Leu Arg Trp Leu Arg Arg Pro
1               5                   10                  15
Glu Asp Arg Ala Phe Ser Arg Ala Ala Met Glu Met Ala Leu Arg Gly
            20                  25                  30
Val Arg Lys Val Leu Cys Val Ala Glu Lys Asn Asp Ala Ala Lys Gly
        35                  40                  45
Ile Ala Asp Leu Leu Ser Asn Gly Arg Met Arg Arg Glu Gly Leu
    50                  55                  60
Ser Lys Phe Asn Lys Ile Tyr Glu Phe Asp Tyr His Leu Tyr Gly Gln
65                  70                  75                  80
Asn Val Thr Met Val Met Thr Ser Val Ser Gly His Leu Leu Ala His
                85                  90                  95
Asp Phe Gln Met Gln Phe Arg Lys Trp Gln Ser Cys Asn Pro Leu Val
            100                 105                 110
Leu Phe Glu Ala Glu Ile Glu Lys Tyr Cys Pro Glu Asn Phe Val Asp
        115                 120                 125
Ile Lys Lys Thr Leu Glu Arg Glu Thr Arg Gln Cys Gln Ala Leu Val
    130                 135                 140
Ile Trp Thr Asp Cys Asp Arg Glu Gly Glu Asn Ile Gly Phe Glu Ile
145                 150                 155                 160
Ile His Val Cys Lys Ala Val Lys Pro Asn Leu Gln Val Leu Arg Ala
                165                 170                 175
Arg Phe Ser Glu Ile Thr Pro His Ala Val Arg Thr Ala Cys Glu Asn
            180                 185                 190
Leu Thr Glu Pro Asp Gln Arg Val Ser Asp Ala Val Asp Val Arg Gln
        195                 200                 205
Glu Leu Asp Leu Arg Ile Gly Ala Ala Phe Thr Arg Phe Gln Thr Leu
    210                 215                 220
Arg Leu Gln Arg Ile Phe Pro Glu Val Leu Ala Glu Gln Leu Ile Ser
225                 230                 235                 240
Tyr Gly Ser Cys Gln Phe Pro Thr Leu Gly Phe Val Val Glu Arg Phe
                245                 250                 255
Lys Ala Ile Gln Ala Phe Val Pro Glu Ile Phe His Arg Ile Lys Val
            260                 265                 270
Thr His Asp His Lys Asp Gly Ile Val Glu Phe Asn Trp Lys Arg His
        275                 280                 285
Arg Leu Phe Asn His Thr Ala Cys Leu Val Leu Tyr Gln Leu Cys Val
    290                 295                 300
Glu Asp Pro Met Ala Thr Val Val Glu Val Arg Ser Lys Pro Lys Ser
305                 310                 315                 320
Lys Trp Arg Pro Gln Ala Leu Asp Thr Val Glu Leu Glu Lys Leu Ala
                325                 330                 335
Ser Arg Lys Leu Arg Ile Asn Ala Lys Glu Thr Met Arg Ile Ala Glu
            340                 345                 350
```

```
Lys Leu Tyr Thr Gln Gly Tyr Ile Ser Tyr Pro Arg Thr Glu Thr Asn
        355                 360                 365

Ile Phe Pro Arg Asp Leu Asn Leu Thr Val Leu Val Glu Gln Gln Thr
    370                 375                 380

Pro Asp Pro Arg Trp Gly Ala Phe Ala Gln Ser Ile Leu Glu Arg Gly
385                 390                 395                 400

Gly Pro Thr Pro Arg Asn Gly Asn Lys Ser Asp Gln Ala His Pro Pro
                405                 410                 415

Ile His Pro Thr Lys Tyr Thr Asn Asn Leu Gln Gly Asp Glu Gln Arg
                420                 425                 430

Leu Tyr Glu Phe Ile Val Arg His Phe Leu Ala Cys Cys Ser Gln Asp
        435                 440                 445

Ala Gln Gly Gln Glu Thr Thr Val Glu Ile Asp Ile Ala Gln Glu Arg
    450                 455                 460

Phe Val Ala His Gly Leu Met Ile Leu Ala Arg Asn Tyr Leu Asp Val
465                 470                 475                 480

Tyr Pro Tyr Asp His Trp Ser Asp Lys Ile Leu Pro Val Tyr Glu Gln
                485                 490                 495

Gly Ser His Phe Gln Pro Ser Thr Val Glu Met Val Asp Gly Glu Thr
                500                 505                 510

Ser Pro Pro Lys Leu Leu Thr Glu Ala Asp Leu Ile Ala Leu Met Glu
            515                 520                 525

Lys His Gly Ile Gly Thr Asp Ala Thr His Ala Glu His Ile Glu Thr
        530                 535                 540

Ile Lys Ala Arg Met Tyr Val Gly Leu Thr Pro Asp Lys Arg Phe Leu
545                 550                 555                 560

Pro Gly His Leu Gly Met Gly Leu Val Glu Gly Tyr Asp Ser Met Gly
                565                 570                 575

Tyr Glu Met Ser Lys Pro Asp Leu Arg Ala Glu Leu Glu Ala Asp Leu
                580                 585                 590

Lys Leu Ile Cys Asp Gly Lys Lys Asp Lys Phe Val Val Leu Arg Gln
        595                 600                 605

Gln Val Gln Lys Tyr Lys Gln Val Phe Ile Glu Ala Val Ala Lys Ala
    610                 615                 620

Lys Lys Leu Asp Glu Ala Leu Ala Gln Tyr Phe Gly Asn Gly Thr Glu
625                 630                 635                 640

Leu Ala Gln Gln Glu Asp Ile Tyr Pro Ala Met Pro Glu Pro Ile Arg
                645                 650                 655

Lys Cys Pro Gln Cys Asn Lys Asp Met Val Leu Lys Thr Lys Lys Asn
                660                 665                 670

Gly Gly Phe Tyr Leu Ser Cys Met Gly Phe Pro Glu Cys Arg Ser Ala
                675                 680                 685

Val Trp Leu Pro Asp Ser Val Leu Glu Ala Ser Arg Asp Ser Ser Val
        690                 695                 700

Cys Pro Val Cys Gln Pro His Pro Val Tyr Arg Leu Lys Leu Lys Phe
705                 710                 715                 720

Lys Arg Gly Ser Leu Pro Pro Thr Met Pro Leu Glu Phe Val Cys Cys
                725                 730                 735

Ile Gly Gly Cys Asp Asp Thr Leu Arg Glu Ile Leu Asp Leu Arg Phe
                740                 745                 750

Ser Gly Gly Pro Pro Arg Ala Ser Gln Pro Ser Gly Arg Leu Gln Ala
                755                 760                 765
```

```
Asn Gln Ser Leu Asn Arg Met Asp Asn Ser Gln His Pro Gln Pro Ala
    770                 775                 780
Asp Ser Arg Gln Thr Gly Ser Ser Lys Ala Leu Ala Gln Thr Leu Pro
785                 790                 795                 800
Pro Pro Thr Ala Ala Gly Glu Ser Asn Ser Val Thr Cys Asn Cys Gly
                805                 810                 815
Gln Glu Ala Val Leu Leu Thr Val Arg Lys Glu Gly Pro Asn Arg Gly
            820                 825                 830
Arg Gln Phe Phe Lys Cys Asn Gly Gly Ser Cys Asn Phe Leu Trp
        835                 840                 845
Ala Asp Ser Pro Asn Pro Gly Ala Gly Pro Pro Ala Leu Ala Tyr
    850                 855                 860
Arg Pro Leu Gly Ala Ser Leu Gly Cys Pro Gly Pro Gly Ile His
865                 870                 875                 880
Leu Gly Gly Phe Gly Asn Pro Gly Asp Gly Ser Gly Thr Ser
                885                 890                 895
Cys Leu Cys Ser Gln Pro Ser Val Thr Arg Thr Val Lys Asp Gly
            900                 905                 910
Pro Asn Lys Gly Arg Gln Phe His Thr Cys Ala Lys Pro Arg Glu Gln
        915                 920                 925
Gln Cys Gly Phe Phe Gln Trp Val Asp Glu Asn Thr Ala Pro Gly Thr
    930                 935                 940
Ser Gly Ala Pro Ser Trp Thr Gly Asp Arg Gly Arg Thr Leu Glu Ser
945                 950                 955                 960
Glu Ala Arg Ser Lys Arg Pro Arg Ala Ser Ser Ser Asp Met Gly Ser
                965                 970                 975
Thr Ala Lys Lys Pro Arg Lys Cys Ser Leu Cys His Gln Pro Gly His
            980                 985                 990
Thr Arg Pro Phe Cys Pro Gln Asn  Arg
        995                 1000

<210> SEQ ID NO 49
<211> LENGTH: 998
<212> TYPE: PRT
<213> ORGANISM: Danio rerio

<400> SEQUENCE: 49

Met Asn Val Leu Phe Arg Ala Leu Arg Lys Thr Val Asn Ser Arg Phe
1               5                   10                  15
Tyr Arg His Ile Ser Val Ser Met Ile Arg Arg Thr Gln Ile Lys Lys
            20                  25                  30
Val Leu Cys Val Ala Glu Lys Asn Asp Ala Ala Lys Gly Ile Ala Glu
        35                  40                  45
Ile Met Ser Asn Gly Arg Ser Arg Arg Glu Gly Cys Ser Val Tyr
    50                  55                  60
Asn Lys Ile Tyr Glu Tyr Glu Tyr Asn Leu Phe Gly Gln Asn Val Thr
65                  70                  75                  80
Val Asn Met Thr Ser Val Ser Gly His Leu Leu Ala Leu Glu Phe Lys
                85                  90                  95
Ala Pro Phe Gln Lys Trp His Ser Cys Ser Pro Val Leu Leu Phe Asp
            100                 105                 110
Ala Glu Val Glu Lys Tyr Cys Pro Glu Asn Phe Ile Pro Ile Lys Arg
        115                 120                 125
Thr Leu Glu Arg Glu Val Arg Gln Cys Gln Ala Leu Ile Val Trp Thr
    130                 135                 140
```

```
Asp Cys Asp Arg Glu Gly Glu Asn Ile Gly Phe Glu Ile Ile Asp Val
145                 150                 155                 160

Cys Lys Ala Val Lys Pro Asn Ile Gln Val Phe Arg Ala Arg Phe Ser
                165                 170                 175

Glu Ile Thr Pro Asn Ser Ile Arg Arg Ala Cys Glu Thr Leu Thr Glu
            180                 185                 190

Pro Asp Ile Asn Val Ser Asp Ala Val Asp Val Arg Gln Glu Leu Asp
        195                 200                 205

Leu Arg Ile Gly Ala Ser Phe Thr Arg Phe Gln Thr Leu Arg Leu Gln
    210                 215                 220

Lys Ile Phe Pro Glu Ser Leu Ser Asp Gln Leu Ile Ser Tyr Gly Ser
225                 230                 235                 240

Cys Gln Phe Pro Thr Leu Gly Phe Val Val Glu Arg Phe Lys Ala Ile
                245                 250                 255

Gln Ala Phe Ile Pro Glu Thr Phe Phe Lys Ile Lys Val Val His Glu
            260                 265                 270

Pro Asn Glu Glu Glu Ser Val Glu Phe Asn Trp Lys Arg His Arg Leu
        275                 280                 285

Phe Asn His Thr Ala Cys Leu Val Leu Tyr Gln Met Cys Met Glu Glu
    290                 295                 300

Pro Met Ala Lys Val Ile Ser Val Thr Ser Lys Pro Lys Ser Lys Trp
305                 310                 315                 320

Arg Pro Leu Pro Leu Asp Thr Val Glu Leu Glu Lys Leu Ala Ser Arg
                325                 330                 335

Lys Leu Arg Ile Ser Ala Lys Glu Thr Met Lys Ile Ala Glu Lys Leu
            340                 345                 350

Tyr Thr Gln Gly Phe Ile Ser Tyr Pro Arg Thr Glu Thr Asn Met Phe
        355                 360                 365

Pro Gln Asn Leu Asn Leu Thr Arg Leu Val Glu Gln Gln Thr Gln Asp
    370                 375                 380

Gln Glu Trp Gly Asn Phe Ala Gln Arg Ile Leu Glu Ser Gly Gly Pro
385                 390                 395                 400

Thr Pro Arg Asn Gly Asn Lys Ser Asp Gln Ala His Pro Pro Ile His
                405                 410                 415

Pro Thr Lys Tyr Thr Asn Gly Leu Gln Gly Asn Glu Lys Arg Leu Tyr
            420                 425                 430

Glu Phe Ile Val Arg His Phe Leu Ala Cys Cys Ser Lys Asp Ala Gln
        435                 440                 445

Gly Gln Glu Val Thr Val Glu Ile Asp Ile Ala Glu Glu Arg Phe Ser
    450                 455                 460

Ala Ser Gly Leu Thr Ile Ile Ala Arg Asn Tyr Leu Glu Val Tyr Pro
465                 470                 475                 480

Tyr Asp Lys Trp Tyr Asn Lys Val Ile Pro Ser Tyr Ser Pro Asn Thr
                485                 490                 495

Thr Phe Gln Pro Thr Ala Ile Glu Met Val Glu Gly Gln Thr Ser Pro
            500                 505                 510

Pro Gln Leu Leu Thr Glu Ala Asp Leu Ile Ser Leu Met Glu Lys His
        515                 520                 525

Gly Ile Gly Thr Asp Ala Thr His Ala Glu His Ile Glu Thr Ile Lys
    530                 535                 540

Ser Arg Met Tyr Val Gly Leu Thr Ala Asp Gln Arg Phe Leu Pro Gly
545                 550                 555                 560
```

```
Glu Leu Gly Met Gly Leu Val Glu Gly Tyr Asn Ser Met Gly Tyr Glu
                565                 570                 575

Met Ser Lys Pro Asp Leu Arg Ala Glu Leu Glu Ala Asp Leu Lys Leu
            580                 585                 590

Val Ser Glu Gly Arg Lys Asn Lys Ala Ser Val Leu Ser Tyr His Val
            595                 600                 605

Ala Lys Tyr Lys Ala Val Phe Ile Glu Ser Val Arg Lys Ala Lys Lys
        610                 615                 620

Leu Asp Glu Ala Leu Ser Asn Tyr Leu Gly Pro Ala Gln Glu Ile Ala
625                 630                 635                 640

Glu Gln Glu Gln Val Glu Leu Glu Ile Pro Leu Pro Val Arg Lys Cys
                645                 650                 655

Pro Gln Cys Asn Arg Asp Met Val Leu Lys Lys Lys Asp Ser Thr
                660                 665                 670

Gly Met Leu Leu Ser Cys Leu Gly Tyr Pro Ala Cys Lys Ala Ala Val
            675                 680                 685

Trp Phe Pro Asp Thr Val Leu Glu Val Ser Arg Asp Glu Ser Ile Cys
        690                 695                 700

Pro Thr Cys Arg Pro His Pro Val His Met Leu Lys Phe Lys Phe Lys
705                 710                 715                 720

Arg Gly Ser Leu Pro Pro Met Met Pro Leu Glu Phe Val Gly Cys Ile
                725                 730                 735

Gly Gly Cys Asp Asp Thr Leu Arg Glu Val Leu Asn Leu Lys Tyr Leu
                740                 745                 750

Arg Gly Arg Asp Ala Glu Ser Ala Pro Gln Ala Asn Asn Ser Ser Arg
            755                 760                 765

Ser Ser Gln His His Ile His Arg Thr Ser Ser Ala Pro Pro Pro Ser
        770                 775                 780

Arg Val Glu Asn Ile Arg Pro Pro Ala Pro Arg Pro Arg Ala Asp Pro
785                 790                 795                 800

Gly Leu Gln Pro Pro Ser Thr Gln Gly Gly Ala Ile Val Cys Asn
                805                 810                 815

Cys Gly Gln Asp Ala Leu Leu Leu Thr Val Arg Lys Glu Gly Pro Asn
            820                 825                 830

Gln Gly Arg Gln Phe Tyr Lys Cys Asn Thr Gly Asp Cys Lys Phe Phe
        835                 840                 845

Leu Trp Ala Asp Gln Pro Pro Glu Gln Gly Val Pro Glu Arg Asn Arg
850                 855                 860

Gly Pro Leu Ser Gln Asn Val Gln Pro Pro Arg Pro Ser Asn Gly Phe
865                 870                 875                 880

Gly Asn Val Ser Gln Gln Arg Gln Asn His Arg Gly Ser Gly Gly Asp
                885                 890                 895

Glu Gly Glu Thr Met Cys Asn Cys Asn Glu Pro Ser Val Thr Arg Thr
            900                 905                 910

Val Met Lys Glu Gly Pro Asn Lys Gly Arg Met Phe His Thr Cys Gly
        915                 920                 925

Lys Pro Arg Asp Gln Gln Cys Gly Phe Phe Gln Trp Ala Asn Glu Asn
930                 935                 940

Val Ala Pro Ala Thr Ala Phe Ser Gly Gly Asn Gly Lys Pro Ser
945                 950                 955                 960

Gly Asn Lys Lys Ala Ser Thr Thr Ser Val Lys Pro Pro Thr Ala Lys
                965                 970                 975

Arg Gln Arg Thr Cys Gly Ile Cys His Glu Pro Gly His Thr Arg Val
```

-continued

```
                980             985             990

Thr Cys Pro Gln Ala His
        995

<210> SEQ ID NO 50
<211> LENGTH: 759
<212> TYPE: PRT
<213> ORGANISM: Caenorhabditis elegans

<400> SEQUENCE: 50

Met Lys Arg Ala Leu Phe Val Ala Glu Lys Asn Asp Val Ala Lys Gly
1               5                   10                  15

Val Ala Ala Ile Leu Ser Asn Gly Thr Ala Asn Arg Arg Glu Gly Arg
            20                  25                  30

Ser Lys Phe Asn Lys Ile Tyr Thr Leu Asn Thr Glu Leu Phe Gly Gln
        35                  40                  45

Gln Thr Ala Ile Ser Val Thr Ser Val Ser Gly His Met Met Asn Phe
    50                  55                  60

Gln Phe His Glu Asn Met Ser Asn Trp Gln Thr Ala Ser Met Val Glu
65                  70                  75                  80

Leu Phe Arg Ala Pro Val Arg His Val Val Thr Pro Glu Met Lys Leu
                85                  90                  95

Ile Glu Gln Thr Leu Arg Glu Gln Ala Gln Arg His Asp Ile Leu Val
            100                 105                 110

Val Trp Thr Asp Cys Asp Arg Glu Gly Glu Ala Ile Gly Ala Glu Ile
        115                 120                 125

Val Lys Val Cys Arg Asp Ser Asn Arg Arg Leu Asp Ile Phe Arg Ala
    130                 135                 140

Arg Phe Ser Glu Ile Thr Lys Ala Ala Ile Thr Arg Ala Ala Arg Asn
145                 150                 155                 160

Leu Ile Arg Leu Asp Glu Lys Thr Val Ala Ala Val Asp Cys Arg Ser
                165                 170                 175

Glu Leu Asp Leu Arg Ile Gly Ser Ala Phe Thr Arg Leu Gln Thr Leu
            180                 185                 190

His Leu Arg Asn Arg Phe Arg Asp Leu Leu Gly Gln Asn Asp Thr Ser
        195                 200                 205

Gln Val Ile Ser Tyr Gly Ser Cys Gln Phe Pro Thr Leu Gly Phe Val
    210                 215                 220

Thr Asp Arg Tyr Lys Met Ile Glu Asn Phe Val Ser Glu Pro Phe Trp
225                 230                 235                 240

Lys Leu Ile Val Glu His Thr Arg Glu Ser His Lys Val Glu Phe Leu
                245                 250                 255

Trp Asp Arg Asn Arg Leu Phe Asp Arg Asp Thr Val Asp Ile Leu His
            260                 265                 270

Asp Glu Cys Lys Glu Thr Lys Glu Ala His Val Glu Lys Val Ala Lys
        275                 280                 285

Lys Pro Lys Ser Lys Trp Arg Pro Gln Ala Leu Asp Thr Val Glu Leu
    290                 295                 300

Glu Lys Leu Gly Ile Ser Lys Leu Arg Met Ser Ala Lys Gln Thr Met
305                 310                 315                 320

Gln Val Ala Glu Lys Leu Tyr Ser Lys Gly Phe Ile Ser Tyr Pro Arg
                325                 330                 335

Thr Glu Thr Asn Lys Phe Pro Ala Gly Leu Asn Leu Thr Pro Leu Val
            340                 345                 350
```

```
Gln Gln Gln Thr Gln Ser Asn Ile Trp Gly Asp Phe Ala Asn Glu Val
            355                 360                 365
Leu Gln Asn Gly Val Asn Pro Arg Asn Gly Arg Lys Ser Asp Glu Ala
        370                 375                 380
His Pro Pro Ile His Pro Leu Lys Phe Thr Glu Lys His Gln Leu Gln
385                 390                 395                 400
Gly Asp Asp Trp Lys Val Tyr Glu Leu Val Arg His Phe Leu Ala
                405                 410                 415
Cys Val Ser Gln Asp Ala Gln Gly Glu Thr Met Val Asn Leu Thr
                420                 425                 430
Val Gly Thr Glu Lys Phe His Ala Ser Gly Leu Arg Ile Arg Asp Met
        435                 440                 445
Gly Tyr Leu Lys Val Tyr Val Tyr Glu Lys Trp Gly Asn Arg Leu Leu
        450                 455                 460
Pro Thr Tyr Thr Glu Gly Glu Arg Phe Thr Asp Phe Glu Leu Lys Ile
465                 470                 475                 480
Gly Asp Gly Lys Thr Gln Ala Pro Asp Phe Leu Thr Glu Ala Asp Leu
                485                 490                 495
Ile Ser Leu Met Asp Lys Tyr Gly Ile Gly Thr Asp Ala Thr His Ala
                500                 505                 510
Glu His Ile Glu Lys Ile Lys Thr Arg Glu Tyr Ile Gly Val Arg Pro
        515                 520                 525
Asp Gly Lys Leu Ile Pro Ser Phe Leu Gly Leu Ala Leu Val Asp Gly
        530                 535                 540
Tyr Asp Asp Met Gly Phe Ala Met Ser Lys Pro Asp Leu Arg Ala Asn
545                 550                 555                 560
Leu Glu Ile Gly Leu Lys Glu Ile Cys Asp Gly Arg Arg Gln Lys Gln
                565                 570                 575
Glu Val Leu Asp Glu Gln Ile Gly Lys Tyr Arg Ala Ile Phe Val Glu
                580                 585                 590
Ser Glu Arg Lys Ile Gly Val Leu Ser Gln Ser Leu Gln Arg Tyr Leu
        595                 600                 605
Asp Lys Asn Asn Gln Ala Gly Gly Pro Gly Gly Pro Gly Gly Gly
        610                 615                 620
Gly Gly Pro Pro Arg Gly Pro Gly Gly Gly Gly Gly Pro Thr
625                 630                 635                 640
Gly Pro Pro Ala Pro Pro Lys Pro Pro Ala Lys Pro Arg Gly Arg Pro
                645                 650                 655
Pro Arg Lys Ser Ile Ser Pro Ala Val Lys Asn Gly His Asp Asp Pro
                660                 665                 670
Glu Asn Asp Thr Ile Val Thr Leu Ser Glu Val Phe Gly Ser Met Ser
                675                 680                 685
Asn Pro Lys Pro Ala Arg Lys Pro Arg Ala Pro Arg Lys Ser Ala Ala
        690                 695                 700
Pro Lys Glu Gln Glu Glu Glu Glu Val Phe Cys Gln Cys Pro Glu
705                 710                 715                 720
Pro Met Arg Ala Val Thr Lys Val Val Gln Lys Glu Gly Pro Asn Lys
                725                 730                 735
Gly Lys Lys Phe Tyr Thr Cys Ser Leu Pro Tyr Thr Ser Glu Lys
                740                 745                 750
Cys Asn Phe Phe Lys Trp Ala
        755
```

<210> SEQ ID NO 51
<211> LENGTH: 622
<212> TYPE: PRT
<213> ORGANISM: Schizosaccharomyces pombe

<400> SEQUENCE: 51

| | | | | | | | | | | | | | | | |
|---|---|---|---|---|---|---|---|---|---|---|---|---|---|---|---|
| Met | Arg | Val | Leu | Cys | Val | Ala | Glu | Lys | Asn | Ser | Ile | Ala | Lys | Ser | Val |
| 1 | | | | 5 | | | | | 10 | | | | | 15 | |
| Ala | Ser | Ile | Leu | Gly | Gly | His | Val | Arg | Arg | Asp | Thr | Arg | Ser | | |
| | | | 20 | | | | 25 | | | | | 30 | | | |
| Lys | Tyr | Val | Lys | Asn | Tyr | Asp | Phe | Ser | Phe | Asn | Phe | Gly | Gly | Asn | Val |
| | | | 35 | | | | | 40 | | | | | 45 | | |
| Gly | Ser | Ser | Asp | Val | Thr | Met | Thr | Ser | Val | Ser | Gly | His | Leu | Thr | Glu |
| | 50 | | | | | | 55 | | | | | 60 | | | |
| Ala | Ser | Phe | Pro | Ser | Glu | Tyr | Ser | Ser | Trp | Ser | Ser | Val | Pro | Gln | Asp |
| 65 | | | | | 70 | | | | | 75 | | | | | 80 |
| Val | Leu | Phe | Asp | Ala | Gln | Ile | Ile | Thr | Ser | Val | Ser | Lys | Asn | Ala | Glu |
| | | | | 85 | | | | | 90 | | | | | 95 | |
| Val | Leu | Ala | Asp | Asn | Ile | Lys | Lys | Glu | Ala | Arg | Asn | Ala | Gln | Tyr | Leu |
| | | | | 100 | | | | | 105 | | | | | 110 | |
| Tyr | Ile | Trp | Thr | Asp | Cys | Asp | Arg | Glu | Gly | Glu | His | Ile | Gly | Val | Glu |
| | | | 115 | | | | | 120 | | | | | 125 | | |
| Ile | Ser | Asn | Val | Ala | Arg | Ala | Ser | Asn | Pro | Ser | Ile | Gln | Val | Ile | Arg |
| | 130 | | | | | 135 | | | | | 140 | | | | |
| Ala | Asp | Phe | Asn | Asn | Leu | Glu | Arg | Ser | His | Ile | Ile | Ser | Ala | Ala | Lys |
| 145 | | | | | 150 | | | | | 155 | | | | | 160 |
| Arg | Pro | Arg | Asp | Val | Ser | Lys | Asn | Ala | Ala | Asp | Ala | Val | Asp | Ala | Arg |
| | | | | 165 | | | | | 170 | | | | | 175 | |
| Ile | Glu | Leu | Asp | Phe | Arg | Leu | Gly | Ala | Ile | Phe | Thr | Arg | Leu | Gln | Thr |
| | | | 180 | | | | | 185 | | | | | 190 | | |
| Ile | Gln | Leu | Gln | Lys | Ser | Phe | Asp | Ile | Leu | Gly | Asn | Lys | Ile | Ile | Ser |
| | | 195 | | | | | 200 | | | | | 205 | | | |
| Tyr | Gly | Pro | Cys | Gln | Phe | Pro | Thr | Leu | Gly | Phe | Val | Val | Asp | Arg | Trp |
| 210 | | | | | 215 | | | | | 220 | | | | | |
| Gln | Arg | Val | Glu | Asp | Phe | Val | Pro | Glu | Thr | Tyr | Trp | His | Leu | Arg | Phe |
| 225 | | | | | 230 | | | | | 235 | | | | | 240 |
| Val | Asp | Lys | Arg | Gln | Gly | Lys | Thr | Ile | Gln | Phe | Asn | Trp | Glu | Arg | Ala |
| | | | | 245 | | | | | 250 | | | | | 255 | |
| Lys | Val | Phe | Asp | Arg | Leu | Thr | Thr | Met | Ile | Ile | Leu | Glu | Asn | Cys | Leu |
| | | | 260 | | | | | 265 | | | | | 270 | | |
| Glu | Cys | Lys | Thr | Ala | Lys | Val | Val | Asn | Ile | Thr | Gln | Lys | Pro | Lys | Thr |
| | | 275 | | | | | 280 | | | | | 285 | | | |
| Lys | Tyr | Lys | Pro | Leu | Pro | Leu | Ser | Thr | Val | Glu | Leu | Thr | Lys | Leu | Gly |
| | 290 | | | | | 295 | | | | | 300 | | | | |
| Pro | Lys | His | Leu | Arg | Ile | Ser | Ala | Lys | Lys | Thr | Leu | Glu | Leu | Ala | Glu |
| 305 | | | | | 310 | | | | | 315 | | | | | 320 |
| Asn | Leu | Tyr | Thr | Asn | Gly | Phe | Val | Ser | Tyr | Pro | Arg | Thr | Glu | Thr | Asp |
| | | | | 325 | | | | | 330 | | | | | 335 | |
| Gln | Phe | Asp | Ser | Ser | Met | Asn | Leu | His | Ala | Ile | Ile | Gly | Lys | Leu | Thr |
| | | | 340 | | | | | 345 | | | | | 350 | | |
| Gly | Ala | Gln | Glu | Trp | Asp | Ser | Tyr | Ala | Glu | Gly | Leu | Leu | Ala | Gly | Asp |
| | | 355 | | | | | 360 | | | | | 365 | | | |
| Tyr | Arg | Pro | Pro | Arg | Lys | Gly | Lys | His | Asn | Asp | Arg | Ala | His | Pro | Pro |
| 370 | | | | | 375 | | | | | 380 | | | | | |

```
Ile His Pro Val Gln Met Val His Arg Ser Ala Leu Pro Ser Gln Asp
385                 390                 395                 400

His Trp Lys Val Tyr Glu Leu Ile Thr Arg Arg Phe Leu Ala Cys Cys
                405                 410                 415

Ser Asp Asn Ala Lys Gly Ala Glu Thr Leu Val Gln Val Lys Met Glu
            420                 425                 430

Glu Glu Leu Phe Ser Lys Lys Gly Leu Leu Val Thr Glu Lys Asn Tyr
        435                 440                 445

Leu Glu Val Tyr Pro Tyr Glu Lys Trp Glu Ser Ser Asp Gln Leu Pro
450                 455                 460

Glu Tyr Arg Leu His Glu Glu Phe Gln Pro His Ile Leu Asp Met Met
465                 470                 475                 480

Asp Ser Ser Thr Ser Ser Pro Ser Tyr Ile Thr Glu Pro Glu Leu Ile
                485                 490                 495

Ala Leu Met Asp Ala Asn Gly Ile Gly Thr Asp Ala Thr Met Ala Glu
            500                 505                 510

His Ile Glu Lys Val Gln Glu Arg Glu Tyr Val Ile Lys Arg Lys Lys
        515                 520                 525

Arg Gly Gln Gly Val Thr Glu Phe Val Pro Ser Ser Leu Gly Val Ala
530                 535                 540

Leu Ala Lys Gly Tyr Asp Glu Ile Gly Leu Glu Trp Ser Leu Thr Lys
545                 550                 555                 560

Pro Phe Leu Arg Lys Glu Met Glu Val Gln Leu Lys Asn Ile Glu Asn
                565                 570                 575

Gly Gln Leu Asn Arg Asn Val Leu Val His Met Ile Leu Thr Gln Phe
            580                 585                 590

Arg Asp Val Phe His Leu Thr Lys Gln Arg Phe Asp Cys Leu Lys Asn
        595                 600                 605

Ser Cys Arg Val Tyr Leu Met Ser His Asn Glu Pro Gln Thr
610                 615                 620

<210> SEQ ID NO 52
<211> LENGTH: 656
<212> TYPE: PRT
<213> ORGANISM: Saccharomyces cerevisiae

<400> SEQUENCE: 52

Met Lys Val Leu Cys Val Ala Glu Lys Asn Ser Ile Ala Lys Ala Val
1               5                   10                  15

Ser Gln Ile Leu Gly Gly Gly Arg Ser Thr Ser Arg Asp Ser Gly Tyr
            20                  25                  30

Met Tyr Val Lys Asn Tyr Asp Phe Met Phe Ser Gly Phe Pro Phe Ala
        35                  40                  45

Arg Asn Gly Ala Asn Cys Glu Val Thr Met Thr Ser Val Ala Gly His
50                  55                  60

Leu Thr Gly Ile Asp Phe Ser His Asp Ser His Gly Trp Gly Lys Cys
65                  70                  75                  80

Ala Ile Gln Glu Leu Phe Asp Ala Pro Leu Asn Glu Ile Met Asn Asn
                85                  90                  95

Asn Gln Lys Lys Ile Ala Ser Asn Ile Lys Arg Glu Ala Arg Asn Ala
            100                 105                 110

Asp Tyr Leu Met Ile Trp Thr Asp Cys Asp Arg Glu Gly Glu Tyr Ile
        115                 120                 125

Gly Trp Glu Ile Trp Gln Glu Ala Lys Arg Gly Asn Arg Leu Ile Gln
130                 135                 140
```

```
Asn Asp Gln Val Tyr Arg Ala Val Phe Ser His Leu Glu Arg Gln His
145                 150                 155                 160

Ile Leu Asn Ala Ala Arg Asn Pro Ser Arg Leu Asp Met Lys Ser Val
                165                 170                 175

His Ala Val Gly Thr Arg Ile Glu Ile Asp Leu Arg Ala Gly Val Thr
            180                 185                 190

Phe Thr Arg Leu Leu Thr Glu Thr Leu Arg Asn Lys Leu Arg Asn Gln
        195                 200                 205

Ala Thr Met Thr Lys Asp Gly Ala Lys His Arg Gly Gly Asn Lys Asn
    210                 215                 220

Asp Ser Gln Val Val Ser Tyr Gly Thr Cys Gln Phe Pro Thr Leu Gly
225                 230                 235                 240

Phe Val Val Asp Arg Phe Glu Arg Ile Arg Asn Phe Val Pro Glu Glu
                245                 250                 255

Phe Trp Tyr Ile Gln Leu Val Val Glu Asn Lys Asp Asn Gly Gly Thr
            260                 265                 270

Thr Thr Phe Gln Trp Asp Arg Gly His Leu Phe Asp Arg Leu Ser Val
        275                 280                 285

Leu Thr Phe Tyr Glu Thr Cys Ile Glu Thr Ala Gly Asn Val Ala Gln
    290                 295                 300

Val Val Asp Leu Lys Ser Lys Pro Thr Thr Lys Tyr Arg Pro Leu Pro
305                 310                 315                 320

Leu Thr Thr Val Glu Leu Gln Lys Asn Cys Ala Arg Tyr Leu Arg Leu
                325                 330                 335

Asn Ala Lys Gln Ser Leu Asp Ala Ala Glu Lys Leu Tyr Gln Lys Gly
            340                 345                 350

Phe Ile Ser Tyr Pro Arg Thr Glu Thr Asp Thr Phe Pro His Ala Met
        355                 360                 365

Asp Leu Lys Ser Leu Val Glu Lys Gln Ala Gln Leu Asp Gln Leu Ala
    370                 375                 380

Ala Gly Gly Arg Thr Ala Trp Ala Ser Tyr Ala Ala Ser Leu Leu Gln
385                 390                 395                 400

Pro Glu Asn Thr Ser Asn Asn Lys Phe Lys Phe Pro Arg Ser Gly
                405                 410                 415

Ser His Asp Asp Lys Ala His Pro Pro Ile His Pro Ile Val Ser Leu
            420                 425                 430

Gly Pro Glu Ala Asn Val Ser Pro Val Glu Arg Arg Val Tyr Glu Tyr
        435                 440                 445

Val Ala Arg His Phe Leu Ala Cys Cys Ser Glu Asp Ala Lys Gly Gln
    450                 455                 460

Ser Met Thr Leu Val Leu Asp Trp Ala Val Glu Arg Phe Ser Ala Ser
465                 470                 475                 480

Gly Leu Val Val Leu Glu Arg Asn Phe Leu Asp Val Tyr Pro Trp Ala
                485                 490                 495

Arg Trp Glu Thr Thr Lys Gln Leu Pro Arg Leu Glu Met Asn Ala Leu
            500                 505                 510

Val Asp Ile Ala Lys Ala Glu Met Lys Ala Gly Thr Thr Ala Pro Pro
        515                 520                 525

Lys Pro Met Thr Glu Ser Glu Leu Ile Leu Leu Met Asp Thr Asn Gly
    530                 535                 540

Ile Gly Thr Asp Ala Thr Ile Ala Glu His Ile Asp Lys Ile Gln Val
545                 550                 555                 560
```

-continued

```
Arg Asn Tyr Val Arg Ser Glu Lys Val Gly Lys Glu Thr Tyr Leu Gln
            565                 570                 575

Pro Thr Thr Leu Gly Val Ser Leu Val His Gly Phe Glu Ala Ile Gly
            580                 585                 590

Leu Glu Asp Ser Phe Ala Lys Pro Phe Gln Arg Arg Glu Met Glu Gln
            595                 600                 605

Asp Leu Lys Lys Ile Cys Glu Gly His Ala Ser Lys Thr Asp Val Val
            610                 615                 620

Lys Asp Ile Val Glu Lys Tyr Arg Lys Tyr Trp His Lys Thr Asn Ala
625                 630                 635                 640

Cys Lys Asn Thr Leu Leu Gln Val Tyr Asp Arg Val Lys Ala Ser Met
            645                 650                 655
```